US009422572B2

(12) United States Patent
Allen et al.

(10) Patent No.: US 9,422,572 B2
(45) Date of Patent: Aug. 23, 2016

(54) PLANTS WITH IMPROVED AGRONOMIC TRAITS

(75) Inventors: Stephen M Allen, Wilmington, DE (US); Rajeev Gupta, Johnston, IA (US); Shuping Jiao, Johnston, IA (US); Robert B Meeley, Des Moines, IA (US); Dilbag S Multani, Urbandale, IA (US); Robert Williams, Hockessin, DE (US)

(73) Assignees: PIONEER HI-BRED INTERNATIONAL INC, Johnston, IA (US); E I DU PONT DE NEMOURS AND COMPANY, Wilmington, DE (US)

( * ) Notice: Subject to any disclaimer, the term of this patent is extended or adjusted under 35 U.S.C. 154(b) by 60 days.

(21) Appl. No.: 13/819,619

(22) PCT Filed: Jun. 27, 2012

(86) PCT No.: PCT/US2012/044434

§ 371 (c)(1), (2), (4) Date: Feb. 27, 2013

(87) PCT Pub. No.: WO2013/006345

PCT Pub. Date: Jan. 10, 2013

(65) Prior Publication Data

US 2013/0232642 A1 Sep. 5, 2013

Related U.S. Application Data

(60) Provisional application No. 61/503,852, filed on Jul. 1, 2011.

(51) Int. Cl.

*C12N 15/82* (2006.01)
*C07K 14/415* (2006.01)

(52) U.S. Cl.

CPC .......... *C12N 15/8274* (2013.01); *C07K 14/415* (2013.01); *C12N 15/8261* (2013.01); *C12N 15/8273* (2013.01)

(58) Field of Classification Search

None

See application file for complete search history.

(56) References Cited

U.S. PATENT DOCUMENTS

| | | | | |
|---|---|---|---|---|
| 2004/0031072 | A1 * | 2/2004 | La Rosa et al. | 800/278 |
| 2004/0123343 | A1 | 6/2004 | LaRosa et al. | |
| 2011/0061129 | A1 | 3/2011 | Tumer et al. | |

OTHER PUBLICATIONS

Keskin et al., 2004, Protein Science 13: 1043-1055.*

Guo et al., 2004, Proceedings of the National Academy of Sciences USA 101: 9205-9210.*

Thornton et al., 2000, Nature Structural Biology, structural genomic supplement, Nov. 2000: 991-994.*

Blazquez et al., 2001, EMBO Reports 21: 1078-1082.*

* cited by examiner

*Primary Examiner* — David T Fox
*Assistant Examiner* — Bratislav Stankovic
(74) *Attorney, Agent, or Firm* — Pioneer Hi-Bred Intl Inc.

(57) ABSTRACT

Isolated polynucleotides and polypeptides and recombinant DNA constructs useful for conferring drought tolerance, compositions (such as plants or seeds) comprising these recombinant DNA constructs, and methods utilizing these recombinant DNA constructs. The recombinant DNA construct comprises a polynucleotide operably linked to a promoter that is functional in a plant, wherein said polynucleotide encodes a PRE2 polypeptide.

3 Claims, 18 Drawing Sheets

A. pre2 at 8-10 leaves stage
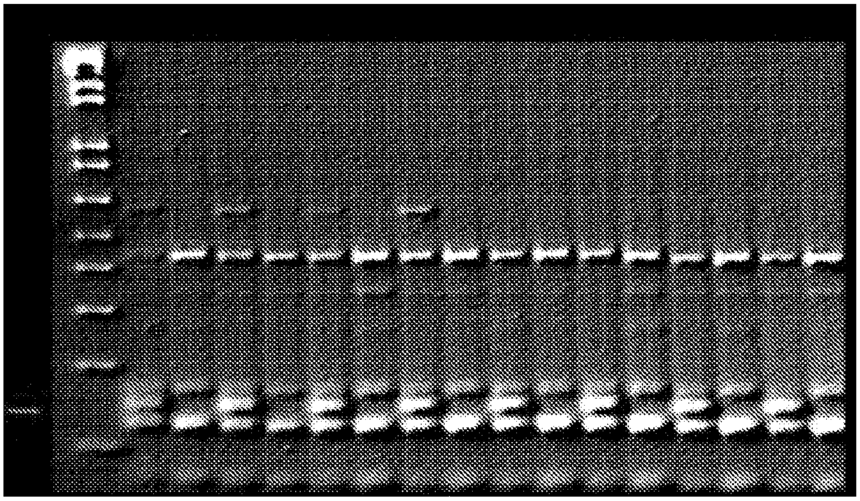
B.
FIG. 1

Molecular<sup>pre2</sup> cterization *ZmPRE2* mRNA Expression in *pre2* Mutant

RT-PCR using Gene Specific primers primers (from exon1 + exon2)

Adding bp in mRNA
373 bp (232 + 1 pre2 TIR)
160 bp (19 + 141)
122 bp (all Mu-TIR)
WT Predicted Polypeptides
113* aa
49* aa
113* aa
1271 aa

A.

| Flat ID | score (2 sigma) | Deviation |
|---|---|---|
| PREESKOAT3VS SIB3 | 2.149 | 7.289 |
| PREESKOAT2VS SIB2 | 1.912 | 6.564 |
| PREESKOAT4VS SIB4 | 1.374 | 4.736 |
| PREESKOAT1VS SIB1 | 1.54 | 4.497 |
| [illegible] | [illegible] | [illegible] |

- All 4 flats are positive (A "score [2 sigma]" greater than 0.9 and a positive deviation considered an outlier in this assay)
- 35S:ZmPRE2 Ox in Arabidopsis show hypersensitivity to drought

B.

| | 1 KO | 1 Wt sib | 2 KO | 2 Wt sib | 3 KO | 3 Wt sib | 4 KO | 4 Wt sib |
|---|---|---|---|---|---|---|---|---|
| Count | 27 | 25 | 27 | 28 | 27 | 27 | 29 | 22 |
| Average | 42306 | 51523 | 34563 | 47275 | 34590 | 44766 | 36295 | 44063 |
| Avg diff | | -9217 | | -12713 | | -10176 | | -7767 |

| EVENT | CCM | | days to shed | | days to silk | | ear area 8DAS (sq cm) | | ear length 8DAS (cm) | | ear width 8DAS (cm) | | silk count | |
|---|---|---|---|---|---|---|---|---|---|---|---|---|---|---|
| | P | % v NULL | P | % v NULL | P | % v NULL | P | % v NULL | P | % v NULL | P | % v NULL | P | % v NULL |
| 1.4 | 0.383 | -6.2% | 0.385 | -0.7% | 0.245 | -2.2% | 0.204 | -7.8% | 0.276 | -5.6% | 0.064 | -5.4% | 0.051 | -11.9% |
| 1.5 | **0.809** | **1.8%** | **0.248** | **1.0%** | **0.351** | **1.8%** | **0.062** | **11.7%** | **0.073** | **9.4%** | **0.576** | **1.6%** | **0.101** | **10.5%** |
| 2.5 | **0.989** | **0.1%** | **0.000** | **5.1%** | **0.000** | **11.2%** | **0.000** | **25.1%** | **0.004** | **15.2%** | **0.132** | **4.5%** | **0.174** | **8.6%** |

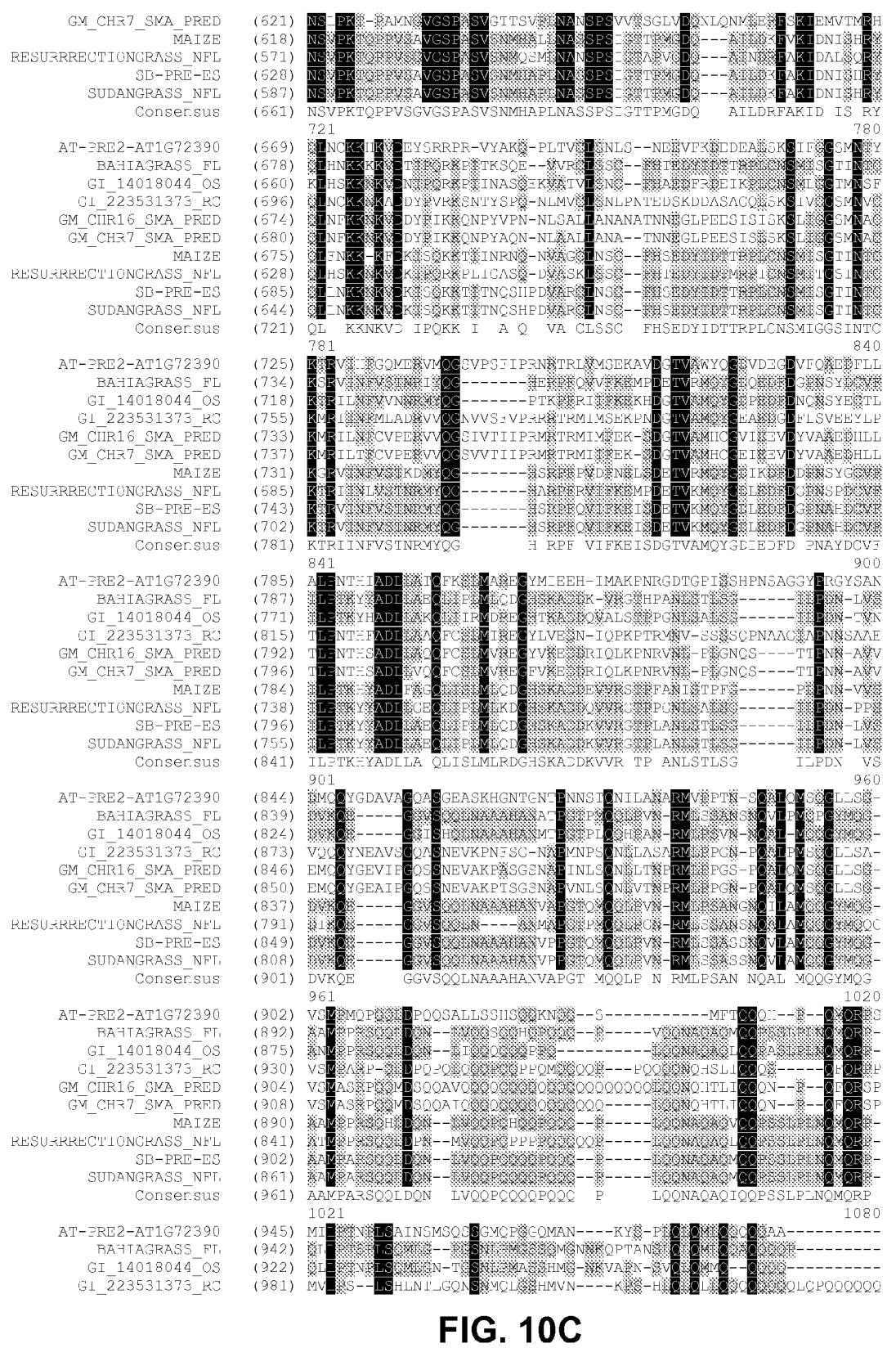

```
     GM_CHR7_SMA_PRED  (621) NSIPKS-SAMNSVGSPASVGTTSVPLNANSPSVVSSGLVDQNLQNMLESFSKIEMVTMRH
                MAIZE  (618) NSVPKTQPPVSAVGSPASVSNMHALLNASPSPIGTTPMGDQ---AILDKFVKIDNISHRY
RESURRECTIONGRASS_NFL  (571) NSVPKTQPPVSGVGSPASVSNMQSMLNANSPSIGTAPVGDQ---AINDRFAKIDALSQRY
            SB-PRE-ES  (628) NSVPKTQPPVSAVGSPASVSNMHAPLNASSPSIGTTPMGDQ---AILDKFAKIDNISHRY
       SUDANGRASS_NFL  (587) NSVPKTQPPVSAVGSPASVSNMHAPLNASSPSIGTTPMGDQ---AILDKFAKIDNISHRY
            Consensus  (661) NSVPKTQPPVSGVGSPASVSNMHAPLNASSPSIGTTPMGDQ   AILDRFAKID IS RY
                             721                                                       780
    AT-PRE2-AT1G72390  (669) QLNQKKIKVDEYSRRPR-VYAKQ-PLTVSLNLS--NEEVFKDEDEALSKSIFGGSMNTY
        BAHIAGRASS_FL  (678) QLHNKKKVDTIPQRKPITKSQE--VVRCLSSC--FHSEDYIDTTRPLCNSMISGTINTC
       GI_14018044_OS  (660) KLHSKKKVDNIPQRKPIINASQEKVATVLNSC--FHAEDFREIKPLCNSMLGGTMNSF
      GI_223531373_RC  (696) QLNCKKKAIDYIVRKSNTYSPQ-NLMVQLSNLPNTEDSKDDASACQLSKSIVGGSMNVS
    GM_CHR16_SMA_PRED  (674) QLNFKKKVDDYPIKKQNPYVPN-NLSALLANANATNNEGLPEESISISKSLIGGSMNAG
     GM_CHR7_SMA_PRED  (680) QLNFKKKVDDYPIKKQNPYAQN-NLAALLANA--TNNEGLPEESISLSKSLIGGSMNAG
                MAIZE  (675) QLFNKK-KFDKISQKKTIINRNQ-NVACLNSC--FHSEDYIDTTRPLCNSMISGTINTC
RESURRECTIONGRASS_NFL  (628) QLHSKKKVDKIPQRKPLIGASQ-DVASKLSSC--FHTEDYIDIMRPICNSMICSINTC
            SB-PRE-ES  (685) QLLNKKKVDKISQKKTITNQSHPDVARCLNSC--FHSEDYIDTTRPLCNSMISGTINTC
       SUDANGRASS_NFL  (644) QLLNKKKVDKISQKKTITNQSHPDVARCLNSC--FHSEDYIDTTRPLCNSMISGTINTC
            Consensus  (721) QL  KKNKVD IPQKK I  A Q  VA CLSSC  FHSEDYIDTTRPLCNSMIGGSINTC
                             781                                                       840
    AT-PRE2-AT1G72390  (725) KTRVILPGQMERVMQGSVPSFIPRNRTRLMMSEKAVDGTVAWYQGSVDEGDVFQAEEFLL
        BAHIAGRASS_FL  (734) KSRVINFVSTNRIYQG-------HERPFQVVFKEMPDETVRMQYGQEDFDGPNSYDCVF
       GI_14018044_OS  (718) KTRILNFVVNNRMYQG-------PTKPPRIIFKEKHDGTVAMQYGPEDFDNQNSYEGTL
      GI_223531373_RC  (755) KMRILNRMLADRVVQGNVVSEVPRRRTRMIMSEKPNDGTVAMQYGEAEEGDFLSVEEYLP
    GM_CHR16_SMA_PRED  (733) KMRILNFCVPERVVQGSIVTIIPRMRTRMIMFEK-SDGTVAMHQGVIEEVDYVAAEEHLL
     GM_CHR7_SMA_PRED  (737) KMRILTFCVPEQVVQGSVVTIIPRMRTRMIIFEK-SDGTVAMHQGEIEEVDYVAAEEHLL
                MAIZE  (731) KGRVINFVSTKDMYQG-------HSRPFPVDFNELSDETVRMQYGIKDEDDPNSYGCVF
RESURRECTIONGRASS_NFL  (685) KTRIINLVSTNRMYQG-------HARPFRVIFKEMPDETVKMQYGLEDFDGPNSPDCVF
            SB-PRE-ES  (743) KTRVINFVSTNRMYQG-------HSRPFQVIFKEISDETVKMQYGRLEDFDGPNAHDCVF
       SUDANGRASS_NFL  (702) KTRVINFVSTNRMYQG-------HSRPFQVIFKEISDETVKMQYGRLEDFDGPNAHDCVF
            Consensus  (781) KTRIINFVSTNRMYQG       H RPF VIFKEISDGTVAMQYGDIEDFD PNAYDCVF
                             841                                                       900
    AT-PRE2-AT1G72390  (785) ALENTHIADLLATQFKSIMAREGYMIEEH-IMAKPNRGDTGPIESHPNSAGGYPRGYSAN
        BAHIAGRASS_FL  (787) ILPTKYYADLLAEQLISLMLQDGHSKAEK-VRGTHPANLSTLSS------ILPDN-LVS
       GI_14018044_OS  (771) ILPTKYHADLLAKQLIIRMDREGHTKASDQVALSTPPGNLSALSS------ILPDN-TVN
      GI_223531373_RC  (815) TLENTHFADLLAAQFCSLMIREGYLVESN-IQPKPTRMNV-SS-SCQPNAACSAPNNSAAE
    GM_CHR16_SMA_PRED  (792) TLENTHSADLLAQQFCSLMVREGYVKEESRIQLKPNRVNL-PSGNQS----TTPNN-AVV
     GM_CHR7_SMA_PRED  (796) TLENTHSADLLVQQFCSLMVREGFVKEESRIQLKPNRVNL-PSGNQS----TTPNN-AVV
                MAIZE  (784) ILPTKYHADLIFAGQLISLMLQDGHSKADEVVRSEPFANISTPFS------PIPNN-VVS
RESURRECTIONGRASS_NFL  (738) ILPTKYYADLLCEQLIPLMLKDGHSKADQVVRGTPPGNISALSS------ILPDN-PPS
            SB-PRE-ES  (796) ILPTKYYADLLAEQLIPLMLQDGHSKADKVVRGTPLANLSTLSS------ILPDN-LVS
       SUDANGRASS_NFL  (755) ILPTKYYADLLAEQLIPLMLQDGHSKADKVVRGTPLANLSTLSS------ILPDN-LVS
            Consensus  (841) ILPTKHYADLLA QLISLMLRDGHSKADKVVR TP ANLSTLSG      ILPDN VS
                             901                                                       960
    AT-PRE2-AT1G72390  (844) EMQQYGDAVAGQASGEASKHGNTGNTPNNSIQNILANARMVSPTN-SQALQMSQGLLSG-
        BAHIAGRASS_FL  (839) DVKQE-----GGVSQQLNAAAHANATPGTPVQQLPVN-RMLSSANSNQVLPMQPGYMQG-
       GI_14018044_OS  (824) DVKQE-----GGISHQQLNAAAHAAMTPSTPLQQHPAN-RMLPSVN-NQAL-MQQGYMQG-
      GI_223531373_RC  (873) VQQQYNEAVSGQASNEVKPNFSC-NAPMNPSQNLASARMLPPCN-PQALPMSQGLLSA-
    GM_CHR16_SMA_PRED  (846) EMQQYGEVIPGQSSNEVAKPASGSNAPINLSQNLTSPRMLPPGS-PQALQMSQGLLSG-
     GM_CHR7_SMA_PRED  (850) EMQQYGEAIPGQSSNEVAKPTSGSNAPVNLSQNLVTSPRMLPPGN-PQALQMSQGLLSG-
                MAIZE  (837) DVKQE-----GGVSQQLNAAAHANVAPGTQMQQLPVN-RMLPSANGNQILAMQQGYMQG-
RESURRECTIONGRASS_NFL  (791) DIKQE-----GGVSQQLN----AAMAPGTPVQQLPQN-RMLSSANSNQALAMQQGYMQQQ
            SB-PRE-ES  (849) DVKQE-----GGVSQQLNAAAHANVPPGTQMQQLPVN-RMLSSASSNQVLAMQQGYMQG-
       SUDANGRASS_NFL  (808) DVKQE-----GGVSQQLNAAAHANVPPGTQMQQLPVN-RMLSSASSNQVLAMQQGYMQG-
            Consensus  (901) DVKQE     GGVSQQLNAAAHANVAPGT MQQLP N RMLPSAN NQAL MQQGYMQG
                             961                                                       1020
    AT-PRE2-AT1G72390  (902) VSMPMQPQQQLDPQQSALLSSHSQQKNQQ--S-----------MFTQQQH--P--QMQRPS
        BAHIAGRASS_FL  (892) AAMPPSQQLDQN--LVQQSQQHQPQQQ--P-----VQQNAQAQMQQPSSLPLNQMQRP-
       GI_14018044_OS  (875) ANMPPSQQLDQN--LIQQQQQQPPQ----------LQQNAQAQLQQPASLPLNQMQRP-
      GI_223531373_RC  (930) VSMPAMP-QLDPQPQLQQQPQQPPQMQQQQH---PQQQQNQHSLIQQQQ------QFQRPP
    GM_CHR16_SMA_PRED  (904) VSMASSPQQMDSQQAVQQQQQQQQQQQQQQQQQQQQQLQQNQHTLIQQQN--P--QFQRSP
     GM_CHR7_SMA_PRED  (908) VSMASSPQQMDSQQATQQQQQQQQQQQQQQQ-----LQQNQHTLIQQQN--P--QFQRSP
                MAIZE  (890) AAMPPSQQHIDQN--LVQQPQHQQPQQQ--P-----LQQNAQAQVQQPSSLPLNQMQRP-
RESURRECTIONGRASS_NFL  (841) ATMPPSQQLDPN--MVQQPQPPPPQQQQQP-----LQQNAQAQLQQPSSLPLNQMQRP-
            SB-PRE-ES  (902) AAMPASQQLDQN--LVQQPQQQQPQQQ--P-----LQQNAQAQMQQPSSLPLNQMQRP-
       SUDANGRASS_NFL  (861) AAMPASQQLDQN--LVQQPQQQQPQQQ--P-----LQQNAQAQMQQPSSLPLNQMQRP-
            Consensus  (961) AAMPARSQQLDQN  LVQQPQQQQPQQQ  P     LQQNAQAQIQQPSSLPLNQMQRP
                             1021                                                      1080
    AT-PRE2-AT1G72390  (945) MIPPTNPLSAINSMSQSSGMQPSGQMAN----KYS-PIQLQMSQQQQAA----------
        BAHIAGRASS_FL  (942) QTPPTSTLSQMQS--PQSNPVMPSSQMQNNKQPTANPLQLQMLQQQQQQQ---------
       GI_14018044_OS  (922) QLPPTNPLSQMQGN-TQSNLSMASSHMQ-NKVAPN-SVQLQMQ--QQQQ----------
      GI_223531373_RC  (981) MVPHS--LSHLNTLGQNSNMQLSSHMVN----KPS-HLQLQLSQQQQQQQLQPQQQQQQ
```

FIG. 10C

```
   GM_CHR16_SMA_PRED  (960) MMLGTNQLSHLNPVGQNSNMPLGNHMLN----KPS-ALQMQMFQQQQQ-----------
    GM_CHR7_SMA_PRED  (959) MMLGTNQLSHLNPVGQNSNMPLGNHMLN----RPS-ALQLQMFQQQQQQ----------
               MAIZE  (940) QVLPTSPLSQMLG--PGSNLPMGSSQIGKNKAPPT-SLQLQMLQ-AQPQQP---------
RESURRECTIONGRASS_NFL (893) QILPTSPLSQMMG--PGSNLPMGSSQMGNNKSAPT-SLQLQMLQQAQQQQP---------
           SB-PRE-ES  (952) QLLPTSPLSQMLG--PGSNLTMGSSQIGNNKAPPS-SLQLQMLQ-AQQQQP---------
      SUDANGRASS_NFL  (911) QLLPTSPLSQMLG--PGSNLTMGSSQIGNNKAPPS-SLQLQMLQ-AQQQQP---------
           Consensus (1021) QLLPTSPLSQMLG  PGSNLPMGSSQIG NK  PS SLQLQMLQQAQQQQP
                            1081                                                    1140
   AT-PRE2-AT1G72390  (990) -----VQKKIMMGLGSGVGMGMGMG---MGMGMGSMGNSIAGLGALGNQLNMAG-RGMGG
      BAHIAGRASS_FL   (991) ---------------MSRKGMMGLG---SAMNMGNMVNNVVSVGGL---MG--NVR----
     GI_14018044_OS   (967) ----------------SRKMMMGLG---SPANMGNMVNNVVGLNNIGNVMGMGNVR----
    GI_223531373_RC  (1034) QQQQQQQQQQQQPQMQQRKMMMGLG---TAMGMGNMGNNMVGLGGLSNAMSIGGARAMGG
   GM_CHR16_SMA_PRED (1004) ------------PQMQ-RKMMMGLG---QAVGMGNLRNNLVGLAPMGNPMGMGGARGIGG
    GM_CHR7_SMA_PRED (1004) ------QQQQQQPQMQ-RKMMMGLG---QAVGMGNLRNNLVGLAPMGNPMGMGGVRGIGG
               MAIZE  (987) ---------------MSRKVMMGLG---SAMNMGNMVNNVVGLGGLGNVMGMGNVR----
RESURRECTIONGRASS_NFL (941) ---------------MSRKVMMGLGGLGSAMNMSNMVNNVVGLGGIGNVMGMGNVR----
           SB-PRE-ES  (999) ---------------MSRKVMMGLG---SAMNMGNMVNNVVGLGGLGNVMGMGNVR----
      SUDANGRASS_NFL  (958) ---------------MSRKVMMGLG---SAMNMGNMVNNVVGLGGLGNVMGMGNVR----
           Consensus (1081)                MSRKMMMGLG   SAMNMGNMVNNVVGLGGLGNVMGMGNVR
                            1141                                                    1200
   AT-PRE2-AT1G72390 (1041) TGISSSMS-VPGIGNMGQNPMNLNPASNLN-AISQQLRSGALTSQQ-NALFTQIRMGMAN
      BAHIAGRASS_FL  (1024) -PISSPMGSMSGLGNN-TNPMNMGMPSNLA---AG-LRPG-MSAAT----IAKMRM---A
     GI_14018044_OS  (1004) -PMSSPMGNMSGLGNN-PNQMSLGMVSSLS---APGIRPG-MTHAA----IAKMRMGLIQ
    GI_223531373_RC  (1091) PGISGSMAPISGMNNVGQNQINLSQTTNLPNVISQHFRAGQVTSQQ-AAYLSKLRMAQ-N
   GM_CHR16_SMA_PRED (1048) SGISAPMTSIAGMGNMGQSPMNLSQTSNITNSISQQFRSGSLNAAASADLISRLRLVHSN
    GM_CHR7_SMA_PRED (1054) SGISAPMTSIAGMGNMGQNPMNLSQTSNITNSISQQFRSGSINAAASADLLSKLRLVHQN
               MAIZE (1025) -PISSPMASMSGLGNN-SNPMNMGMASNLA---AAGLRPG-MNPAA----IAKVRMG-LA
RESURRECTIONGRASS_NFL (982) -PISSPMGSMS-LGNN-SNPMNLGMTSNLA---AAGLRPG-MNPAT----LAKMRM---A
           SB-PRE-ES (1037) -PISSPMGSMSGLGNN-SNPMNMGMASNLA---AAGLRPG-MNPAT----FAKMRIG-LA
      SUDANGRASS_NFL  (996) -PISSPMGSMSGLGNN-SNPMNMGMASNLA---AAGLRPG-MNPAT----FAKMRIG-LA
           Consensus (1141)  PISSPMGSMSGLGNN SNPMNLGM SNLA   AAGLRPG MNPA    IAKMRMG  A
                            1201                                                    1260
   AT-PRE2-AT1G72390 (1098) RGGVMGAPQ-TGISGVSG-TRQMHPS-SAGLSMLDQN----RANLQRAAAMGNMGPPKLM
      BAHIAGRASS_FL  (1070) QQRAG-MYPQTGMVGMPGSSSPILPS-SANLIMMNHPLNRSNLNPLQRAMMSSMGPPKMP
     GI_14018044_OS  (1054) QQRAAGIYPQTSMVGMPGSSSPILPG-SANLSMMNQ-LNRSNINPLQRAMMG---PPKMP
    GI_223531373_RC  (1149) RTSMLGAPQ-SGIAGMSG-ARQMHPG-SAGLSMLGQSLNRAKMNPMQRSAMGPMGPPKLM
   GM_CHR16_SMA_PRED (1108) RQSMLGSPQ-SNLASISG-ARQIHPGATPSLSMLGR------ANTMQR-PIGPMGPPKMM
    GM_CHR7_SMA_PRED (1114) RQGMLGSSQ-SNIASISG-ARQIHPGGTPSLSMLGR------ANTMQR-PIGPMGPPKIM
               MAIZE (1074) QQRAAGMYP--GMVGMPGSSSSILPS-SAGLSMMGQPLNRGNLGPLQRAMMSSMGPPKMP
RESURRECTIONGRASS_NFL (1028) QQRAAGTYPQTGMVGMPGSSSPVS--------MMGHPLNRSNLNPLQRAMMSSMGPPKTP
           SB-PRE-ES (1086) QQRAAGMYP--GMVGMTGSSSPILPS-SAGLSMMGQPLNRSNLGPLQRAMMSSMGPPKIP
      SUDANGRASS_NFL (1045) QQRAAGMYP--GMVGMPGSSSPILPS-SAGLSMMGQPLNRSNLGPLQRAMMSSMGPPKIP
           Consensus (1201) QQRAAGMYP TGMVGMPGSSSPILPS SAGLSMMGQPLNRSNLNPLQRAMMSSMGPPKIP
                            1261                                                    1320
   AT-PRE2-AT1G72390 (1151) PGMMNLYMNQQQQQQQ-----------LQQ-------------QPQQQQLQHQQQLQQPM
      BAHIAGRASS_FL  (1128) SGNFQLNPQQQMQLQQLQQQQQ---LQQNPQQQQQLQQQQQQQLQQQQQQQLPQQQL
     GI_14018044_OS  (1109) SSNYPLTPQQQMQLQQQFQQNP----LQQQQ-------------LQQLQQQQQQQQ-QQQI
    GI_223531373_RC  (1206) AG-MNLYMNQQQQQQQQQLQLQQQQQFQQQQ-------------QQQQQQQQQQQQLQQLQ
   GM_CHR16_SMA_PRED (1159) AG-MNLYMSQQQQHQ---------------------------QPQQQQQQHQQQLQLQQ
    GM_CHR7_SMA_PRED (1165) AG-MNLYMSQQQQQH-----------QQP-------------QPQQQQQQHQQQLQLQQ
               MAIZE (1131) SGNFQLNAQQQIHLQHQLQQ------LQQNP-------------QQQLQQLQQQQQIQQLQ
RESURRECTIONGRASS_NFL (1080) SGNFPLNAQQQMQLQQQLQQQQQ--LQQNP-------------Q-QQQQLQQQQ--QQQL
           SB-PRE-ES (1143) SGNFQLNAQQQMQLQQQLQQQQQ---LQQNPQQQQQ-LHQNPQQQQLQQLQQQQQIQQQL
      SUDANGRASS_NFL (1102) SGNFQLNAQQQMQLQQQLQQQQQ---LQQNPQQQQQ-LHQNPQQQQLQQLQQQQQIQQQL
           Consensus (1261) SGNFNLN QQQMQLQQQLQQQQQ   LQQNP             QQQQQQQQQQQQLQQQL
                            1321                                                    1380
   AT-PRE2-AT1G72390 (1187) SQPSQQLAQSPQQQQQLQ-QHEQPQ-QAQQQQQATASPLQSVLSPPQVGSPS-AGITQQQ
      BAHIAGRASS_FL  (1185) ------------QQMQQLQQQQLQQQLQLQQQQQQMGSPRQQA----QVGSPA--GSQQSL
     GI_14018044_OS  (1152) ------------QQQQQQQQQQQQQQQIQQQQQQMGSPLQQAA---QVGSPA--GSQQSL
    GI_223531373_RC  (1252) ------------QQQQQLQ-QQQQQQ-MQQQQQQDPSSSLQAVVSSSQVGSPSTMGIPQLN
   GM_CHR16_SMA_PRED (1190) ------------HMQQQLQ-QQQQQ--------QETTSQLQSVVSPPQVGSPS-MGVPPLN
    GM_CHR7_SMA_PRED (1200) ------------HMQQQLQ-QQQQQ---------ETTSQLQAVVSPPQVGSPS-MGIPPMN
               MAIZE (1173) ------------QQQQ----QQLQQQ-QLQQQQQ-MGSPLQQA----QVGSPA--GSQQSP
RESURRECTIONGRASS_NFL (1123) ------------QQSPQ---QQHQQ-QMQQQLQ--------------Q----------QQLQ
           SB-PRE-ES (1199) ------------QQQQQLQ-QQLQQQ-QQQQQQQQMGSPLQQA----QVGSPA--GSQQSL
      SUDANGRASS_NFL (1158) ------------QQQQQLQ-QQLQQQ-QQQQQQQQMGSPLQQA----QVGSPA--GSQQSL
           Consensus (1321)             QQQQQLQ QQLQQQ Q QQQQQ MGSPLQQA    QVGSPA  GSQQSN
                            1381                                                    1440
   AT-PRE2-AT1G72390 (1244) LQQSSPQQMSQRTPMSPQQVNQRTPMSPQISSGAMHPMS--TSNLEGQP---ASPQLSSQ
      BAHIAGRASS_FL  (1228) MMQQQ----------LSPPQMGQHAAMSPQLSSGTLQQMSNNVANPVATPGPPPSPQLSSQ
     GI_14018044_OS  (1196) VMSQHQQ--------LSPQQ---MAAMSPQLSSGTMQQVNNNVINHVATPGPPPSPQLSSQ
```

FIG. 10D

```
        GI_223531373_RC  (1299) QQQQPQQQP------SPQQMSQRTPMSPQISSSAIHAMS--AGNPEACP---ASPQLSSQ
     GM_CHR16_SMA_PRED  (1229) --QQTQQQA------SPQQMSQRTPMSPQMSSSAIHAMS--AGNPLACP---ASPQLSSQ
      GM_CHR7_SMA_PRED  (1238) --QQAQQQA------NPQQMSQRTPMSPQMSSSAIHAMN--AGNPEACP---ASPQLSSQ
                 MAIZE  (1210) MMQQQQQQQQQ---ISPQQMGQQAAMSPQLSSGTLQQMSNNVANPVATPGPPPSPQLSSG
RESURRRECTIONGRASS_NFL  (1146) QLQQQ-------------------------------QQ----------------------
             SB-PRE-ES  (1240) MMQQQQQ-------ISPQQMGQQAAMSPQLSSGTLQQMSNNVVNPVATPGPPPSPQLSSQ
        SUDANGRASS_NFL  (1199) MMQQQQQ-------ISPQQMGQQAAMSPQLSSGTLQQMSNNVVNPVATPGPPPSPQLSSQ
             Consensus  (1381) MMQQQQQ       ISPQQM Q AAMSPQLSSGTLQQMSNNVGNPVATPGPPPSPQLSSQ
                                1441                               1475
      AT-PRE2-AT1G72390  (1299) TMGSVGS-ITNSPMELQGPKNNSAGNNS-------
        BAHIAGRASS_FL  (1279) THGSVNS-IANSPMEQLQGANKGGPGSM-------
        GI_14018044_OS  (1246) THGSVNS-IANSPMEQLQGANKGGPGSM-------
        GI_223531373_RC  (1348) ILGSVGS-ITNSPMELQGVNKSNSVNNA-------
     GM_CHR16_SMA_PRED  (1276) TLGSVSS-ITNSPMDMQGVNKSNSNAQ--------
      GM_CHR7_SMA_PRED  (1285) TLGSVSS-ITNSPMDMQGVNKSNSNAQ--------
                 MAIZE  (1267) QQHS-------------------------------
RESURRRECTIONGRASS_NFL  (1153) -----------------------------------
             SB-PRE-ES  (1293) THGSEGVNTGQDHYVFFVVVNEVKLGVLYTYTLDR
        SUDANGRASS_NFL  (1252) THGSVSS-IANSPMEQLQGASKGGPGSM-------
             Consensus  (1441) T GSV S I NSPME          G
```

FIG. 10E

```
                                  110         122
AT-PRE-ES-AT1G72390      (95)  KVLHPYDRAAEGL
BAHIAGRASS_FL           (105)  KTLHPYDRASEKL
GI_14018044_OS          (100)  KTLHPYDKASEKL
GI_223531373_RC         (103)  KLLHPYDKTSETL
GM_CHR16_SMA_PRED        (95)  KSLHPYDRSSESL
GM_CHR7_SMA_PRED         (95)  KLLHPYDRSSESL
MAIZE                    (99)  KTLHPYDRASEKL
RESURRRECTIONGRASS_NFL   (56)  KTLHPYDRASEKL
SB-PRE-ES               (108)  KTLHPYDRASEKL
SUDANGRASS_NFL           (67)  KTLHPYDRASEKL
Consensus               (110)  KTLHPYDRASEKL
```

$KX_1LHPYD\ X_2X_3X_4E\ X_5L$ (Conserved Domain 1 – SEQ ID NO: 27)

X1 -- T,L,S,V

X2 -- R,K

X3 -- A,S,T

X4 -- S,A

X5 -- K,S,T,G

```
                               215            230
AT-PRE-ES-AT1G72390     (192)  LQPELCLDPLPRLDRL
BAHIAGRASS_FL           (210)  LQPELCLDPTPKLDRL
GI_14018044_OS          (205)  LQPALCLDPTPKLDRL
GI_223531373_RC         (208)  LQPQLCLDPTPKLDRL
GM_CHR16_SMA_PRED       (198)  LQPKLHLDPTPKLDRL
GM_CHR7_SMA_PRED        (199)  LQPKLHLDPTPKLDRL
MAIZE                   (204)  LQPELCLDPTPKLDRL
RESURRRECTIONGRASS_NFL  (161)  LQPELCLDPTPKLDRL
SB-PRE-ES               (213)  LQPELCLDPTPKLDRL
SUDANGRASS_NFL          (172)  LQPELCLDPTPKLDRL
Consensus               (215)  LQPELCLDPTPKLDRL
```

$LQPX_1LX_2LDPX_3PX_4LDRL$ (Conserved Domain 2 – SEQ ID NO: 28)

```
                                     588       598
     AT-PRE-ES-AT1G72390     (547)   SPLSSKSGEFS
          BAHIAGRASS_FL      (550)   SPVSSKSGEIS
         GI_14018044_OS      (531)   SPVSSKSGEIS
        GI_223531373_RC      (568)   SPLSSKSGEFS
      GM_CHR16_SMA_PRED      (549)   SPLSSKSGEFS
       GM_CHR7_SMA_PRED      (555)   SPLSSKSGEFS
                  MAIZE      (547)   SPVSSKSGELS
RESURRRECTIONGRASS_NFL       (500)   SPVSSKSGEIS
              SB-PRE-ES      (557)   SPVSSKSGEIS
        SUDANGRASS_NFL       (516)   SPVSSKSGEIS
              Consensus      (588)   SPVSSKSGEIS
```

$SPX^1SSKSGEX^2S$ (Conserved Domain 3 – SEQ ID NO: 29)

X1 -- V,L

X2 -- I,F,L

```
                                     673                692
     AT-PRE-ES-AT1G72390     (624)   VGSPVSVNTISVPVNARSPS
          BAHIAGRASS_FL      (633)   VGSPASVSNMHAPLNASSPS
         GI_14018044_OS      (615)   VGSPASVSNMHAVLNASSPS
        GI_223531373_RC      (651)   VGSPASVSNMSVPLNANSPS
      GM_CHR16_SMA_PRED      (626)   VGSPVSVGTTSVPLNANSPS
       GM_CHR7_SMA_PRED      (632)   VGSPASVGTTSVPLNANSPS
                  MAIZE      (630)   VGSPASVSNMHALLNASSPS
RESURRRECTIONGRASS_NFL       (583)   VGSPASVSNMQSMLNANSPS
              SB-PRE-ES      (640)   VGSPASVSNMHAPLNASSPS
        SUDANGRASS_NFL       (599)   VGSPASVSNMHAPLNASSPS
              Consensus      (673)   VGSPASVSNMHAPLNASSPS
```

$VGSPX_1SVX_2X_3X_4X_5X_6X_7X_8NAX_9SPS$ (Conserved Domain 4 – SEQ ID NO: 30)

```
                                 842                    863
   AT-PRE-ES-AT1G72390   (786)  LPNTHIADLLATQFKSLMAREG
        BAHIAGRASS_FL    (788)  LPTKYYADLLAEQLIPLMLQDG
       GI_14018044_OS    (772)  LPTKYHADLLAKQLIIRMDREG
      GI_223531373_RC    (816)  LPNTHFADLLAAQFCSLMIREG
    GM_CHR16_SMA_PRED    (793)  LPNTHSADLLAQQFCSLMVREG
     GM_CHR7_SMA_PRED    (797)  LPNTHSADLLVQQFCSLMVREG
                MAIZE    (785)  LPTKHYADLFAGQLISLMLQDG
RESURRRECTIONGRASS_NFL   (739)  LPTKYYADLLGEQLIPLMLKDG
            SB-PRE-ES    (797)  LPTKYYADLLAEQLIPLMLQDG
       SUDANGRASS_NFL    (756)  LPTKYYADLLAEQLIPLMLQDG
            Consensus    (842)  LPTKHYADLLA QLISLMLRDG
```

$LPX_1X_2X_3X_4ADLX_5X_6X_7QX_8X_9X_{10}X_{11}MX_{12}X_{13}X_{14}G$ (Conserved Domain 5 – SEQ ID NO: 31)

SEQUENCE LISTING

```
<160> NUMBER OF SEQ ID NOS: 51

<210> SEQ ID NO 1
<211> LENGTH: 11674
<212> TYPE: DNA
<213> ORGANISM: Zea mays

<400> SEQUENCE: 1

aaagtagcat atttactgga ttctcctagt ttaagcttat ttgataatct aatgcatatg     60

ttgttctttt gatcacatct gttatttgtt tgatcattga ataacttcaa ttaacactta    120

tgtttcttag tgcctcacat ttttttaaaa tcgatatctc tcttgatatg cactaagttg    180

aaaggagaat tcatgataca tttatgcaat tagtgatcca cttgatatat gataacattg    240

tcttagaaaa ggatcattag ttgtagaact ctctcttgtg cgtgggggag gtgagggatg    300
```

-continued

```
agggtctctg atttgctgcc tatggtaccc gtgcgttaat caaaaatatt atgtgaagac    360
aagagacaat caataaaaaa ttttgagata tttttggtga ataatttacg tgggtattgt    420
tgtgagccgt cgcaacgcac gggtaaccgg ctagtctaaa ctctaaagca gagctgttcc    480
gtacagagtt ttggaataaa gctattatga aatactctgc caaattttct agagtcgcaa    540
acatcctcta attatttgag acaattgttg gagcgagtcc acgcatgcaa gcgagtcctg    600
acggtataaa cccagtccat cagtccgatc tgtacattta ccggttgatt ggttccctgt    660
gtccgtggct gcacgctcgc ccgagcctgg ctggtcagat acatgcgttt tggcggtacg    720
agcggatgca gacaattagc cttcaaatgg cttgttttgc atcggcttgt gcagcccacg    780
ccttcgatgt gcaggcaacc aaacatacgc tcaggtaaag tcaatgcatg cagtgatcta    840
ggataaaacg atgcgaccaa ccaatcatat gattagcgta tgtggtcgcc gttcctgtgt    900
ttgttaacct cacaaatcat agataggcaa aactgtctcg atttttttcc agcccggcgt    960
caccgtacac cgatctctcc ccccccaccc caccccccaac atgctgcctc cgcccacggt   1020
agtagccgcg agccgaccga cgctcgtcga cgcgggtacg gggcgagtcg gtcatgctcc   1080
tgacctttct ctacatgtgc cgtcgaggag gacatggtgg cacctgccac acttaggtta   1140
tcttggcgat gaggagtcca ggtctgttat attggacaat catggctcgt agcgtgacag   1200
cagtcagcat atgctatgga gttgtggtgg tgttgtgtcg cttcagcggg ttcagggctg   1260
ggaagacact cacattctct cgtccgtctc ggactgacgc ctggtgcggg tgcctctcag   1320
tttggagctg ctccgactgg gcttctttct ccgcttgtgt gctctctccc tatatatcta   1380
tcggtataat acatatgtcg cctccagatg ccaaggtctt cgtcgtgtcc ttctccgaca   1440
acgaacaggt atgtccgcct ctttccttcc cctcttgctc tacgaaacct tggaagtgga   1500
ggaggcgagc tctgatttgc tgtctatggt acccgtgcgt taataaaaaa atattatgtg   1560
aagactagag acaatcaata aaaaaatttt gagatatttt tggtgaataa tttacgtggg   1620
tattgttgtg agccgtcgca atgcacgggt aaccggctag tctaaactct aaagcagagc   1680
tgttccgtac agagttttgg aataaaacta ttatgaaata ctctaccaaa ttttctagag   1740
tcgcaaacat cctctaatta tttgagacaa ttgttggagc gagtcaacgc atgcaagcga   1800
gtcctggtat aaacccaatc catcagtccg atctatatat ttaccggctg attggttccc   1860
tgtgtccgtg gctgcacgcc tgcccgagcc tgactggtcg gatatatgcg ttttggcggt   1920
acgaacggat gcatgcaatt agcctttaaa tgacttgttt tgtatcggct tgtgcagccc   1980
acgtcttcga tgtgcaggca accaaacata cactcagtta aagtcaatgc gtgcagtgat   2040
ctaggacaaa acgatgaaac caaccaatcg tatgattagc gtatgcggcc gccgttcctg   2100
cgtttgttaa cctcacaaat catagatagg caaaactgtc acgatttttt tccagcccgg   2160
cgtcaccgta caccgatctc tccccccccc cccgccaccc accccccacc accacgcccg   2220
acctcgtccg cggtgaaggt caaggagacg gcggaggaag cctgacaacc gtgtggatgg   2280
ggatctcgtt caagctgtcg aaggtcgggg tccgcgtgca cccggccgcg cgctcggcgt   2340
ccgcggcggt ggcggaaaag ccgggcgcgg gtgggaagga gggttcgctg tctgagtcga   2400
cacgcgaggt gaggcgctcg tggcttctat cgcttgcttg tttggtttgt gtgtcgcttc   2460
gagatggttt gggtgccaac agtggggggt gggggggggg ggggggatca aggagcggaa   2520
agcaatttgt cgaggaactg atgaaaaatc tgacctcgat ttttttgtt ttcaggcgaa   2580
tttcgttaat tcgctacaag gattaatatt tttggtgatt tcggctcgaa agcttgcgtt   2640
ggacaatcaa tcgcattttc gtttggagtg gtcaaatcct tcggaaggac tgaacattca   2700
```

-continued

```
aagacttttt tttggggggg gggggactcg tactttttcc ctcttttttt gggtttaagc   2760
tcgttttttt ggatggctat gtgtagcagt tcggctatag tagctgaggg tgccaatttg   2820
gcctgcttga actcagtatc taccaaacaa ctatttgtct tgtgcaacac tctagctaat   2880
tgtttgttat caattacctt acttttgatt gtctattggg tttagagcat tcaggtgtgg   2940
tttccaaggg attgacctaa tggggcgttt ggatccattc attttagagg aactgaaatt   3000
tacttaataa agtaacctat ttagcttgga atttgacatt ccaccacttt acaaagttta   3060
gatataagcc tatctcaaat ttatggagta gaggatgaga aataatttta tatatcagta   3120
gaatatgttt ctactctgca acttatagga cgctcttcga ctcactactt tataaaaatg   3180
tagcacataa atatcccgac atcttgttaa taatagtata caaatatatt ttacataaaa   3240
ccgtattagc ttaattgatg tgcctaaatt acttttatta gaatggaatt caattccaag   3300
gatctaaacg aggcaaagta tttgccatga agcaagggca atgctcctaa tttccaataa   3360
acataggatc accaatactg gagattcttt tgagttgtac tagtatctgt tgagaccagg   3420
gatgttatct tgtccagctc tttctgttgc acccttgctt tagtattgaa gtaccttata   3480
attttagttg gagcaatcaa gcaatgtaaa attagctagt attggcatgg ataggtgtac   3540
ctgaagtgct aaacttcaag tggacagtag atgatccaaa tcttgttgcc agatcttttg   3600
ttagcttaaa tgattggaga gaagatactt gcaacatgtt taaaaaaataa tttattttgt  3660
tttgttggtt ttcttgttgt attcgctttt tgttaatttg aatttgactg caattctctt   3720
ttctccatga taactgggtt ttactatgat ggaatgctca tttaatctct ttgtgcagga   3780
caaaagaaaa gatgtcaatg gcatcaaaat tttaccagca tgctccaaag aaattttgcc   3840
aggtattttg gacaatttaa gattttttg tctgtatcaa ttttgccagg ctttgttgtt   3900
gttttgtatt tagtctatgt tatgcactca acattgtatt gcagatcatg aggtttcttt   3960
cacattgagc ctctatgaga gaggttatct catttcaaag tcagcacccg tgagttcttc   4020
atctggaaat ttatgtagcg aatttcagtt actattcttg ttgcattgtt ttttctggaa   4080
ttcaagagaa aggcattcaa ctatgaatat attcctgaca taaaatacat atatgttcag   4140
atggatccta gtcagacctc aattcaggac ggcaaaacac tgcatcccta tgatagagca   4200
tcagaaaagt tgttctctgt aagtatggta tcacttgctt gcaagttttg ttttagttgt   4260
gtccttggat gacatgtcca tactccatag ttcatgcaat gccataccaa aaatttggag   4320
ccaaattagg tgtgaaaacc aaccaaattt ggttcatacc gcatttactt tatttttagt   4380
atgaacacga atttgaattg cttgaaatat gagttattgt atgttgtaat gtcaaatatg   4440
gatagagttg gggcaatgtt tgaggtctgt ttggaatgca ggaatttcat aggaggaata   4500
ggggaaaatt ctcgtgtttg gaacacatga atttcatagg ggtaggggta aaatcttgtg   4560
ttccaacagg gctttataat ttccaatcaa atgcaaaaac ttgtcactga gattctatcc   4620
aattgtagtc atttccattt atctttgtca tcgaaagaaa cgggagttca cattaaattt   4680
gtggaattct tcaaactaag gcttatgaca gtgaaatatg tatattttct ttaccaaatt   4740
cgaatataaa tagctggggt aaaccaaaac tttggatggc aaaaagtcta taccatattt   4800
gcatcaatat tgtttatgca aacctgaaat aatttcaggt tggcgcaaaa ttatgaaatt   4860
tggttggatg gaatatctat cgagtatggt atagtactat agtcacacat atttcttttg   4920
cgctctcaac caagaatgtc aaatctcatc tgaaaaaaaa acaaaaatga gaagaatgtt   4980
tcaaggaagt tttcaaatga gcacctctta catggtgatg aagttttatt cttctatagg   5040
```

-continued

```
actatatgat tgcaacattg gtgcgaccat atagtttgac cttagcatcc tgtaggctgt   5100
agccaagagc ccaagtttcc tgtgtatgag tattttcata tactaccata ttagacgttt   5160
tgagtactag acaaatatgt ttgctttgtt ttttagcctc ctaactgatc gaccaggttt   5220
atccatttag ctgtctaaag ataaaaattg atatacatga ctaattataa ttacatgagt   5280
ttcctcgtga tctgcaggct atcgaagctg ggaggctacc tggcgatatt tttgatgaga   5340
taccaagcaa gtactataat ggatcagttg tttgtgaggt aagttgtttt atcacacata   5400
agaaaggcta tgcatgcaat gctattgaac tgcaacatgc tgaaaccttc tgaaatttat   5460
tctcttataa gttgtggttg gtttctctga tacatggttc aaaaagcatg ctggtacaat   5520
ttctgtactg aggatttatg ctatatggga gaaatccttc tttaaaagaa aaactagaag   5580
tttggtgagc tttactgacg acatgttcta taatatgcca acctaccagt actgtaccaa   5640
ccttttttcta acacttattt cagaaacaac cgttatgcat tatcatgaag catcatgttg   5700
tgtcatgtgc tcatggtcat gtgctactgt accttattga taagagacca ttgagtcttt   5760
agcagtactt cattgtctta catcgacata agtaatgagt tctctttcta gatacatgac   5820
taccgaaagc atgtgtccaa ccaagcgcct gcatcatctg ctgagctagg atcaccaatt   5880
gtgaataaag tacgactgcg aatgaccttt gaaaatgttg taaaggacat tacccttcta   5940
tctgatgatt cctggagtta cagggatttt atggtaagta tgctgtggta acatctattc   6000
tatgagttag aatctcaaca tggctcattt tggcatctgt actcgtagtc tttatactct   6060
aggatctata ggaaattgct tattgagaat gtattaactg aatttagggc atgtttggat   6120
acatgggcta attgctagct aaaattggtt ctagtgcatc caaacaggag ggctaataga   6180
tgggttaatt ttttagccaa gtctccaact agctgttagc caaccgtagt taatttgggc   6240
taatttttag ctccaactag taactattca tgtatccaaa cgggccctta atcatttgtg   6300
tacctaatac tcagcaattg taaagttagt tcttcaataa ctgattagta acactggaat   6360
agcatgatac agtaacaaaa atgtaaaata tatgtatggt tggataacta attgaacttc   6420
tgaaacagag taacctgaaa tttcagttgc tgcaatttaa ctttctttgc tgaaccatat   6480
gggctattct gatatgcatg tttatctagg aagctgaggc ttgtattttg agagctctac   6540
aaccggaact ttgcttagac cccacaccta aactggatcg acttcatcag gatcctgttc   6600
cgcataaggt atggacacat gctgaaaaga aatattatca tggtaggtac atatgtctca   6660
aactaagtct cttatgttaa ttgcagttga gccttggtat agggaaaaag aggaggctga   6720
ggcaaaatcc tgaagttgtc acatccagtc acatgtctca tggtaaaaag gtttgcattg   6780
ataggttacc tgaaagtgcc aaagctgatg agatgggcat cactagcagt aatgcagctc   6840
agcaggttgg tggtaacatt accatccaaa atatgtcagt ctcaggtggt tctcagacac   6900
ttagaccaaa taattcttca caagatgctg ccagaacgct tttgcctcaa tctggtctac   6960
agcaaacctt gtgttattct gctgctggta atgatcatat ggcaggacca cctgccaatt   7020
tttctggaac cagttcatgc atttcatctc atcagagcct gattggttac agtgactctg   7080
tggctgccaa cagccttcta tctgtgaaga gggaaatgca ggatgcctcg cttcaagatc   7140
ctaagagaat aaagcgaact ggtggtattg atgatgtaca gcagcagcag ataaggcctc   7200
aacccccttgg tgggcaggag atgcaatgga agaaccatca actgcatcca caattagatg   7260
ttaaggggat gcagtatgca tcttcactga gtggtcagag atatccttct tcgatgatga   7320
acaacatgca agatccagga tcttccttat attttagtca tcagcaaaat ttgagatacg   7380
atgctaagca agagcagatg gatggttctg ataagtcaaa agacaccttg cagtctatgg   7440
```

```
cacctgaaac ttccatgctg gatcagcagc aatcccaatc tcaacattta ccacaacaat   7500
cagtggcaag aaataatgtt ccaaacatgg gacagtggca aaatactcgg ttcgcagctg   7560
agaaggactt caaaaaagaa gacataattc agagaagaaa gttagcacct agctctcgtg   7620
cccctactgg gcctgtgatt cagtctccag tgtcctcgaa atctggagag ttatcaggca   7680
gttcaatggg tggccagttt ggttctgctg tgacatcagc tgtaacaggg gtacagaaag   7740
ataaatttgc tgcaaattcc ggtactgcag ttggatttcc ttctgtagct tccagtccta   7800
gtgattccat gcaccgaata caacagcctg ctgttgcttc ctcaaagagg aaaacaaatt   7860
ctgtccccaa aactcaaccg cctgtgagtg ctgttgggtc tccagccagt gtttcaaaca   7920
tgcatgcgct gctgaatgca agcagtccat cgattgggac cacacctatg ggagaccaag   7980
caatccttga taaatttgtg aaaattgata acatttccca tcggtatagc ataatttcta   8040
catctgctcc ctcccttcac gaatttttgt tgtcactttc ctttctattc ttagtttctt   8100
tggaagtctg tcatgggaga ctttttaagg aagttttggg ttgcacggtg tgaatttgat   8160
gtctaggcta ttttaaagct gagattcagc cctattactt tggatggtca cacaaaaaaa   8220
tgtcaggcta taatgtgcaa atgaactgtt tcaattcttt atcaaagtta atcaacattt   8280
taacctaaat aactagtccc tccagttcaa attgtaagtt gttttggttt tttagatacc   8340
tggttttcac tgtgtatata gacatagcac acatctaggt gcatagcaga acctatgtac   8400
ctagaaaagt caaaacaact tacaatttga aattgaggga atgcctaaca aaataaaagg   8460
gtgaagagtt aaaacatctt ttttaggacc ggagtttcta aaaaaaaccc cggctgggga   8520
gtgaaagacc accctcctgg tattaatgct tggagttgac actcaaggat gcacacaacc   8580
cactgatggc taacaagaga ccgaaacatt gatcctagcc gagaaaatcc ccgacccatc   8640
actaacgggt caacgtcaac cgtccactct gcaatgaccc aatcagaggg tggcgtagag   8700
gacatcgtaa cccgagagcg gatgaggcac atcgagggga ttcttttaac caagccggaa   8760
aattcatttc tgagaagaat cgaacccaag acttgtaggt gctactcgga agcccttaac   8820
caataggccc tttcgcggac cggattttct caactaacta aaaacctgaa gaaagctttg   8880
tgagtctaaa catgcttttt tagtattgaa tctcatgtac aaagtgtctt ggtacctttt   8940
atcagttgtt acaacgtaca aatgtggact atttagtcag tttggtctgt agataccata   9000
aagtttgttt aaatattgaa tttcttgaag tgaagtcagc aatgcatata caacagcaac   9060
aaagcctttt agtcccaatt aagttgtggg taggctaaag ctaaaaccta actatgcatg   9120
tatgtttttt tttgatatag atctcattat aaagtggcac ataactggca cttgtggacg   9180
atttgaaata tttcattttt ggccattgca ttgtgataat atttttttct acatgcagtg   9240
atcgttgtgt attcttttca ggtaccagct tttcaataag aagaagtttg ataaaatatc   9300
tcaaaagaaa accattatca atcgaaacca aaatgtagct ggttgtctca acagttgttt   9360
ccattctgag gattatatag ataccacaag acctctttgt aattctatga ttagtggaac   9420
tataaacaca tgcaagggta gggtaataaa ctttgtgagc acaaaagaca tgtaccaagg   9480
tatgctctat agacattttg ctgaaaaggt ccccaggaaa gaaaagccac agcaccttca   9540
gttaatctga ttcacattgt catacaggtc attcaaggcc attcccggtt gattttaacg   9600
aactgtctga tgaaactgta agaatgcaat atggagatat aaaagatttt gatgatccaa   9660
attcatatgg ttgtgtattc atattaccga caaaggtttg ttgttatctc tcaaggtttc   9720
cctgttgtcc tttgtagcat aaaggccctg aaacactagg gcataatatt taactgctct   9780
```

-continued

```
atttctgtcc taacttttca attatttgct ctggcagcac tatgctgact tgtttgcggg   9840

gcagcttatt tcccttgtaa gttagataac cctaaagccc tgaatagtaa agatgttaag   9900

tcaatcttct cattaacttt cgtacttttt gctctagatg ttgcaagatg gacattctaa   9960

agctgacgat gaagttgtgc gtagcacccc ttttgctaac atcagtacac cctttggacc  10020

tttaccaaac aacgtagtga gtgatgtaaa gcaagaggga ggtgtaagcc aacaacttaa  10080

tgccgcagcc catgcaaatg tggcacctgg aacacaaatg caacagcttc ctgtcaatag  10140

gatgcttcca tctgcaaatg gcaaccagat tctagcaatg cagcaaggtt atatgcaagg  10200

ggcagccatg cctccaagga gccagcatct tgaccaaaat ttggttcagc agccgcagca  10260

ccaacagcca caacagcaac cactgcagca aaatgctcaa gcccaggtgc agcaaccatc  10320

atctcttcca ctgaaccaga tgcaaagacc tcaggttctg cctacgagcc cattatctca  10380

gatgttgggg cctggctcaa atctcccaat gggctcaagt cagataggta agaataaggc  10440

tcctcccaca tctttgcagc ttcaaatgct acaggcacaa ccccaacaac ctatgtctag  10500

gaaagtgatg atggggcttg gctcagccat gaacatgggc aatatggtta acaatgttgt  10560

tggtcttggt ggcctcggaa atgttatggg aatgggcaac gtgcggccaa tatcttcccc  10620

catggcatcg atgtcaggct taggtaacaa ttccaatcca atgaacatgg gaatggcatc  10680

caatcttgct gcagctggac ttcggccagg catgaaccct gctgctattg ccaaggtgcg  10740

tatggggttg gcacagcaaa gggcagcagg catgtaccct ggaatggttg gaatgcctgg  10800

aagcagctca tcaatccttc ctagttcagc tggcttgtct atgatgggcc agccgctaaa  10860

cagaggcaac cttggccccc tccagagggc catgatgtcg tctatgggcc ctccaaaaat  10920

gccaggaggt aactttcagc tgaatgctca acagcaaata cacctccagc atcagttgca  10980

gcagctccaa cagaacccac agcagcagct ccaacagcta cagcaacagc aacaaataca  11040

acaactgcag cagcagcagc agcagcagct ccaacaacag caactgcagc agcaacaaca  11100

aatgggatct ccgttacagc aggcacaggt gggctcacct gctggctcac agcaatcgcc  11160

gatgatgcag cagcagcagc agcagcagca gcagataagc cctcagcaga tgggacagca  11220

ggctgcaatg agcccccagt tgagctcagg aactctgcag caaatgagca ataacgtggc  11280

caaccctgta gccactccag gccctcctcc aagcccgcag ctgagctccg gtcaacagca  11340

tagctaactc cccgatggag cagctgcaag gcgccattaa gggaggtcct ggtagtagta  11400

accggagtcc acttcttgcc tatggaaggt gtaaacactg accaagatca ctctgttctc  11460

ttgtttgctg tggtaaatga ggttaaatta ggtgtgttat aagttatagg ccatagagga  11520

cagctttaag gaccagcttt atgcttggat ttttatgctg tacattgtag ttagtaggaa  11580

tggtgtgttg gagctcggta atcagttcta tgcaagcatt attcaattgg acagttttct  11640

actcttgtag cttcatgttt aaatttaaat taaa                              11674
```

```
<210> SEQ ID NO 2
<211> LENGTH: 4164
<212> TYPE: DNA
<213> ORGANISM: Zea mays

<400> SEQUENCE: 2

atggggatct cgttcaagct gtcgaaggtc ggggtccgcg tgcacccggc cgcgcgctcg     60

gcgtccgcgg cggtggcgga aaagccgggc gcgggtggga aggagggttc gctgtctgag    120

tcgacacgcg aggacaaaag aaaagatgtc aatggcatca aaattttacc agcatgctcc    180

aaagaaattt tgccagatca tgaggtttct ttcacattga gcctctatga gagaggttat    240
```

-continued

```
ctcatttcaa agtcagcacc catggatcct agtcagacct caattcagga cggcaaaaca    300
ctgcatccct atgatagagc atcagaaaag ttgttctctg ctatcgaagc tgggaggcta    360
cctggcgata tttttgatga gataccaagc aagtactata atggatcagt tgtttgtgag    420
atacatgact accgaaagca tgtgtccaac caagcgcctg catcatctgc tgagctagga    480
tcaccaattg tgaataaagt acgactgcga atgacctttg aaaatgttgt aaaggacatt    540
acccttctat ctgatgattc ctggagttac agggatttta tggaagctga ggcttgtatt    600
ttgagagctc tacaaccgga actttgctta gaccccacac ctaaactgga tcgacttcat    660
caggatcctg ttccgcataa gttgagcctt ggtataggga aaaagaggag gctgaggcaa    720
aatcctgaag ttgtcacatc cagtcacatg tctcatggta aaaaggtttg cattgatagg    780
ttacctgaaa gtgccaaagc tgatgagatg ggcatcacta gcagtaatgc agctcagcag    840
gttggtggta acattaccat ccaaaatatg tcagtctcag gtggttctca gacacttaga    900
ccaaataatt cttcacaaga tgctgccaga acgcttttgc ctcaatctgg tctacagcaa    960
accttgtgtt attctgctgc tggtaatgat catatggcag gaccacctgc caatttttct   1020
ggaaccagtt catgcatttc atctcatcag agcctgattg gttacagtga ctctgtggct   1080
gccaacagcc ttctatctgt gaagagggaa atgcaggatg cctcgcttca agatcctaag   1140
agaataaagc gaactggtgg tattgatgat gtacagcagc agcagataag gcctcaaccc   1200
cttggtgggc aggagatgca atggaagaac catcaactgc atccacaatt agatgttaag   1260
gggatgcagt atgcatcttc actgagtggt cagagatatc cttcttcgat gatgaacaac   1320
atgcaagatc caggatcttc cttatatttt agtcatcagc aaaatttgag atacgatgct   1380
aagcaagagc agatggatgg ttctgataag tcaaaagaca ccttgcagtc tatggcacct   1440
gaaacttcca tgctggatca gcagcaatcc caatctcaac atttaccaca acaatcagtg   1500
gcaagaaata atgttccaaa catgggacag tggcaaaata ctcggttcgc agctgagaag   1560
gacttcaaaa aagaagacat aattcagaga agaaagttag cacctagctc tcgtgcccct   1620
actgggcctg tgattcagtc tccagtgtcc tcgaaatctg gagagttatc aggcagttca   1680
atgggtggcc agtttggttc tgctgtgaca tcagctgtaa caggggtaca gaaagataaa   1740
tttgctgcaa attccggtac tgcagttgga tttccttctg tagcttccag tcctagtgat   1800
tccatgcacc gaatacaaca gcctgctgtt gcttcctcaa agaggaaaac aaattctgtc   1860
cccaaaactc aaccgcctgt gagtgctgtt gggtctccag ccagtgtttc aaacatgcat   1920
gcgctgctga atgcaagcag tccatcgatt gggaccacac ctatgggaga ccaagcaatc   1980
cttgataaat ttgtgaaaat tgataacatt tcccatcggt accagctttt caataagaag   2040
aagtttgata aaatatctca aaagaaaacc attatcaatc gaaaccaaaa tgtagctggt   2100
tgtctcaaca gttgtttcca ttctgaggat tatatagata ccacaagacc tctttgtaat   2160
tctatgatta gtggaactat aaacacatgc aagggtaggg taataaactt tgtgagcaca   2220
aaagacatgt accaaggtca ttcaaggcca ttcccggttg attttaacga actgtctgat   2280
gaaactgtaa gaatgcaata tggagatata aaagattttg atgatccaaa ttcatatggt   2340
tgtgtattca tattaccgac aaagcactat gctgacttgt ttgcggggca gcttatttcc   2400
cttatgttgc aagatggaca ttctaaagct gacgatgaag ttgtgcgtag cacccctttt   2460
gctaacatca gtacaccctt tggaccttta ccaaacaacg tagtgagtga tgtaaagcaa   2520
gagggaggtg taagccaaca acttaatgcc gcagcccatg caaatgtggc acctggaaca   2580
```

-continued

```
caaatgcaac agcttcctgt caataggatg cttccatctg caaatggcaa ccagattcta   2640

gcaatgcagc aaggttatat gcaaggggca gccatgcctc caaggagcca gcatcttgac   2700

caaaatttgg ttcagcagcc gcagcaccaa cagccacaac agcaaccact gcagcaaaat   2760

gctcaagccc aggtgcagca accatcatct cttccactga accagatgca aagacctcag   2820

gttctgccta cgagcccatt atctcagatg ttggggcctg gctcaaatct cccaatgggc   2880

tcaagtcaga taggtaagaa taaggctcct cccacatctt tgcagcttca aatgctacag   2940

gcacaacccc aacaacctat gtctaggaaa gtgatgatgg ggcttggctc agccatgaac   3000

atgggcaata tggttaacaa tgttgttggt cttggtggcc tcggaaatgt tatgggaatg   3060

ggcaacgtgc ggccaatatc ttcccccatg gcatcgatgt caggcttagg taacaattcc   3120

aatccaatga acatgggaat ggcatccaat cttgctgcag ctggacttcg gccaggcatg   3180

aaccctgctg ctattgccaa ggtgcgtatg gggttggcac agcaaagggc agcaggcatg   3240

taccctggaa tggttggaat gcctggaagc agctcatcaa tccttcctag ttcagctggc   3300

ttgtctatga tgggccagcc gctaaacaga ggcaaccttg gcccccctcca gagggccatg   3360

atgtcgtcta tgggccctcc aaaaatgcca ggaggtaact ttcagctgaa tgctcaacag   3420

caaatacacc tccagcatca gttgcagcag ctccaacaga acccacagca gcagctccaa   3480

cagctacagc aacagcaaca aatacaacaa ctgcagcagc agcagcagca gcagctccaa   3540

caacagcaac tgcagcagca acaacaaatg ggatctccgt tacagcaggc acaggtgggc   3600

tcacctgctg gctcacagca atcgccgatg atgcagcagc agcagcagca gcagcagcag   3660

ataagccctc agcagatggg acagcaggct gcaatgagcc cccagttgag ctcaggaact   3720

ctgcagcaaa tgagcaataa cgtggccaac cctgtagcca ctccaggccc tcctccaagc   3780

ccgcagctga gctccggtca acagcatagc taactccccg atggagcagc tgcaaggcgc   3840

cattaaggga ggtcctggta gtagtaaccg gagtccactt cttgcctatg gaaggtgtaa   3900

acactgacca agatcactct gttctcttgt ttgctgtggt aaatgaggtt aaattaggtg   3960

tgttataagt tataggccat agaggacagc tttaaggacc agctttatgc ttggattttt   4020

atgctgtaca ttgtagttag taggaatggt gtgttggagc tcggtaatca gttctatgca   4080

agcattattc aattggacag ttttctactc ttgtagcttc atgtttaaat ttaaattaaa   4140

aaaaaaaaaa aaaaaaaaaa aaaa                                           4164
```

<210> SEQ ID NO 3
<211> LENGTH: 1270
<212> TYPE: PRT
<213> ORGANISM: Zea mays

<400> SEQUENCE: 3

```
Met Gly Ile Ser Phe Lys Leu Ser Lys Val Gly Val Arg Val His Pro
1               5                   10                  15

Ala Ala Arg Ser Ala Ser Ala Ala Val Ala Glu Lys Pro Gly Ala Gly
            20                  25                  30

Gly Lys Glu Gly Ser Leu Ser Glu Ser Thr Arg Glu Asp Lys Arg Lys
        35                  40                  45

Asp Val Asn Gly Ile Lys Ile Leu Pro Ala Cys Ser Lys Glu Ile Leu
    50                  55                  60

Pro Asp His Glu Val Ser Phe Thr Leu Ser Leu Tyr Glu Arg Gly Tyr
65                  70                  75                  80

Leu Ile Ser Lys Ser Ala Pro Met Asp Pro Ser Gln Thr Ser Ile Gln
                85                  90                  95
```

```
Asp Gly Lys Thr Leu His Pro Tyr Asp Arg Ala Ser Glu Lys Leu Phe
            100                 105                 110

Ser Ala Ile Glu Ala Gly Arg Leu Pro Gly Asp Ile Phe Asp Glu Ile
        115                 120                 125

Pro Ser Lys Tyr Tyr Asn Gly Ser Val Val Cys Glu Ile His Asp Tyr
    130                 135                 140

Arg Lys His Val Ser Asn Gln Ala Pro Ala Ser Ser Ala Glu Leu Gly
145                 150                 155                 160

Ser Pro Ile Val Asn Lys Val Arg Leu Arg Met Thr Phe Glu Asn Val
                165                 170                 175

Val Lys Asp Ile Thr Leu Leu Ser Asp Asp Ser Trp Ser Tyr Arg Asp
            180                 185                 190

Phe Met Glu Ala Glu Ala Cys Ile Leu Arg Ala Leu Gln Pro Glu Leu
        195                 200                 205

Cys Leu Asp Pro Thr Pro Lys Leu Asp Arg Leu His Gln Asp Pro Val
    210                 215                 220

Pro His Lys Leu Ser Leu Gly Ile Gly Lys Lys Arg Arg Leu Arg Gln
225                 230                 235                 240

Asn Pro Glu Val Val Thr Ser Ser His Met Ser His Gly Lys Lys Val
                245                 250                 255

Cys Ile Asp Arg Leu Pro Glu Ser Ala Lys Ala Asp Glu Met Gly Ile
            260                 265                 270

Thr Ser Ser Asn Ala Ala Gln Gln Val Gly Gly Asn Ile Thr Ile Gln
        275                 280                 285

Asn Met Ser Val Ser Gly Gly Ser Gln Thr Leu Arg Pro Asn Asn Ser
    290                 295                 300

Ser Gln Asp Ala Ala Arg Thr Leu Leu Pro Gln Ser Gly Leu Gln Gln
305                 310                 315                 320

Thr Leu Cys Tyr Ser Ala Ala Gly Asn Asp His Met Ala Gly Pro Pro
                325                 330                 335

Ala Asn Phe Ser Gly Thr Ser Ser Cys Ile Ser Ser His Gln Ser Leu
            340                 345                 350

Ile Gly Tyr Ser Asp Ser Val Ala Ala Asn Ser Leu Leu Ser Val Lys
        355                 360                 365

Arg Glu Met Gln Asp Ala Ser Leu Gln Asp Pro Lys Arg Ile Lys Arg
    370                 375                 380

Thr Gly Gly Ile Asp Asp Val Gln Gln Gln Gln Ile Arg Pro Gln Pro
385                 390                 395                 400

Leu Gly Gly Gln Glu Met Gln Trp Lys Asn His Gln Leu His Pro Gln
                405                 410                 415

Leu Asp Val Lys Gly Met Gln Tyr Ala Ser Ser Leu Ser Gly Gln Arg
            420                 425                 430

Tyr Pro Ser Ser Met Met Asn Asn Met Gln Asp Pro Gly Ser Ser Leu
        435                 440                 445

Tyr Phe Ser His Gln Gln Asn Leu Arg Tyr Asp Ala Lys Gln Glu Gln
    450                 455                 460

Met Asp Gly Ser Asp Lys Ser Lys Asp Thr Leu Gln Ser Met Ala Pro
465                 470                 475                 480

Glu Thr Ser Met Leu Asp Gln Gln Gln Ser Gln Ser Gln His Leu Pro
                485                 490                 495

Gln Gln Ser Val Ala Arg Asn Asn Val Pro Asn Met Gly Gln Trp Gln
            500                 505                 510
```

-continued

```
Asn Thr Arg Phe Ala Ala Glu Lys Asp Phe Lys Lys Glu Asp Ile Ile
        515                 520                 525

Gln Arg Arg Lys Leu Ala Pro Ser Ser Arg Ala Pro Thr Gly Pro Val
    530                 535                 540

Ile Gln Ser Pro Val Ser Ser Lys Ser Gly Glu Leu Ser Gly Ser Ser
545                 550                 555                 560

Met Gly Gly Gln Phe Gly Ser Ala Val Thr Ser Ala Val Thr Gly Val
                565                 570                 575

Gln Lys Asp Lys Phe Ala Ala Asn Ser Gly Thr Ala Val Gly Phe Pro
            580                 585                 590

Ser Val Ala Ser Ser Pro Ser Asp Ser Met His Arg Ile Gln Gln Pro
        595                 600                 605

Ala Val Ala Ser Ser Lys Arg Lys Thr Asn Ser Val Pro Lys Thr Gln
    610                 615                 620

Pro Pro Val Ser Ala Val Gly Ser Pro Ala Ser Val Ser Asn Met His
625                 630                 635                 640

Ala Leu Leu Asn Ala Ser Ser Pro Ser Ile Gly Thr Thr Pro Met Gly
                645                 650                 655

Asp Gln Ala Ile Leu Asp Lys Phe Val Lys Ile Asp Asn Ile Ser His
            660                 665                 670

Arg Tyr Gln Leu Phe Asn Lys Lys Lys Phe Asp Lys Ile Ser Gln Lys
        675                 680                 685

Lys Thr Ile Ile Asn Arg Asn Gln Asn Val Ala Gly Cys Leu Asn Ser
    690                 695                 700

Cys Phe His Ser Glu Asp Tyr Ile Asp Thr Thr Arg Pro Leu Cys Asn
705                 710                 715                 720

Ser Met Ile Ser Gly Thr Ile Asn Thr Cys Lys Gly Arg Val Ile Asn
                725                 730                 735

Phe Val Ser Thr Lys Asp Met Tyr Gln Gly His Ser Arg Pro Phe Pro
            740                 745                 750

Val Asp Phe Asn Glu Leu Ser Asp Glu Thr Val Arg Met Gln Tyr Gly
        755                 760                 765

Asp Ile Lys Asp Phe Asp Asp Pro Asn Ser Tyr Gly Cys Val Phe Ile
    770                 775                 780

Leu Pro Thr Lys His Tyr Ala Asp Leu Phe Ala Gly Gln Leu Ile Ser
785                 790                 795                 800

Leu Met Leu Gln Asp Gly His Ser Lys Ala Asp Asp Glu Val Val Arg
                805                 810                 815

Ser Thr Pro Phe Ala Asn Ile Ser Thr Pro Phe Gly Pro Leu Pro Asn
            820                 825                 830

Asn Val Val Ser Asp Val Lys Gln Glu Gly Gly Val Ser Gln Gln Leu
        835                 840                 845

Asn Ala Ala Ala His Ala Asn Val Ala Pro Gly Thr Gln Met Gln Gln
    850                 855                 860

Leu Pro Val Asn Arg Met Leu Pro Ser Ala Asn Gly Asn Gln Ile Leu
865                 870                 875                 880

Ala Met Gln Gln Gly Tyr Met Gln Gly Ala Ala Met Pro Pro Arg Ser
                885                 890                 895

Gln His Leu Asp Gln Asn Leu Val Gln Gln Pro Gln His Gln Gln Pro
            900                 905                 910

Gln Gln Gln Pro Leu Gln Gln Asn Ala Gln Ala Gln Val Gln Gln Pro
        915                 920                 925

Ser Ser Leu Pro Leu Asn Gln Met Gln Arg Pro Gln Val Leu Pro Thr
```

-continued

```
    930                 935                 940

Ser Pro Leu Ser Gln Met Leu Gly Pro Gly Ser Asn Leu Pro Met Gly
945                 950                 955                 960

Ser Ser Gln Ile Gly Lys Asn Lys Ala Pro Pro Thr Ser Leu Gln Leu
                965                 970                 975

Gln Met Leu Gln Ala Gln Pro Gln Gln Pro Met Ser Arg Lys Val Met
            980                 985                 990

Met Gly Leu Gly Ser Ala Met Asn  Met Gly Asn Met Val  Asn Asn Val
        995                 1000                1005

Val Gly  Leu Gly Gly Leu Gly  Asn Val Met Gly Met  Gly Asn Val
    1010                 1015                1020

Arg Pro  Ile Ser Ser Pro Met  Ala Ser Met Ser Gly  Leu Gly Asn
    1025                 1030                1035

Asn Ser  Asn Pro Met Asn Met  Gly Met Ala Ser Asn  Leu Ala Ala
    1040                 1045                1050

Ala Gly  Leu Arg Pro Gly Met  Asn Pro Ala Ala Ile  Ala Lys Val
    1055                 1060                1065

Arg Met  Gly Leu Ala Gln Gln  Arg Ala Ala Gly Met  Tyr Pro Gly
    1070                 1075                1080

Met Val  Gly Met Pro Gly Ser  Ser Ser Ser Ile Leu  Pro Ser Ser
    1085                 1090                1095

Ala Gly  Leu Ser Met Met Gly  Gln Pro Leu Asn Arg  Gly Asn Leu
    1100                 1105                1110

Gly Pro  Leu Gln Arg Ala Met  Met Ser Ser Met Gly  Pro Pro Lys
    1115                 1120                1125

Met Pro  Gly Gly Asn Phe Gln  Leu Asn Ala Gln Gln  Gln Ile His
    1130                 1135                1140

Leu Gln  His Gln Leu Gln Gln  Leu Gln Gln Asn Pro  Gln Gln Gln
    1145                 1150                1155

Leu Gln  Gln Leu Gln Gln Gln  Gln Gln Ile Gln Gln  Leu Gln Gln
    1160                 1165                1170

Gln Gln  Gln Gln Gln Leu Gln  Gln Gln Gln Leu Gln  Gln Gln Gln
    1175                 1180                1185

Gln Met  Gly Ser Pro Leu Gln  Gln Ala Gln Val Gly  Ser Pro Ala
    1190                 1195                1200

Gly Ser  Gln Gln Ser Pro Met  Met Gln Gln Gln Gln  Gln Gln Gln
    1205                 1210                1215

Gln Gln  Ile Ser Pro Gln Gln  Met Gly Gln Gln Ala  Ala Met Ser
    1220                 1225                1230

Pro Gln  Leu Ser Ser Gly Thr  Leu Gln Gln Met Ser  Asn Asn Val
    1235                 1240                1245

Ala Asn  Pro Val Ala Thr Pro  Gly Pro Pro Pro Ser  Pro Gln Leu
    1250                 1255                1260

Ser Ser  Gly Gln Gln His Ser
    1265                 1270
```

<210> SEQ ID NO 4
<211> LENGTH: 4170
<212> TYPE: DNA
<213> ORGANISM: Oryza sativa

<400> SEQUENCE: 4

```
atggggatct cgttcaagct gtccaaggtg ggcgtccggg tccaccccgc cgcgcgggtg      60

gccgccccgg cgccggcggc ggtcgcggcg gagaaggcgg ccgagaagga ggcgaagcgc     120
```

-continued

```
gaggatggtg ttgttgaaag agctagtgat gccaatggca tcacgatttc accagcatgc    180
tctaggataa ttttgccaga gcacgaggtt tccttcactt tcagtctgta tgatagaggc    240
tatctcattg caaagtcagc agcgatggat ccttgccagc catcaataca ggatggaaaa    300
acacttcatc cctatgacaa ggcgtctgaa aaattgtttt ctgcaattga atctgggaga    360
ctgcctgaag atatacttga tgagatacca agcaagtact acaatggatc agtcatctgt    420
gagatacgtg attatcgaaa gcatgcttcc aatcaagcac ctgcaccatc tgctgagcta    480
ggactacctg ttgtgaataa agtgaggctg caaatgactt ttgaaaatgt tgtaagggac    540
attcctcggc tatctgatga ttcctggagt taccgagatt tcatggaagc tgaggcacgg    600
attgtgaaag ttctacaacc agcactttgt ttagatccta ctcctaagtt ggaccgactt    660
tgtcaggatc ctgttcctca taagctgaac cttggtattg gaaaaaagag aaggctaagg    720
cagaatcctg aagttgttgt cacatccaat aacatgtctc atggcaaaaa ggtgtgcata    780
gacagggttt ctgaaaatat gaaatcagat gagatgggta tttcaggtgg caatgctgtt    840
catcaaggcc ttgataacac tgccatccaa aatatgtcag gtggctctca gacatttaga    900
ccagctaatt tttcaatgct gtcccaaacc agtatccagc aaactgtcaa ttatcctgct    960
attggtaatg atcgtggggc agggactcct atgaactatg ctggaatcaa ttcaagcatt   1020
tcatctccac aaaacttgat ggcttacaat gagacaacca atggcctttt atctgtgaag   1080
agagaaatgg cagatgcccc actacaagac cctaagagag taaaaacaac ggtcagtgtt   1140
gatgatatgc agcagcagca gcaaacaagg catcagccag ctggacttgg tgggcaggag   1200
atgcagtgga agaatcaaca gctgcagcaa ttagatgtca agggcatgca gtatgctgct   1260
tcggttgggc agagatatac tcatcctcat gtgcaagaac cagcttccat ttattcgaac   1320
cagctaggta tgagatatgg agctaagcaa gagcagatgg atggcatgga caagtcaaaa   1380
gacaccttgc aagctatggc acctgaaaat tctgtgctgg atcaacaaca acctcaggcc   1440
ccacatttgt cacagcaagc aggcccacga aacatgcaac agtggcagaa tcctcgtttt   1500
tcaggtgaga aggacttgaa gaaagaagaa atgcttcaga gaaggaagat agctgctact   1560
tctcgtgtct cttctgtacc aatggttcag tctccagtct cctcaaaatc tggggagata   1620
tcaagcagtt caatgagtgc ccagtttggc gctgctgtga catctgctgt aatgggatca   1680
cagaaagaca agttccctgc aaattccaat cctgcagtag tgggctatcc ccctgttgct   1740
tctagcccta gtgattcaat gcaccggatg cagcagcctt cagttgctcc ttcaaagaga   1800
aaatcaaatt ctgttcccaa aactcaaccg cctgtgagtg gtgtagggtc tccagccagt   1860
gtttcaaaca tgcatgctgt actgaatgct agcagcccat caattgggac tgcacctatg   1920
ggtgatcaag caatccttga gagatttgtc aaaattgatg ccatatctca aaggtgcaag   1980
ctgcacagca agaagaacaa agttgacaat atacctcaga gaaaaccgat tatcaatgca   2040
agccaagaga aagttgctac agttctctcc aattgctttc atgctgaaga ttttagagat   2100
gaaataaaac ctctttgtaa ctctatgttg ggtggaacaa tgaattcctt taagactaga   2160
atactaaact ttgtggtcaa caaccgcatg taccaaggcc ctacaaagcc attccgtatc   2220
attttcaagg agaagcatga tggaacagtg gcgatgcaat atggagatcc agaagatttt   2280
gacaatcaga actcatatga gtgtacactg atattgccca ccaagtacca cgctgatctg   2340
cttgcgaagc aacttattat ccggatggac cgagaaggcc ataccaaggc agacgatcaa   2400
gttgcgctta gcacccctcc tggtaacctc agtgcattat caggaatttt accagacaac   2460
```

-continued acggtaaatg atgtgaaaca agaaggtggt attagccatc agctaaatgc tgcagctcat 2520
gcaaatatga cacctggaac ccctttacaa caacaccctg ccaataggat gcttccatct 2580
gtgaataacc aagcgttaat gcagcaagga tacatgcagg gggcaaacat gcctccgagg 2640
agtcaacagc ttgaccagaa tttgattcag cagcagcaac agcagccgcc gcagctgcag 2700
caaaatgcac aagcacaact gcagcaacca gcatctcttc ctctcaacca gatgcagaga 2760
cctcaacttc taccaacgaa cccattatct cagatgctgg ggaatactgg ctccaatctt 2820
ccgatggcct caagccacat gggtaacaag gtcgctccta attctgtgca gcttcagatg 2880
atgcagcagc agcaacagtc gaggaaaatg atgatgggcc tcggctcgcc tgccaacatg 2940
ggtaatatgg ttaacaatgt tgttggcctc aacaatattg gaaatgttat gggaatgggc 3000
aatgtgcggc caatgtcgtc cccaatggga aacatgtcag gcttagggaa caaccccaat 3060
cagatgagcc ttggaatggt atccagtctc tctgcacctg ggattcgtcc aggtatgaca 3120
catgctgcta ttgccaagat gcgaatgggg ttgatacagc agcaaagagc agcaggcatt 3180
tacccccaga ctagcatggt cggaatgcct gggagcagtt ctccgattct tcctggttct 3240
gccaatttgt ccatgatgaa tcagctaaac agaagcaaca ttaacccttt gcagcgggcc 3300
atgatgggtc caccaaagat gccaggcagt aattacccgt tgactccgca acagcaaatg 3360
caactccagc aacagttcca acagaacccg ctgcagcagc agcaactgca gcaactccaa 3420
caacagcagc agcaacaaca acaacagcaa atccagcagc agcagcagca gcaacagcaa 3480
cagcagcagc agcagcagca aattcagcag cagcaacaac aaatgggctc tccgttacag 3540
caggcggcac aggtgggctc acctgctggt tcgcagcagt cattggtgat gtcgcagcat 3600
cagcaaataa gcccacagca aatggccgcg atgagtccac agctgagctc aggcaccatg 3660
cagcaagtga ataacaatgt tatcaaccac gtagccacac caggccctcc tcctagcccg 3720
cagctcagct cacagaccca tgggtcggtc aacagcatcg caaactcccc aatggagcag 3780
ttgcaaggtg ccaataaagg aggtccaggg agcatgtagt gacggcaaat aattgtttct 3840
gtgatggaca tacaaaataa tgcaaggtat aaatatcggc agtgatcagc actttttctt 3900
atttgttgtg gtaaatgatg ttaaagttag gtgtcctgta agttatagcc aatagatgaa 3960
gatattatgg aggatcagcc ttacgcaggg atttctgatg ttgtagattt tagataatga 4020
aattagtacc tttaggggat tggtactgat gaaagttttg ttcaatggga ctactttctt 4080
gtttaaatta attatcaagt ttgtgtaata gctatgtaac cgtggtgctt attaataagt 4140
atcttcattt gattgtggaa attttgccct 4170

<210> SEQ ID NO 5
<211> LENGTH: 1272
<212> TYPE: PRT
<213> ORGANISM: Oryza sativa

<400> SEQUENCE: 5

Met Gly Ile Ser Phe Lys Leu Ser Lys Val Gly Val Arg Val His Pro
1 5 10 15

Ala Ala Arg Val Ala Ala Pro Ala Pro Ala Ala Val Ala Ala Glu Lys
20 25 30

Ala Ala Glu Lys Glu Ala Lys Arg Glu Asp Gly Val Val Glu Arg Ala
35 40 45

Ser Asp Ala Asn Gly Ile Thr Ile Ser Pro Ala Cys Ser Arg Ile Ile
50 55 60

Leu Pro Glu His Glu Val Ser Phe Thr Phe Ser Leu Tyr Asp Arg Gly

-continued

```
65                  70                  75                  80

Tyr Leu Ile Ala Lys Ser Ala Ala Met Asp Pro Cys Gln Pro Ser Ile
                85                  90                  95

Gln Asp Gly Lys Thr Leu His Pro Tyr Asp Lys Ala Ser Glu Lys Leu
            100                 105                 110

Phe Ser Ala Ile Glu Ser Gly Arg Leu Pro Glu Asp Ile Leu Asp Glu
        115                 120                 125

Ile Pro Ser Lys Tyr Tyr Asn Gly Ser Val Ile Cys Glu Ile Arg Asp
    130                 135                 140

Tyr Arg Lys His Ala Ser Asn Gln Ala Pro Ala Pro Ser Ala Glu Leu
145                 150                 155                 160

Gly Leu Pro Val Val Asn Lys Val Arg Leu Gln Met Thr Phe Glu Asn
                165                 170                 175

Val Val Arg Asp Ile Pro Arg Leu Ser Asp Asp Ser Trp Ser Tyr Arg
            180                 185                 190

Asp Phe Met Glu Ala Glu Ala Arg Ile Val Lys Val Leu Gln Pro Ala
        195                 200                 205

Leu Cys Leu Asp Pro Thr Pro Lys Leu Asp Arg Leu Cys Gln Asp Pro
    210                 215                 220

Val Pro His Lys Leu Asn Leu Gly Ile Gly Lys Lys Arg Arg Leu Arg
225                 230                 235                 240

Gln Asn Pro Glu Val Val Val Thr Ser Asn Asn Met Ser His Gly Lys
                245                 250                 255

Lys Val Cys Ile Asp Arg Val Ser Glu Asn Met Lys Ser Asp Glu Met
            260                 265                 270

Gly Ile Ser Gly Gly Asn Ala Val His Gln Gly Leu Asp Asn Thr Ala
        275                 280                 285

Ile Gln Asn Met Ser Gly Gly Ser Gln Thr Phe Arg Pro Ala Asn Phe
    290                 295                 300

Ser Met Leu Ser Gln Thr Ser Ile Gln Gln Thr Val Asn Tyr Pro Ala
305                 310                 315                 320

Ile Gly Asn Asp Arg Gly Ala Gly Thr Pro Met Asn Tyr Ala Gly Ile
                325                 330                 335

Asn Ser Ser Ile Ser Ser Pro Gln Asn Leu Met Ala Tyr Asn Glu Thr
            340                 345                 350

Thr Asn Gly Leu Leu Ser Val Lys Arg Glu Met Ala Asp Ala Pro Leu
        355                 360                 365

Gln Asp Pro Lys Arg Val Lys Thr Thr Val Ser Val Asp Asp Met Gln
    370                 375                 380

Gln Gln Gln Gln Thr Arg His Gln Pro Ala Gly Leu Gly Gly Gln Glu
385                 390                 395                 400

Met Gln Trp Lys Asn Gln Gln Leu Gln Gln Leu Asp Val Lys Gly Met
                405                 410                 415

Gln Tyr Ala Ala Ser Val Gly Gln Arg Tyr Thr His Pro His Val Gln
            420                 425                 430

Glu Pro Ala Ser Ile Tyr Ser Asn Gln Leu Gly Met Arg Tyr Gly Ala
        435                 440                 445

Lys Gln Glu Gln Met Asp Gly Met Asp Lys Ser Lys Asp Thr Leu Gln
    450                 455                 460

Ala Met Ala Pro Glu Asn Ser Val Leu Asp Gln Gln Gln Pro Gln Ala
465                 470                 475                 480

Pro His Leu Ser Gln Gln Ala Gly Pro Arg Asn Met Gln Gln Trp Gln
                485                 490                 495
```

-continued

```
Asn Pro Arg Phe Ser Gly Glu Lys Asp Leu Lys Lys Glu Glu Met Leu
            500                 505                 510

Gln Arg Arg Lys Ile Ala Ala Thr Ser Arg Val Ser Ser Val Pro Met
        515                 520                 525

Val Gln Ser Pro Val Ser Ser Lys Ser Gly Glu Ile Ser Ser Ser Ser
    530                 535                 540

Met Ser Ala Gln Phe Gly Ala Ala Val Thr Ser Ala Val Met Gly Ser
545                 550                 555                 560

Gln Lys Asp Lys Phe Pro Ala Asn Ser Asn Pro Ala Val Val Gly Tyr
                565                 570                 575

Pro Pro Val Ala Ser Ser Pro Ser Asp Ser Met His Arg Met Gln Gln
            580                 585                 590

Pro Ser Val Ala Pro Ser Lys Arg Lys Ser Asn Ser Val Pro Lys Thr
        595                 600                 605

Gln Pro Pro Val Ser Gly Val Gly Ser Pro Ala Ser Val Ser Asn Met
    610                 615                 620

His Ala Val Leu Asn Ala Ser Ser Pro Ser Ile Gly Thr Ala Pro Met
625                 630                 635                 640

Gly Asp Gln Ala Ile Leu Glu Arg Phe Val Lys Ile Asp Ala Ile Ser
                645                 650                 655

Gln Arg Cys Lys Leu His Ser Lys Lys Asn Lys Val Asp Asn Ile Pro
            660                 665                 670

Gln Arg Lys Pro Ile Ile Asn Ala Ser Gln Glu Lys Val Ala Thr Val
        675                 680                 685

Leu Ser Asn Cys Phe His Ala Glu Asp Phe Arg Asp Glu Ile Lys Pro
    690                 695                 700

Leu Cys Asn Ser Met Leu Gly Gly Thr Met Asn Ser Phe Lys Thr Arg
705                 710                 715                 720

Ile Leu Asn Phe Val Val Asn Asn Arg Met Tyr Gln Gly Pro Thr Lys
                725                 730                 735

Pro Phe Arg Ile Ile Phe Lys Glu Lys His Asp Gly Thr Val Ala Met
            740                 745                 750

Gln Tyr Gly Asp Pro Glu Asp Phe Asp Asn Gln Asn Ser Tyr Glu Cys
        755                 760                 765

Thr Leu Ile Leu Pro Thr Lys Tyr His Ala Asp Leu Leu Ala Lys Gln
    770                 775                 780

Leu Ile Ile Arg Met Asp Arg Glu Gly His Thr Lys Ala Asp Asp Gln
785                 790                 795                 800

Val Ala Leu Ser Thr Pro Pro Gly Asn Leu Ser Ala Leu Ser Gly Ile
                805                 810                 815

Leu Pro Asp Asn Thr Val Asn Asp Val Lys Gln Glu Gly Gly Ile Ser
            820                 825                 830

His Gln Leu Asn Ala Ala Ala His Ala Asn Met Thr Pro Gly Thr Pro
        835                 840                 845

Leu Gln Gln His Pro Ala Asn Arg Met Leu Pro Ser Val Asn Asn Gln
    850                 855                 860

Ala Leu Met Gln Gln Gly Tyr Met Gln Gly Ala Asn Met Pro Pro Arg
865                 870                 875                 880

Ser Gln Gln Leu Asp Gln Asn Leu Ile Gln Gln Gln Gln Gln Gln Pro
                885                 890                 895

Pro Gln Leu Gln Gln Asn Ala Gln Ala Gln Leu Gln Gln Pro Ala Ser
            900                 905                 910
```

```
Leu Pro Leu Asn Gln Met Gln Arg Pro Gln Leu Leu Pro Thr Asn Pro
        915                 920                 925

Leu Ser Gln Met Leu Gly Asn Thr Gly Ser Asn Leu Pro Met Ala Ser
    930                 935                 940

Ser His Met Gly Asn Lys Val Ala Pro Asn Ser Val Gln Leu Gln Met
945                 950                 955                 960

Met Gln Gln Gln Gln Gln Ser Arg Lys Met Met Met Gly Leu Gly Ser
                965                 970                 975

Pro Ala Asn Met Gly Asn Met Val Asn Asn Val Val Gly Leu Asn Asn
            980                 985                 990

Ile Gly Asn Val Met Gly Met Gly  Asn Val Arg Pro Met  Ser Ser Pro
        995                 1000                1005

Met Gly  Asn Met Ser Gly Leu  Gly Asn Asn Pro Asn  Gln Met Ser
    1010                1015                1020

Leu Gly  Met Val Ser Ser Leu  Ser Ala Pro Gly Ile  Arg Pro Gly
    1025                1030                1035

Met Thr  His Ala Ala Ile Ala  Lys Met Arg Met Gly  Leu Ile Gln
    1040                1045                1050

Gln Gln  Arg Ala Ala Gly Ile  Tyr Pro Gln Thr Ser  Met Val Gly
    1055                1060                1065

Met Pro  Gly Ser Ser Ser Pro  Ile Leu Pro Gly Ser  Ala Asn Leu
    1070                1075                1080

Ser Met  Met Asn Gln Leu Asn  Arg Ser Asn Ile Asn  Pro Leu Gln
    1085                1090                1095

Arg Ala  Met Met Gly Pro Pro  Lys Met Pro Gly Ser  Asn Tyr Pro
    1100                1105                1110

Leu Thr  Pro Gln Gln Gln Met  Gln Leu Gln Gln Gln  Phe Gln Gln
    1115                1120                1125

Asn Pro  Leu Gln Gln Gln Gln  Leu Gln Gln Leu Gln  Gln Gln Gln
    1130                1135                1140

Gln Gln  Gln Gln Gln Gln Gln  Ile Gln Gln Gln Gln  Gln Gln Gln
    1145                1150                1155

Gln Gln  Gln Gln Gln Gln Gln  Gln Gln Ile Gln Gln  Gln Gln Gln
    1160                1165                1170

Gln Met  Gly Ser Pro Leu Gln  Gln Ala Ala Gln Val  Gly Ser Pro
    1175                1180                1185

Ala Gly  Ser Gln Gln Ser Leu  Val Met Ser Gln His  Gln Gln Ile
    1190                1195                1200

Ser Pro  Gln Gln Met Ala Ala  Met Ser Pro Gln Leu  Ser Ser Gly
    1205                1210                1215

Thr Met  Gln Gln Val Asn Asn  Asn Val Ile Asn His  Val Ala Thr
    1220                1225                1230

Pro Gly  Pro Pro Pro Ser Pro  Gln Leu Ser Ser Gln  Thr His Gly
    1235                1240                1245

Ser Val  Asn Ser Ile Ala Asn  Ser Pro Met Glu Gln  Leu Gln Gly
    1250                1255                1260

Ala Asn  Lys Gly Gly Pro Gly  Ser Met
    1265                1270
```

<210> SEQ ID NO 6
<211> LENGTH: 3984
<212> TYPE: DNA
<213> ORGANISM: Sorghum bicolor

<400> SEQUENCE: 6

-continued

```
atggggatct cgttcaagct gtccaaggtc ggggtccgcg tgcacccggc cgcgcgctcg     60
gcgtccgcgg cgctggcaca ggcggcggag gcggaaaagc cggccacggg ggagaaggag    120
gggtccctgt ctgagtcgag acgcgaggac aacttcgttg agagaggaaa agatgtcaat    180
ggaatcaaaa ttttaccagc gtgctccaag gaaattttgc cagatcatga ggtttctttc    240
acatttagcc tctatgagag aggttatctc atttcaaagt cagcatctat ggatcctagt    300
cagacctcaa tccaggacag caaaacactg catccctatg atagagcatc ggaaaagtta    360
ttctctgcca ttgaagctgg aaggctacca ggcgatattc ttgatgagat accaagcaag    420
tactataatg gatcagttgt ttgtgagata cgtgactacc gaaagcatgt gtccaaccaa    480
gcgcctgcat catctgctga gctaggttta cctattgtga ataaagtgcg actacgaatg    540
acctttgaga atgttgtaaa ggacattacc cttctatctg atgattcctg gacttacagg    600
gattttgtgg aagctgaggc tcgcattgtg agagctctac aaccagaact ttgcttagac    660
cctacaccta aactggatcg actttgtcag gatcctgttc cgcataagtt gagcctcggt    720
ataggaaaaa agaggaggct gaggcaaaat cctgaagttg ttgtcacatc cagtaacatg    780
tctcatggta aaaaggtttg cattgatagg ttacctgaaa atgccaaagt tgatgacatg    840
ggcatcacca gcagtaatgc agctcagcag gttggtgata acattaccat ccaaaatatc    900
tcggtctcgg gtggttctca gacacttaga ccaaataatt cttcacaaga tgctgccaga    960
atgcttttgt cccaatctgg tctacagcaa gcattaagtt attctgctgc tggtaatgat   1020
cgtatggcag gactgcctgc caatttttct ggaatcaatt caagcatttc atctccccag   1080
agcatgattg gttacaatga cactgtggct gccaatggcc ttctatctgt gaagagagaa   1140
atgcaagatg ccccgcttca agatcctaag agaataaagc caactggtgg cattgatgat   1200
gtacagcagc agcagataag gcctcaaccc cttggtgggc tggagatgca atggaagaac   1260
catcaactgc atccacaatt agatgtcaag ggatgcagt atgcatcttc actgagtggt    1320
cagagatatc cttcttcgat gatgaacaac atgcaagatc caggatcttc cttatatttc   1380
aatcatcagc aaaatttgag atacggtgct aagcaagagc agatggatgg ttctgataag   1440
tcgaaagacg ccttgcagtc tatggcacct gaaagttcca tgctggatca gcagcaatcc   1500
caggctcaac atttaccaca gcaatcagcg gcaagaaaca atgttccaaa catgggacag   1560
tggcaaaata ctcggttcgc agctgagaag gacttgaaaa aagaagaaat aattccaaga   1620
agaaaattag cacctagctc tcgtgcccct tctgggccta tggttcagtc tccagtgtcc   1680
tcgaaatctg gagagatatc aagcagttca atgggtggcc agtttggttc tgctgtgaca   1740
tcagctgtaa taggggcaca gaaagataaa tttgctgcaa attccagtgc tgcagttgga   1800
tttccttctg tagcttccag ccctaatgat tccatgcacc gaatacaaca gccagctgtt   1860
gcttcctcaa agaggaaaac aaattctgtc cccaaaactc aaccgcctgt gagtgctgtt   1920
gggtctccag ccagtgtttc aaatatgcat gctccgctga atgcgagcag cccatcgatt   1980
gggaccacac ctatgggaga ccaagcaatc cttgataaat ttgcaaaaat tgataatatt   2040
tcccatcggt accagcttct caataagaag aacaaggttg ataaaatatc tcaaaagaaa   2100
accattacca atcaaagtca tccagatgta gctagatgtc tcaatagttg tttccattct   2160
gaggattata tagatacaac aagacctctt tgtaattcta tgattagtgg aactataaac   2220
acgtgcaaga ctagggtaat aaactttgtg agcacaaacc gcatgtacca aggtcattca   2280
aggccattcc aggttatttt caaggaaatt tctgatgaaa ctgtaaaaat gcaatatgga   2340
```

-continued

```
gatctagaag attttgatgg tccgaatgcg catgattgtg tattcatatt accaacaaag   2400

tactatgctg acttgcttgc agagcagctt attcccctta tgttgcaaga tgggcattct   2460

aaagctgatg ataaagtcgt gcgcggcacc ccccttgcta acctcagtac gctgtctgga   2520

attttaccag acaatttagt gagtgatgta aagcaagagg gaggtgtaag ccaacaactt   2580

aatgctgcag cccatgcaaa tgtgccacct ggaacacaga tgcaacagct tcctgtcaat   2640

aggatgcttt catctgcgag tagcaaccag gttctagcaa tgcagcaagg ttatatgcaa   2700

ggggcagcca tgcctgcaag gagccagcaa cttgaccaaa atttggttca gcagccgcag   2760

cagcaacagc cacagcagca gccactgcag caaaatgctc aagcccagat gcagcaacca   2820

tcctctcttc cactgaacca gatgcaaaga cctcagcttc tgcccacgag cccattatca   2880

cagatgttgg ggcctggctc aaatctcaca atgggctcaa gccagatagg taacaataag   2940

gctcctcctt catccttgca gcttcagatg ctacaggcac aacagcaaca acctatgtct   3000

aggaaagtga tgatgggcct cggctcagcc atgaacatgg gcaatatggt taacaatgtt   3060

gttggtcttg gtggccttgg taatgttatg ggaatgggca acgtgcgtcc aatatcctcc   3120

cccatgggat cgatgtcagg cttaggtaac aattccaatc caatgaacat gggaatggca   3180

tccaatcttg ctgcagctgg acttcggcca ggtatgaacc ctgctacttt tgccaagatg   3240

cgtatcggtt tggcacaaca aagggcagca ggcatgtatc ctggaatggt tggaatgcct   3300

ggaagcagct ctccaatcct tcctagttca gctggcttat ctatgatggg ccagccgcta   3360

aacagaagca accttggtcc cctgcagagg gccatgatgt cgtctatggg ccctccaaaa   3420

attccaggag gtaactttca gctgaacgcg caacagcaaa tgcagctcca gcagcagttg   3480

cagcagcagc agcagctcca acagaacccc cagcaacagc agcagctcca tcagaacccg   3540

cagcagcagc aactgcagca gctacagcaa cagcaacaaa tacagcaaca actgcagcag   3600

cagcagcagc tccaacaaca actgcagcag caacagcagc agcaacaaca acaacaaatg   3660

ggatctccgt tacagcaggc acaggtgggc tcacctgctg gctcgcagca gtcgctgatg   3720

atgcagcagc agcagcagat aagcccacag caaatgggac agcaggctgc catgagcccc   3780

cagttgagct caggaacgct gcagcaaatg agcaataacg tggtcaaccc tgtagccact   3840

ccaggtcctc ccccaagccc gcagctgagc tcccagaccc atgggtcgga aggtgtaaac   3900

actggccaag atcactatgt tttctttgtt gtggtaaatg aggttaaatt aggtgtgtta   3960

tacatttaca ttcttgacag ataa                                          3984
```

<210> SEQ ID NO 7
<211> LENGTH: 1327
<212> TYPE: PRT
<213> ORGANISM: Sorghum bicolor

<400> SEQUENCE: 7

```
Met Gly Ile Ser Phe Lys Leu Ser Lys Val Gly Val Arg Val His Pro
1               5                   10                  15

Ala Ala Arg Ser Ala Ser Ala Ala Leu Ala Gln Ala Ala Glu Ala Glu
            20                  25                  30

Lys Pro Ala Thr Gly Glu Lys Glu Gly Ser Leu Ser Glu Ser Arg Arg
        35                  40                  45

Glu Asp Asn Phe Val Glu Arg Gly Lys Asp Val Asn Gly Ile Lys Ile
    50                  55                  60

Leu Pro Ala Cys Ser Lys Glu Ile Leu Pro Asp His Glu Val Ser Phe
65                  70                  75                  80
```

-continued

```
Thr Phe Ser Leu Tyr Glu Arg Gly Tyr Leu Ile Ser Lys Ser Ala Ser
                85                  90                  95

Met Asp Pro Ser Gln Thr Ser Ile Gln Asp Ser Lys Thr Leu His Pro
            100                 105                 110

Tyr Asp Arg Ala Ser Glu Lys Leu Phe Ser Ala Ile Glu Ala Gly Arg
        115                 120                 125

Leu Pro Gly Asp Ile Leu Asp Glu Ile Pro Ser Lys Tyr Tyr Asn Gly
    130                 135                 140

Ser Val Val Cys Glu Ile Arg Asp Tyr Arg Lys His Val Ser Asn Gln
145                 150                 155                 160

Ala Pro Ala Ser Ser Ala Glu Leu Gly Leu Pro Ile Val Asn Lys Val
                165                 170                 175

Arg Leu Arg Met Thr Phe Glu Asn Val Val Lys Asp Ile Thr Leu Leu
            180                 185                 190

Ser Asp Asp Ser Trp Thr Tyr Arg Asp Phe Val Glu Ala Glu Ala Arg
        195                 200                 205

Ile Val Arg Ala Leu Gln Pro Glu Leu Cys Leu Asp Pro Thr Pro Lys
    210                 215                 220

Leu Asp Arg Leu Cys Gln Asp Pro Val Pro His Lys Leu Ser Leu Gly
225                 230                 235                 240

Ile Gly Lys Lys Arg Arg Leu Arg Gln Asn Pro Glu Val Val Val Thr
                245                 250                 255

Ser Ser Asn Met Ser His Gly Lys Lys Val Cys Ile Asp Arg Leu Pro
            260                 265                 270

Glu Asn Ala Lys Val Asp Asp Met Gly Ile Thr Ser Ser Asn Ala Ala
        275                 280                 285

Gln Gln Val Gly Asp Asn Ile Thr Ile Gln Asn Ile Ser Val Ser Gly
    290                 295                 300

Gly Ser Gln Thr Leu Arg Pro Asn Asn Ser Ser Gln Asp Ala Ala Arg
305                 310                 315                 320

Met Leu Leu Ser Gln Ser Gly Leu Gln Gln Ala Leu Ser Tyr Ser Ala
                325                 330                 335

Ala Gly Asn Asp Arg Met Ala Gly Leu Pro Ala Asn Phe Ser Gly Ile
            340                 345                 350

Asn Ser Ser Ile Ser Ser Pro Gln Ser Met Ile Gly Tyr Asn Asp Thr
        355                 360                 365

Val Ala Ala Asn Gly Leu Leu Ser Val Lys Arg Glu Met Gln Asp Ala
    370                 375                 380

Pro Leu Gln Asp Pro Lys Arg Ile Lys Pro Thr Gly Gly Ile Asp Asp
385                 390                 395                 400

Val Gln Gln Gln Gln Ile Arg Pro Gln Pro Leu Gly Gly Leu Glu Met
                405                 410                 415

Gln Trp Lys Asn His Gln Leu His Pro Gln Leu Asp Val Lys Gly Met
            420                 425                 430

Gln Tyr Ala Ser Ser Leu Ser Gly Gln Arg Tyr Pro Ser Ser Met Met
        435                 440                 445

Asn Asn Met Gln Asp Pro Gly Ser Ser Leu Tyr Phe Asn His Gln Gln
    450                 455                 460

Asn Leu Arg Tyr Gly Ala Lys Gln Glu Gln Met Asp Gly Ser Asp Lys
465                 470                 475                 480

Ser Lys Asp Ala Leu Gln Ser Met Ala Pro Glu Ser Ser Met Leu Asp
                485                 490                 495

Gln Gln Gln Ser Gln Ala Gln His Leu Pro Gln Gln Ser Ala Ala Arg
```

-continued

```
            500                 505                 510

Asn Asn Val Pro Asn Met Gly Gln Trp Gln Asn Thr Arg Phe Ala Ala
        515                 520                 525

Glu Lys Asp Leu Lys Lys Glu Glu Ile Ile Pro Arg Arg Lys Leu Ala
    530                 535                 540

Pro Ser Ser Arg Ala Pro Ser Gly Pro Met Val Gln Ser Pro Val Ser
545                 550                 555                 560

Ser Lys Ser Gly Glu Ile Ser Ser Ser Ser Met Gly Gly Gln Phe Gly
                565                 570                 575

Ser Ala Val Thr Ser Ala Val Ile Gly Ala Gln Lys Asp Lys Phe Ala
            580                 585                 590

Ala Asn Ser Ser Ala Ala Val Gly Phe Pro Ser Val Ala Ser Ser Pro
        595                 600                 605

Asn Asp Ser Met His Arg Ile Gln Gln Pro Ala Val Ala Ser Ser Lys
    610                 615                 620

Arg Lys Thr Asn Ser Val Pro Lys Thr Gln Pro Pro Val Ser Ala Val
625                 630                 635                 640

Gly Ser Pro Ala Ser Val Ser Asn Met His Ala Pro Leu Asn Ala Ser
                645                 650                 655

Ser Pro Ser Ile Gly Thr Thr Pro Met Gly Asp Gln Ala Ile Leu Asp
            660                 665                 670

Lys Phe Ala Lys Ile Asp Asn Ile Ser His Arg Tyr Gln Leu Leu Asn
        675                 680                 685

Lys Lys Asn Lys Val Asp Lys Ile Ser Gln Lys Lys Thr Ile Thr Asn
    690                 695                 700

Gln Ser His Pro Asp Val Ala Arg Cys Leu Asn Ser Cys Phe His Ser
705                 710                 715                 720

Glu Asp Tyr Ile Asp Thr Thr Arg Pro Leu Cys Asn Ser Met Ile Ser
                725                 730                 735

Gly Thr Ile Asn Thr Cys Lys Thr Arg Val Ile Asn Phe Val Ser Thr
            740                 745                 750

Asn Arg Met Tyr Gln Gly His Ser Arg Pro Phe Gln Val Ile Phe Lys
        755                 760                 765

Glu Ile Ser Asp Glu Thr Val Lys Met Gln Tyr Gly Asp Leu Glu Asp
    770                 775                 780

Phe Asp Gly Pro Asn Ala His Asp Cys Val Phe Ile Leu Pro Thr Lys
785                 790                 795                 800

Tyr Tyr Ala Asp Leu Leu Ala Glu Gln Leu Ile Pro Leu Met Leu Gln
                805                 810                 815

Asp Gly His Ser Lys Ala Asp Asp Lys Val Val Arg Gly Thr Pro Leu
            820                 825                 830

Ala Asn Leu Ser Thr Leu Ser Gly Ile Leu Pro Asp Asn Leu Val Ser
        835                 840                 845

Asp Val Lys Gln Glu Gly Gly Val Ser Gln Gln Leu Asn Ala Ala Ala
    850                 855                 860

His Ala Asn Val Pro Pro Gly Thr Gln Met Gln Gln Leu Pro Val Asn
865                 870                 875                 880

Arg Met Leu Ser Ser Ala Ser Ser Asn Gln Val Leu Ala Met Gln Gln
                885                 890                 895

Gly Tyr Met Gln Gly Ala Ala Met Pro Ala Arg Ser Gln Gln Leu Asp
            900                 905                 910

Gln Asn Leu Val Gln Gln Pro Gln Gln Gln Gln Pro Gln Gln Gln Pro
        915                 920                 925
```

```
Leu Gln Gln Asn Ala Gln Ala Gln Met Gln Gln Pro Ser Ser Leu Pro
    930                 935                 940

Leu Asn Gln Met Gln Arg Pro Gln Leu Leu Pro Thr Ser Pro Leu Ser
945                 950                 955                 960

Gln Met Leu Gly Pro Gly Ser Asn Leu Thr Met Gly Ser Ser Gln Ile
                965                 970                 975

Gly Asn Asn Lys Ala Pro Pro Ser Ser Leu Gln Leu Gln Met Leu Gln
            980                 985                 990

Ala Gln Gln Gln Gln Pro Met Ser  Arg Lys Val Met Met  Gly Leu Gly
        995                 1000                1005

Ser Ala  Met Asn Met Gly Asn  Met Val Asn Asn Val  Val Gly Leu
    1010                1015                1020

Gly Gly  Leu Gly Asn Val Met  Gly Met Gly Asn Val  Arg Pro Ile
    1025                1030                1035

Ser Ser  Pro Met Gly Ser Met  Ser Gly Leu Gly Asn  Asn Ser Asn
    1040                1045                1050

Pro Met  Asn Met Gly Met Ala  Ser Asn Leu Ala Ala  Ala Gly Leu
    1055                1060                1065

Arg Pro  Gly Met Asn Pro Ala  Thr Phe Ala Lys Met  Arg Ile Gly
    1070                1075                1080

Leu Ala  Gln Gln Arg Ala Ala  Gly Met Tyr Pro Gly  Met Val Gly
    1085                1090                1095

Met Pro  Gly Ser Ser Ser Pro  Ile Leu Pro Ser Ser  Ala Gly Leu
    1100                1105                1110

Ser Met  Met Gly Gln Pro Leu  Asn Arg Ser Asn Leu  Gly Pro Leu
    1115                1120                1125

Gln Arg  Ala Met Met Ser Ser  Met Gly Pro Pro Lys  Ile Pro Gly
    1130                1135                1140

Gly Asn  Phe Gln Leu Asn Ala  Gln Gln Gln Met Gln  Leu Gln Gln
    1145                1150                1155

Gln Leu  Gln Gln Gln Gln Gln  Leu Gln Gln Asn Pro  Gln Gln Gln
    1160                1165                1170

Gln Gln  Leu His Gln Asn Pro  Gln Gln Gln Gln Leu  Gln Gln Leu
    1175                1180                1185

Gln Gln  Gln Gln Gln Ile Gln  Gln Gln Leu Gln Gln  Gln Gln Gln
    1190                1195                1200

Leu Gln  Gln Gln Leu Gln Gln  Gln Gln Gln Gln Gln  Gln Gln Gln
    1205                1210                1215

Gln Met  Gly Ser Pro Leu Gln  Gln Ala Gln Val Gly  Ser Pro Ala
    1220                1225                1230

Gly Ser  Gln Gln Ser Leu Met  Met Gln Gln Gln Gln  Gln Ile Ser
    1235                1240                1245

Pro Gln  Gln Met Gly Gln Gln  Ala Ala Met Ser Pro  Gln Leu Ser
    1250                1255                1260

Ser Gly  Thr Leu Gln Gln Met  Ser Asn Asn Val Val  Asn Pro Val
    1265                1270                1275

Ala Thr  Pro Gly Pro Pro Pro  Ser Pro Gln Leu Ser  Ser Gln Thr
    1280                1285                1290

His Gly  Ser Glu Gly Val Asn  Thr Gly Gln Asp His  Tyr Val Phe
    1295                1300                1305

Phe Val  Val Val Asn Glu Val  Lys Leu Gly Val Leu  Tyr Ile Tyr
    1310                1315                1320
```

```
Ile Leu  Asp Arg
    1325


<210> SEQ ID NO 8
<211> LENGTH: 4500
<212> TYPE: DNA
<213> ORGANISM: Paspalum notatum

<400> SEQUENCE: 8

caaccgcgtc tcccaacacc gagctcacct catcacacgc ccctctcctc ccccctaacc      60

ccctcgctcg tcggcggcga gagagacggc ggcggaggct gtggagcagg aagcctaggt     120

gtacgccgcg gggcggcgtc ccctgtgggg atggggatct cgttcaagat atccaaggtc     180

ggcgtccgcg tgcacccggg cgcgcgctcg gcttcagcga cgcaggcgca ggcggaaaag     240

ccggccgcgg tcgacaagga gggatccgtg tctgactcga gaggcgaggg tgactttgtt     300

gagggagcaa aagatatcaa tggaatcata atttcaccag catgctcgag ggaaatttcg     360

cctgatcatg aggtttcttt cacattcagc ctttatgaca gaggttatct catttcaaag     420

tcagcagcta tggattccaa ccagacctca attcaggatg gtaaaacact acatccctat     480

gatagagcat cagaaaagtt attctcttct attgaagctg ggaggctgcc tggtgatatt     540

cttgatgata taccaagcaa gtactacagt gggtcagttg tttgtgagat acgtgactac     600

agaaagcatg tgtccaatca agttcctgca tcatctgctg agctaggatt acctatcgtg     660

aataaagtac aactgcgaat gacctttgag aatgttgtga aagacatttc acttctatct     720

gatgattcct ggagttacag ggattttgtg gaagctgagg ctcgtattgt gagagtccta     780

caaccagaac tttgcttaga ccctactcct aaactggatc gactttatca ggatcctgtt     840

cctcataagt tgagccttgg tattggaaag aagaggaggc tgaggcaaaa tcctgaagtt     900

gttgtcacat ccagtaacat gtctcatggt aaaaaagttt gcattgatag gttacctgaa     960

aataccaaag cagatgaaat gggcatcgca ggcagtaatg cagctcacca ggttggtgat    1020

aacataacca tccaaaatat tccgggtggt catcagccac ttagaccaaa taatgcttca    1080

caagatgctg ccagaatgct attgtcccaa acccaacctg gtatacagca aacagtaagt    1140

tattctgcca ttggtaatga tcgtatggca ggaccacctg ccaatttttc tggaatcagt    1200

tcaagcattt catctcctca gagcatgatt ggttacaatg acactgtttc tgccaatggc    1260

cttctatctg tgaagaggga aatgcaagat gttccacttc aagatcctaa gagaataaag    1320

ccaactggtg gtactgatga cgtacagcag cagcagacaa ggcatcaacc ccttggtggg    1380

caggagatgc aatggaagaa tcaactgcat ccacaattag atgtcaaggg gatgcagtat    1440

gcatcttcat tgagtagtca gagatatcct acttcgttga tgaacaatat gcaagattca    1500

ggatcttcct tctatttcaa tcagcaaggt ttgagataca gtgctaagca ggagcagatg    1560

gatggttccg ataggtcgaa agatgcattg cagtctatgg cacctgaaag ttctatgctg    1620

gaccagcagc agtcccaggc tcaacattta tcacagcaat cagcagcaag aaataatgtt    1680

ccaaacatgg cacagtggca gaatagggca gctgagaagg acctgaaaaa agaagaaata    1740

attcagagaa gaaagttagc acctagctct cgtgcccctt ctgggccaat ggttcagtct    1800

ccagtgtcct caaaatctgg agagatatca agcagttcca tgggtggtca gttcggttct    1860

gctgtgacat cagctgtaat aggggcacag aaagataaat ttgctgcaaa ttccagtgct    1920

gcagttggat acccttcagt agtttccagt cctagtgatt ccatgcaccg aatacaacaa    1980

cctgctgttg ctccttcaaa gaggaaatca aattctgtcc ctaaaaatca accacctgtg    2040
```

-continued

```
agcgctgttg ggtctccagc tagtgtttca aatatgcacg ctccgctgaa tgcaagcagc   2100
ccatcagttg gcaccgcacc tatgggagac caagcaatcc ttgataaatt tgcaaaaatt   2160
gaaaatcttt cccatcggta ccagcttcac aataagaaga agaaggttga tacgatacct   2220
caaagaaaac ccataaccaa aagccaagaa gtcgttagat gtctgtccag ttgttttcat   2280
actgaggatt atatagatac aacaagacct ctttgtaatt ctatgattag tggaactata   2340
aacacatgca agagtagggt aataaacttt gtgagcacaa accgcattta ccaaggtcat   2400
gaaaggccat tccaggttgt ctttaaggaa atgcctgatg aaactgtgag aatgcaatat   2460
ggagatcaag aagattttga tggcccgaat tcatatgatt gtgtattcat attaccaacg   2520
aagtactatg ctgacttgct tgcagagcag cttatacccc tgatgttgca agatgggcat   2580
tctaaagctg atgataaagt tcgtggcacc catcctgcta acctcagtac actgtcagga   2640
attttaccag acaatttagt gagtgacgta aagcaagagg gaggtgtaag ccagcaactt   2700
aatgctgcag cccatgcaaa tgcgacacct ggaacaccaa tgcaacaact tcctgtcaat   2760
aggatgcttt catctgcaaa tagcaaccag gttctaccaa tgcagccagg gtatatgcaa   2820
ggggcagcca tgcctccaag gagtcaacaa cttgaccaaa atttggttca gcagtcacag   2880
cagcaccagc cacagcagca accagtgcag caaaatgctc aagcacagat gcagcaacct   2940
tcttctcttc cactcaacca gatgcagaga cctcaacttc taccaacaag cccattatct   3000
cagatgttgg ggcctggctc aaatctccca atgggctcaa gtcaaatggg taacaataag   3060
cagcctacag ccaattcctt gcagcttcag atgctacagc aagcacaaca gcaacagcct   3120
atgtctagga aagggatgat ggggcttggc tcagccatga acatgggcaa tatggttaac   3180
aatgtcgtta gtgtcggtgg cctaatgggc aatgtgcggc caatatcctc ccccatggga   3240
tcgatgtcag gcttaggcaa caataccaat ccaatgaaca tgggaatgcc atcaaacctt   3300
gctgctggac ttcggccagg tatgagcgca gctactattg ccaagatgcg aatggcacag   3360
caaagggcag gcatgtatcc tcagactgga atggttggaa tgcctggcag cagctctcca   3420
atccttccta gttcagctaa cttgaccatg atgaatcatc cgctaaatag gagcaacctc   3480
aaccccctgc aaagggccat gatgtcttct atgggccctc caaagatgcc aggaggtaac   3540
tttcagctga acccccagca gcaaatgcag ctccagcagc tgcagcagca gcagcagcag   3600
ctccaacaga acccacagca gcagcagcag cagctccaac agcagcagca gcagcagcag   3660
ctccagcagc agcagcagca gcagctccca cagcaacaac tgcagcaaat gcaacagcta   3720
cagcagcagc agctgcaaca acagctgcag ctgcagcaac agcaacagca aatgggatct   3780
ccacggcagc aggcgcaggt gggatcacca gctggctcgc agcagtcgtt gatgatgcag   3840
cagcagataa gccctccgca aatgggacag catgctgcaa tgagccccca gttgagctca   3900
ggaactctgc agcaaatgag caacaacgtg gccaaccctg tagccactcc aggtccgccc   3960
ccaagcccgc aactgagctc ccagacgcat gggtcagtga acagcattgc caactcccca   4020
atggagcagc tgcaaggcgc caataaggga ggaccaggta gcatgtaata actggaaata   4080
ctttggttca cttcttggcc agtatgatat atagtaggaa ggtgtaaaga ttggccatga   4140
tcactgtgat ttcttgttgt gataaatggg attaattagg tgtgttgtaa gttatagatc   4200
atagacggta ccttgtaaga actggcttta tggttggatt cttgatgtta tagattgtag   4260
ttagtaggag tggtgtgtgt aggcgctggg caatcggtac tggggcaagc attgttcaat   4320
tggacagtgt tctcttctgg tgtttaaatt gaaatgatca gagaattgtg aactgctaca   4380
taggttcgcc agtagttttg ctatgtttct atcttgtaac gtttgcaatc gcaatatgat   4440
```

ccctgacaaa cactgctaaa cgtttcgacc tgttctgttt ctttcacggc ttattgcagc 4500

<210> SEQ ID NO 9
<211> LENGTH: 1305
<212> TYPE: PRT
<213> ORGANISM: Paspalum notatum

<400> SEQUENCE: 9

```
Met Gly Ile Ser Phe Lys Ile Ser Lys Val Gly Val Arg Val His Pro
1               5                   10                  15

Gly Ala Arg Ser Ala Ser Ala Thr Gln Ala Gln Ala Glu Lys Pro Ala
            20                  25                  30

Ala Val Asp Lys Glu Gly Ser Val Ser Asp Ser Arg Gly Glu Gly Asp
        35                  40                  45

Phe Val Glu Gly Ala Lys Asp Ile Asn Gly Ile Ile Ser Pro Ala
    50                  55                  60

Cys Ser Arg Glu Ile Ser Pro Asp His Glu Val Ser Phe Thr Phe Ser
65                  70                  75                  80

Leu Tyr Asp Arg Gly Tyr Leu Ile Ser Lys Ser Ala Ala Met Asp Ser
                85                  90                  95

Asn Gln Thr Ser Ile Gln Asp Gly Lys Thr Leu His Pro Tyr Asp Arg
            100                 105                 110

Ala Ser Glu Lys Leu Phe Ser Ser Ile Glu Ala Gly Arg Leu Pro Gly
        115                 120                 125

Asp Ile Leu Asp Asp Ile Pro Ser Lys Tyr Tyr Ser Gly Ser Val Val
    130                 135                 140

Cys Glu Ile Arg Asp Tyr Arg Lys His Val Ser Asn Gln Val Pro Ala
145                 150                 155                 160

Ser Ser Ala Glu Leu Gly Leu Pro Ile Val Asn Lys Val Gln Leu Arg
                165                 170                 175

Met Thr Phe Glu Asn Val Val Lys Asp Ile Ser Leu Leu Ser Asp Asp
            180                 185                 190

Ser Trp Ser Tyr Arg Asp Phe Val Glu Ala Glu Ala Arg Ile Val Arg
        195                 200                 205

Val Leu Gln Pro Glu Leu Cys Leu Asp Pro Thr Pro Lys Leu Asp Arg
    210                 215                 220

Leu Tyr Gln Asp Pro Val Pro His Lys Leu Ser Leu Gly Ile Gly Lys
225                 230                 235                 240

Lys Arg Arg Leu Arg Gln Asn Pro Glu Val Val Val Thr Ser Ser Asn
                245                 250                 255

Met Ser His Gly Lys Lys Val Cys Ile Asp Arg Leu Pro Glu Asn Thr
            260                 265                 270

Lys Ala Asp Glu Met Gly Ile Ala Gly Ser Asn Ala Ala His Gln Val
        275                 280                 285

Gly Asp Asn Ile Thr Ile Gln Asn Ile Pro Gly Gly His Gln Pro Leu
    290                 295                 300

Arg Pro Asn Asn Ala Ser Gln Asp Ala Ala Arg Met Leu Leu Ser Gln
305                 310                 315                 320

Thr Gln Pro Gly Ile Gln Gln Thr Val Ser Tyr Ser Ala Ile Gly Asn
                325                 330                 335

Asp Arg Met Ala Gly Pro Pro Ala Asn Phe Ser Gly Ile Ser Ser Ser
            340                 345                 350

Ile Ser Ser Pro Gln Ser Met Ile Gly Tyr Asn Asp Thr Val Ser Ala
        355                 360                 365
```

-continued

```
Asn Gly Leu Leu Ser Val Lys Arg Glu Met Gln Asp Val Pro Leu Gln
    370                 375                 380

Asp Pro Lys Arg Ile Lys Pro Thr Gly Gly Thr Asp Asp Val Gln Gln
385                 390                 395                 400

Gln Gln Thr Arg His Gln Pro Leu Gly Gly Gln Glu Met Gln Trp Lys
                405                 410                 415

Asn Gln Leu His Pro Gln Leu Asp Val Lys Gly Met Gln Tyr Ala Ser
            420                 425                 430

Ser Leu Ser Ser Gln Arg Tyr Pro Thr Ser Leu Met Asn Asn Met Gln
        435                 440                 445

Asp Ser Gly Ser Ser Phe Tyr Phe Asn Gln Gln Gly Leu Arg Tyr Ser
    450                 455                 460

Ala Lys Gln Glu Gln Met Asp Gly Ser Asp Arg Ser Lys Asp Ala Leu
465                 470                 475                 480

Gln Ser Met Ala Pro Glu Ser Ser Met Leu Asp Gln Gln Gln Ser Gln
                485                 490                 495

Ala Gln His Leu Ser Gln Gln Ser Ala Ala Arg Asn Asn Val Pro Asn
            500                 505                 510

Met Ala Gln Trp Gln Asn Arg Ala Ala Glu Lys Asp Leu Lys Lys Glu
        515                 520                 525

Glu Ile Ile Gln Arg Arg Lys Leu Ala Pro Ser Ser Arg Ala Pro Ser
    530                 535                 540

Gly Pro Met Val Gln Ser Pro Val Ser Ser Lys Ser Gly Glu Ile Ser
545                 550                 555                 560

Ser Ser Ser Met Gly Gly Gln Phe Gly Ser Ala Val Thr Ser Ala Val
                565                 570                 575

Ile Gly Ala Gln Lys Asp Lys Phe Ala Ala Asn Ser Ser Ala Ala Val
            580                 585                 590

Gly Tyr Pro Ser Val Val Ser Ser Pro Ser Asp Ser Met His Arg Ile
        595                 600                 605

Gln Gln Pro Ala Val Ala Pro Ser Lys Arg Lys Ser Asn Ser Val Pro
    610                 615                 620

Lys Asn Gln Pro Pro Val Ser Ala Val Gly Ser Pro Ala Ser Val Ser
625                 630                 635                 640

Asn Met His Ala Pro Leu Asn Ala Ser Ser Pro Ser Val Gly Thr Ala
                645                 650                 655

Pro Met Gly Asp Gln Ala Ile Leu Asp Lys Phe Ala Lys Ile Glu Asn
            660                 665                 670

Leu Ser His Arg Tyr Gln Leu His Asn Lys Lys Lys Lys Val Asp Thr
        675                 680                 685

Ile Pro Gln Arg Lys Pro Ile Thr Lys Ser Gln Glu Val Val Arg Cys
    690                 695                 700

Leu Ser Ser Cys Phe His Thr Glu Asp Tyr Ile Asp Thr Thr Arg Pro
705                 710                 715                 720

Leu Cys Asn Ser Met Ile Ser Gly Thr Ile Asn Thr Cys Lys Ser Arg
                725                 730                 735

Val Ile Asn Phe Val Ser Thr Asn Arg Ile Tyr Gln Gly His Glu Arg
            740                 745                 750

Pro Phe Gln Val Val Phe Lys Glu Met Pro Asp Glu Thr Val Arg Met
        755                 760                 765

Gln Tyr Gly Asp Gln Glu Asp Phe Asp Gly Pro Asn Ser Tyr Asp Cys
    770                 775                 780
```

-continued

```
Val Phe Ile Leu Pro Thr Lys Tyr Tyr Ala Asp Leu Leu Ala Glu Gln
785                 790                 795                 800

Leu Ile Pro Leu Met Leu Gln Asp Gly His Ser Lys Ala Asp Asp Lys
                805                 810                 815

Val Arg Gly Thr His Pro Ala Asn Leu Ser Thr Leu Ser Gly Ile Leu
            820                 825                 830

Pro Asp Asn Leu Val Ser Asp Val Lys Gln Glu Gly Gly Val Ser Gln
        835                 840                 845

Gln Leu Asn Ala Ala Ala His Ala Asn Ala Thr Pro Gly Thr Pro Met
    850                 855                 860

Gln Gln Leu Pro Val Asn Arg Met Leu Ser Ser Ala Asn Ser Asn Gln
865                 870                 875                 880

Val Leu Pro Met Gln Pro Gly Tyr Met Gln Gly Ala Ala Met Pro Pro
                885                 890                 895

Arg Ser Gln Gln Leu Asp Gln Asn Leu Val Gln Gln Ser Gln Gln His
            900                 905                 910

Gln Pro Gln Gln Gln Pro Val Gln Gln Asn Ala Gln Ala Gln Met Gln
        915                 920                 925

Gln Pro Ser Ser Leu Pro Leu Asn Gln Met Gln Arg Pro Gln Leu Leu
    930                 935                 940

Pro Thr Ser Pro Leu Ser Gln Met Leu Gly Pro Gly Ser Asn Leu Pro
945                 950                 955                 960

Met Gly Ser Ser Gln Met Gly Asn Asn Lys Gln Pro Thr Ala Asn Ser
                965                 970                 975

Leu Gln Leu Gln Met Leu Gln Gln Ala Gln Gln Gln Gln Pro Met Ser
            980                 985                 990

Arg Lys Gly Met Met Gly Leu Gly  Ser Ala Met Asn Met  Gly Asn Met
        995                 1000                 1005

Val Asn  Asn Val Val Ser Val  Gly Gly Leu Met Gly  Asn Val Arg
    1010                 1015                 1020

Pro Ile  Ser Ser Pro Met Gly  Ser Met Ser Gly Leu  Gly Asn Asn
    1025                 1030                 1035

Thr Asn  Pro Met Asn Met Gly  Met Pro Ser Asn Leu  Ala Ala Gly
    1040                 1045                 1050

Leu Arg  Pro Gly Met Ser Ala  Ala Thr Ile Ala Lys  Met Arg Met
    1055                 1060                 1065

Ala Gln  Gln Arg Ala Gly Met  Tyr Pro Gln Thr Gly  Met Val Gly
    1070                 1075                 1080

Met Pro  Gly Ser Ser Ser Pro  Ile Leu Pro Ser Ser  Ala Asn Leu
    1085                 1090                 1095

Thr Met  Met Asn His Pro Leu  Asn Arg Ser Asn Leu  Asn Pro Leu
    1100                 1105                 1110

Gln Arg  Ala Met Met Ser Ser  Met Gly Pro Pro Lys  Met Pro Gly
    1115                 1120                 1125

Gly Asn  Phe Gln Leu Asn Pro  Gln Gln Gln Met Gln  Leu Gln Gln
    1130                 1135                 1140

Leu Gln  Gln Gln Gln Gln Gln  Leu Gln Gln Asn Pro  Gln Gln Gln
    1145                 1150                 1155

Gln Gln  Gln Leu Gln Gln Gln  Gln Gln Gln Gln Gln  Leu Gln Gln
    1160                 1165                 1170

Gln Gln  Gln Gln Gln Leu Pro  Gln Gln Gln Leu Gln  Gln Met Gln
    1175                 1180                 1185

Gln Leu  Gln Gln Gln Gln Leu  Gln Gln Gln Leu Gln  Leu Gln Gln
```

```
    1190                1195                1200

Gln Gln  Gln Gln Met Gly Ser  Pro Arg Gln Gln Ala  Gln Val Gly
    1205                1210                1215

Ser Pro  Ala Gly Ser Gln Gln  Ser Leu Met Met Gln  Gln Gln Ile
    1220                1225                1230

Ser Pro  Pro Gln Met Gly Gln  His Ala Ala Met Ser  Pro Gln Leu
    1235                1240                1245

Ser Ser  Gly Thr Leu Gln Gln  Met Ser Asn Asn Val  Ala Asn Pro
    1250                1255                1260

Val Ala  Thr Pro Gly Pro Pro  Pro Ser Pro Gln Leu  Ser Ser Gln
    1265                1270                1275

Thr His  Gly Ser Val Asn Ser  Ile Ala Asn Ser Pro  Met Glu Gln
    1280                1285                1290

Leu Gln  Gly Ala Asn Lys Gly  Gly Pro Gly Ser Met
    1295                1300                1305
```

<210> SEQ ID NO 10
<211> LENGTH: 4062
<212> TYPE: DNA
<213> ORGANISM: Sorghum bicolor subsp. drummondii

<400> SEQUENCE: 10

```
tccctgtctg agtcgagacg cgaggacaac ttcgttgaga gaggaaaaga tgtcaatgga     60
atcaaaattt taccagcgtg ctccaaggaa attttgccag atcatgaggt ttctttcaca    120
tttagcctct atgagagagg ttatctcatt tcaaagtcag catctatgga tcctagtcag    180
acctcaatcc aggacagcaa aacactgcat ccctatgata gagcatcgga aaagttattc    240
tctgccattg aagctggaag gctaccaggc gatattcttg atgagatacc aagcaagtac    300
tataatggat cagttgtttg tgagatacgt gactaccgaa agcatgtgtc caaccaagcg    360
cctgcatcat ctgctgagct aggtttacct attgtgaata aagtgcgact acgaatgacc    420
tttgagaatg ttgtaaagga cattaccctt ctatctgatg attcctggac ttacagggat    480
tttgtggaag ctgaggctcg cattgtgaga gctctacaac cagaactttg cttagaccct    540
acacctaaac tggatcgact ttgtcaggat cctgttccgc ataagttgag cctcggtata    600
ggaaaaaaga ggaggctgag gcaaaatcct gaagttgttg tcacatccag taacatgtct    660
catggtaaaa aggtttgcat tgataggtta cctgaaaatg ccaaagttga tgacatgggc    720
atcaccagca gtaatgcagc tcagcaggtt ggtgataaca ttaccatcca aaatatctcg    780
gtctcgggtg gttctcagac acttagacca aataattctt cacaagatgc tgccagaatg    840
cttttgtccc aatctggtct acagcaagca ttaagttatt ctgctgctgg taatgatcgt    900
atggcaggac tgcctgccaa tttttctgga atcaattcaa gcatttcatc tccccagagc    960
atgattggtt acaatgacac tgtggctgcc aatggccttc tatctgtgaa gagagaaatg   1020
caagatgccc cgcttcaaga tcctaagaga ataaagccaa ctggtggcat tgatgatgta   1080
cagcagcagc agataaggcc tcaacccctt ggtgggctgg agatgcaatg gaagaaccat   1140
caactgcatc cacaattaga tgtcaagggg atgcagtatg catcttcact gagtggtcag   1200
agatatcctt cttcgatgat gaacaacatg caagatccag gatcttcctt atatttcaat   1260
catcagcaaa atttgagata cggtgctaag caagagcaga tggatggttc tgataagtcg   1320
aaagacgcct tgcagtctat ggcacctgaa agttccatgc tggatcagca gcaatcccag   1380
gctcaacatt taccacagca atcagcggca agaaacaatg ttccaaacat gggacagtgg   1440
```

-continued

```
caaaatactc ggttcgcagc tgagaaggac ttgaaaaaag aagaaataat tccaagaaga   1500
aaattagcac ctagctctcg tgccccttct gggcctatgg ttcagtctcc agtgtcctcg   1560
aaatctggag agatatcaag cagttcaatg ggtggccagt ttggttctgc tgtgacatca   1620
gctgtaatag gggcacagaa agataaattt gctgcaaatt ccagtgctgc agttggattt   1680
ccttctgtag cttccagccc taatgattcc atgcaccgaa tacaacagcc agctgttgct   1740
tcctcaaaga ggaaaacaaa ttctgtcccc aaaactcaac cgcctgtgag tgctgttggg   1800
tctccagcca gtgtttcaaa tatgcatgct ccgctgaatg cgagcagccc atcgattggg   1860
accacaccta tgggagacca agcaatcctt gataaattgg caaaaattga taatatttcc   1920
catcggtacc agcttctcaa taagaagaac aaggttgata aaatatctca aaagaaaacc   1980
attaccaatc aaagtcatcc agatgtagct agatgtctca atagttgttt ccattctgag   2040
gattatatag atacaacaag acctctttgt aattctatga ttagtggaac tataaacacg   2100
tgcaagacta gggtaataaa ctttgtgagc acaaaccgca tgtaccaagg tcattcaagg   2160
ccattccagg ttattttcaa ggaaatttct gatgaaactg taaaaatgca atatggagat   2220
ctagaagatt ttgatggtcc gaatgcgcat gattgtgtat tcatattacc aacaaagtac   2280
tatgctgact tgcttgcaga gcagcttatt ccccttatgt tgcaagatgg gcattctaaa   2340
gctgatgata aagtcgtgcg cggcaccccc cttgctaacc tcagtacgct gtctggaatt   2400
ttaccagaca atttagtgag tgatgtaaag caagagggag gtgtaagcca acaacttaat   2460
gctgcagccc atgcaaatgt gccacctgga acacagatgc aacagcttcc tgtcaatagg   2520
atgctttcat ctgcgagtag caaccaggtt ctagcaatgc agcaaggtta tatgcaaggg   2580
gcagccatgc ctgcaaggag ccagcaactt gaccaaaatt tggttcagca gccgcagcag   2640
caacagccac agcagcagcc actgcagcaa aatgctcaag cccagatgca gcaaccatcc   2700
tctcttccac tgaaccagat gcaaagacct cagcttctgc ccacgagccc attatcacag   2760
atgttggggc ctggctcaaa tctcacaatg ggctcaagcc agataggtaa caataaggct   2820
cctccttcat ccttgcagct tcagatgcta caggcacaac agcaacaacc tatgtctagg   2880
aaagtgatga tgggcctcgg ctcagccatg aacatgggca atatggttaa caatgttgtt   2940
ggtcttggtg gccttggtaa tgttatggga atgggcaacg tgcgtccaat atcctccccc   3000
atgggatcga tgtcaggctt aggtaacaat tccaatccaa tgaacatggg aatggcatcc   3060
aatcttgctg cagctggact tcggccaggt atgaaccctg ctacttttgc caagatgcgt   3120
atcggtttgg cacaacaaag ggcagcaggc atgtatcctg gaatggttgg aatgcctgga   3180
agcagctctc caatccttcc tagttcagct ggcttatcta tgatgggcca gccgctaaac   3240
agaagcaacc ttggtcccct gcagagggcc atgatgtcgt ctatgggccc tccaaaaatt   3300
ccaggaggta actttcagct gaacgcgcaa cagcaaatgc agctccagca gcagttgcag   3360
cagcagcagc agctccaaca gaacccccag caacagcagc agctccatca gaacccgcag   3420
cagcagcaac tgcagcagct acagcaacag caacaaatac agcaacaact gcagcagcag   3480
cagcagctcc aacaacaact gcagcagcaa cagcagcagc aacaacaaca acaaatggga   3540
tctccgttac agcaggcaca ggtgggctca cctgctggct cgcagcagtc gctgatgatg   3600
cagcagcagc agcagataag cccacagcaa atgggacagc aggctgccat gagcccccag   3660
ttgagctcag gaacgctgca gcaaatgagc aataacgtgg tcaaccctgt agccactcca   3720
ggtcctcccc caagcccgca gctgagctcc cagacccatg ggtcggtaag cagcatagct   3780
aactccccga tggagcagct gcaaggcgcc agtaagggag gtcccggtag catgtaacca   3840
```

```
caaataattg gttcacttct ttgcctatat atacagtgta ggaaggtgta aacactggcc   3900

aagatcacta tgttttcttt gttgtggtaa atgaggttaa attaggtgtg ttatagtaag   3960

ttatagacca tagatgatag cttgttaagg accgaccatc tttatgcatg gatttctatg   4020

ctgtagattg tagttagtag gaatggtagt cagttcttgt ga                      4062


<210> SEQ ID NO 11
<211> LENGTH: 1278
<212> TYPE: PRT
<213> ORGANISM: Paspalum notatum

<400> SEQUENCE: 11

Ser Leu Ser Glu Ser Arg Arg Glu Asp Asn Phe Val Glu Arg Gly Lys
1               5                   10                  15

Asp Val Asn Gly Ile Lys Ile Leu Pro Ala Cys Ser Lys Glu Ile Leu
            20                  25                  30

Pro Asp His Glu Val Ser Phe Thr Phe Ser Leu Tyr Glu Arg Gly Tyr
        35                  40                  45

Leu Ile Ser Lys Ser Ala Ser Met Asp Pro Ser Gln Thr Ser Ile Gln
    50                  55                  60

Asp Ser Lys Thr Leu His Pro Tyr Asp Arg Ala Ser Glu Lys Leu Phe
65                  70                  75                  80

Ser Ala Ile Glu Ala Gly Arg Leu Pro Gly Asp Ile Leu Asp Glu Ile
                85                  90                  95

Pro Ser Lys Tyr Tyr Asn Gly Ser Val Val Cys Glu Ile Arg Asp Tyr
            100                 105                 110

Arg Lys His Val Ser Asn Gln Ala Pro Ala Ser Ser Ala Glu Leu Gly
        115                 120                 125

Leu Pro Ile Val Asn Lys Val Arg Leu Arg Met Thr Phe Glu Asn Val
    130                 135                 140

Val Lys Asp Ile Thr Leu Leu Ser Asp Asp Ser Trp Thr Tyr Arg Asp
145                 150                 155                 160

Phe Val Glu Ala Glu Ala Arg Ile Val Arg Ala Leu Gln Pro Glu Leu
                165                 170                 175

Cys Leu Asp Pro Thr Pro Lys Leu Asp Arg Leu Cys Gln Asp Pro Val
            180                 185                 190

Pro His Lys Leu Ser Leu Gly Ile Gly Lys Lys Arg Arg Leu Arg Gln
        195                 200                 205

Asn Pro Glu Val Val Val Thr Ser Ser Asn Met Ser His Gly Lys Lys
    210                 215                 220

Val Cys Ile Asp Arg Leu Pro Glu Asn Ala Lys Val Asp Asp Met Gly
225                 230                 235                 240

Ile Thr Ser Ser Asn Ala Ala Gln Gln Val Gly Asp Asn Ile Thr Ile
                245                 250                 255

Gln Asn Ile Ser Val Ser Gly Gly Ser Gln Thr Leu Arg Pro Asn Asn
            260                 265                 270

Ser Ser Gln Asp Ala Ala Arg Met Leu Leu Ser Gln Ser Gly Leu Gln
        275                 280                 285

Gln Ala Leu Ser Tyr Ser Ala Ala Gly Asn Asp Arg Met Ala Gly Leu
    290                 295                 300

Pro Ala Asn Phe Ser Gly Ile Asn Ser Ser Ile Ser Ser Pro Gln Ser
305                 310                 315                 320

Met Ile Gly Tyr Asn Asp Thr Val Ala Ala Asn Gly Leu Leu Ser Val
                325                 330                 335
```

```
Lys Arg Glu Met Gln Asp Ala Pro Leu Gln Asp Pro Lys Arg Ile Lys
            340                 345                 350

Pro Thr Gly Gly Ile Asp Asp Val Gln Gln Gln Gln Ile Arg Pro Gln
        355                 360                 365

Pro Leu Gly Gly Leu Glu Met Gln Trp Lys Asn His Gln Leu His Pro
    370                 375                 380

Gln Leu Asp Val Lys Gly Met Gln Tyr Ala Ser Ser Leu Ser Gly Gln
385                 390                 395                 400

Arg Tyr Pro Ser Ser Met Met Asn Asn Met Gln Asp Pro Gly Ser Ser
                405                 410                 415

Leu Tyr Phe Asn His Gln Gln Asn Leu Arg Tyr Gly Ala Lys Gln Glu
            420                 425                 430

Gln Met Asp Gly Ser Asp Lys Ser Lys Asp Ala Leu Gln Ser Met Ala
        435                 440                 445

Pro Glu Ser Ser Met Leu Asp Gln Gln Gln Ser Gln Ala Gln His Leu
    450                 455                 460

Pro Gln Gln Ser Ala Ala Arg Asn Asn Val Pro Asn Met Gly Gln Trp
465                 470                 475                 480

Gln Asn Thr Arg Phe Ala Ala Glu Lys Asp Leu Lys Lys Glu Glu Ile
                485                 490                 495

Ile Pro Arg Arg Lys Leu Ala Pro Ser Ser Arg Ala Pro Ser Gly Pro
            500                 505                 510

Met Val Gln Ser Pro Val Ser Ser Lys Ser Gly Glu Ile Ser Ser Ser
        515                 520                 525

Ser Met Gly Gly Gln Phe Gly Ser Ala Val Thr Ser Ala Val Ile Gly
    530                 535                 540

Ala Gln Lys Asp Lys Phe Ala Ala Asn Ser Ser Ala Ala Val Gly Phe
545                 550                 555                 560

Pro Ser Val Ala Ser Ser Pro Asn Asp Ser Met His Arg Ile Gln Gln
                565                 570                 575

Pro Ala Val Ala Ser Ser Lys Arg Lys Thr Asn Ser Val Pro Lys Thr
            580                 585                 590

Gln Pro Pro Val Ser Ala Val Gly Ser Pro Ala Ser Val Ser Asn Met
        595                 600                 605

His Ala Pro Leu Asn Ala Ser Ser Pro Ser Ile Gly Thr Thr Pro Met
    610                 615                 620

Gly Asp Gln Ala Ile Leu Asp Lys Phe Ala Lys Ile Asp Asn Ile Ser
625                 630                 635                 640

His Arg Tyr Gln Leu Leu Asn Lys Lys Asn Lys Val Asp Lys Ile Ser
                645                 650                 655

Gln Lys Lys Thr Ile Thr Asn Gln Ser His Pro Asp Val Ala Arg Cys
            660                 665                 670

Leu Asn Ser Cys Phe His Ser Glu Asp Tyr Ile Asp Thr Thr Arg Pro
        675                 680                 685

Leu Cys Asn Ser Met Ile Ser Gly Thr Ile Asn Thr Cys Lys Thr Arg
    690                 695                 700

Val Ile Asn Phe Val Ser Thr Asn Arg Met Tyr Gln Gly His Ser Arg
705                 710                 715                 720

Pro Phe Gln Val Ile Phe Lys Glu Ile Ser Asp Glu Thr Val Lys Met
                725                 730                 735

Gln Tyr Gly Asp Leu Glu Asp Phe Asp Gly Pro Asn Ala His Asp Cys
            740                 745                 750
```

-continued

```
Val Phe Ile Leu Pro Thr Lys Tyr Tyr Ala Asp Leu Leu Ala Glu Gln
        755                 760                 765

Leu Ile Pro Leu Met Leu Gln Asp Gly His Ser Lys Ala Asp Asp Lys
    770                 775                 780

Val Val Arg Gly Thr Pro Leu Ala Asn Leu Ser Thr Leu Ser Gly Ile
785                 790                 795                 800

Leu Pro Asp Asn Leu Val Ser Asp Val Lys Gln Glu Gly Gly Val Ser
                805                 810                 815

Gln Gln Leu Asn Ala Ala Ala His Ala Asn Val Pro Pro Gly Thr Gln
            820                 825                 830

Met Gln Gln Leu Pro Val Asn Arg Met Leu Ser Ser Ala Ser Ser Asn
        835                 840                 845

Gln Val Leu Ala Met Gln Gln Gly Tyr Met Gln Gly Ala Ala Met Pro
    850                 855                 860

Ala Arg Ser Gln Gln Leu Asp Gln Asn Leu Val Gln Gln Pro Gln Gln
865                 870                 875                 880

Gln Gln Pro Gln Gln Gln Pro Leu Gln Gln Asn Ala Gln Ala Gln Met
                885                 890                 895

Gln Gln Pro Ser Ser Leu Pro Leu Asn Gln Met Gln Arg Pro Gln Leu
            900                 905                 910

Leu Pro Thr Ser Pro Leu Ser Gln Met Leu Gly Pro Gly Ser Asn Leu
        915                 920                 925

Thr Met Gly Ser Ser Gln Ile Gly Asn Asn Lys Ala Pro Pro Ser Ser
    930                 935                 940

Leu Gln Leu Gln Met Leu Gln Ala Gln Gln Gln Gln Pro Met Ser Arg
945                 950                 955                 960

Lys Val Met Met Gly Leu Gly Ser Ala Met Asn Met Gly Asn Met Val
                965                 970                 975

Asn Asn Val Val Gly Leu Gly Gly Leu Gly Asn Val Met Gly Met Gly
            980                 985                 990

Asn Val Arg Pro Ile Ser Ser Pro  Met Gly Ser Met Ser  Gly Leu Gly
        995                 1000                 1005

Asn Asn  Ser Asn Pro Met Asn  Met Gly Met Ala Ser  Asn Leu Ala
    1010                 1015                 1020

Ala Ala  Gly Leu Arg Pro Gly  Met Asn Pro Ala Thr  Phe Ala Lys
    1025                 1030                 1035

Met Arg  Ile Gly Leu Ala Gln  Gln Arg Ala Ala Gly  Met Tyr Pro
    1040                 1045                 1050

Gly Met  Val Gly Met Pro Gly  Ser Ser Ser Pro Ile  Leu Pro Ser
    1055                 1060                 1065

Ser Ala  Gly Leu Ser Met Met  Gly Gln Pro Leu Asn  Arg Ser Asn
    1070                 1075                 1080

Leu Gly  Pro Leu Gln Arg Ala  Met Met Ser Ser Met  Gly Pro Pro
    1085                 1090                 1095

Lys Ile  Pro Gly Gly Asn Phe  Gln Leu Asn Ala Gln  Gln Gln Met
    1100                 1105                 1110

Gln Leu  Gln Gln Gln Leu Gln  Gln Gln Gln Gln Leu  Gln Gln Asn
    1115                 1120                 1125

Pro Gln  Gln Gln Gln Gln Leu  His Gln Asn Pro Gln  Gln Gln Gln
    1130                 1135                 1140

Leu Gln  Gln Leu Gln Gln Gln  Gln Gln Ile Gln Gln  Gln Leu Gln
    1145                 1150                 1155

Gln Gln  Gln Gln Leu Gln Gln  Gln Leu Gln Gln Gln  Gln Gln Gln
```

```
    1160                1165                1170

Gln Gln  Gln Gln Gln Met Gly  Ser Pro Leu Gln Gln  Ala Gln Val
    1175                1180                1185

Gly Ser  Pro Ala Gly Ser Gln  Gln Ser Leu Met Met  Gln Gln Gln
    1190                1195                1200

Gln Gln  Ile Ser Pro Gln Gln  Met Gly Gln Gln Ala  Ala Met Ser
    1205                1210                1215

Pro Gln  Leu Ser Ser Gly Thr  Leu Gln Gln Met Ser  Asn Asn Val
    1220                1225                1230

Val Asn  Pro Val Ala Thr Pro  Gly Pro Pro Pro Ser  Pro Gln Leu
    1235                1240                1245

Ser Ser  Gln Thr His Gly Ser  Val Ser Ser Ile Ala  Asn Ser Pro
    1250                1255                1260

Met Glu  Gln Leu Gln Gly Ala  Ser Lys Gly Gly Pro  Gly Ser Met
    1265                1270                1275


<210> SEQ ID NO 12
<211> LENGTH: 3458
<212> TYPE: DNA
<213> ORGANISM: Resurrection grass

<400> SEQUENCE: 12

gttgacagag caaataatat caatggcgtc aaaattttta cagggtgctc caacgaaatt     60

ttgccagagc atgaggtttc tttcacattc agcctctatg acagaggtta tctcatttca    120

aagtcaccag caatggatcc tagccagacc tcagttcagg atggcaaaac actgcatccc    180

tatgatagag catcggaaaa attattctca gctattgaag ctggaaggct acctggcgat    240

attcttgatg agataccaag caagtactat aatggatcag ttgtttgtga gatacgtgac    300

taccgaaagc gtatatccaa tcaaacgcct gcgtcatctg ctgagctagg acttcccatc    360

gtgaataaag tacgtctgcg gatgacattt gagaacgttg tgaaggacat tacactgcta    420

tctgatgatt cttggagtta cagggatttt gtggaagctg aggcacgtat tgtcagagct    480

ctacaaccag aactttgctt agaccctact cctaaattgg accggctttg tcaggatcct    540

gtccctcata agttgaacct tggtattgga aaaaagagga ggatgaggca aaatcctgaa    600

gttgttgtca catccagtaa catgtctcat ggcaaaaagg tgtgcattga taggttgtct    660

gaaaacggca aagcagatga gatgggcatc acaggtggca atgcagctca ccaggctgtt    720

gatagtgtta ccattcagaa tacttcaggt gttcctcaac cacttagacc aaataattct    780

tcacaagatg ctgccagaat gcttttgtcg caatctggta tacagcaaac tatgagttat    840

tctgctgtgg gcaatgatcg tatggcagga tctcctgcca attttactgg aatcagttca    900

agtatttcat ctcctcagaa catgatgact tacaatgatg ccgcctctgc caacggcctt    960

ctttctgtga agagggaaat gcaagatgct ccactgcaag atcctaataa gagaataaag   1020

tctggtggca ttgatgatgc acagcagcag cagttgaggc ctcaatccct tggcggacag   1080

gagatgcaat ggaagaacca acagctgcat ccacaattag aggtcaaggg gatgcagtat   1140

gctgcttctt cattgggtgg tcagagatat ccttctccga tgatgaacaa tatgccagat   1200

tcaggagctt ccttctattt caatcagcag ggtatgagat atggggctaa gcaagagcag   1260

atggatggtt ctgataggtt gaaagacagc ttggcacctg aaggttctat gctggatcag   1320

cagcagtccc aggctcaact cttgtcacaa caatcaactg caagaaacaa tattcccaac   1380

atgacacagt ggcagaatac caggttttca gttgagaagg acatgaaaaa agatgaaatt   1440
```

```
aaccagagaa gaaagttagc tcccaactcc cgtgcccctt ctgggccaat ggttcagtct   1500
ccagtgtcct ctaaatctgg agagatatct agcagttcaa tgggtggtca gtttggttct   1560
gctgtgacat cagctgcaat aggggtacaa aaagataagt ttgcagcaaa ctccagtgct   1620
gcagttggat acccttctgt agcttcgagc cctagtgatt ctatgcaccg ggtacaacag   1680
cccgctgttg ctccttcaaa gaggaaaaca aattcagttc caaaaactca accacctgtg   1740
agcggtgtag ggtctccagc cagtgtttca aatatgcagt ctatgctgaa tgctaacagc   1800
ccatcgattg ggaccgcacc tgtgggagac caagcgatca acgatagatt cgcgaaaatt   1860
gatgctcttt cccagcggta ccagctgcat agtaagaaga acaaagttga taagatacca   1920
caaaggaaac ccctgattgg tgcaagccaa gatgtagcta gtaaactctc cagttgcttc   1980
catacagagg attatataga tacaatgaga cctatctgta attctatgat tactggatca   2040
ataaacacgt gcaagactag aataattaat cttgtgagca caaaccgcat gtaccaaggt   2100
catgcgaggc cattccgggt cattttcaag gaaatgcctg atgaaactgt aaaaatgcaa   2160
tatggggatt tagaagattt tgatggtccg aactcaccgg attgtgtatt catattacca   2220
acgaagtact atgccgactt gctcggagag caacttattc ccctgatgtt gaaagatggt   2280
cattcgaagg cagatgatca agttgttcgt ggcacccctc ctggcaacct cagcgcacta   2340
tcaggaattt taccagacaa tccaccaagt gacataaagc aagagggagg tgtaagccag   2400
caactcaatg caaatatggc acctggaaca ccgatgcaac agcttcctgg caataggatg   2460
ctttcatctg caaatagcaa ccaggcccta gcaatgcagc aaggttacat gcaacaaggg   2520
gcaaccatgc ctccaaggag tcaacaactt gacccaaata tggtccagca gccgcagcca   2580
ccgccgcctc agcagcagca gcaaccgctg cagcaaaatg ctcaagcaca gcttcagcaa   2640
ccatcatctc ttcctctcaa ccagatgcag agacctcaaa tattaccaac gagcccatta   2700
tctcagatga tggggcctgg ttccaatctt ccaatgggct caagccagat gggtaacaat   2760
aagtctgctc ctacttccct tcagcttcag atgctacagc aggcacagca gcaacagcct   2820
atgtctagga aggtgatgat ggggcttggc ggacttggtt cagccatgaa catgagcaac   2880
atggttaaca atgtcgtggg cctcggtggt attggaaatg ttatgggaat gggcaatgtg   2940
aggccaattt cctccccgat gggatcaatg tccttgggca acaattccaa tccaatgaac   3000
cttggaatga catcaaacct agctgcagcc ggacttcgtc caggcatgaa ccctgctact   3060
cttgcgaaga tgcgtatggc acagcaaagg gcagcaggaa tatatcccca gactggaatg   3120
gttggaatgc ctgggagcag ttctcctgtg tccatgatgg gccatccatt gaatcgaagc   3180
aacctcaacc cattgcagag ggccatgatg tcttccatgg gccctccgaa gataccagga   3240
ggtaactttc cgctgaacgc tcaacagcaa atgcagctac aacagcagtt gcaacagcag   3300
cagcagcagc tccagcagaa cccacagcag caacagcaac tacagcagca gcagcagcag   3360
cagctccaac agagcccaca gcagcagctt catcagcagc aaatgcaaca acagctacag   3420
cagcaacagc tgcaacaact acagcagcag cagcaaca                         3458
```

```
<210> SEQ ID NO 13
<211> LENGTH: 1152
<212> TYPE: PRT
<213> ORGANISM: Resurrection grass

<400> SEQUENCE: 13

Val Asp Arg Ala Asn Asn Ile Asn Gly Val Lys Ile Phe Thr Gly Cys
1               5                   10                  15
```

-continued

```
Ser Asn Glu Ile Leu Pro Glu His Glu Val Ser Phe Thr Phe Ser Leu
            20                  25                  30

Tyr Asp Arg Gly Tyr Leu Ile Ser Lys Ser Pro Ala Met Asp Pro Ser
        35                  40                  45

Gln Thr Ser Val Gln Asp Gly Lys Thr Leu His Pro Tyr Asp Arg Ala
    50                  55                  60

Ser Glu Lys Leu Phe Ser Ala Ile Glu Ala Gly Arg Leu Pro Gly Asp
65                  70                  75                  80

Ile Leu Asp Glu Ile Pro Ser Lys Tyr Tyr Asn Gly Ser Val Val Cys
                85                  90                  95

Glu Ile Arg Asp Tyr Arg Lys Arg Ile Ser Asn Gln Thr Pro Ala Ser
            100                 105                 110

Ser Ala Glu Leu Gly Leu Pro Ile Val Asn Lys Val Arg Leu Arg Met
        115                 120                 125

Thr Phe Glu Asn Val Val Lys Asp Ile Thr Leu Leu Ser Asp Asp Ser
    130                 135                 140

Trp Ser Tyr Arg Asp Phe Val Glu Ala Glu Ala Arg Ile Val Arg Ala
145                 150                 155                 160

Leu Gln Pro Glu Leu Cys Leu Asp Pro Thr Pro Lys Leu Asp Arg Leu
                165                 170                 175

Cys Gln Asp Pro Val Pro His Lys Leu Asn Leu Gly Ile Gly Lys Lys
            180                 185                 190

Arg Arg Met Arg Gln Asn Pro Glu Val Val Val Thr Ser Ser Asn Met
        195                 200                 205

Ser His Gly Lys Lys Val Cys Ile Asp Arg Leu Ser Glu Asn Gly Lys
    210                 215                 220

Ala Asp Glu Met Gly Ile Thr Gly Gly Asn Ala Ala His Gln Ala Val
225                 230                 235                 240

Asp Ser Val Thr Ile Gln Asn Thr Ser Gly Val Pro Gln Pro Leu Arg
                245                 250                 255

Pro Asn Asn Ser Ser Gln Asp Ala Ala Arg Met Leu Leu Ser Gln Ser
            260                 265                 270

Gly Ile Gln Gln Thr Met Ser Tyr Ser Ala Val Gly Asn Asp Arg Met
        275                 280                 285

Ala Gly Ser Pro Ala Asn Phe Thr Gly Ile Ser Ser Ser Ile Ser Ser
    290                 295                 300

Pro Gln Asn Met Met Thr Tyr Asn Asp Ala Ala Ser Ala Asn Gly Leu
305                 310                 315                 320

Leu Ser Val Lys Arg Glu Met Gln Asp Ala Pro Leu Gln Asp Pro Asn
                325                 330                 335

Lys Arg Ile Lys Ser Gly Gly Ile Asp Asp Ala Gln Gln Gln Gln Leu
            340                 345                 350

Arg Pro Gln Ser Leu Gly Gly Gln Glu Met Gln Trp Lys Asn Gln Gln
        355                 360                 365

Leu His Pro Gln Leu Glu Val Lys Gly Met Gln Tyr Ala Ala Ser Ser
    370                 375                 380

Leu Gly Gly Gln Arg Tyr Pro Ser Pro Met Met Asn Asn Met Pro Asp
385                 390                 395                 400

Ser Gly Ala Ser Phe Tyr Phe Asn Gln Gln Gly Met Arg Tyr Gly Ala
                405                 410                 415

Lys Gln Glu Gln Met Asp Gly Ser Asp Arg Leu Lys Asp Ser Leu Ala
            420                 425                 430

Pro Glu Gly Ser Met Leu Asp Gln Gln Gln Ser Gln Ala Gln Leu Leu
```

```
        435                 440                 445

Ser Gln Gln Ser Thr Ala Arg Asn Asn Ile Pro Asn Met Thr Gln Trp
    450                 455                 460

Gln Asn Thr Arg Phe Ser Val Glu Lys Asp Met Lys Lys Asp Glu Ile
465                 470                 475                 480

Asn Gln Arg Arg Lys Leu Ala Pro Asn Ser Arg Ala Pro Ser Gly Pro
                485                 490                 495

Met Val Gln Ser Pro Val Ser Ser Lys Ser Gly Glu Ile Ser Ser Ser
            500                 505                 510

Ser Met Gly Gly Gln Phe Gly Ser Ala Val Thr Ser Ala Ala Ile Gly
        515                 520                 525

Val Gln Lys Asp Lys Phe Ala Ala Asn Ser Ser Ala Ala Val Gly Tyr
    530                 535                 540

Pro Ser Val Ala Ser Ser Pro Ser Asp Ser Met His Arg Val Gln Gln
545                 550                 555                 560

Pro Ala Val Ala Pro Ser Lys Arg Lys Thr Asn Ser Val Pro Lys Thr
                565                 570                 575

Gln Pro Pro Val Ser Gly Val Gly Ser Pro Ala Ser Val Ser Asn Met
            580                 585                 590

Gln Ser Met Leu Asn Ala Asn Ser Pro Ser Ile Gly Thr Ala Pro Val
        595                 600                 605

Gly Asp Gln Ala Ile Asn Asp Arg Phe Ala Lys Ile Asp Ala Leu Ser
    610                 615                 620

Gln Arg Tyr Gln Leu His Ser Lys Lys Asn Lys Val Asp Lys Ile Pro
625                 630                 635                 640

Gln Arg Lys Pro Leu Ile Gly Ala Ser Gln Asp Val Ala Ser Lys Leu
                645                 650                 655

Ser Ser Cys Phe His Thr Glu Asp Tyr Ile Asp Thr Met Arg Pro Ile
            660                 665                 670

Cys Asn Ser Met Ile Thr Gly Ser Ile Asn Thr Cys Lys Thr Arg Ile
        675                 680                 685

Ile Asn Leu Val Ser Thr Asn Arg Met Tyr Gln Gly His Ala Arg Pro
    690                 695                 700

Phe Arg Val Ile Phe Lys Glu Met Pro Asp Glu Thr Val Lys Met Gln
705                 710                 715                 720

Tyr Gly Asp Leu Glu Asp Phe Asp Gly Pro Asn Ser Pro Asp Cys Val
                725                 730                 735

Phe Ile Leu Pro Thr Lys Tyr Tyr Ala Asp Leu Leu Gly Glu Gln Leu
            740                 745                 750

Ile Pro Leu Met Leu Lys Asp Gly His Ser Lys Ala Asp Asp Gln Val
        755                 760                 765

Val Arg Gly Thr Pro Pro Gly Asn Leu Ser Ala Leu Ser Gly Ile Leu
    770                 775                 780

Pro Asp Asn Pro Pro Ser Asp Ile Lys Gln Glu Gly Gly Val Ser Gln
785                 790                 795                 800

Gln Leu Asn Ala Asn Met Ala Pro Gly Thr Pro Met Gln Gln Leu Pro
                805                 810                 815

Gly Asn Arg Met Leu Ser Ser Ala Asn Ser Asn Gln Ala Leu Ala Met
            820                 825                 830

Gln Gln Gly Tyr Met Gln Gln Gly Ala Thr Met Pro Pro Arg Ser Gln
        835                 840                 845

Gln Leu Asp Pro Asn Met Val Gln Gln Pro Gln Pro Pro Pro Pro Gln
    850                 855                 860
```

```
Gln Gln Gln Gln Pro Leu Gln Gln Asn Ala Gln Ala Gln Leu Gln Gln
865                 870                 875                 880

Pro Ser Ser Leu Pro Leu Asn Gln Met Gln Arg Pro Gln Ile Leu Pro
                885                 890                 895

Thr Ser Pro Leu Ser Gln Met Met Gly Pro Gly Ser Asn Leu Pro Met
            900                 905                 910

Gly Ser Ser Gln Met Gly Asn Asn Lys Ser Ala Pro Thr Ser Leu Gln
        915                 920                 925

Leu Gln Met Leu Gln Gln Ala Gln Gln Gln Gln Pro Met Ser Arg Lys
    930                 935                 940

Val Met Met Gly Leu Gly Gly Leu Gly Ser Ala Met Asn Met Ser Asn
945                 950                 955                 960

Met Val Asn Asn Val Val Gly Leu Gly Gly Ile Gly Asn Val Met Gly
                965                 970                 975

Met Gly Asn Val Arg Pro Ile Ser Ser Pro Met Gly Ser Met Ser Leu
            980                 985                 990

Gly Asn Asn Ser Asn Pro Met Asn  Leu Gly Met Thr Ser  Asn Leu Ala
        995                 1000                1005

Ala Ala  Gly Leu Arg Pro Gly  Met Asn Pro Ala Thr  Leu Ala Lys
    1010                1015                1020

Met Arg  Met Ala Gln Gln Arg  Ala Ala Gly Ile Tyr  Pro Gln Thr
    1025                1030                1035

Gly Met  Val Gly Met Pro Gly  Ser Ser Ser Pro Val  Ser Met Met
    1040                1045                1050

Gly His  Pro Leu Asn Arg Ser  Asn Leu Asn Pro Leu  Gln Arg Ala
    1055                1060                1065

Met Met  Ser Ser Met Gly Pro  Pro Lys Ile Pro Gly  Gly Asn Phe
    1070                1075                1080

Pro Leu  Asn Ala Gln Gln Gln  Met Gln Leu Gln Gln  Gln Leu Gln
    1085                1090                1095

Gln Gln  Gln Gln Gln Leu Gln  Gln Asn Pro Gln Gln  Gln Gln Gln
    1100                1105                1110

Leu Gln  Gln Gln Gln Gln Gln  Gln Leu Gln Gln Ser  Pro Gln Gln
    1115                1120                1125

Gln Leu  His Gln Gln Gln Met  Gln Gln Gln Leu Gln  Gln Gln Gln
    1130                1135                1140

Leu Gln  Gln Leu Gln Gln Gln  Gln Gln
    1145                1150
```

<210> SEQ ID NO 14
<211> LENGTH: 3978
<212> TYPE: DNA
<213> ORGANISM: Arabidopsis thaliana

<400> SEQUENCE: 14

```
atgggtgtct cgtttaagat atcgaaggtt ggtagaaagt ttcgacctaa gatttctact      60

gaattggcta ctcctgattc cccaaaagca atcgttctat ctgggaaacc aaaggccact     120

gatgatagca atattggcga tgtttccggg ttttcgaagc catctttacc cgatatatct     180

ccagatcatg aagtttcctt catattgagc ctctatccaa atgggtactc tataggaaaa     240

acctctgagg ctatgcaaca gatatcgttt cgagatgttc caaaggtctt acatccgtat     300

gatagggcag cagagggtct cctttcggct attgaggctg gcaggcttcc tggggacatt     360

ttggaagata taccttgcaa atttgtggat ggggtggtta tatgtgaggt gcatgactat     420
```

cggaaacata cctcatctca agtctctcct gtgataaata aattgcgcct taagatgtca 480
ctcgagaatg tggtaaaaga tattccatca atgtcagaca actcatggac gtacggtgat 540
ctcatggaag tggagtccag gatattaaaa gccttacaac ctgaactctg tctggatcct 600
ttacccagac ttgataggct gagtaaaaat cctttgactg ctaagctcga tttgtcgctt 660
tctactttgc ggagaaagag attaaggcaa atggcagaag tgacagtcat gtctcagaat 720
aagattcagg ggaaaaaggt gtgcattgat cggcttcctg aaagttcaga gcgaggaaat 780
ttgccagggc atttgataat gcagcaaacc aataacaacc aggctattca aaaccttggt 840
actaatatgc tggcgggatt aagaagtcag ccgttgcaag atgcaccaaa ttcctctctg 900
gccttggtac cacctcagca acaaaggtac atgggaattg gaagtacaag aaacacgcag 960
gatcaaggat caaattctgt cagtgtctct ggcgcttcgc ctggtggact agatgcgatg 1020
ctgccttatg gctctgatag tatgaaccct ggtacatctt ttcatagaaa gagagaaagt 1080
caagaaggac aaatgtcttc tatgcctggc ttgaataagc gaacaagggt ttcacatatg 1140
ggtcctgatg ggttccgca gcaacagtta gggcaacgta tggatggcct tcatggatcc 1200
gatacaaatt ggaaaaatac gcttctacaa caccaagaca tgctaggcag aagtattcag 1260
tatccaaata caagtattca gaggttttca ccacaccaaa tggaagggt tatgaatcag 1320
gaaggtggtc ccatgcaatt tccagcttca caacaggggg gaatgaaata cacttcaaaa 1380
gaggagccat ttgagactgg taaaattgat ggcggcacca gaaacaatat tccgggggtg 1440
ggaagtgatg caaatgattt agatccacgt attcagtcaa ggatgcccca taatgcattc 1500
attagatcaa atttccctca aacatcctgg aatgttaatc ctggccagca gattgaaaaa 1560
gagccgaaaa aagaagaaca atttagtcgt aggatatcgg ctcaaagtcc tcgtttgtcg 1620
gcaggtggtc caccgcagtc cccactttca tcgaagtctg gtgagttttc tggtggttca 1680
atggggaccc actatggagc agttgcagca gctcagaagg acaaggctgt tacttctatt 1740
cctgctattg gtgctactca gtcagtgggt tctagtgcta atgaagctat gcagcaaagg 1800
caacaccaag cccaaatggc tgcaaaacgg agaacaaatt ctcttcctaa gacgcaagtt 1860
attagcactg ttggttctcc tgttagtgtc aatactatta gtgtcccagt taatgcaagg 1920
agcccttcag tgggacccca aactttgggc gatcacgcaa tcttggacag attttcaaag 1980
attgaacgag ttgctgctag gtaccaacta aactgcaaaa agcataaggt ggatgagtac 2040
tctcgaagac ctcgcgtgta tgctaaacag ccccttactg tttgtttatc aaacctgtct 2100
aacgaagagg tcttcaaaga cgaggacgaa gcattatcaa aatctatatt tggtggcagt 2160
atgaatacat acaagaccag agtcattcac tttggtcaga tggaacgtgt aatgcaaggt 2220
tcggtccctt ccttcatccc tagaaaccga acaagactgg tgatgtcaga gaaggccgtc 2280
gatgggacag tagcatggta tcaaggggac gtagatgaag gggatgtttt tcaggctgaa 2340
gattttctct tagcgttgcc caatacacac atcgccgatc tacttgctac tcaatttaaa 2400
tcactgatgg cccgtgaagg atacatgatt gaagaacata ttatggcaaa gccaaaccgt 2460
ggggatactg gcccaatcag cagccatcca aattctgcgg gtggttatcc aagaggttat 2520
tctgcaaacg atatgcaaca gtatggagat gcagttgcag ggcaagcgtc tggtgaggca 2580
tcaaaacatg ggaatactgg aaatacgccg aataactcaa cccagaatat tcttgcaaat 2640
gcaaggatgg ttcctccaac aaattctcaa gccttgcaaa tgtctcaagg actgctgtct 2700
ggtgtctcca tgcctatgca accacaacag cttgacccac aacagtcagc gctactgtca 2760

```
tcacattcac agcagaaaaa tcaacagtca atgtttacac agcaacagca tccacaaatg   2820
cagagacctt ccatgatact gcctacaaat ccactatcag ccatcaactc gatgagccag   2880
agctctggta tgcagccggg tggtcagatg gccaacaagt attcgcctct ccaactgcag   2940
atgttacagc agcagcagca ggcggcagtg cagaagaaga taatgatggg gctaggatca   3000
ggtgtaggca tgggtatggg tatgggcatg ggtatgggta tgggaagcat gggaaatagt   3060
attgctgggc ttggagcttt aggcaaccaa ttgaatatgg caggaagagg tatgggggga   3120
accggaatct catcgtcaat gtctgttcct ggcatcggta atatgggcca gaacccaatg   3180
aatctgaatc cagcatcaaa tttgaatgct ataagccagc aactccgatc tggtgcatta   3240
acaccacaac aaaacgctct gtttacacag attaggatgg gcatggcaaa ccgaggaggt   3300
gtaatgggtg ctcctcaaac cgggataagt ggcgtgtcag gtactaggca gatgcacccc   3360
agctcagctg gtctttccat gttggatcag aacagagcta atctgcagcg agctgctgct   3420
atgggtaaca tgggcccacc caagctgatg cctggaatga tgaatcttta catgaatcaa   3480
caacaacagc agcagcaact ccagcagcaa ccccaacaac aacagttgca gcatcagcaa   3540
cagttacagc agcctatgtc tcagccatct cagcagctag ctcagtctcc gcagcagcag   3600
cagcagctac aacaacatga acagcctcaa caagcacagc agcagcagca ggcaacagca   3660
tcccctcttc agtctgtact atcaccaccc caagtagggt caccatcagc tggaattacc   3720
caacagcagc tacaacagtc cagtccccag caaatgagtc agagaactcc aatgagtccc   3780
cagcaagtga accaaagaac tcctatgagt cctcagataa gctcgggtgc aatgcatccc   3840
atgagcacaa gcaacctcga gggttgtcca gcgagtccac agcttagctc tcagacaatg   3900
ggttctgttg gtagcatcac taattctcca atggagcttc aaggtcccaa aaacaactct   3960
gctggtaata attcttga                                                 3978
```

<210> SEQ ID NO 15
<211> LENGTH: 1325
<212> TYPE: PRT
<213> ORGANISM: Arabidopsis thaliana

<400> SEQUENCE: 15

```
Met Gly Val Ser Phe Lys Ile Ser Lys Val Gly Arg Lys Phe Arg Pro
1               5                   10                  15

Lys Ile Ser Thr Glu Leu Ala Thr Pro Asp Ser Pro Lys Ala Ile Val
            20                  25                  30

Leu Ser Gly Lys Pro Lys Ala Thr Asp Asp Ser Asn Ile Gly Asp Val
        35                  40                  45

Ser Gly Phe Ser Lys Pro Ser Leu Pro Asp Ile Ser Pro Asp His Glu
    50                  55                  60

Val Ser Phe Ile Leu Ser Leu Tyr Pro Asn Gly Tyr Ser Ile Gly Lys
65                  70                  75                  80

Thr Ser Glu Ala Met Gln Gln Ile Ser Phe Arg Asp Val Pro Lys Val
                85                  90                  95

Leu His Pro Tyr Asp Arg Ala Ala Glu Gly Leu Leu Ser Ala Ile Glu
            100                 105                 110

Ala Gly Arg Leu Pro Gly Asp Ile Leu Glu Asp Ile Pro Cys Lys Phe
        115                 120                 125

Val Asp Gly Val Val Ile Cys Glu Val His Asp Tyr Arg Lys His Thr
    130                 135                 140

Ser Ser Gln Val Ser Pro Val Ile Asn Lys Leu Arg Leu Lys Met Ser
145                 150                 155                 160
```

-continued

```
Leu Glu Asn Val Val Lys Asp Ile Pro Ser Met Ser Asp Asn Ser Trp
                165                 170                 175

Thr Tyr Gly Asp Leu Met Glu Val Glu Ser Arg Ile Leu Lys Ala Leu
            180                 185                 190

Gln Pro Glu Leu Cys Leu Asp Pro Leu Pro Arg Leu Asp Arg Leu Ser
        195                 200                 205

Lys Asn Pro Leu Thr Ala Lys Leu Asp Leu Ser Leu Ser Thr Leu Arg
    210                 215                 220

Arg Lys Arg Leu Arg Gln Met Ala Glu Val Thr Val Met Ser Gln Asn
225                 230                 235                 240

Lys Ile Gln Gly Lys Lys Val Cys Ile Asp Arg Leu Pro Glu Ser Ser
                245                 250                 255

Glu Arg Gly Asn Leu Pro Gly His Leu Ile Met Gln Gln Thr Asn Asn
            260                 265                 270

Asn Gln Ala Ile Gln Asn Leu Gly Thr Asn Met Leu Ala Gly Leu Arg
        275                 280                 285

Ser Gln Pro Leu Gln Asp Ala Pro Asn Ser Ser Leu Ala Leu Val Pro
    290                 295                 300

Pro Gln Gln Gln Arg Tyr Met Gly Ile Gly Ser Thr Arg Asn Thr Gln
305                 310                 315                 320

Asp Gln Gly Ser Asn Ser Val Ser Val Ser Gly Ala Ser Pro Gly Gly
                325                 330                 335

Leu Asp Ala Met Leu Pro Tyr Gly Ser Asp Ser Met Asn Pro Gly Thr
            340                 345                 350

Ser Phe His Arg Lys Arg Glu Ser Gln Glu Gly Gln Met Ser Ser Met
        355                 360                 365

Pro Gly Leu Asn Lys Arg Thr Arg Val Ser His Met Gly Pro Asp Gly
    370                 375                 380

Val Pro Gln Gln Gln Leu Gly Gln Arg Met Asp Gly Leu His Gly Ser
385                 390                 395                 400

Asp Thr Asn Trp Lys Asn Thr Leu Leu Gln His Gln Asp Met Leu Gly
                405                 410                 415

Arg Ser Ile Gln Tyr Pro Asn Thr Ser Ile Gln Arg Phe Ser Pro His
            420                 425                 430

Gln Met Glu Gly Val Met Asn Gln Glu Gly Gly Pro Met Gln Phe Pro
        435                 440                 445

Ala Ser Gln Gln Gly Gly Met Lys Tyr Thr Ser Lys Glu Glu Pro Phe
    450                 455                 460

Glu Thr Gly Lys Ile Asp Gly Gly Thr Arg Asn Asn Ile Pro Gly Val
465                 470                 475                 480

Gly Ser Asp Ala Asn Asp Leu Asp Pro Arg Ile Gln Ser Arg Met Pro
                485                 490                 495

His Asn Ala Phe Ile Arg Ser Asn Phe Pro Gln Thr Ser Trp Asn Val
            500                 505                 510

Asn Pro Gly Gln Gln Ile Glu Lys Glu Pro Lys Lys Glu Glu Gln Phe
        515                 520                 525

Ser Arg Arg Ile Ser Ala Gln Ser Pro Arg Leu Ser Ala Gly Gly Pro
    530                 535                 540

Pro Gln Ser Pro Leu Ser Ser Lys Ser Gly Glu Phe Ser Gly Gly Ser
545                 550                 555                 560

Met Gly Thr His Tyr Gly Ala Val Ala Ala Ala Gln Lys Asp Lys Ala
                565                 570                 575
```

```
Val Thr Ser Ile Pro Ala Ile Gly Ala Thr Gln Ser Val Gly Ser Ser
            580                 585                 590

Ala Asn Glu Ala Met Gln Gln Arg Gln His Gln Ala Gln Met Ala Ala
        595                 600                 605

Lys Arg Arg Thr Asn Ser Leu Pro Lys Thr Gln Val Ile Ser Thr Val
    610                 615                 620

Gly Ser Pro Val Ser Val Asn Thr Ile Ser Val Pro Val Asn Ala Arg
625                 630                 635                 640

Ser Pro Ser Val Gly Pro Gln Thr Leu Gly Asp His Ala Ile Leu Asp
                645                 650                 655

Arg Phe Ser Lys Ile Glu Arg Val Ala Ala Arg Tyr Gln Leu Asn Cys
            660                 665                 670

Lys Lys His Lys Val Asp Glu Tyr Ser Arg Arg Pro Arg Val Tyr Ala
        675                 680                 685

Lys Gln Pro Leu Thr Val Cys Leu Ser Asn Leu Ser Asn Glu Glu Val
    690                 695                 700

Phe Lys Asp Glu Asp Glu Ala Leu Ser Lys Ser Ile Phe Gly Gly Ser
705                 710                 715                 720

Met Asn Thr Tyr Lys Thr Arg Val Ile His Phe Gly Gln Met Glu Arg
                725                 730                 735

Val Met Gln Gly Ser Val Pro Ser Phe Ile Pro Arg Asn Arg Thr Arg
            740                 745                 750

Leu Val Met Ser Glu Lys Ala Val Asp Gly Thr Val Ala Trp Tyr Gln
        755                 760                 765

Gly Asp Val Asp Glu Gly Asp Val Phe Gln Ala Glu Asp Phe Leu Leu
    770                 775                 780

Ala Leu Pro Asn Thr His Ile Ala Asp Leu Leu Ala Thr Gln Phe Lys
785                 790                 795                 800

Ser Leu Met Ala Arg Glu Gly Tyr Met Ile Glu Glu His Ile Met Ala
                805                 810                 815

Lys Pro Asn Arg Gly Asp Thr Gly Pro Ile Ser Ser His Pro Asn Ser
            820                 825                 830

Ala Gly Gly Tyr Pro Arg Gly Tyr Ser Ala Asn Asp Met Gln Gln Tyr
        835                 840                 845

Gly Asp Ala Val Ala Gly Gln Ala Ser Gly Glu Ala Ser Lys His Gly
    850                 855                 860

Asn Thr Gly Asn Thr Pro Asn Asn Ser Thr Gln Asn Ile Leu Ala Asn
865                 870                 875                 880

Ala Arg Met Val Pro Pro Thr Asn Ser Gln Ala Leu Gln Met Ser Gln
                885                 890                 895

Gly Leu Leu Ser Gly Val Ser Met Pro Met Gln Pro Gln Gln Leu Asp
            900                 905                 910

Pro Gln Gln Ser Ala Leu Leu Ser Ser His Ser Gln Gln Lys Asn Gln
        915                 920                 925

Gln Ser Met Phe Thr Gln Gln Gln His Pro Gln Met Gln Arg Pro Ser
    930                 935                 940

Met Ile Leu Pro Thr Asn Pro Leu Ser Ala Ile Asn Ser Met Ser Gln
945                 950                 955                 960

Ser Ser Gly Met Gln Pro Gly Gly Gln Met Ala Asn Lys Tyr Ser Pro
                965                 970                 975

Leu Gln Leu Gln Met Leu Gln Gln Gln Gln Gln Ala Ala Val Gln Lys
            980                 985                 990

Lys Ile Met Met Gly Leu Gly Ser  Gly Val Gly Met Gly  Met Gly Met
```

-continued

```
        995                 1000                1005

Gly Met Gly Met Gly Met Gly Ser Met Gly Asn Ser Ile Ala Gly
    1010                1015                1020

Leu Gly Ala Leu Gly Asn Gln Leu Asn Met Ala Gly Arg Gly Met
    1025                1030                1035

Gly Gly Thr Gly Ile Ser Ser Ser Met Ser Val Pro Gly Ile Gly
    1040                1045                1050

Asn Met Gly Gln Asn Pro Met Asn Leu Asn Pro Ala Ser Asn Leu
    1055                1060                1065

Asn Ala Ile Ser Gln Gln Leu Arg Ser Gly Ala Leu Thr Pro Gln
    1070                1075                1080

Gln Asn Ala Leu Phe Thr Gln Ile Arg Met Gly Met Ala Asn Arg
    1085                1090                1095

Gly Gly Val Met Gly Ala Pro Gln Thr Gly Ile Ser Gly Val Ser
    1100                1105                1110

Gly Thr Arg Gln Met His Pro Ser Ser Ala Gly Leu Ser Met Leu
    1115                1120                1125

Asp Gln Asn Arg Ala Asn Leu Gln Arg Ala Ala Ala Met Gly Asn
    1130                1135                1140

Met Gly Pro Pro Lys Leu Met Pro Gly Met Met Asn Leu Tyr Met
    1145                1150                1155

Asn Gln Gln Gln Gln Gln Gln Gln Leu Gln Gln Gln Pro Gln Gln
    1160                1165                1170

Gln Gln Leu Gln His Gln Gln Gln Leu Gln Gln Pro Met Ser Gln
    1175                1180                1185

Pro Ser Gln Gln Leu Ala Gln Ser Pro Gln Gln Gln Gln Gln Leu
    1190                1195                1200

Gln Gln His Glu Gln Pro Gln Gln Ala Gln Gln Gln Gln Gln Ala
    1205                1210                1215

Thr Ala Ser Pro Leu Gln Ser Val Leu Ser Pro Pro Gln Val Gly
    1220                1225                1230

Ser Pro Ser Ala Gly Ile Thr Gln Gln Gln Leu Gln Gln Ser Ser
    1235                1240                1245

Pro Gln Gln Met Ser Gln Arg Thr Pro Met Ser Pro Gln Gln Val
    1250                1255                1260

Asn Gln Arg Thr Pro Met Ser Pro Gln Ile Ser Ser Gly Ala Met
    1265                1270                1275

His Pro Met Ser Thr Ser Asn Leu Glu Gly Cys Pro Ala Ser Pro
    1280                1285                1290

Gln Leu Ser Ser Gln Thr Met Gly Ser Val Gly Ser Ile Thr Asn
    1295                1300                1305

Ser Pro Met Glu Leu Gln Gly Pro Lys Asn Asn Ser Ala Gly Asn
    1310                1315                1320

Asn Ser
    1325
```

<210> SEQ ID NO 16
<211> LENGTH: 6411
<212> TYPE: DNA
<213> ORGANISM: Arabidopsis thaliana

<400> SEQUENCE: 16

```
ctttctcttc cgatcgcatc ttcttcaaaa atttcccacc tgtgtttcac aaattccatg      60

tttatgaatt cttcattgct ctattcttag tcacctttga tttctctcgc tttctatccg     120
```

-continued

```
atccaattgt ttgatgatct tctctgtaac aagctcataa ggtttcaatt tctctagctt    180
tcttaaaatt cattcttcga tttcttcaat tctcgtgtct tttttatttc tgtatcgttt    240
attgacagta cctagacagg tttgagcttc atctctctgg agagaatcca tgggtgtctc    300
gtttaagata tcgaaggttg gtagaaagtt tcgacctaag atttctactg aattggctac    360
tcctgattcc ccaaaagcaa tcgttctatc tgggaaacca aaggtaattt aacttagaat    420
tttagttgta ttgtgttcca actaaattcg cttattttgg aaagttatat agaaaattta    480
ttacgtttgg ttcaggccac tgatgatagc aatattggcg atgtttccgg gttttcgaag    540
ccatctttac ccgatatatc tccaggtttg gatctcaacg aaccactttg acacataatg    600
ttttgctaaa ttctagctat gttgaattga gtgcattttg gtttctctgc agatcatgaa    660
gtttccttca tattgagcct ctatccaaat gggtactcta taggaaaaac ctctgaggta    720
tgtactgaga gtctatatga atttatttat cttgtgattt cttgtatttg agttttaaaa    780
ccttcacgtt ttcacaaatt tgagtttttg aataccaggc tatgcaacag atatcgtttc    840
gagatgttcc aaaggtctta catccgtatg atagggcagc agagggtctc ctttcggtaa    900
atctttcgaa ctatgttatt atagacttga tttgaacatg taatcaaagt tttggtgaat    960
gaattcaaag tacttagatt tagtaaatgt gaagatgatg ttttttttcc ccacttgttc   1020
tacccgaata atgcatttca ctgcactact tactcgcgtt ttgttaaata cactttctga   1080
gtttcattct actgagtaaa tgtttttaat ccctttgtac gctttatagg ctattgaggc   1140
tggcaggctt cctggggaca ttttggaaga tataccttgc aaatttgtgg atggggtggt   1200
tatatgtgag gtgagttatc tgcaattatt ttttgggata aagccttcca taagttcttg   1260
gaaacagtcc aaacgtatat aaatatattt aaaaagagct caacagaaat tatctacact   1320
taatcaagat taaaaaaatg tcgtaattat aagtacatgg aagtttatct tccaaactca   1380
attgtacatg tatttgattg tttctgaaac ataatggagt aactgggacc agaagtaaac   1440
ataaaaaacc tagttatact aatttttaat tgactgctgt gtaccatctt acatcatcat   1500
gttttcttta atttttggca catactattg taggtgcatg actatcggaa acatacctca   1560
tctcaagtct ctcctgtgat aaataaattg cgccttaaga tgtcactcga gaatgtggta   1620
aaagatattc catcaatgtc agacaactca tggacgtacg gtgatctcat ggtaatcatg   1680
gtagctcgtg gcttataggt cgtatatctg agcactgaaa ctattatctt ctgtactgat   1740
ccttacatca actgcaggaa gtggagtcca ggatattaaa agccttacaa cctgaactct   1800
gtctggatcc tttacccaga cttgataggc tgagtaaaaa tcctttgact gctaaggtaa   1860
tatctcatta aaaagactcc ttgtgctttc tgttctcagt tgtttattat agtgtctaaa   1920
atgttttttt ttctctactc gatagctcga tttgtcgctt tctactttgc ggagaaagag   1980
attaaggcaa atggcagaag tgacagtcat gtctcagaat aagattcagg ggaaaaaggt   2040
gtgcattgat cggcttcctg aaagttcaga gcgaggaaat ttgccagggc atttgataat   2100
gcagcaaacc aataacaacc aggctattca aaaccttggt actaatatgc tggcgggatt   2160
aagaagtcag ccgttgcaag atgcaccaaa ttcctctctg gccttggtac cacctcagca   2220
acaaaggtac atgggaattg gaagtacaag aaacacgcag gatcaaggat caaattctgt   2280
cagtgtctct ggcgcttcgc ctggtggact agatgcgatg ctgccttatg gctctgatag   2340
tatgaaccct ggtacatctt ttcatagaaa gagagaaagt caagaaggac aaatgtcttc   2400
tatgcctggc ttgaataagc gaacaagggt ttcacatatg ggtcctgatg ggggttccgca  2460
```

-continued

```
gcaacagtta gggcaacgta tggatggcct tcatggatcc gatacaaatt ggaaaaatac   2520
gcttctacaa caccaagaca tgctaggcag aagtattcag tatccaaata caagtattca   2580
gaggttttca ccacaccaaa tggaaggggt tatgaatcag gaaggtggtc ccatgcaatt   2640
tccagcttca caacaggggg gaatgaaata cacttcaaaa gaggagccat ttgagactgg   2700
taaaattgat ggcggcacca gaaacaatat tccgggggtg ggaagtgatg caaatgattt   2760
agatccacgt attcagtcaa ggatgcccca taatgcattc attagatcaa atttccctca   2820
aacatcctgg aatgttaatc ctggccagca gattgaaaaa gagccgaaaa aagaagaaca   2880
atttagtcgt aggatatcgg ctcaaagtcc tcgtttgtcg gcaggtggtc caccgcagtc   2940
cccactttca tcgaagtctg gtgagttttc tggtggttca atggggaccc actatggagc   3000
agttgcagca gctcagaagg acaaggctgt tacttctatt cctgctattg gtgctactca   3060
gtcagtgggt tctagtgcta atgaagctat gcagcaaagg caacaccaag cccaaatggc   3120
tgcaaaacgg agaacaaatt ctcttcctaa gacgcaagtt attagcactg ttggttctcc   3180
tgttagtgtc aatactatta gtgtcccagt taatgcaagg agcccttcag tgggacccca   3240
aactttgggc gatcacgcaa tcttggacag attttcaaag attgaacgag ttgctgctag   3300
gtatgaatgt tatgaaacct ggtttgttga ttttattccc ttcaaattct tttttatgat   3360
ctttactttc acttatgtga tacttctcct gttttgattc tggctttacg ctagagcatt   3420
gctggcattg tcttattctc cttatatcat tgcatttata taaataaata atgtttgttg   3480
gtgcatgaac aagttctata tttcatagat tttatttttt ggttgatcca gtttcttgtt   3540
ccatttttag gtaccaacta aactgcaaaa agcataaggt ggatgagtac tctcgaagac   3600
ctcgcgtgta tgctaaacag cccccttactg tttgtttatc aaacctgtct aacgaagagg   3660
tcttcaaaga cgaggacgaa gcattatcaa aatctatatt tggtggcagt atgaatacat   3720
acaagaccag agtcattcac tttggtcaga tggaacgtgt aatgcaaggt ctgtttttct   3780
tttaactaga tatctggcta ttggtatatt tctttatgtg attgaccaga ctccagtatc   3840
ttttcaggtt cggtcccttc cttcatccct agaaaccgaa caagactggt gatgtcagag   3900
aaggccgtcg atgggacagt agcatggtat caaggggacg tagatgaagg ggatgttttt   3960
caggctgaag attttctctt agcgttgccc aatacagtaa gttcacagga aatttgatag   4020
ttatcatact cccctgcatt cttttttgat cagcaatata tcttcaactt gcatgcacta   4080
ccattcaatg taatgttgat tttacattta gtgatgttta taggttgtcg ggtcatgttc   4140
ttggggttta tgtctctgtt gtgaatgttt tgtgtaatta tgaatatggt tggttggtct   4200
atggatactt ctctcttgtt agttgcttat gctcgtttat ccttcttgtc caatgcgatc   4260
aaaagggaat ggacaatgga ttattaattt ttctcttatg tacgccactt attttctgga   4320
agctatgctg acttgcttat tcctcacttt gtcacagcac atcgccgatc tacttgctac   4380
tcaatttaaa tcactggtat ttctcgagtt ctgaatcaat tatttcatgt tcctggttct   4440
atggtaaagc tacttaaaga ttgatttata tgcttatgca gatggcccgt gaaggataca   4500
tgattgaaga acatattatg gcaaagccaa accgtgggga tactggccca atcagcagcc   4560
atccaaattc tgcgggtggt tatccaagag gttattctgc aaacgatatg caacagtatg   4620
gagatgcagt tgcagggcaa gcgtctggtg aggcatcaaa acatgggaat actggaaata   4680
cgccgaataa ctcaacccag aatattcttg caaatgcaag gatggttcct ccaacaaatt   4740
ctcaagcctt gcaaatgtct caaggactgc tgtctggtgt ctccatgcct atgcaaccac   4800
aacagcttga cccacaacag tcagcgctac tgtcatcaca ttcacagcag aaaaatcaac   4860
```

-continued agtcaatgtt tacacagcaa cagcatccac aaatgcagag accttccatg atactgccta 4920
caaatccact atcagccatc aactcgatga gccagagctc tggtatgcag ccgggtggtc 4980
agatggccaa caagtattcg cctctccaac tgcagatgtt acagcagcag cagcaggcgg 5040
cagtgcagaa gaagataatg atggggctag gatcaggtgt aggcatgggt atgggtatgg 5100
gcatgggtat gggtatggga agcatgggaa atagtattgc tgggcttgga gctttaggca 5160
accaattgaa tatggcagga agaggtatgg ggggaaccgg aatctcatcg tcaatgtctg 5220
ttcctggcat cggtaatatg ggccagaacc caatgaatct gaatccagca tcaaatttga 5280
atgctataag ccagcaactc cgatctggtg cattaacacc acaacaaaac gctctgttta 5340
cacagattag gatgggcatg gcaaaccgag gaggtgtaat gggtgctcct caaaccggga 5400
taagtggcgt gtcaggtact aggcagatgc accccagctc agctggtctt tccatgttgg 5460
atcagaacag agctaatctg cagcgagctg ctgctatggg taacatgggc ccacccaagc 5520
tgatgcctgg aatgatgaat ctttacatga atcaacaaca acagcagcag caactccagc 5580
agcaacccca acaacaacag ttgcagcatc agcaacagtt acagcagcct atgtctcagc 5640
catctcagca gctagctcag tctccgcagc agcagcagca gctacaacaa catgaacagc 5700
ctcaacaagc acagcagcag cagcaggcaa cagcatcccc tcttcagtct gtactatcac 5760
caccccaagt agggtcacca tcagctggaa ttacccaaca gcagctacaa cagtccagtc 5820
cccagcaaat gagtcagaga actccaatga gtccccagca agtgaaccaa agaactccta 5880
tgagtcctca gataagctcg ggtgcaatgc atcccatgag cacaagcaac ctcgagggtt 5940
gtccagcgag tccacagctt agctctcaga caatgggttc tgttggtagc atcactaatt 6000
ctccaatgga gcttcaaggt cccaaaaaca actctgctgg taataattct tgatcaggaa 6060
aactatgatt ttgggtagac attatttatc ttcaggaacc ctttgcttca caacatgagt 6120
tgttatctac attagggaca agcatagaaa gagtttttag tttaccgtct taagttttgc 6180
ttgtacatta agcttttgaa attaaattta gattcatgac caaagcctgt agagaaaaag 6240
taaagaatct gttgtgctct gctagtgaaa ttaagtgcca ctatcattag gttgttgata 6300
taaccactgt ctgcttcaag gctatttgga gatttatttt aagcttaata attaatatat 6360
ctgttttgtt caattgttgt gatttgccac tgctaccttg taaacatggg a 6411

<210> SEQ ID NO 17
<211> LENGTH: 3906
<212> TYPE: DNA
<213> ORGANISM: Glycine max

<400> SEQUENCE: 17
atgggggtct ctttcaaggt gtccaaaacc ggcactaggt ttcgccccaa gtcgattccc 60
caacttcaag atggctcatc cgacaattcc aagtcccaga gtgatcttgt tgaggctggt 120
gaaaacattg ctcagattcc ccagtcatct gtttcatctg aaactctttc attagcagat 180
agggaagctt ctttcacatt gaacctgttt ccagatggtt attctattgg aaaaccctcc 240
gagaatgaag cagctagtca gtcaaaatac caagattttc ccaagtcgtt acatccatat 300
gacaggtcgt ctgagagtct attcttggcc attgagtcag gtcacttgcc tggggatatt 360
cttgatgata tacctgccaa gtatgttgat ggagcactta tatgtgtggt gcatgattat 420
cgaagatgct cttctgataa agggagtagt gtgtctgcag aaagttctac tgttagcaaa 480
gtatgcctca agatgtcgtt ggaaaatatt gtaaaggaca tcccatcgat tactgacaag 540

-continued

```
tcttggacat atggtgattt gatggaagtt gagtcgaaga tactgaaagc attacaacca    600
aaacttcatc tagaccctac tccaaagtta gatcggctgt gtgaaagtcc acttccaaca    660
aagctcaatt tgccaagaaa gcgattaaaa aatatgccag agtttgctgt tacttctacc    720
aataaaattc atgggaagaa agtatgcata gatagagtgc aagaaagctc aattagcaga    780
gtaggtgatg taggaaacac tgcatccaat gctattgtgc agcagaccca tgaaaatcca    840
gccatgcaaa atcttagtcc aaatgttgcc atggccttga gatctaagaa ttttatacct    900
gattcttcca tccctaactt tcctatgatg acccatcaat caagatatgc aatggctgtt    960
ggaactcaga gaagtttgca ggagcaggga cccgctcctt ccattaattc atcagtggct   1020
tctcctgcta cacaatatgc tgataatgca aactcaggtg cctctcttct tggaaaaagg   1080
gataatcaag atggacaagc atcgcctttg tccaatattg ctaaaagaat gaggcctggt   1140
tccactgttg ttgatgcaat gcagcatcag caaataggct cacacgttga agctcttcaa   1200
ggatcagata tgaattggca gaattcattg caacaacaac caatggccag aggtattcag   1260
tatgcaagtg gtggcattca gaagtttcct cagcaggttt ttgaaggggg ggcaaatcaa   1320
gagacagggg caattccctt tgcttctagt cagcagggca tgaggttggt tgccaaggaa   1380
gaacagtttg aaatggaaaa attagatggt gcagaaataa actgcaataa aagtgacatg   1440
gaaatggaaa tgaacaattt agatccacaa caattgcggc ttcagcaacg attgccacag   1500
catgcattca tgaggcctaa tttccctcag gcagcctgga acagtttggg tcagcatatg   1560
ggcaaagaaa caaaaaaaga agaccagctt cagaaaagga aatcagtaca gagtcctcgc   1620
ttatcctccg cggcattacc tcactcccca ttgtcttcga aatcaggtga attttccaat   1680
ggtgcagttg gaccaagttt tggaccatct gcaatggctg ctgcacctgg gacatcacaa   1740
aaagacaagg cagcaatggc ctcagttcct gctactgttg gaactccatc taatgattct   1800
acacaaagac aacatgcaca actagctgca aaacggagat ctaattctct tcccaagacc   1860
ccagcaatga atggagttgg ttctcctgtt agtgttggta caaccagtgt cccattgaat   1920
gcaaatagtc cctcagttgt gacctcgggt tttgttgatc aaaatcttca aaatatgctt   1980
gaaaggttct caaaaattga aatggtgaca atgaggcatc aacttaactt taagaagaac   2040
aaggttgatg actatcccat taagaagcag aatccatatg taccaaataa tctatcagca   2100
cttcttgcta atgctaatgc aactaataat gagggattgc cagaggagtc aatttctatt   2160
tcaaagtcgc ttataggtgg gagtatgaat gcgtgcaaaa tgagaatctt aaatttttgt   2220
gtgcctgagc gtgtagttca aggaagtatt gttactataa ttccgaggat gcgaactagg   2280
atgattatgt ttgaaaaatc tgatggtact gtggctatgc attgtggggt gattgaagaa   2340
gttgattacg tagctgcaga ggatcatctc ctcacattac ccaatactca ttctgcggat   2400
ttgcttgcac aacagttctg ttcactgatg gtacgcgaag gatatgtgaa ggaagatgat   2460
cgaatccaac ttaaaccaaa ccgggtgaac cttccgttgg gcaatcaatc tactacccct   2520
aataatgctg tagttgaaat gcaacaatat ggagaagtca ttcctggtca atcatccaat   2580
gaagttgcaa aaccagctag tggcagtaat gcacctataa acctctctca gaatcttcta   2640
acaaacccaa ggatgttgcc acctggaagc cccccaagcct tacagatgtc ccaaggactt   2700
ctctctggtg tttcaatggc ttcaagacca cagcaaatgg actcacaaca agctgtacag   2760
caacaacagc agcagcagca gcagcaacaa caacaacaac agcagcagca gcagcagctg   2820
caacaaaatc aacacacact cattcaacag cagaatcccc agttccagag gtctcctatg   2880
atgcttggga caaatcagct ttcacactta aatccagttg gacaaaactc caacatgcca   2940
```

-continued

```
ttaggtaatc acatgctcaa caagccttca gctctccaga tgcagatgtt ccaacaacag   3000

caacagcagc ctcaaatgca aaggaaaatg atgatgggac ttggacaagc cgtgggaatg   3060

ggtaacttga gaaataacct agttgggctt gcaccaatgg gcaaccctat gggaatggga   3120

ggtgcgaggg gaataggagg aagtggaatc tcagcaccaa tgacatctat tgctggcatg   3180

ggaaatatgg gtcagagccc aatgaatctt agccagactt caaatattac taattccata   3240

agccaacagt ttaggtccgg atcattaaat gcagcagcat ctgctgacct tatatcaagg   3300

cttagattgg tacattcgaa tcgtcaaagc atgctagggt cccctcagtc taacctagct   3360

agcatctcag gggccagaca aatacaccct ggtgctactc ctagtctttc aatgttgggc   3420

agggctaata caatgcagcg accaattgga cctatgggtc caccaaagat gatggcaggg   3480

atgaatcttt atatgagtca gcagcagcaa catcaacaac cccaacagca gcagcagcaa   3540

caccaacagc aattgcaact ccaacagcat atgcagcagc aattacagca gcaacagcaa   3600

caacaagaaa caacttcaca attgcagtca gttgtttcac ccccacaggt gggatcgcca   3660

tcaatgggcg taccaccatt gaaccaacaa acgcagcagc aagccagccc tcagcaaatg   3720

agtcaacgaa ctccgatgag tccacaaatg agctcaggtg caattcatgc catgagtgct   3780

ggtaatcctg aagcttgtcc agccagtcca cagttgagct ctcagaccct tggctctgtt   3840

agtagcataa caaactcccc tatggacatg caaggtgtta acaagagcaa ctctaatgca   3900

caatga                                                              3906


<210> SEQ ID NO 18
<211> LENGTH: 1301
<212> TYPE: PRT
<213> ORGANISM: Glycine max

<400> SEQUENCE: 18

Met Gly Val Ser Phe Lys Val Ser Lys Thr Gly Thr Arg Phe Arg Pro
1               5                   10                  15

Lys Ser Ile Pro Gln Leu Gln Asp Gly Ser Ser Asp Asn Ser Lys Ser
            20                  25                  30

Gln Ser Asp Leu Val Glu Ala Gly Glu Asn Ile Ala Gln Ile Pro Gln
        35                  40                  45

Ser Ser Val Ser Ser Glu Thr Leu Ser Leu Ala Asp Arg Glu Ala Ser
    50                  55                  60

Phe Thr Leu Asn Leu Phe Pro Asp Gly Tyr Ser Ile Gly Lys Pro Ser
65                  70                  75                  80

Glu Asn Glu Ala Ala Ser Gln Ser Lys Tyr Gln Asp Phe Pro Lys Ser
                85                  90                  95

Leu His Pro Tyr Asp Arg Ser Ser Glu Ser Leu Phe Leu Ala Ile Glu
            100                 105                 110

Ser Gly His Leu Pro Gly Asp Ile Leu Asp Asp Ile Pro Ala Lys Tyr
        115                 120                 125

Val Asp Gly Ala Leu Ile Cys Val Val His Asp Tyr Arg Arg Cys Ser
    130                 135                 140

Ser Asp Lys Gly Ser Ser Val Ser Ala Glu Ser Ser Thr Val Ser Lys
145                 150                 155                 160

Val Cys Leu Lys Met Ser Leu Glu Asn Ile Val Lys Asp Ile Pro Ser
                165                 170                 175

Ile Thr Asp Lys Ser Trp Thr Tyr Gly Asp Leu Met Glu Val Glu Ser
            180                 185                 190
```

```
Lys Ile Leu Lys Ala Leu Gln Pro Lys Leu His Leu Asp Pro Thr Pro
        195                 200                 205

Lys Leu Asp Arg Leu Cys Glu Ser Pro Leu Pro Thr Lys Leu Asn Leu
    210                 215                 220

Pro Arg Lys Arg Leu Lys Asn Met Pro Glu Phe Ala Val Thr Ser Thr
225                 230                 235                 240

Asn Lys Ile His Gly Lys Lys Val Cys Ile Asp Arg Val Gln Glu Ser
                245                 250                 255

Ser Ile Ser Arg Val Gly Asp Val Gly Asn Thr Ala Ser Asn Ala Ile
            260                 265                 270

Val Gln Gln Thr His Glu Asn Pro Ala Met Gln Asn Leu Ser Pro Asn
        275                 280                 285

Val Ala Met Ala Leu Arg Ser Lys Asn Phe Ile Pro Asp Ser Ser Ile
    290                 295                 300

Pro Asn Phe Pro Met Met Thr His Gln Ser Arg Tyr Ala Met Ala Val
305                 310                 315                 320

Gly Thr Gln Arg Ser Leu Gln Glu Gln Gly Pro Ala Pro Ser Ile Asn
                325                 330                 335

Ser Ser Val Ala Ser Pro Ala Thr Gln Tyr Ala Asp Asn Ala Asn Ser
            340                 345                 350

Gly Ala Ser Leu Leu Gly Lys Arg Asp Asn Gln Asp Gly Gln Ala Ser
        355                 360                 365

Pro Leu Ser Asn Ile Ala Lys Arg Met Arg Pro Gly Ser Thr Val Val
    370                 375                 380

Asp Ala Met Gln His Gln Gln Ile Gly Ser His Val Glu Ala Leu Gln
385                 390                 395                 400

Gly Ser Asp Met Asn Trp Gln Asn Ser Leu Gln Gln Gln Pro Met Ala
                405                 410                 415

Arg Gly Ile Gln Tyr Ala Ser Gly Gly Ile Gln Lys Phe Pro Gln Gln
            420                 425                 430

Val Phe Glu Gly Gly Ala Asn Gln Glu Thr Gly Ala Ile Pro Phe Ala
        435                 440                 445

Ser Ser Gln Gln Gly Met Arg Leu Val Ala Lys Glu Glu Gln Phe Glu
    450                 455                 460

Met Glu Lys Leu Asp Gly Ala Glu Ile Asn Cys Asn Lys Ser Asp Met
465                 470                 475                 480

Glu Met Glu Met Asn Asn Leu Asp Pro Gln Gln Leu Arg Leu Gln Gln
                485                 490                 495

Arg Leu Pro Gln His Ala Phe Met Arg Pro Asn Phe Pro Gln Ala Ala
            500                 505                 510

Trp Asn Ser Leu Gly Gln His Met Gly Lys Glu Thr Lys Lys Glu Asp
        515                 520                 525

Gln Leu Gln Lys Arg Lys Ser Val Gln Ser Pro Arg Leu Ser Ser Ala
    530                 535                 540

Ala Leu Pro His Ser Pro Leu Ser Ser Lys Ser Gly Glu Phe Ser Asn
545                 550                 555                 560

Gly Ala Val Gly Pro Ser Phe Gly Pro Ser Ala Met Ala Ala Ala Pro
                565                 570                 575

Gly Thr Ser Gln Lys Asp Lys Ala Ala Met Ala Ser Val Pro Ala Thr
            580                 585                 590

Val Gly Thr Pro Ser Asn Asp Ser Thr Gln Arg Gln His Ala Gln Leu
        595                 600                 605

Ala Ala Lys Arg Arg Ser Asn Ser Leu Pro Lys Thr Pro Ala Met Asn
```

```
    610                 615                 620

Gly Val Gly Ser Pro Val Ser Val Gly Thr Thr Ser Val Pro Leu Asn
625                 630                 635                 640

Ala Asn Ser Pro Ser Val Val Thr Ser Gly Phe Val Asp Gln Asn Leu
                645                 650                 655

Gln Asn Met Leu Glu Arg Phe Ser Lys Ile Glu Met Val Thr Met Arg
            660                 665                 670

His Gln Leu Asn Phe Lys Lys Asn Lys Val Asp Asp Tyr Pro Ile Lys
        675                 680                 685

Lys Gln Asn Pro Tyr Val Pro Asn Asn Leu Ser Ala Leu Leu Ala Asn
    690                 695                 700

Ala Asn Ala Thr Asn Asn Glu Gly Leu Pro Glu Glu Ser Ile Ser Ile
705                 710                 715                 720

Ser Lys Ser Leu Ile Gly Gly Ser Met Asn Ala Cys Lys Met Arg Ile
                725                 730                 735

Leu Asn Phe Cys Val Pro Glu Arg Val Val Gln Gly Ser Ile Val Thr
            740                 745                 750

Ile Ile Pro Arg Met Arg Thr Arg Met Ile Met Phe Glu Lys Ser Asp
        755                 760                 765

Gly Thr Val Ala Met His Cys Gly Val Ile Glu Glu Val Asp Tyr Val
    770                 775                 780

Ala Ala Glu Asp His Leu Leu Thr Leu Pro Asn Thr His Ser Ala Asp
785                 790                 795                 800

Leu Leu Ala Gln Gln Phe Cys Ser Leu Met Val Arg Glu Gly Tyr Val
                805                 810                 815

Lys Glu Asp Asp Arg Ile Gln Leu Lys Pro Asn Arg Val Asn Leu Pro
            820                 825                 830

Leu Gly Asn Gln Ser Thr Thr Pro Asn Asn Ala Val Val Glu Met Gln
        835                 840                 845

Gln Tyr Gly Glu Val Ile Pro Gly Gln Ser Ser Asn Glu Val Ala Lys
    850                 855                 860

Pro Ala Ser Gly Ser Asn Ala Pro Ile Asn Leu Ser Gln Asn Leu Leu
865                 870                 875                 880

Thr Asn Pro Arg Met Leu Pro Pro Gly Ser Pro Gln Ala Leu Gln Met
                885                 890                 895

Ser Gln Gly Leu Leu Ser Gly Val Ser Met Ala Ser Arg Pro Gln Gln
            900                 905                 910

Met Asp Ser Gln Gln Ala Val Gln Gln Gln Gln Gln Gln Gln Gln Gln
        915                 920                 925

Gln Gln Gln Gln Gln Gln Gln Gln Gln Gln Gln Leu Gln Gln Asn Gln
    930                 935                 940

His Thr Leu Ile Gln Gln Gln Asn Pro Gln Phe Gln Arg Ser Pro Met
945                 950                 955                 960

Met Leu Gly Thr Asn Gln Leu Ser His Leu Asn Pro Val Gly Gln Asn
                965                 970                 975

Ser Asn Met Pro Leu Gly Asn His Met Leu Asn Lys Pro Ser Ala Leu
            980                 985                 990

Gln Met Gln Met Phe Gln Gln Gln  Gln Gln Gln Pro Gln  Met Gln Arg
        995                 1000                1005

Lys Met  Met Met Gly Leu Gly  Gln Ala Val Gly Met  Gly Asn Leu
    1010                1015                1020

Arg Asn  Asn Leu Val Gly Leu  Ala Pro Met Gly Asn  Pro Met Gly
    1025                1030                1035
```

-continued

```
Met Gly  Gly Ala Arg Gly Ile  Gly Gly Ser Gly Ile  Ser Ala Pro
    1040                 1045                 1050

Met Thr  Ser Ile Ala Gly Met  Gly Asn Met Gly Gln  Ser Pro Met
    1055                 1060                 1065

Asn Leu  Ser Gln Thr Ser Asn  Ile Thr Asn Ser Ile  Ser Gln Gln
    1070                 1075                 1080

Phe Arg  Ser Gly Ser Leu Asn  Ala Ala Ala Ser Ala  Asp Leu Ile
    1085                 1090                 1095

Ser Arg  Leu Arg Leu Val His  Ser Asn Arg Gln Ser  Met Leu Gly
    1100                 1105                 1110

Ser Pro  Gln Ser Asn Leu Ala  Ser Ile Ser Gly Ala  Arg Gln Ile
    1115                 1120                 1125

His Pro  Gly Ala Thr Pro Ser  Leu Ser Met Leu Gly  Arg Ala Asn
    1130                 1135                 1140

Thr Met  Gln Arg Pro Ile Gly  Pro Met Gly Pro Pro  Lys Met Met
    1145                 1150                 1155

Ala Gly  Met Asn Leu Tyr Met  Ser Gln Gln Gln Gln  His Gln Gln
    1160                 1165                 1170

Pro Gln  Gln Gln Gln Gln Gln  His Gln Gln Gln Leu  Gln Leu Gln
    1175                 1180                 1185

Gln His  Met Gln Gln Gln Leu  Gln Gln Gln Gln Gln  Gln Gln Glu
    1190                 1195                 1200

Thr Thr  Ser Gln Leu Gln Ser  Val Val Ser Pro Pro  Gln Val Gly
    1205                 1210                 1215

Ser Pro  Ser Met Gly Val Pro  Pro Leu Asn Gln Gln  Thr Gln Gln
    1220                 1225                 1230

Gln Ala  Ser Pro Gln Gln Met  Ser Gln Arg Thr Pro  Met Ser Pro
    1235                 1240                 1245

Gln Met  Ser Ser Gly Ala Ile  His Ala Met Ser Ala  Gly Asn Pro
    1250                 1255                 1260

Glu Ala  Cys Pro Ala Ser Pro  Gln Leu Ser Ser Gln  Thr Leu Gly
    1265                 1270                 1275

Ser Val  Ser Ser Ile Thr Asn  Ser Pro Met Asp Met  Gln Gly Val
    1280                 1285                 1290

Asn Lys  Ser Asn Ser Asn Ala  Gln
    1295                 1300
```

```
<210> SEQ ID NO 19
<211> LENGTH: 3933
<212> TYPE: DNA
<213> ORGANISM: Glycine max

<400> SEQUENCE: 19

atgggggtct ccttcaaggt gtccaaaacc ggcactaggt ttcgccctaa gtgcattccc      60

caacttcaag atggcgcatc cgacaattcc aaaccccaga gtgatcttgt tgaggctggt     120

gaaaacattg ctcagattcc caggtcatct gtgtcatctg aaactctttc attagcagat     180

agggaggctt ctttcacatt gaacctgttt ccagatggtt attctattgg aaaaccctcc     240

gagaatgaag cagctaatca gtcaaaatac caagattttc ccaagttgtt acatccatat     300

gataggtcat ctgagagtct tttcttggcc attgagtcag gtcacttgcc tggggatatt     360

cttgatgata tacctgccaa gtatgttgat ggagcactta tatgtgaggt gcatgattat     420

cgaagatgct cttctgaaaa agggggtagt gtgtctgcag aaagttctcc tactgttagc     480
```

-continued

```
aaagtatgcc tcaagatgtc gttggaaaat attgtaaagg acatcccatc gattactgac    540
aagtcttgga catatggtga tctaatggaa gttgaatcga agatactgaa agcattacaa    600
ccaaaacttc atctagaccc tactccaaag ttagatcggc tgtgtgaaag tccgcttcca    660
acgaagctca atttgccaag aaagcgatta aaaaatatgc cagagtttgc tgttacttct    720
actaataaaa ttcatgggaa gaaagtatgc atagatagag tgcaggaaag ctcaattaac    780
agattaggtg atgtaggaaa cactgcatca aatgctattg tgcagcagac ccatgaaaat    840
ccagccatgc agaatcttag tccgaatgtt gccatggcct tgagatctaa gaattttata    900
cctgattctt ccatccctaa ctttcctatg atgtcccatc aatcaagata ttcaatggct    960
gttggaactc agagaagttt gcaggagcag ggaccaactc cttccattaa ttcgttaggg   1020
gcttctcctg ctacacaaga tgtcatgatt tcatatgctg aaaatgcaaa ctcgggtgcc   1080
tctcttcttg gaaaaaggga taatcaagat ggacaagcat cacctttgtc caatattgct   1140
aaaagaatga ggcctgcttc cactgtgctt gatgcaatgc agcatcagca aatagggtca   1200
catgttgaag ctcttcaagg atcagatatg aattggcaga atacattgca acaacaagca   1260
atggccagaa ttcagtatgc aagtggtggc attcaaaagt ttcctcagca ggcttttgaa   1320
ggggggcaa atcaagagac aggggctatt ccctttgctt ctagtcagca gcagggcatg   1380
aggttggttg ccaaggaaga acagtttgaa atggaaaaat tagatggtgc agagataaac   1440
cgcaataaaa gtgagatgga aatggaaatg aacaatttag atccacaaca attacggatt   1500
cagcaacgat tgtcacagca tgcattcatg aggtctaatt tcccccaggc agcctggaac   1560
agtttgggtc agcctatgga gaaagaaaca aaaaaagagg accagcttca gaaaaggaaa   1620
tcagtacaga gtcctcgctt atccaccggg gcattacctc actccccatt gtcttcgaaa   1680
tcaggtgaat tttccaatgg tgcagtagga ccaagttttg gacagtctgc aatggctgct   1740
gtgcctggga catcacaaaa agacaagaca gcaatggtct cagttcctgc tactgttgga   1800
actccatcta atgactctac acaaagacaa catgcacaac tagccgcaaa gcggagatct   1860
aattctcttc ccaagacccc agcaatgaat ggagttggtt ctcccgctag tgttggtaca   1920
accagtgtcc cactgaatgc aaatagtccc tcagttgtga cctcgggttt agttgaccaa   1980
aatcttcaaa atatgcttga aaggttctca aaaattgaaa tggtgacaat gaggcatcaa   2040
cttaacttta agaagaataa ggttgatgac tatcccatta agaagcagaa tccatatgca   2100
caaaataatc tagctgcact tcttgccaat gcaactaata atgagggatt gccagaggag   2160
tcaatttctt tgtcaaagtc gcttattggt gggagtatga atgcatgtaa aatgagaatc   2220
ttaactttct gtgtgcctga gcgtgtagtt caaggaagtg ttgttactat aattccgagg   2280
atgcgaacta ggatgataat atttgagaaa tctgatggta ctgtcgctat gcattgtggg   2340
gagattgaag aagttgatta cgtagctgca gaggatcatc ttctcacatt acccaatact   2400
cattctgcag atttgcttgt acaacagttc tgttcactga tggtacgcga aggatttgtg   2460
aaagaagatg accgaatcca acttaaacca aaccgggtga accttccatt gggcaatcaa   2520
tctactaccc ctaataatgc tgtagttgaa atgcaacaat atggagaagc cattcctggt   2580
caatcatcca atgaagttgc aaaaccaact agtggcagta atgcacctgt aaacctctct   2640
cagaatcttg taacaaatcc aaggatgctg ccacctggaa acccccaagc cttacagatg   2700
tcccaaggac ttctctctgg tgtttcgatg gcttcaagac cacaacaaat ggactcacaa   2760
caagccatac agcagcagca gcagcagcag cagcaacaac aacaacagca gcagctgcaa   2820
caaaatcaac acacactcat tcaacagcag aatccccagt tccagaggtc tcctatgatg   2880
```

```
cttgggacaa atcagctttc acacttaaat ccagttggac aaaactccaa catgccatta   2940

ggtaatcaca tgctgaacag gccttcagct ctccagcttc agatgttcca acaacaacaa   3000

cagcaacagc aacagcagca gcagcagcct caaatgcaaa ggaaaatgat gatgggactc   3060

ggacaagctg tgggaatggg taacttgaga aataacctag ttgggcttgc acccatgggt   3120

aaccctatgg ggatgggagg tgtcagggga ataggaggaa gtggaatctc agcaccaatg   3180

acatctattg ctggcatggg aaatatgggt cagaacccaa tgaatcttag ccagacttca   3240

aatattacta attccataag ccaacagttc aggtccggat cgataaatgc agcagcatct   3300

gctgaccttt tatcaaagct tagattggta catcagaatc gtcaaggcat gctagggtcc   3360

tctcaatcta acatagctag catctcaggg gctagacaaa tacaccctgg tggtactcca   3420

agtctttcaa tgttgggcag ggctaataca atgcagcgac caattggacc tatgggtcca   3480

ccgaagatta tggctgggat gaatctttat atgagtcagc agcagcagca gcaacatcaa   3540

caaccccaac cccaacaaca gcagcagcaa caccaacagc aattgcaact tcagcagcat   3600

atgcagcagc aattacagca gcaacaacaa caagaaacaa cttcacaatt gcaggcagtt   3660

gtttctcccc cacaggtggg atcgccatca atgggcattc caccaatgaa ccaacaagcg   3720

cagcagcaag ccagccctca gcaaatgagt caacgaaccc ctatgagtcc acagatgagc   3780

tcaggtgcga ttcatgccat gaatgctggt aatcctgaag cttgtccagc cagtccacag   3840

ttgagctctc agacccttgg ctctgttagt agcataacaa actcccctat ggacatgcaa   3900

ggtgtcaaca agagcaactc taatgcacaa tga                                3933
```

```
<210> SEQ ID NO 20
<211> LENGTH: 1310
<212> TYPE: PRT
<213> ORGANISM: Glycine max

<400> SEQUENCE: 20

Met Gly Val Ser Phe Lys Val Ser Lys Thr Gly Thr Arg Phe Arg Pro
1               5                   10                  15

Lys Cys Ile Pro Gln Leu Gln Asp Gly Ala Ser Asp Asn Ser Lys Pro
            20                  25                  30

Gln Ser Asp Leu Val Glu Ala Gly Glu Asn Ile Ala Gln Ile Pro Arg
        35                  40                  45

Ser Ser Val Ser Ser Glu Thr Leu Ser Leu Ala Asp Arg Glu Ala Ser
    50                  55                  60

Phe Thr Leu Asn Leu Phe Pro Asp Gly Tyr Ser Ile Gly Lys Pro Ser
65                  70                  75                  80

Glu Asn Glu Ala Ala Asn Gln Ser Lys Tyr Gln Asp Phe Pro Lys Leu
                85                  90                  95

Leu His Pro Tyr Asp Arg Ser Ser Glu Ser Leu Phe Leu Ala Ile Glu
            100                 105                 110

Ser Gly His Leu Pro Gly Asp Ile Leu Asp Asp Ile Pro Ala Lys Tyr
        115                 120                 125

Val Asp Gly Ala Leu Ile Cys Glu Val His Asp Tyr Arg Arg Cys Ser
    130                 135                 140

Ser Glu Lys Gly Gly Ser Val Ser Ala Glu Ser Ser Pro Thr Val Ser
145                 150                 155                 160

Lys Val Cys Leu Lys Met Ser Leu Glu Asn Ile Val Lys Asp Ile Pro
                165                 170                 175

Ser Ile Thr Asp Lys Ser Trp Thr Tyr Gly Asp Leu Met Glu Val Glu
```

-continued

```
            180                 185                 190

Ser Lys Ile Leu Lys Ala Leu Gln Pro Lys Leu His Leu Asp Pro Thr
        195                 200                 205

Pro Lys Leu Asp Arg Leu Cys Glu Ser Pro Leu Pro Thr Lys Leu Asn
    210                 215                 220

Leu Pro Arg Lys Arg Leu Lys Asn Met Pro Glu Phe Ala Val Thr Ser
225                 230                 235                 240

Thr Asn Lys Ile His Gly Lys Lys Val Cys Ile Asp Arg Val Gln Glu
                245                 250                 255

Ser Ser Ile Asn Arg Leu Gly Asp Val Gly Asn Thr Ala Ser Asn Ala
            260                 265                 270

Ile Val Gln Gln Thr His Glu Asn Pro Ala Met Gln Asn Leu Ser Pro
        275                 280                 285

Asn Val Ala Met Ala Leu Arg Ser Lys Asn Phe Ile Pro Asp Ser Ser
    290                 295                 300

Ile Pro Asn Phe Pro Met Met Ser His Gln Ser Arg Tyr Ser Met Ala
305                 310                 315                 320

Val Gly Thr Gln Arg Ser Leu Gln Glu Gln Gly Pro Thr Pro Ser Ile
                325                 330                 335

Asn Ser Leu Gly Ala Ser Pro Ala Thr Gln Asp Val Met Ile Ser Tyr
            340                 345                 350

Ala Glu Asn Ala Asn Ser Gly Ala Ser Leu Leu Gly Lys Arg Asp Asn
        355                 360                 365

Gln Asp Gly Gln Ala Ser Pro Leu Ser Asn Ile Ala Lys Arg Met Arg
    370                 375                 380

Pro Ala Ser Thr Val Leu Asp Ala Met Gln His Gln Gln Ile Gly Ser
385                 390                 395                 400

His Val Glu Ala Leu Gln Gly Ser Asp Met Asn Trp Gln Asn Thr Leu
                405                 410                 415

Gln Gln Gln Ala Met Ala Arg Ile Gln Tyr Ala Ser Gly Gly Ile Gln
            420                 425                 430

Lys Phe Pro Gln Gln Ala Phe Glu Gly Gly Ala Asn Gln Glu Thr Gly
        435                 440                 445

Ala Ile Pro Phe Ala Ser Ser Gln Gln Gln Gly Met Arg Leu Val Ala
    450                 455                 460

Lys Glu Glu Gln Phe Glu Met Glu Lys Leu Asp Gly Ala Glu Ile Asn
465                 470                 475                 480

Arg Asn Lys Ser Glu Met Glu Met Glu Met Asn Asn Leu Asp Pro Gln
                485                 490                 495

Gln Leu Arg Ile Gln Gln Arg Leu Ser Gln His Ala Phe Met Arg Ser
            500                 505                 510

Asn Phe Pro Gln Ala Ala Trp Asn Ser Leu Gly Gln Pro Met Glu Lys
        515                 520                 525

Glu Thr Lys Lys Glu Asp Gln Leu Gln Lys Arg Lys Ser Val Gln Ser
    530                 535                 540

Pro Arg Leu Ser Thr Gly Ala Leu Pro His Ser Pro Leu Ser Ser Lys
545                 550                 555                 560

Ser Gly Glu Phe Ser Asn Gly Ala Val Gly Pro Ser Phe Gly Gln Ser
                565                 570                 575

Ala Met Ala Ala Val Pro Gly Thr Ser Gln Lys Asp Lys Thr Ala Met
            580                 585                 590

Val Ser Val Pro Ala Thr Val Gly Thr Pro Ser Asn Asp Ser Thr Gln
        595                 600                 605
```

-continued

```
Arg Gln His Ala Gln Leu Ala Ala Lys Arg Arg Ser Asn Ser Leu Pro
    610                 615                 620

Lys Thr Pro Ala Met Asn Gly Val Gly Ser Pro Ala Ser Val Gly Thr
625                 630                 635                 640

Thr Ser Val Pro Leu Asn Ala Asn Ser Pro Ser Val Val Thr Ser Gly
                645                 650                 655

Leu Val Asp Gln Asn Leu Gln Asn Met Leu Glu Arg Phe Ser Lys Ile
            660                 665                 670

Glu Met Val Thr Met Arg His Gln Leu Asn Phe Lys Lys Asn Lys Val
        675                 680                 685

Asp Asp Tyr Pro Ile Lys Lys Gln Asn Pro Tyr Ala Gln Asn Asn Leu
    690                 695                 700

Ala Ala Leu Leu Ala Asn Ala Thr Asn Asn Glu Gly Leu Pro Glu Glu
705                 710                 715                 720

Ser Ile Ser Leu Ser Lys Ser Leu Ile Gly Gly Ser Met Asn Ala Cys
                725                 730                 735

Lys Met Arg Ile Leu Thr Phe Cys Val Pro Glu Arg Val Val Gln Gly
            740                 745                 750

Ser Val Val Thr Ile Ile Pro Arg Met Arg Thr Arg Met Ile Ile Phe
        755                 760                 765

Glu Lys Ser Asp Gly Thr Val Ala Met His Cys Gly Glu Ile Glu Glu
    770                 775                 780

Val Asp Tyr Val Ala Ala Glu Asp His Leu Leu Thr Leu Pro Asn Thr
785                 790                 795                 800

His Ser Ala Asp Leu Leu Val Gln Gln Phe Cys Ser Leu Met Val Arg
                805                 810                 815

Glu Gly Phe Val Lys Glu Asp Asp Arg Ile Gln Leu Lys Pro Asn Arg
            820                 825                 830

Val Asn Leu Pro Leu Gly Asn Gln Ser Thr Thr Pro Asn Asn Ala Val
        835                 840                 845

Val Glu Met Gln Gln Tyr Gly Glu Ala Ile Pro Gly Gln Ser Ser Asn
    850                 855                 860

Glu Val Ala Lys Pro Thr Ser Gly Ser Asn Ala Pro Val Asn Leu Ser
865                 870                 875                 880

Gln Asn Leu Val Thr Asn Pro Arg Met Leu Pro Pro Gly Asn Pro Gln
                885                 890                 895

Ala Leu Gln Met Ser Gln Gly Leu Leu Ser Gly Val Ser Met Ala Ser
            900                 905                 910

Arg Pro Gln Gln Met Asp Ser Gln Gln Ala Ile Gln Gln Gln Gln Gln
        915                 920                 925

Gln Gln Gln Gln Gln Gln Gln Gln Gln Gln Leu Gln Gln Asn Gln His
    930                 935                 940

Thr Leu Ile Gln Gln Gln Asn Pro Gln Phe Gln Arg Ser Pro Met Met
945                 950                 955                 960

Leu Gly Thr Asn Gln Leu Ser His Leu Asn Pro Val Gly Gln Asn Ser
                965                 970                 975

Asn Met Pro Leu Gly Asn His Met Leu Asn Arg Pro Ser Ala Leu Gln
            980                 985                 990

Leu Gln Met Phe Gln Gln Gln Gln  Gln Gln Gln Gln Gln  Gln Gln Gln
        995                 1000                1005

Gln Pro  Gln Met Gln Arg Lys  Met Met Met Gly Leu  Gly Gln Ala
    1010                 1015                 1020
```

```
Val Gly  Met Gly Asn Leu Arg  Asn Asn Leu Val Gly  Leu Ala Pro
    1025                 1030                 1035

Met Gly  Asn Pro Met Gly Met  Gly Gly Val Arg Gly  Ile Gly Gly
    1040                 1045                 1050

Ser Gly  Ile Ser Ala Pro Met  Thr Ser Ile Ala Gly  Met Gly Asn
    1055                 1060                 1065

Met Gly  Gln Asn Pro Met Asn  Leu Ser Gln Thr Ser  Asn Ile Thr
    1070                 1075                 1080

Asn Ser  Ile Ser Gln Gln Phe  Arg Ser Gly Ser Ile  Asn Ala Ala
    1085                 1090                 1095

Ala Ser  Ala Asp Leu Leu Ser  Lys Leu Arg Leu Val  His Gln Asn
    1100                 1105                 1110

Arg Gln  Gly Met Leu Gly Ser  Ser Gln Ser Asn Ile  Ala Ser Ile
    1115                 1120                 1125

Ser Gly  Ala Arg Gln Ile His  Pro Gly Gly Thr Pro  Ser Leu Ser
    1130                 1135                 1140

Met Leu  Gly Arg Ala Asn Thr  Met Gln Arg Pro Ile  Gly Pro Met
    1145                 1150                 1155

Gly Pro  Pro Lys Ile Met Ala  Gly Met Asn Leu Tyr  Met Ser Gln
    1160                 1165                 1170

Gln Gln  Gln Gln Gln His Gln  Gln Pro Gln Pro Gln  Gln Gln Gln
    1175                 1180                 1185

Gln Gln  His Gln Gln Gln Leu  Gln Leu Gln Gln His  Met Gln Gln
    1190                 1195                 1200

Gln Leu  Gln Gln Gln Gln Gln  Gln Glu Thr Thr Ser  Gln Leu Gln
    1205                 1210                 1215

Ala Val  Val Ser Pro Pro Gln  Val Gly Ser Pro Ser  Met Gly Ile
    1220                 1225                 1230

Pro Pro  Met Asn Gln Gln Ala  Gln Gln Gln Ala Ser  Pro Gln Gln
    1235                 1240                 1245

Met Ser  Gln Arg Thr Pro Met  Ser Pro Gln Met Ser  Ser Gly Ala
    1250                 1255                 1260

Ile His  Ala Met Asn Ala Gly  Asn Pro Glu Ala Cys  Pro Ala Ser
    1265                 1270                 1275

Pro Gln  Leu Ser Ser Gln Thr  Leu Gly Ser Val Ser  Ser Ile Thr
    1280                 1285                 1290

Asn Ser  Pro Met Asp Met Gln  Gly Val Asn Lys Ser  Asn Ser Asn
    1295                 1300                 1305

Ala Gln
    1310
```

<210> SEQ ID NO 21
<211> LENGTH: 4125
<212> TYPE: DNA
<213> ORGANISM: Ricinus communis

<400> SEQUENCE: 21

```
atgggggttt cttttaaggt atcaaaaact ggtactaggt ttcgtccaaa gcctattact     60

ttaccagagc ctgcgcttga tgaggcctca gagaacacta aggaaagctc tttaattggc    120

tcaaagaatg aatcctcaaa gagaaagctc gaggttgaca ttggtgagga tctctctggt    180

gcttcaagtt catccatcac tgagcacgaa gtttccttca cattgaacct ctactcagat    240

ggatattcta ttgggaagcc ttctgagaat gaggctgcaa atcaggctct actccaagat    300

gtttcaaagt tgttgcatcc atatgataag acatctgaaa ctctcttttt ggcaattgag    360
```

-continued

```
tctggccggt tgcctggaga tattctggat gatataccat gcaagtatgt caacggcaca    420
ctcatgtgtg aggtgcggga ttatcgaaaa tgtgttcctg agcaaggttc tagtattcca    480
tctatgaatg gactccctat tgtaaataga gtacgtctca ggatgtcttt ggagaatgta    540
gtgaaggata ttccattact ctcagataat tcttggactt atggtgattt gatggaagtg    600
gaatcccgga tattgaaagc cttgcagcca caactttgtc tagatcctac tccgaaattg    660
gataggctct gtaatgaccc agctcctaca aagctgagtt taggtatgag cagtttgcgg    720
agaaaaagat taaggcagat gcctgaagtt actgtcacat ctaatagcag aatccatggc    780
aagaaagttt gcatagatcg agtgccagaa agctcaaatg gcaggttagg agattcagca    840
atcatttccg ggaatatgtt gccacaaagt ggtcaggaga atctgactac tcaaaacctt    900
ggtccaagca acctgttagc tctaggagca agaagcttta tatcagatgg caatgttcca    960
gcaatgcctt tggtagcaca gcaatcaagg tatcaaatgg gggtgagtac cccaagaagt   1020
atgcaggatc aagggtcagg gtctcttgtt aatatttcag gagcttcccc tgccacgcag   1080
gatatgatga ttgcatatgg tgacactatg aatcctgggg cttcacttca tagtaaaaag   1140
gagaatcaag atgggcaaat gtctccctta tccagtttga ataagagagc taggcttacc   1200
tcagtggctc ctgatgggat tcatcagcag cagatagggc caaacatgga tagtgttaat   1260
gcatcagatt tgaactggaa aaattcttta ctacatcaac aggcaatggc aagaggaatt   1320
cactatgcta atgcaggtat tcagaagtat ccccagcaga tgtttgaagg ggttatgaat   1380
caaaatgctg tgccagcatc attttctgct gcacagccag gtttaagatt tggtccgaag   1440
gaagaacagt ttgaaacaga aaagctggat ggctcagaga tcagtcaggg taaaaatgat   1500
atccagatct tggagacaga aacaggccat cttgaccctc aagtgtcacg gctacaacaa   1560
agattaccac cacatcacat gagatctaat ttccctcagg cagcatggaa caatcttagc   1620
caagattcaa ggaaggatga tcaattccag aagaggaaaa ctgtgcaaag tcctcggtta   1680
tcagctgggg ctttgcctca atcaccattg tcatctaaat ctggagaatt ttctagtggc   1740
tctgctgggg cccactttgg agctgttgca gcaactactg ctcttggatc atctcaaaag   1800
gagaagtctg ctgtcacttc ggttcctgct gttggcggca ccccatcctt gacttccagt   1860
gctaatgact ccttgcaacg gcaacaccag gcccaagttg ctgcaaaacg gagatccaac   1920
tcccttccaa aaactccagt aatgagtggg gttggctccc ctgcaagtgt tagtaatatg   1980
agtgttccat taaatgcaaa tagtccttct gttggaaccc cgactatggt tgatcaaacc   2040
atgcttgaaa ggttctcaaa gattgagatg gtgactgtga ggcatcaact caactgcaag   2100
aaaaataaag ctgatgacta ccctgtgagg aaatccaaca catattcacc tcaaaatctt   2160
atggtttgtc tctcaaattt acccaacact gaggattcaa aagatgatgc tagtgcaggg   2220
caattatcga agtcaattgt aggtggcagc atgaatgtct gcaagatgag aattataaac   2280
tttatgctgg cagatcgagt tgttcaaggg aatgttgttt cttttgttcc tcggagacgg   2340
actagaatga tcatgtcaga gaagccaaat gatggtacag tagcaatgca atatggagaa   2400
gcagaggatg gtgattttct atctgtagag gagtatcttc ctacattgcc caatactcat   2460
tttgcggatt tgcttgcggc acaattttgt tcactgatga ttcgtgaagg atatcttgtg   2520
gaagataata ttcaaccaaa gcctacccgc atgaatgttt cctcaagtag ccaaccaaat   2580
gctgccggaa tcgcacctaa taattcagca gctgaggtgc agcagcaata caatgaggca   2640
gtctcaggtc aggcatccaa tgaagtaaag ccaaatttta gtggtaatgc acccatgaat   2700
```

-continued

```
ccatcccaga atctattagc aagtgccagg atgctgcctc ctggaaaccc tcaagcctta   2760
ccgatgtctc aaggtctctt gtctgcagtt tcaatgccag ctagaccaca actagaccca   2820
caaccacaac tgcagcagca gcctcaacaa ccaccacaaa tgcagcagca gcaaccacca   2880
caacagcaac aaaatcaaca ttccttaatt caacagcaat cacagttcca gaggccacca   2940
atggtgcttc catctctctc tcacttgaat acacttgggc agaattcaaa catgcagctg   3000
gggagtcaca tggtcaacaa gccttcgcat ctccagcttc agctgttaca gcagcaacag   3060
cagcagcagc agcttcaacc acagcagcaa caacagcagc agcagcaaca gcagcagcag   3120
cagcaacagc agcagccaca gatgcaacaa aggaaaatga tgatgggact tgggacagca   3180
atgggcatgg gaaatatggg caacaatatg gttggcctag gaggcctgag taatgccatg   3240
ggcattggag gtgcaagggc aatgggaggg cctggaatct cgggatcaat ggcacctata   3300
tccggcatga acaatgtggg tcagaaccaa atcaatttga gccaaactac aaatcttcca   3360
aacgttataa gtcagcattt ccgcgcagga caagtaactc cacaacaggc tgcttaccta   3420
tcaaaactta ggatggcgca aaacagaaca agtatgctag ggccccctca gtcaggcata   3480
gctgggatgt caggagccag acagatgcac ccaggttctg caggtctttc aatgctgggc   3540
cagtctctga accgtgctaa catgaaccca atgcaacgga gtgcaatggg gcctatgggt   3600
ccaccgaaat tgatggcagg gatgaatctc tatatgaacc aacagcaaca gcagcagcag   3660
caactgcaat tacaacagca gcaacaattc cagcagcaac agcaacagca acagcagcag   3720
cagcagcagc aacagcaatt acagcagcta cagcagcagc aacagcaatt acagcagcag   3780
cagcaacaac agatgcagca acagcagcag caagatccat cctcatccct acaggctgtt   3840
gtttcgtctt cacaagtagg ctcaccatca accatgggaa ttccgcaact gaaccaacag   3900
caacaacccc aacaacagcc tagtccacaa caaatgagcc aacggacgcc aatgagccca   3960
caaattagtt caggagcaat ccatgcaatg agtgctggta atccagaggc ttgtcctgcc   4020
agtccacagt tgagctcaca gactcttggc tcagtaggaa gcatcacaaa ctctccgatg   4080
gagctccaag gtgtaaacaa aagcaactct gttaataatg catag                    4125
```

<210> SEQ ID NO 22
<211> LENGTH: 1374
<212> TYPE: PRT
<213> ORGANISM: Ricinus communis

<400> SEQUENCE: 22

```
Met Gly Val Ser Phe Lys Val Ser Lys Thr Gly Thr Arg Phe Arg Pro
1               5                   10                  15

Lys Pro Ile Thr Leu Pro Glu Pro Ala Leu Asp Glu Ala Ser Glu Asn
            20                  25                  30

Thr Lys Glu Ser Ser Leu Ile Gly Ser Lys Asn Glu Ser Ser Lys Arg
        35                  40                  45

Lys Leu Glu Val Asp Ile Gly Glu Asp Leu Ser Gly Ala Ser Ser Ser
    50                  55                  60

Ser Ile Thr Glu His Glu Val Ser Phe Thr Leu Asn Leu Tyr Ser Asp
65                  70                  75                  80

Gly Tyr Ser Ile Gly Lys Pro Ser Glu Asn Glu Ala Ala Asn Gln Ala
                85                  90                  95

Leu Leu Gln Asp Val Ser Lys Leu Leu His Pro Tyr Asp Lys Thr Ser
            100                 105                 110

Glu Thr Leu Phe Leu Ala Ile Glu Ser Gly Arg Leu Pro Gly Asp Ile
        115                 120                 125
```

-continued

```
Leu Asp Asp Ile Pro Cys Lys Tyr Val Asn Gly Thr Leu Met Cys Glu
    130                 135                 140

Val Arg Asp Tyr Arg Lys Cys Val Pro Glu Gln Gly Ser Ser Ile Pro
145                 150                 155                 160

Ser Met Asn Gly Leu Pro Ile Val Asn Arg Val Arg Leu Arg Met Ser
                165                 170                 175

Leu Glu Asn Val Val Lys Asp Ile Pro Leu Leu Ser Asp Asn Ser Trp
            180                 185                 190

Thr Tyr Gly Asp Leu Met Glu Val Glu Ser Arg Ile Leu Lys Ala Leu
        195                 200                 205

Gln Pro Gln Leu Cys Leu Asp Pro Thr Pro Lys Leu Asp Arg Leu Cys
    210                 215                 220

Asn Asp Pro Ala Pro Thr Lys Leu Ser Leu Gly Met Ser Ser Leu Arg
225                 230                 235                 240

Arg Lys Arg Leu Arg Gln Met Pro Glu Val Thr Val Thr Ser Asn Ser
                245                 250                 255

Arg Ile His Gly Lys Lys Val Cys Ile Asp Arg Val Pro Glu Ser Ser
            260                 265                 270

Asn Gly Arg Leu Gly Asp Ser Ala Ile Ile Ser Gly Asn Met Leu Pro
        275                 280                 285

Gln Ser Gly Gln Glu Asn Leu Thr Thr Gln Asn Leu Gly Pro Ser Asn
    290                 295                 300

Leu Leu Ala Leu Gly Ala Arg Ser Phe Ile Ser Asp Gly Asn Val Pro
305                 310                 315                 320

Ala Met Pro Leu Val Ala Gln Gln Ser Arg Tyr Gln Met Gly Val Ser
                325                 330                 335

Thr Pro Arg Ser Met Gln Asp Gln Gly Ser Gly Ser Leu Val Asn Ile
            340                 345                 350

Ser Gly Ala Ser Pro Ala Thr Gln Asp Met Met Ile Ala Tyr Gly Asp
        355                 360                 365

Thr Met Asn Pro Gly Ala Ser Leu His Ser Lys Lys Glu Asn Gln Asp
    370                 375                 380

Gly Gln Met Ser Pro Leu Ser Ser Leu Asn Lys Arg Ala Arg Leu Thr
385                 390                 395                 400

Ser Val Ala Pro Asp Gly Ile His Gln Gln Gln Ile Gly Pro Asn Met
                405                 410                 415

Asp Ser Val Asn Ala Ser Asp Leu Asn Trp Lys Asn Ser Leu Leu His
            420                 425                 430

Gln Gln Ala Met Ala Arg Gly Ile His Tyr Ala Asn Ala Gly Ile Gln
        435                 440                 445

Lys Tyr Pro Gln Gln Met Phe Glu Gly Val Met Asn Gln Asn Ala Val
    450                 455                 460

Pro Ala Ser Phe Ser Ala Ala Gln Pro Gly Leu Arg Phe Gly Pro Lys
465                 470                 475                 480

Glu Glu Gln Phe Glu Thr Glu Lys Leu Asp Gly Ser Glu Ile Ser Gln
                485                 490                 495

Gly Lys Asn Asp Ile Gln Ile Leu Glu Thr Glu Thr Gly His Leu Asp
            500                 505                 510

Pro Gln Val Ser Arg Leu Gln Gln Arg Leu Pro Pro His His Met Arg
        515                 520                 525

Ser Asn Phe Pro Gln Ala Ala Trp Asn Asn Leu Ser Gln Asp Ser Arg
    530                 535                 540
```

-continued

Lys Asp Asp Gln Phe Gln Lys Arg Lys Thr Val Gln Ser Pro Arg Leu
545 550 555 560

Ser Ala Gly Ala Leu Pro Gln Ser Pro Leu Ser Ser Lys Ser Gly Glu
565 570 575

Phe Ser Ser Gly Ser Ala Gly Ala His Phe Gly Ala Val Ala Ala Thr
580 585 590

Thr Ala Leu Gly Ser Ser Gln Lys Glu Lys Ser Ala Val Thr Ser Val
595 600 605

Pro Ala Val Gly Gly Thr Pro Ser Leu Thr Ser Ser Ala Asn Asp Ser
610 615 620

Leu Gln Arg Gln His Gln Ala Gln Val Ala Ala Lys Arg Arg Ser Asn
625 630 635 640

Ser Leu Pro Lys Thr Pro Val Met Ser Gly Val Gly Ser Pro Ala Ser
645 650 655

Val Ser Asn Met Ser Val Pro Leu Asn Ala Asn Ser Pro Ser Val Gly
660 665 670

Thr Pro Thr Met Val Asp Gln Thr Met Leu Glu Arg Phe Ser Lys Ile
675 680 685

Glu Met Val Thr Val Arg His Gln Leu Asn Cys Lys Lys Asn Lys Ala
690 695 700

Asp Asp Tyr Pro Val Arg Lys Ser Asn Thr Tyr Ser Pro Gln Asn Leu
705 710 715 720

Met Val Cys Leu Ser Asn Leu Pro Asn Thr Glu Asp Ser Lys Asp Asp
725 730 735

Ala Ser Ala Gly Gln Leu Ser Lys Ser Ile Val Gly Gly Ser Met Asn
740 745 750

Val Cys Lys Met Arg Ile Ile Asn Phe Met Leu Ala Asp Arg Val Val
755 760 765

Gln Gly Asn Val Val Ser Phe Val Pro Arg Arg Arg Thr Arg Met Ile
770 775 780

Met Ser Glu Lys Pro Asn Asp Gly Thr Val Ala Met Gln Tyr Gly Glu
785 790 795 800

Ala Glu Asp Gly Asp Phe Leu Ser Val Glu Glu Tyr Leu Pro Thr Leu
805 810 815

Pro Asn Thr His Phe Ala Asp Leu Leu Ala Ala Gln Phe Cys Ser Leu
820 825 830

Met Ile Arg Glu Gly Tyr Leu Val Glu Asp Asn Ile Gln Pro Lys Pro
835 840 845

Thr Arg Met Asn Val Ser Ser Ser Ser Gln Pro Asn Ala Ala Gly Ile
850 855 860

Ala Pro Asn Asn Ser Ala Ala Glu Val Gln Gln Gln Tyr Asn Glu Ala
865 870 875 880

Val Ser Gly Gln Ala Ser Asn Glu Val Lys Pro Asn Phe Ser Gly Asn
885 890 895

Ala Pro Met Asn Pro Ser Gln Asn Leu Leu Ala Ser Ala Arg Met Leu
900 905 910

Pro Pro Gly Asn Pro Gln Ala Leu Pro Met Ser Gln Gly Leu Leu Ser
915 920 925

Ala Val Ser Met Pro Ala Arg Pro Gln Leu Asp Pro Gln Pro Gln Leu
930 935 940

Gln Gln Gln Pro Gln Gln Pro Pro Gln Met Gln Gln Gln Gln Pro Pro
945 950 955 960

Gln Gln Gln Gln Asn Gln His Ser Leu Ile Gln Gln Gln Ser Gln Phe

-continued

```
                965                 970                 975

Gln Arg Pro Pro Met Val Leu Pro Ser Leu Ser His Leu Asn Thr Leu
            980                 985                 990

Gly Gln Asn Ser Asn Met Gln Leu  Gly Ser His Met Val  Asn Lys Pro
        995                 1000                1005

Ser His  Leu Gln Leu Gln Leu  Leu Gln Gln Gln Gln  Gln Gln Gln
    1010                 1015                 1020

Gln Leu  Gln Pro Gln Gln Gln  Gln Gln Gln Gln Gln  Gln Gln Gln
    1025                 1030                 1035

Gln Gln  Gln Gln Gln Gln Gln  Pro Gln Met Gln Gln  Arg Lys Met
    1040                 1045                 1050

Met Met  Gly Leu Gly Thr Ala  Met Gly Met Gly Asn  Met Gly Asn
    1055                 1060                 1065

Asn Met  Val Gly Leu Gly Gly  Leu Ser Asn Ala Met  Gly Ile Gly
    1070                 1075                 1080

Gly Ala  Arg Ala Met Gly Gly  Pro Gly Ile Ser Gly  Ser Met Ala
    1085                 1090                 1095

Pro Ile  Ser Gly Met Asn Asn  Val Gly Gln Asn Gln  Ile Asn Leu
    1100                 1105                 1110

Ser Gln  Thr Thr Asn Leu Pro  Asn Val Ile Ser Gln  His Phe Arg
    1115                 1120                 1125

Ala Gly  Gln Val Thr Pro Gln  Gln Ala Ala Tyr Leu  Ser Lys Leu
    1130                 1135                 1140

Arg Met  Ala Gln Asn Arg Thr  Ser Met Leu Gly Ala  Pro Gln Ser
    1145                 1150                 1155

Gly Ile  Ala Gly Met Ser Gly  Ala Arg Gln Met His  Pro Gly Ser
    1160                 1165                 1170

Ala Gly  Leu Ser Met Leu Gly  Gln Ser Leu Asn Arg  Ala Asn Met
    1175                 1180                 1185

Asn Pro  Met Gln Arg Ser Ala  Met Gly Pro Met Gly  Pro Pro Lys
    1190                 1195                 1200

Leu Met  Ala Gly Met Asn Leu  Tyr Met Asn Gln Gln  Gln Gln Gln
    1205                 1210                 1215

Gln Gln  Gln Leu Gln Leu Gln  Gln Gln Gln Gln Phe  Gln Gln Gln
    1220                 1225                 1230

Gln Gln  Gln Gln Gln Gln Gln  Gln Gln Gln Gln Gln  Gln Leu Gln
    1235                 1240                 1245

Gln Leu  Gln Gln Gln Gln Gln  Gln Leu Gln Gln Gln  Gln Gln Gln
    1250                 1255                 1260

Gln Met  Gln Gln Gln Gln Gln  Gln Asp Pro Ser Ser  Ser Leu Gln
    1265                 1270                 1275

Ala Val  Val Ser Ser Ser Gln  Val Gly Ser Pro Ser  Thr Met Gly
    1280                 1285                 1290

Ile Pro  Gln Leu Asn Gln Gln  Gln Gln Pro Gln Gln  Gln Pro Ser
    1295                 1300                 1305

Pro Gln  Gln Met Ser Gln Arg  Thr Pro Met Ser Pro  Gln Ile Ser
    1310                 1315                 1320

Ser Gly  Ala Ile His Ala Met  Ser Ala Gly Asn Pro  Glu Ala Cys
    1325                 1330                 1335

Pro Ala  Ser Pro Gln Leu Ser  Ser Gln Thr Leu Gly  Ser Val Gly
    1340                 1345                 1350

Ser Ile  Thr Asn Ser Pro Met  Glu Leu Gln Gly Val  Asn Lys Ser
    1355                 1360                 1365
```

Asn Ser Val Asn Asn Ala
1370

<210> SEQ ID NO 23
<211> LENGTH: 784
<212> TYPE: DNA
<213> ORGANISM: Brassica oleracea

<400> SEQUENCE: 23
gcagtatgaa ccccggtcca tcttttcata gaaagagaga aagccaagaa gtacaactgt 60
cttctatgcc tggtttgaat aagcgaacaa gggtttctca catgggtcct gatatggttc 120
cacagcaaca gttagggcaa cgcatggatg gtcctcatgg aaccgataca aattggaaaa 180
atgcgcttct acaacaagac atgctccgta gaagtattca atatccaaat gcaaatatgc 240
agaggttttc accccagcaa attggaggag ctatgaatca ggaagctggt cccatgcagt 300
ttccagcttc acaacagggg ccaatgcgtt acacttcgaa agaggagcca tttgagacgg 360
gtaaaattga tggtaatatc agaaacaata tgccaggagt gggaagcgat gcaaatgatt 420
tggatccgcg tattcagcct aggatgcccc ataatgtatt taacagatca aatttccctc 480
agacatcctg gaatgctaat ccaggccagc agattgaaaa agacctcaaa aaagaagaac 540
aattcagtag aagggtatcg tctcaaagcc ctcgtttatc agcaggtgct cctccacagt 600
ccccgctttc atcgaagtct ggagagtttt ctggtggttc aatggggacc cattatggag 660
cagttgcggc agctcaaaag gacaaagctg ttacttcaat tcctatcggt gctgctcagt 720
ccgtgggttc tagtggtaat gatgctatgc agcaaaaggc acaccaaatg gctccaaaac 780
gtag 784

<210> SEQ ID NO 24
<211> LENGTH: 1072
<212> TYPE: DNA
<213> ORGANISM: Brassica rapa

<400> SEQUENCE: 24
gatcgccttg ctgaaagttc atagcgagga agtatgcagg gacatttgtt gatgcatcaa 60
acccatcaca accaggcttt tcaaaatgtt ggtacgaaca tgccggtggg attaataaat 120
caggccttgc aagatgcgcc aacttcccca ctgcctttgg tacaacctca gcaacaaatg 180
tacctgggaa ctggaaatat tagaaacatg caggatcaat gatctgaatg ctgtcagtgt 240
ctctggagct tcgcctggag gactagatgc aatgttgcct tatgcctctg acagtatgaa 300
ccccggtcca tcttttcata gaaagagaga cagccaagaa gtacaactgt cttctatgcc 360
tggtttgaat aagcgaacaa gggtttctca catgggtcct gatatggttc cacagcaaca 420
gttagggcaa cgcatggatg gtcctcatgg aaccgataca aattggaaaa atgcgcttct 480
acaacaagac atgctccgta gaagtattca atatccaaat gcaaatatgc agaggttttc 540
accccagcaa attggaggag ctatgaatca ggaagctggt cccatgcagt ttccagcttc 600
acaacagggg ccaatgcgtt acacttcgaa agaggagcca tttgagacgg gtaaaattga 660
tggtaatatc agaaacaata tgccaggagt gggaagcgat gcaaatgatt tggatccgcg 720
tattcagcct aggatgcccc ataatgtatt taacagatca aatttccctc agacatcctg 780
gaatgctaat ccaggccagc agattgaaaa agacctcaaa aaagaagaac aattcagtag 840
aagggtatcg tctcaaagcc ctcgtttatc agcaggtgct cctccacagt ccccgctttc 900
atcgaagtct ggagagtttt ctggtggttc aatggggacc cattatggag cagttgcggc 960
agctcaaaag gacaaagctg ttacttcaat tcctatcggt gctgctcagt ccgtgggttc 1020
tagtggtaat gatgctatgc agcaaaaggc acaccaaatg gctccaaaac gt 1072

<210> SEQ ID NO 25
<211> LENGTH: 1336
<212> TYPE: DNA
<213> ORGANISM: Brassica napus

<400> SEQUENCE: 25
agagctctgg catggcgctg ggtggtcaga tgaccaacaa ccattcgcct catcaactgc 60
agatgttgca gcaccacgcg gcgattcaga ggaagatgat gatggggcaa caggggtcag 120
gtgtagccat gaatatggga atgggaagca tgggcaacag tattgctgcg cttggggctt 180
ttggcaacca aatgaatatg gcgggaagag ggcttggagg aaccggaatc acatcgtcaa 240
tgtctcttcc tggcatcaat aacatggggc agaacccaat gaatcatcca gcgtcaaatt 300
tgaatgttat aagccagcaa ctccgatctg gtgctttaac accacaacag agtgccgctg 360
tgtttacaaa tcttaggttg gcgaaccgag gaggtggaat gggtgctccc caagccggga 420
tgagtggcgt gtcaggtgcc aggcagatgc accccagctc tgctggtcta tctatgatgg 480
atccgaatac attaaaccga gctaacctgc agcgagctat gggtaaacat gggtccacct 540
aagctgatgc ctggaatgaa tccttacatg aatcaacagc aactccagca gcagcaaccc 600
caacagcaac agttgcagca tcagcaacag ctacagcaac ctatgtctca gcagcaagct 660
cagtctcagc agctacaaca acttgagctg cctcagcaac aacagcaaca gcagcaacag 720
gcaacagcct cgcctcttca gtctgtgcta tcaccacccc aagtaagttc gccatcagct 780
ggaattacac agcagcagct gcaacagtcc agtccccagc aaatgagcca gagaactccg 840
atgagtcccc agcaaatgaa ccaaagaact ccaatgagtc cgcaacaaat gagtcaaaga 900
acccctatga gtcctcagat aagctcgggt acgatgcacc ccatgagcac aagcaacctg 960
gaggcttgtc cagcaagtcc acagctaagt tctcagacac atggatctgt tggtagcatc 1020
gccaattccc caatggagct tcaaggtccc aagaacaact ctgctagtac taataatccc 1080
taatcaagaa acataatgat tagtttaaga aaagcccttt tatcttcaaa acatgggttg 1140
taattgaacc tggcaaagca tttgaagttt tttgtgtcac agttttaagt tttgcgtgta 1200
cataaattaa ttaagcttgt gcttgtagag aaagtaaaca atcctttgtg ctttgcaagt 1260
gaaaatgcta gccgctatta ttaggttgtt gatatgtaat gctatctaga gattttgtga 1320
tgctagattg taaact 1336

<210> SEQ ID NO 26
<211> LENGTH: 2802
<212> TYPE: DNA
<213> ORGANISM: Glycine max
<220> FEATURE:
<221> NAME/KEY: misc_feature
<222> LOCATION: (359)..(359)
<223> OTHER INFORMATION: where n is A, G, C or T
<220> FEATURE:
<221> NAME/KEY: misc_feature
<222> LOCATION: (1387)..(1387)
<223> OTHER INFORMATION: where n is A, G, C or T

<400> SEQUENCE: 26
acgagggaag aacagtttga aatggaaaaa ttagatggtg cagaaataaa ctgcaataaa 60
agtgacatgg aaatggaaat gaacaattta gatccacaac aattgcggct tcagcaacga 120

-continued

```
ttgccacagc atgcattcat gaggcctaat ttccctcagg cagcctggaa cagtttgggt    180
cagcatatgg gcaaagaaac aaaaaaagaa gaccagcttc agaaaaggaa atcagtacag    240
agtcctcgct tatcctccgc ggcattacct cactccccat tgtcttcgaa atcaggtgaa    300
ttttccaatg gtgcagttgg accaagtttt ggaccatctg caatggctgc tgcacctgng    360
acatcacaaa aagacaaggc agcaatggcc tcagttcctg ctactgttgg aactccatct    420
aatgattcta cacaaagaca acatgcacaa ctagctgcaa aacggagatc taattctctt    480
cccaagaccc cagcaatgaa tggagttggt tctcctgtta gtgttggtac aaccagtgtc    540
ccattgaatg caaatagtcc ctcagttgtg acctcgggtt ttgttgatca aaatcttcaa    600
aatatgcttg aaaggttctc aaaaattgaa atggtgacaa tgaggcatca acttaacttt    660
aagaagaaca aggttgatga ctatcccatt aagaagcaga atccatatgt accaaataat    720
ctatcagcac ttcttgctaa tgctaatgca actaataatg agggattgcc agaggagtca    780
atttctattt caaagtcgct tataggtggg agtatgaatg cgtgcaaaat gagaatctta    840
aatttttgtg tgcctgagcg tgtagttcaa ggaagtattg ttactataat tccgaggatg    900
cgaactagga tgattatgtt tgaaaaatct gatggtactg tggctatgca ttgtggggag    960
attgaagaag ttgattacgt agctgcagag gatcatctcc tcacattacc caatactcat   1020
tctgcagatt tgcttgtaca acagttctgt tcactgatgg tacgcgaagg atttgtgaaa   1080
gaagatgacc gaatccaact taaaccaaac cgggtgaacc ttccattggg caatcaatct   1140
actaccccta ataatgctgt agttgaaatg caacaatatg gagaagccat tcctggtcaa   1200
tcatccaatg aagttgcaaa accaactagt ggcagtaatg cacctgtaaa cctctctcag   1260
aatcttgtaa caaatccaag gatgctgcca cctggaaacc cccaagcctt acagatgtcc   1320
caaggacttc tctctggtgt ttcgatggct tcaagaccac aacaaatgga ctcacaacaa   1380
gccatanaaa tcaacacaca ctcattcaac agcagaatcc ccagttccag aggtctccta   1440
tgatgcttgg gacaaatcag ctttcacact taaatccagt tggacaaaac tccaacatgc   1500
cattaggtaa tcacatgctc aacaagcctt cagctctcca gatgcagatg ttccaacaac   1560
agcaacagca gcctcaaatg caaaggaaaa tgatgatggg acttggacaa gccgtgggaa   1620
tgggtaactt gagaaataac ctagttgggc ttgcaccaat gggcaaccct atgggaatgg   1680
gaggtgcgag gggaatagga ggaagtggaa tctcatcacc aatgacatct attgctggca   1740
tgggaaatat gggtcagagc ccaatgaatc ttagccagac ttcaaatatt actaattcca   1800
taagccaaca gtttaggtcc ggatcattaa atgcagcagc atctgctgac cttatatcaa   1860
ggcttagatt ggtacattcg aatcgtcaaa gcatgctagg gtcccctcag tctaacctag   1920
ctagcatctc aggggccaga caaatacacc ctggtgctac tcctagtctt tcaatgttgg   1980
gcagggctaa tacaatgcag cgaccaattg gacctatggg tccaccaaag atgatggcag   2040
ggatgaatct ttatatgagt cagcagcagc aacatcaaca accccaacag cagcagcagc   2100
aacaccaaca gcaattgcaa ctccaacagc atatgcagca gcaattacag cagcaacagc   2160
aacaacaaga aacaacttca caattgcagt cagttgtttc acccccacag gtgggatcgc   2220
catcaatggg cgtaccacca ttgaaccaac aaacgcagca gcaagccagc cctcagcaaa   2280
tgagtcaacg aactccgatg agtccacaaa tgagctcagg tgcaattcat gccatgagtg   2340
ctggtaatcc tgaagcttgt ccagccagtc cacagttgag ctctcagacc cttggctctg   2400
ttagtagcat aacaaactcc cctatggaca tgcaaggtgt taacaagagc aactctaatg   2460
cacaatgaag ctacaaagcc taaattgtcc aaatcagtgc ccctgtcacc taagttgttg   2520
```

```
gaaactgttg aagcaaataa tgttgaatat tggtgcattg aatcatacca gaaaatgata   2580

attatttact tatgaataaa caaagcatat tgaataaata tgctgctctt ttgtaactct   2640

agggggaatc acatgcatta ttatgtcagt tgtgaatagt ttcttgtttt cttttgctct   2700

cattaaacac atcagtgtaa cttttaggat atttaggcca agattaacat gtattagtct   2760

aggtacttta tggagtgcag tagcaaactt attttttgt aa                       2802


<210> SEQ ID NO 27
<211> LENGTH: 13
<212> TYPE: PRT
<213> ORGANISM: Artificial Sequence
<220> FEATURE:
<223> OTHER INFORMATION: Conserved sequence motifs
<220> FEATURE:
<221> NAME/KEY: MISC_FEATURE
<222> LOCATION: (2)..(2)
<223> OTHER INFORMATION: Where X is T,L,S,V
<220> FEATURE:
<221> NAME/KEY: MISC_FEATURE
<222> LOCATION: (8)..(8)
<223> OTHER INFORMATION: Where X is R, K
<220> FEATURE:
<221> NAME/KEY: MISC_FEATURE
<222> LOCATION: (9)..(9)
<223> OTHER INFORMATION: Where X is A, S, T
<220> FEATURE:
<221> NAME/KEY: MISC_FEATURE
<222> LOCATION: (10)..(10)
<223> OTHER INFORMATION: Where X is S, A
<220> FEATURE:
<221> NAME/KEY: MISC_FEATURE
<222> LOCATION: (12)..(12)
<223> OTHER INFORMATION: Where X is K, S, T, G

<400> SEQUENCE: 27

Lys Xaa Leu His Pro Tyr Asp Xaa Xaa Xaa Glu Xaa Leu
1               5                   10


<210> SEQ ID NO 28
<211> LENGTH: 16
<212> TYPE: PRT
<213> ORGANISM: Artificial Sequence
<220> FEATURE:
<223> OTHER INFORMATION: Conserved Domains
<220> FEATURE:
<221> NAME/KEY: MISC_FEATURE
<222> LOCATION: (4)..(4)
<223> OTHER INFORMATION: Where X is -- E,K,Q,A
<220> FEATURE:
<221> NAME/KEY: MISC_FEATURE
<222> LOCATION: (6)..(6)
<223> OTHER INFORMATION: Where X is C, H
<220> FEATURE:
<221> NAME/KEY: MISC_FEATURE
<222> LOCATION: (10)..(10)
<223> OTHER INFORMATION: Where X is T, L
<220> FEATURE:
<221> NAME/KEY: MISC_FEATURE
<222> LOCATION: (12)..(12)
<223> OTHER INFORMATION: Where X is K, R

<400> SEQUENCE: 28

Leu Gln Pro Xaa Leu Xaa Leu Asp Pro Xaa Pro Xaa Leu Asp Arg Leu
1               5                   10                  15


<210> SEQ ID NO 29
<211> LENGTH: 11
<212> TYPE: PRT
<213> ORGANISM: Artificial Sequence
<220> FEATURE:
```

<223> OTHER INFORMATION: Conserved Domains
<220> FEATURE:
<221> NAME/KEY: MISC_FEATURE
<222> LOCATION: (3)..(3)
<223> OTHER INFORMATION: Where X is V or L
<220> FEATURE:
<221> NAME/KEY: MISC_FEATURE
<222> LOCATION: (10)..(10)
<223> OTHER INFORMATION: Where X is I, F or L

<400> SEQUENCE: 29

Ser Pro Xaa Ser Ser Lys Ser Gly Glu Xaa Ser
1               5                   10

<210> SEQ ID NO 30
<211> LENGTH: 20
<212> TYPE: PRT
<213> ORGANISM: Artificial Sequence
<220> FEATURE:
<223> OTHER INFORMATION: Conserved Domains
<220> FEATURE:
<221> NAME/KEY: MISC_FEATURE
<222> LOCATION: (5)..(5)
<223> OTHER INFORMATION: Where X is V or A
<220> FEATURE:
<221> NAME/KEY: MISC_FEATURE
<222> LOCATION: (8)..(8)
<223> OTHER INFORMATION: Where X is S, G, or N
<220> FEATURE:
<221> NAME/KEY: MISC_FEATURE
<222> LOCATION: (9)..(9)
<223> OTHER INFORMATION: Where X is N or T
<220> FEATURE:
<221> NAME/KEY: MISC_FEATURE
<222> LOCATION: (10)..(10)
<223> OTHER INFORMATION: Where X is M, T or I
<220> FEATURE:
<221> NAME/KEY: MISC_FEATURE
<222> LOCATION: (11)..(11)
<223> OTHER INFORMATION: Where X is H, S or Q
<220> FEATURE:
<221> NAME/KEY: MISC_FEATURE
<222> LOCATION: (12)..(12)
<223> OTHER INFORMATION: Where X is A, V or S
<220> FEATURE:
<221> NAME/KEY: MISC_FEATURE
<222> LOCATION: (13)..(13)
<223> OTHER INFORMATION: Where X is P, M, L or V
<220> FEATURE:
<221> NAME/KEY: MISC_FEATURE
<222> LOCATION: (14)..(14)
<223> OTHER INFORMATION: Where X is L or V
<220> FEATURE:
<221> NAME/KEY: MISC_FEATURE
<222> LOCATION: (17)..(17)
<223> OTHER INFORMATION: Where X is S, N or R

<400> SEQUENCE: 30

Val Gly Ser Pro Xaa Ser Val Xaa Xaa Xaa Xaa Xaa Xaa Xaa Asn Ala
1               5                   10                  15

Xaa Ser Pro Ser
            20

<210> SEQ ID NO 31
<211> LENGTH: 22
<212> TYPE: PRT
<213> ORGANISM: Artificial Sequence
<220> FEATURE:
<223> OTHER INFORMATION: Conserved Domains
<220> FEATURE:
<221> NAME/KEY: MISC_FEATURE
<222> LOCATION: (3)..(3)
<223> OTHER INFORMATION: Where X is N or T
<220> FEATURE:

```
<221> NAME/KEY: MISC_FEATURE
<222> LOCATION: (4)..(4)
<223> OTHER INFORMATION: Where X is T or K
<220> FEATURE:
<221> NAME/KEY: MISC_FEATURE
<222> LOCATION: (5)..(5)
<223> OTHER INFORMATION: Where X is H or Y
<220> FEATURE:
<221> NAME/KEY: MISC_FEATURE
<222> LOCATION: (6)..(6)
<223> OTHER INFORMATION: Where X is Y, S, F, H or I
<220> FEATURE:
<221> NAME/KEY: MISC_FEATURE
<222> LOCATION: (10)..(10)
<223> OTHER INFORMATION: Where X is L or F
<220> FEATURE:
<221> NAME/KEY: MISC_FEATURE
<222> LOCATION: (11)..(11)
<223> OTHER INFORMATION: Where X is A, G or V
<220> FEATURE:
<221> NAME/KEY: MISC_FEATURE
<222> LOCATION: (12)..(12)
<223> OTHER INFORMATION: Where X is E, K, A, Q, G or T
<220> FEATURE:
<221> NAME/KEY: MISC_FEATURE
<222> LOCATION: (14)..(14)
<223> OTHER INFORMATION: Where X is L or F
<220> FEATURE:
<221> NAME/KEY: MISC_FEATURE
<222> LOCATION: (15)..(15)
<223> OTHER INFORMATION: Where X is I, C or K
<220> FEATURE:
<221> NAME/KEY: MISC_FEATURE
<222> LOCATION: (16)..(16)
<223> OTHER INFORMATION: Where X is S, P or I
<220> FEATURE:
<221> NAME/KEY: MISC_FEATURE
<222> LOCATION: (17)..(17)
<223> OTHER INFORMATION: Where X is L or R
<220> FEATURE:
<221> NAME/KEY: MISC_FEATURE
<222> LOCATION: (19)..(19)
<223> OTHER INFORMATION: Where X is L, V, I, A or D
<220> FEATURE:
<221> NAME/KEY: MISC_FEATURE
<222> LOCATION: (20)..(20)
<223> OTHER INFORMATION: Where X is R, Q or K
<220> FEATURE:
<221> NAME/KEY: MISC_FEATURE
<222> LOCATION: (21)..(21)
<223> OTHER INFORMATION: Where X is D or E

<400> SEQUENCE: 31

Leu Pro Xaa Xaa Xaa Xaa Ala Asp Leu Xaa Xaa Xaa Gln Xaa Xaa Xaa
1               5                   10                  15

Xaa Met Xaa Xaa Xaa Gly
            20


<210> SEQ ID NO 32
<211> LENGTH: 49
<212> TYPE: PRT
<213> ORGANISM: Artificial Sequence
<220> FEATURE:
<223> OTHER INFORMATION: Conserved Regions

<400> SEQUENCE: 32

Met Ser Leu Glu Asn Ile Val Lys Asp Ile Pro Ser Ile Ser Asp Asn
1               5                   10                  15

Ser Trp Thr Tyr Gly Asp Leu Met Glu Val Glu Ser Lys Ile Leu Lys
            20                  25                  30

Ala Leu Gln Pro Lys Leu His Leu Asp Pro Thr Pro Lys Leu Asp Arg
        35                  40                  45
```

Leu

<210> SEQ ID NO 33
<211> LENGTH: 12
<212> TYPE: PRT
<213> ORGANISM: Artificial Sequence
<220> FEATURE:
<223> OTHER INFORMATION: Conserved Regions

<400> SEQUENCE: 33

```
Ser Trp Thr Tyr Gly Asp Leu Met Glu Val Glu Ser
1               5                   10
```

<210> SEQ ID NO 34
<211> LENGTH: 20
<212> TYPE: PRT
<213> ORGANISM: Artificial Sequence
<220> FEATURE:
<223> OTHER INFORMATION: Conserved Regions

<400> SEQUENCE: 34

```
Ser Trp Thr Tyr Gly Asp Leu Met Glu Val Glu Ser Lys Ile Leu Lys
1               5                   10                  15

Ala Leu Gln Pro
            20
```

<210> SEQ ID NO 35
<211> LENGTH: 13
<212> TYPE: PRT
<213> ORGANISM: Artificial Sequence
<220> FEATURE:
<223> OTHER INFORMATION: Conserved Regions

<400> SEQUENCE: 35

```
Gly Lys Lys Val Cys Ile Asp Arg Val Gln Glu Ser Ser
1               5                   10
```

<210> SEQ ID NO 36
<211> LENGTH: 23
<212> TYPE: PRT
<213> ORGANISM: Artificial Sequence
<220> FEATURE:
<223> OTHER INFORMATION: Conserved Regions

<400> SEQUENCE: 36

```
Gln Ser Pro Arg Leu Ser Ala Gly Ala Leu Pro Gln Ser Pro Leu Ser
1               5                   10                  15

Ser Lys Ser Gly Glu Phe Ser
            20
```

<210> SEQ ID NO 37
<211> LENGTH: 11
<212> TYPE: PRT
<213> ORGANISM: Artificial Sequence
<220> FEATURE:
<223> OTHER INFORMATION: Conserved Regions

<400> SEQUENCE: 37

```
Ser Pro Leu Ser Ser Lys Ser Gly Glu Phe Ser
1               5                   10
```

<210> SEQ ID NO 38
<211> LENGTH: 15
<212> TYPE: PRT
<213> ORGANISM: Artificial Sequence
<220> FEATURE:

-continued

<223> OTHER INFORMATION: Conserved Regions

<400> SEQUENCE: 38

Ala Gln Leu Ala Ala Lys Arg Arg Ser Asn Ser Leu Pro Lys Thr
1 5 10 15

<210> SEQ ID NO 39
<211> LENGTH: 19
<212> TYPE: PRT
<213> ORGANISM: Artificial Sequence
<220> FEATURE:
<223> OTHER INFORMATION: Conserved Regions

<400> SEQUENCE: 39

Val Gly Ser Pro Val Ser Val Gly Thr Thr Ser Val Pro Leu Asn Ala
1 5 10 15

Asn Ser Pro

<210> SEQ ID NO 40
<211> LENGTH: 18
<212> TYPE: PRT
<213> ORGANISM: Artificial Sequence
<220> FEATURE:
<223> OTHER INFORMATION: Conserved Regions

<400> SEQUENCE: 40

Arg Phe Ser Lys Ile Glu Met Val Thr Met Arg His Gln Leu Asn Phe
1 5 10 15

Lys Lys

<210> SEQ ID NO 41
<211> LENGTH: 22
<212> TYPE: PRT
<213> ORGANISM: Artificial Sequence
<220> FEATURE:
<223> OTHER INFORMATION: Conserved Regions

<400> SEQUENCE: 41

Leu Pro Asn Thr His Ser Ala Asp Leu Leu Ala Gln Gln Phe Cys Ser
1 5 10 15

Leu Met Val Arg Glu Gly
20

<210> SEQ ID NO 42
<211> LENGTH: 15
<212> TYPE: PRT
<213> ORGANISM: Artificial Sequence
<220> FEATURE:
<223> OTHER INFORMATION: Conserved Regions

<400> SEQUENCE: 42

Gln Ala Leu Gln Met Ser Gln Gly Leu Leu Ser Gly Val Ser Met
1 5 10 15

<210> SEQ ID NO 43
<211> LENGTH: 53
<212> TYPE: PRT
<213> ORGANISM: Artificial Sequence
<220> FEATURE:
<223> OTHER INFORMATION: Conserved Regions

<400> SEQUENCE: 43

Ser Pro Gln Gln Met Ser Gln Arg Thr Pro Met Ser Pro Gln Ile Ser
1 5 10 15

Ser Gly Ala Ile His Ala Met Ser Ala Gly Asn Pro Glu Ala Cys Pro
20 25 30

Ala Ser Pro Gln Leu Ser Ser Gln Thr Leu Gly Ser Val Ser Ser Ile
35 40 45

Thr Asn Ser Pro Met
50

<210> SEQ ID NO 44
<211> LENGTH: 23
<212> TYPE: PRT
<213> ORGANISM: Artificial Sequence
<220> FEATURE:
<223> OTHER INFORMATION: Conserved Regions

<400> SEQUENCE: 44

Cys Pro Ala Ser Pro Gln Leu Ser Ser Gln Thr Leu Gly Ser Val Ser
1 5 10 15

Ser Ile Thr Asn Ser Pro Met
20

<210> SEQ ID NO 45
<211> LENGTH: 195
<212> TYPE: PRT
<213> ORGANISM: Artificial Sequence
<220> FEATURE:
<223> OTHER INFORMATION: Conserved Regions

<400> SEQUENCE: 45

His Glu Val Ser Phe Thr Phe Ser Leu Tyr Asp Arg Gly Tyr Leu Ile
1 5 10 15

Ser Lys Ser Ala Ala Met Asp Pro Ser Gln Thr Ser Ile Gln Asp Gly
20 25 30

Lys Thr Leu His Pro Tyr Asp Arg Ala Ser Glu Lys Leu Phe Ser Ala
35 40 45

Ile Glu Ala Gly Arg Leu Pro Gly Asp Ile Leu Asp Glu Ile Pro Ser
50 55 60

Lys Tyr Tyr Asn Gly Ser Val Val Cys Glu Ile Arg Asp Tyr Arg Lys
65 70 75 80

His Val Ser Asn Gln Ala Pro Ala Ser Ser Ala Glu Leu Gly Leu Pro
85 90 95

Ile Val Asn Lys Val Arg Leu Arg Met Thr Phe Glu Asn Val Val Lys
100 105 110

Asp Ile Thr Leu Leu Ser Asp Asp Ser Trp Ser Tyr Arg Asp Phe Val
115 120 125

Glu Ala Glu Ala Arg Ile Val Arg Ala Leu Gln Pro Glu Leu Cys Leu
130 135 140

Asp Pro Thr Pro Lys Leu Asp Arg Leu Cys Gln Asp Pro Val Pro His
145 150 155 160

Lys Leu Ser Leu Gly Ile Gly Lys Lys Arg Arg Leu Arg Gln Asn Pro
165 170 175

Glu Val Val Val Thr Ser Ser Asn Met Ser His Gly Lys Lys Val Cys
180 185 190

Ile Asp Arg
195

<210> SEQ ID NO 46
<211> LENGTH: 35
<212> TYPE: PRT
<213> ORGANISM: Artificial Sequence
<220> FEATURE:
<223> OTHER INFORMATION: Conserved Regions

<400> SEQUENCE: 46

Leu Cys Leu Asp Pro Thr Pro Lys Leu Asp Arg Leu Cys Gln Asp Pro
1 5 10 15

Val Pro His Lys Leu Ser Leu Gly Ile Gly Lys Lys Arg Arg Leu Arg
20 25 30

Gln Asn Pro
35

<210> SEQ ID NO 47
<211> LENGTH: 12
<212> TYPE: PRT
<213> ORGANISM: Artificial Sequence
<220> FEATURE:
<223> OTHER INFORMATION: Conserved Regions

<400> SEQUENCE: 47

Leu Cys Leu Asp Pro Thr Pro Lys Leu Asp Arg Leu
1 5 10

<210> SEQ ID NO 48
<211> LENGTH: 22
<212> TYPE: PRT
<213> ORGANISM: Artificial Sequence
<220> FEATURE:
<223> OTHER INFORMATION: Conserved Regions

<400> SEQUENCE: 48

Gln Asp Pro Val Pro His Lys Leu Ser Leu Gly Ile Gly Lys Lys Arg
1 5 10 15

Arg Leu Arg Gln Asn Pro
20

<210> SEQ ID NO 49
<211> LENGTH: 450
<212> TYPE: DNA
<213> ORGANISM: Artificial Sequence
<220> FEATURE:
<223> OTHER INFORMATION: RNAi target sequence

<400> SEQUENCE: 49
ctgaatcaca ggcccagtag gggcacgaga gctaggtgct aactttcttc tctgaattat 60
gtcttctttt ttgaagtcct tctcagctgc gaaccgagta ttttgccact gtcccatgtt 120
tggaacatta tttcttgcca ctgattgttg tggtaaatgt tgagattggg attgctgctg 180
atccagcatg gaagtttcag gtgccataga ctgcaaggcg tcttttgact tatcagaacc 240
atccatctgc tcctgcttag catcgtatct caaattttgc tgatgactaa aatataagga 300
agatcctgga tcttgcatgt tgttcatcat cgaagaagga tatctctgac cactcagtga 360
agatgcatac tgcatcccct tgacatctaa ttgtggatgc agttgatggt tcttccattg 420
catctcctgc ccaccaaggg gttgaggcct 450

<210> SEQ ID NO 50
<211> LENGTH: 450
<212> TYPE: DNA
<213> ORGANISM: Artificial Sequence
<220> FEATURE:
<223> OTHER INFORMATION: RNAi target sequence repeat -continued

<400> SEQUENCE: 50

```
aggcctcaac cccttggtgg gcaggagatg caatggaaga accatcaact gcatccacaa     60

ttagatgtca aggggatgca gtatgcatct tcactgagtg gtcagagata tccttcttcg    120

atgatgaaca acatgcaaga tccaggatct tccttatatt ttagtcatca gcaaaatttg    180

agatacgatg ctaagcagga gcagatggat ggttctgata agtcaaaaga cgccttgcag    240

tctatggcac ctgaaacttc catgctggat cagcagcaat cccaatctca acatttacca    300

caacaatcag tggcaagaaa taatgttcca aacatgggac agtggcaaaa tactcggttc    360

gcagctgaga aggacttcaa aaaagaagac ataattcaga gaagaaagtt agcacctagc    420

tctcgtgccc ctactgggcc tgtgattcag                                     450
```

<210> SEQ ID NO 51
<211> LENGTH: 147
<212> TYPE: DNA
<213> ORGANISM: Artificial Sequence
<220> FEATURE:
<223> OTHER INFORMATION: GmPre2 RNAi target sequence

<400> SEQUENCE: 51

```
gcagcagctg caacaaaatc aacacacact cattcaacag cagaatcccc agttccagag     60

gtctcctatg atgcttggga caaatcagct ttcacactta aatccagttg gacaaaactc    120

caacatgcca ttaggtaatc acatgct                                        147
```

PLANTS WITH IMPROVED AGRONOMIC TRAITS

FIELD

The field of disclosure relates to plant breeding and genetics and, in particular, relates to recombinant DNA constructs useful in plants for conferring improved agronomic traits.

BACKGROUND

Improving agronomic traits in crop plants is beneficial to farmers. Several factors crop yield. Abiotic stress is the primary cause of crop loss worldwide, causing average yield losses of more than 50% for major crops. Among the various abiotic stresses, drought is a major factor that limits crop productivity worldwide. Exposure of plants to a water-limiting environment during various developmental stages appears to activate various physiological and developmental changes. Molecular mechanisms of abiotic stress responses and the genetic regulatory networks of drought stress tolerance have been studied.

Natural responses to abiotic stress vary among plant species and among varieties and cultivars within a plant species. Certain species, varieties or cultivars are more tolerant to abiotic stress such as drought than others. Transgenic approaches including overexpression and downregulation are evaluated for engineering drought tolerance in crop plants. Nitrogen utilization efficiency also affects crop yield, especially where the application of nitrogen fertilizer is limited.

SUMMARY

Methods and compositions to increase yield and stress tolerance in plants are disclosed. In an embodiment, reduced activity or expression of Pre2 gene results in increased tolerance to drought and improved nitrogen utilization.

A method of altering an agronomic trait or parameter of a plant, the method includes expressing a polynucleotide that down-regulates the endogenous expression of a messenger RNA encoding a polypeptide, wherein the polypeptide includes a conserved domain selected from the group consisting of SEQ ID NOS: 27-48. In an embodiment, the agronomic trait or parameter is selected from the group consisting of drought tolerance, increased nitrogen use efficiency, and increased yield. In an embodiment, the suppression of endogenous expression of the messenger RNA is by RNAi.

In an embodiment, the expression of the endogenous Pre2 gene or production of its protein is reduced by anti-sense expression, co-suppression, dsRNA, ribozymes, microRNA, genome editing, targeted promoter inactivation, site-directed mutagenesis and knock-outs.

In an embodiment, a plant comprising in its genome a recombinant DNA construct comprising a polynucleotide operably linked to at least one regulatory element, wherein said polynucleotide comprises a nucleotide sequence selected from the group consisting of: (a) a nucleotide sequence encoding a polypeptide with drought tolerance activity, wherein the polypeptide has an amino acid sequence of at least 60%, 80%, 85%, 90%, 95% or 100% sequence identity, based on the Clustal W method of alignment with pairwise alignment default parameters (GAP PENALTY=10, GAP LENGTH PENALTY=0.2, DELAY DEVERGENT SEQS (%)=30%, DNA TRANSITION WEIGHT=0.5, PROTEIN WEIGHT MATRIX "Gonnet Series"), when compared to a sequence selected from the group consisting of SEQ ID NOS: 3, 5, 7, 9, 11, 13, 15, 18, 20 and 22; (b) a nucleotide sequence encoding a polypeptide with drought tolerance activity, wherein the nucleotide sequence is hybridizable under stringent conditions with a DNA molecule comprising the full complement to a sequence selected from the group consisting of SEQ ID NOS: 1, 2, 4, 6, 8, 10, 12, 14, 16, 17, 19, 21, 23-26; (c) a nucleotide sequence encoding a polypeptide with drought tolerance activity, wherein the nucleotide sequence is derived from a sequence selected from the group consisting of SEQ ID NOS: 1, 2, 4, 6, 8, 10, 12, 14, 16, 17, 19, 21, 23-26 by alteration of one or more nucleotides by at least one method selected from the group consisting of: deletion, substitution, addition and insertion; (d) a nucleotide sequence encoding a polypeptide wherein the amino acid sequence of the polypeptide comprises a sequence selected from the group consisting of SEQ ID NOS: 3, 5, 7, 9, 11, 13, 15, 18, 20 and 22; and (e) a nucleotide sequence comprising a sequence selected from the group consisting of SEQ ID NOS: 1, 2, 4, 6, 8, 10, 12, 14, 16, 17, 19, 21, 23-26; and wherein said plant exhibits increased drought tolerance when compared to a control plant not comprising said recombinant DNA construct. The plant may be a monocot or dicot.

In another embodiment, a plant comprising in its genome a recombinant DNA construct comprising a polynucleotide operably linked to at least one regulatory element, wherein said polynucleotide comprises a nucleotide sequence selected from the group consisting of: (a) a nucleotide sequence encoding a polypeptide with drought tolerance activity, wherein the polypeptide has an amino acid sequence of at least 60%, 80%, 85%, 90%, 95% or 100% sequence identity, based on the Clustal W method of alignment with pairwise alignment default parameters (GAP PENALTY=10, GAP LENGTH PENALTY=0.2, DELAY DEVERGENT SEQS (%)=30%, DNA TRANSITION WEIGHT=0.5, PROTEIN WEIGHT MATRIX "Gonnet Series"), when compared to a sequence selected from the group consisting of SEQ ID NOS: 3, 5, 7, 9, 11, 13, 15, 18, 20 and 22; (b) a nucleotide sequence encoding a polypeptide with drought tolerance activity, wherein the nucleotide sequence is hybridizable under stringent conditions with a DNA molecule comprising the full complement to a sequence selected from the group consisting of SEQ ID NOS: 1, 2, 4, 6, 8, 10, 12, 14, 16, 17, 19, 21, 23-26; (c) a nucleotide sequence encoding a polypeptide with drought tolerance activity, wherein the nucleotide sequence is derived from a sequence selected from the group consisting of SEQ ID NOS: 1, 2, 4, 6, 8, 10, 12, 14, 16, 17, 19, 21, 23-26 by alteration of one or more nucleotides by at least one method selected from the group consisting of: deletion, substitution, addition and insertion; (d) a nucleotide sequence encoding a polypeptide wherein the amino acid sequence of the polypeptide comprises a sequence selected from the group consisting of SEQ ID NOS: 3, 5, 7, 9, 11, 13, 15, 18, 20 and 22; and (e) a nucleotide sequence comprising a sequence selected from the group consisting of SEQ ID NOS: 1, 2, 4, 6, 8, 10, 12, 14, 16, 17, 19, 21, 23-26; and wherein said plant exhibits an increase in yield when compared to a control plant not comprising said recombinant DNA construct. The plant may exhibit said increase in yield when compared, under water limiting conditions, to said control plant not comprising said recombinant DNA construct. The plant may be a monocot or dicot.

In another embodiment, a method of increasing drought tolerance in a plant, comprising: (a) introducing into a regenerable plant cell a recombinant DNA construct comprising a polynucleotide operably linked to at least one regulatory element, wherein said polynucleotide comprises a nucleotide sequence selected from the group consisting of: (i) a nucleotide sequence encoding a polypeptide with drought tolerance activity, wherein the polypeptide has an amino acid sequence of at least 60%, 80%, 85%, 90%, 95% or 100% sequence identity, based on the Clustal W method of alignment with pairwise alignment default parameters (GAP PENALTY=10, GAP LENGTH PENALTY=0.2, DELAY DEVERGENT SEQS (%)=30%, DNA TRANSITION WEIGHT=0.5, PROTEIN WEIGHT MATRIX "Gonnet Series"), when compared to a sequence selected from the group consisting of SEQ ID NOS: 3, 5, 7, 9, 11, 13, 15, 18, 20 and 22; (ii) a nucleotide sequence encoding a polypeptide with drought tolerance activity, wherein the nucleotide sequence is hybridizable under stringent conditions with a DNA molecule comprising the full complement to a sequence selected from the group consisting of SEQ ID NOS: 1, 2, 4, 6, 8, 10, 12, 14, 16, 17, 19, 21, 23-26; (iii) a nucleotide sequence encoding a polypeptide with drought tolerance activity, wherein the nucleotide sequence is a sequence selected from the group consisting of SEQ ID NOS: 1, 2, 4, 6, 8, 10, 12, 14, 16, 17, 19, 21, 23-26 by alteration of one or more nucleotides by at least one method selected from the group consisting of: deletion, substitution, addition and insertion; (iv) a nucleotide sequence encoding a polypeptide wherein the amino acid sequence of the polypeptide comprises a sequence selected from the group consisting of SEQ ID NOS: 3, 5, 7, 9, 11, 13, 15, 18, 20 and 22; and (v) a nucleotide sequence comprising a sequence selected from the group consisting of SEQ ID NOS: 1, 2, 4, 6, 8, 10, 12, 14, 16, 17, 19, 21, 23-26; and (b) regenerating a transgenic plant from the regenerable plant cell after step (a), wherein the transgenic plant comprises in its genome the recombinant DNA construct and exhibits increased drought tolerance when compared to a control plant not comprising the recombinant DNA construct. The method may further comprise: (c) obtaining a progeny plant derived from the transgenic plant, wherein said progeny plant comprises in its genome the recombinant DNA construct and exhibits increased drought tolerance when compared to a control plant not comprising the recombinant DNA construct.

In another embodiment, a method of evaluating drought tolerance in a plant, comprising: (a) obtaining a transgenic plant, wherein the transgenic plant comprises in its genome a recombinant DNA construct comprising a polynucleotide operably linked to at least one regulatory element, wherein said polynucleotide comprises a nucleotide sequence selected from the group consisting of: (i) a nucleotide sequence encoding a polypeptide with drought tolerance activity, wherein the polypeptide has an amino acid sequence of at least 60%, 80%, 85%, 90%, 95% or 100% sequence identity, based on the Clustal W method of alignment with pairwise alignment default parameters (GAP PENALTY=10, GAP LENGTH PENALTY=0.2, DELAY DEVERGENT SEQS (%)=30%, DNA TRANSITION WEIGHT=0.5, PROTEIN WEIGHT MATRIX "Gonnet Series"), when compared to a sequence selected from the group consisting of SEQ ID NOS: 3, 5, 7, 9, 11, 13, 15, 18, 20 and 22; (ii) a nucleotide sequence encoding a polypeptide with drought tolerance activity, wherein the nucleotide sequence is hybridizable under stringent conditions with a DNA molecule comprising the full complement of a sequence selected from the group consisting of SEQ ID NOS: 1, 2, 4, 6, 8, 10, 12, 14, 16, 17, 19, 21, 23-26; (iii) a nucleotide sequence encoding a polypeptide with drought tolerance activity, wherein the nucleotide sequence is a sequence selected from the group consisting of SEQ ID NOS: 1, 2, 4, 6, 8, 10, 12, 14, 16, 17, 19, 21, 23-26 by alteration of one or more nucleotides by at least one method selected from the group consisting of: deletion, substitution, addition and insertion; (iv) a nucleotide sequence encoding a polypeptide wherein the amino acid sequence of the polypeptide comprises a sequence selected from the group consisting of SEQ ID NOS: 3, 5, 7, 9, 11, 13, 15, 18, 20 and 22; and (v) a nucleotide sequence comprising a sequence selected from the group consisting of SEQ ID NOS: 1, 2, 4, 6, 8, 10, 12, 14, 16, 17, 19, 21, 23-26; and (b) obtaining a progeny plant derived from the transgenic plant of (a), wherein the progeny plant comprises in its genome the recombinant DNA construct; and (c) evaluating the progeny plant for drought tolerance compared to a control plant not comprising the recombinant DNA construct.

In another embodiment, a method of determining an alteration of an agronomic characteristic in a plant, comprising: (a) obtaining a transgenic plant, wherein the transgenic plant comprises in its genome a recombinant DNA construct comprising a polynucleotide operably linked to at least one regulatory element, wherein said polynucleotide comprises a nucleotide sequence selected from the group consisting of: (i) a nucleotide sequence encoding a polypeptide with drought tolerance activity, wherein the polypeptide has an amino acid sequence of at least 60%, 80%, 85%, 90%, 95% or 100% sequence identity, based on the Clustal W method of alignment with pairwise alignment default parameters (GAP PENALTY=10, GAP LENGTH PENALTY=0.2, DELAY DEVERGENT SEQS (%)=30%, DNA TRANSITION WEIGHT=0.5, PROTEIN WEIGHT MATRIX "Gonnet Series"), when compared to a sequence selected from the group consisting of SEQ ID NOS: 3, 5, 7, 9, 11, 13, 15, 18, 20 and 22; (ii) a nucleotide sequence encoding a polypeptide with drought tolerance activity, wherein the nucleotide sequence is hybridizable under stringent conditions with a DNA molecule comprising the full complement of a sequence selected from the group consisting of SEQ ID NOS: 1, 2, 4, 6, 8, 10, 12, 14, 16, 17, 19, 21, 23-26; (iii) a nucleotide sequence encoding a polypeptide with drought tolerance activity, wherein the nucleotide sequence is a sequence selected from the group consisting of SEQ ID NOS: 1, 2, 4, 6, 8, 10, 12, 14, 16, 17, 19, 21, 23-26 by alteration of one or more nucleotides by at least one method selected from the group consisting of: deletion, substitution, addition and insertion; (iv) a nucleotide sequence encoding a polypeptide wherein the amino acid sequence of the polypeptide comprises a sequence selected from the group consisting of SEQ ID NOS: 3, 5, 7, 9, 11, 13, 15, 18, 20 and 22; and (v) a nucleotide sequence comprising a sequence selected from the group consisting of SEQ ID NOS: 1, 2, 4, 6, 8, 10, 12, 14, 16, 17, 19, 21, 23-26; and (b) obtaining a progeny plant derived from the transgenic plant of step (a), wherein the progeny plant comprises in its genome the recombinant DNA construct; and (c) determining whether the progeny plant exhibits an alteration of at least one agronomic characteristic when compared to a control plant not comprising the recombinant DNA construct. Said determining step (c) may comprise determining whether the transgenic plant exhibits an alteration of at least one agronomic characteristic when compared, under water limiting conditions, to a control plant not comprising the recombinant DNA construct. Said at least one agronomic trait may be yield and furthermore may be an increase in yield.

In another embodiment, an isolated polynucleotide comprising a nucleotide sequence selected from the group consisting of: (a) a nucleotide sequence encoding a polypeptide with drought tolerance activity, wherein the polypeptide has an amino acid sequence of at least 60%, 80%, 85%, 90% or 95% sequence identity, based on the Clustal W method of alignment with pairwise alignment default parameters (GAP PENALTY=10, GAP LENGTH PENALTY=0.2, DELAY DEVERGENT SEQS (%)=30%, DNA TRANSITION WEIGHT=0.5, PROTEIN WEIGHT MATRIX "Gonnet Series"), when compared to a sequence selected from the group consisting of SEQ ID NOS: 3, 5, 7, 9, 11, 13, 15, 18, 20 and 22; b) a nucleotide sequence encoding a polypeptide with drought tolerance activity, wherein the nucleotide sequence is hybridizable under stringent conditions with a DNA molecule comprising the full complement of a sequence selected from the group consisting of SEQ ID NOS: 1, 2, 4, 6, 8, 10, 12, 14, 16, 17, 19, 21, 23-26; (c) a nucleotide sequence encoding a polypeptide with drought tolerance activity, wherein the nucleotide sequence is a sequence selected from the group consisting of SEQ ID NOS: 1, 2, 4, 6, 8, 10, 12, 14, 16, 17, 19, 21, 23-26 by alteration of one or more nucleotides by at least one method selected from the group consisting of: deletion, substitution, addition and insertion; (d) a nucleotide sequence encoding a polypeptide wherein the amino acid sequence of the polypeptide comprises a sequence selected from the group consisting of SEQ ID NOS: 3, 5, 7, 9, 11, 13, 15, 18, 20 and 22; and (e) a nucleotide sequence comprising a sequence selected from the group consisting of SEQ ID NOS: 1, 2, 4, 6, 8, 10, 12, 14, 16, 17, 19, 21, 23-26.

In another embodiment, an isolated polynucleotide comprising the full complement of the nucleotide sequence of the disclosure, wherein the full complement and the nucleotide sequence of the disclosure consist of the same number of nucleotides and are 100% complementary.

In another embodiment, a recombinant DNA construct comprising the isolated polynucleotide of the disclosure operably linked to at least one regulatory element.

In another embodiment, a cell comprising the recombinant DNA construct of the disclosure, wherein the cell is selected from the group consisting of a bacterial cell, a yeast cell, and insect cell and a plant cell.

In another embodiment, a plant or a seed comprising the recombinant DNA construct of the disclosure. The plant or seed may be a monocot or a dicot plant or seed.

In another embodiment, a method for isolating a polypeptide encoded by the recombinant DNA construct of the disclosure, wherein the method comprises the following: (a) transforming a cell with the recombinant DNA construct of the disclosure; (b) growing the transformed cell of step (a) under conditions suitable for expression of the recombinant DNA construct; and (c) isolating the polypeptide from the transformed cell of step (b).

In another embodiment, an isolated polypeptide selected from the group consisting of: (a) a polypeptide with drought tolerance activity, wherein the polypeptide has an amino acid sequence of at least 60%, 80%, 85%, 90% or 95% sequence identity, based on the Clustal W method of alignment with pairwise alignment default parameters (GAP PENALTY=10, GAP LENGTH PENALTY=0.2, DELAY DEVERGENT SEQS (%)=30%, DNA TRANSITION WEIGHT=0.5, PROTEIN WEIGHT MATRIX "Gonnet Series"), when compared to a sequence selected from the group consisting of SEQ ID NOS: 3, 5, 7, 9, 11, 13, 15, 18, 20 and 22; (b) a polypeptide with drought tolerance activity, wherein the amino acid sequence is a sequence selected from the group consisting of SEQ ID NOS: 1, 2, 4, 6, 8, 10, 12, 14, 16, 17, 19, 21, 23-26; by alteration of one or more amino acids by at least one method selected from the group consisting of: deletion, substitution, addition and insertion; and (c) a polypeptide wherein the amino acid sequence of the polypeptide comprises a sequence selected from the group consisting of SEQ ID NOS: 3, 5, 7, 9, 11, 13, 15, 18, 20 and 22.

In another embodiment, a vector that includes the polynucleotide of the disclosure is described.

In another embodiment, a method for producing a transgenic plant comprising transforming a plant cell with the recombinant DNA construct of the disclosure and regenerating a transgenic plant from the transformed plant cell.

In another embodiment, the present disclosure includes any of the plants of the present disclosure wherein the plant is selected from the group consisting of: maize, soybean, sunflower, sorghum, canola, wheat, alfalfa, cotton, rice, barley, millet, sugarcane, switchgrass, tobacco, potato and sugar beet.

In another embodiment, the present disclosure includes any of the methods of the present disclosure wherein the plant is selected from the group consisting of: maize, soybean, sunflower, sorghum, canola, wheat, alfalfa, cotton, rice, barley, millet, sugarcane, switchgrass, tobacco, potato and sugar beet.

In another embodiment, the present disclosure includes seed of any of the plants of the present disclosure, wherein said seed comprises in its genome a recombinant DNA construct comprising a polynucleotide operably linked to at least one regulatory element, wherein said polynucleotide encodes a polypeptide having an amino acid sequence of at least 60% sequence identity, based on the Clustal W method of alignment, when compared to a sequence selected from the group consisting of SEQ ID NOS: 3, 5, 7, 9, 11, 13, 15, 18, 20 and 22; and wherein a plant produced from said seed exhibits either an increased drought tolerance, or an increase in yield, or both, when compared to a control plant not comprising said recombinant DNA construct.

A method of identifying a plant that exhibits increased drought tolerance or an improved agronomic parameter, the method includes screening a population of maize plants for drought tolerance or enhanced nitrogen utilization efficiency and analyzing the sequence of a polynucleotide encoding a protein comprising SEQ ID NO: 3 and identifying the plant with drought tolerance or enhanced nitrogen utilization efficiency.

A method of identifying alleles in maize plants or germplasm that are associated with enhanced tolerance to drought and/or increased nitrogen use efficiency comprising:

(a) obtaining a population of maize plants, wherein one or more plants exhibit differing levels of enhanced tolerance to drought and/or increased nitrogen use efficiency;
(b) evaluating allelic variations with respect to the polynucleotide sequence encoding a protein comprising SEQ ID NO: 3 or in the genomic region that regulates the expression of the polynucleotide encoding the protein;
(c) obtaining phenotypic values of enhanced tolerance to drought and/or increased nitrogen use efficiency for a plurality of maize plants in the population;
(d) associating the allelic variations in the genomic associated with SEQ ID NO: 1 with said tolerance; and
(e) identifying the alleles that are associated with enhanced tolerance.

A transgenic plant includes in its genome a recombinant construct, the recombinant construct comprising a genetic element that reduces the expression of an endogenous gene, wherein the endogenous gene encodes a polypeptide that comprises an amino acid sequence of SEQ ID NO: 3 or a sequence that is 90% identical to SEQ ID NO: 3. In an embodiment, the genetic element includes a RNAi construct.

A plant comprising in its genome a genetic modification that results in the reduced expression of a gene that encodes a polypeptide that comprises an amino acid sequence of SEQ ID NO: 3 or a sequence that is 95% identical to SEQ ID NO: 3 or the reduced activity of the polypeptide, wherein the plant shows one or more improved agronomic parameters that contribute to drought tolerance or yield. In an embodiment, the plant is a maize plant.

BRIEF DESCRIPTION OF THE DRAWINGS AND SEQUENCE LISTING

The disclosure can be more fully understood from the following detailed description and the accompanying drawings and Sequence Listing which form a part of this application.

FIG. 1 shows the phenotype of pre-mature senescence (pre2) mutation (1A) and co-segregation analysis using SAIFF (Selective Amplification of Insertion Flanking Fragments) protocol to isolate a candidate gene responsible for the pre2 mutant phenotype in corn (1B).

The multiple alignment of dicot Prc2 sequences.

FIG. 2 shows RT-PCR and Southern blot analyses of Pre2 candidate gene: Reverse transcriptase-polymerase chain reaction (RT-PCR) of pre2 mutant showing four transcripts with variable intensities as compared to one in WT-sib (2A). Cloning and sequence analysis of these transcripts were due to interference of the Mutator resulting into differential splicing in mutant mature RNA (2C). Southern blot analysis of pre2-2 mutant allele indicates a tight linkage between the pre2 mutant phenotype with the polymorphism in the candidate gene (2B).

Figure 10A:
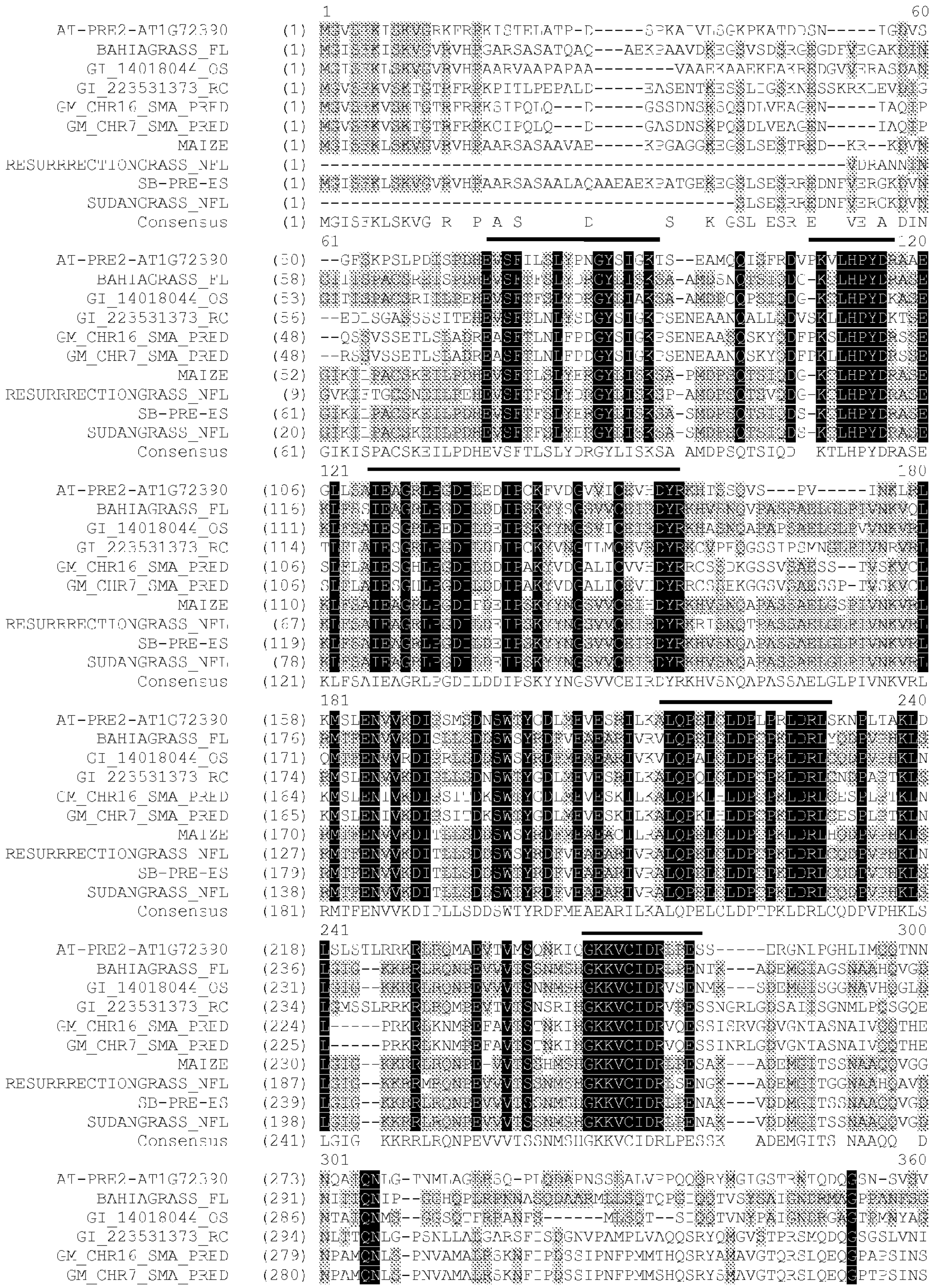
Figure 10B:
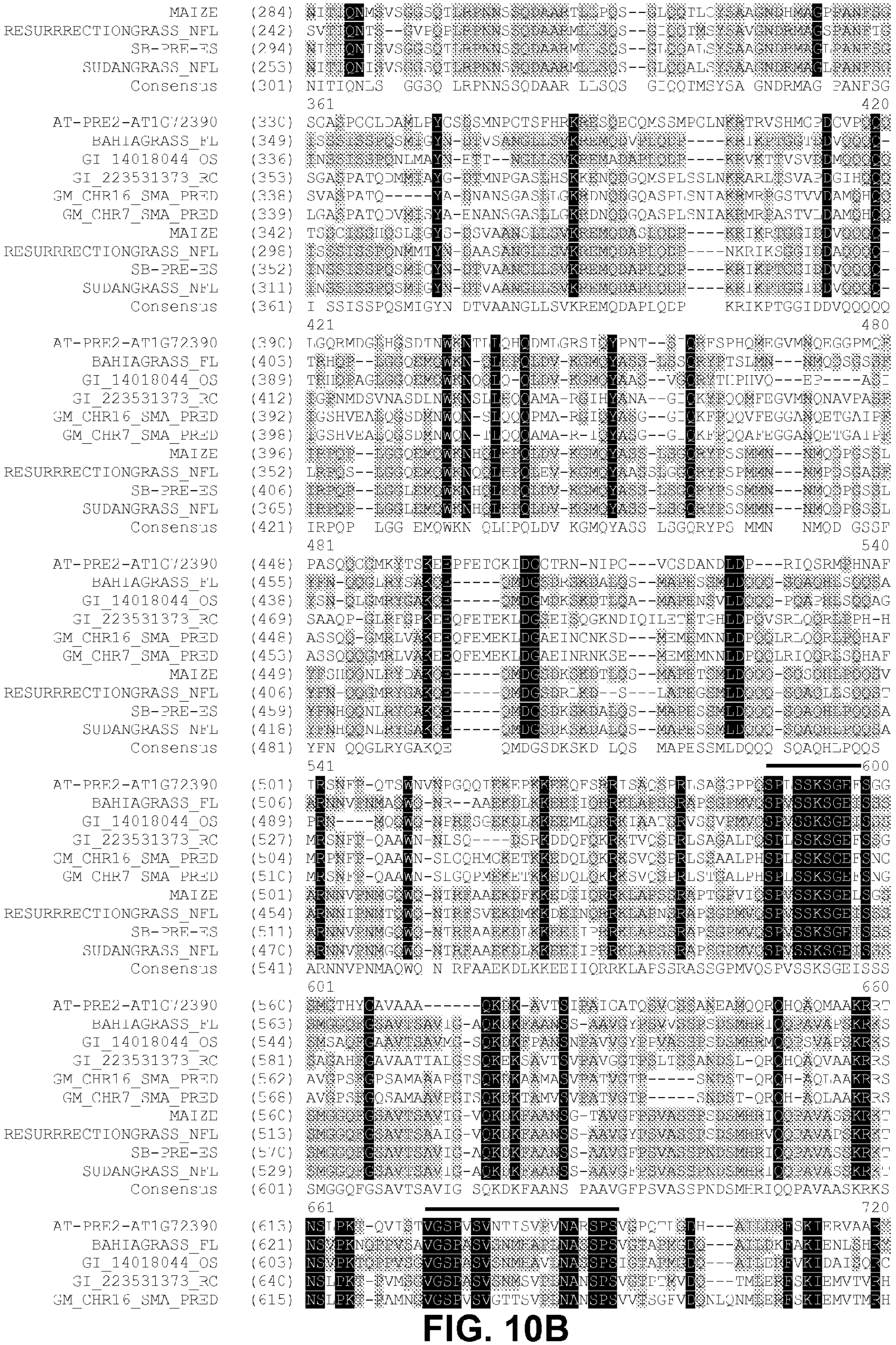

FIG. 10 (A-E) shows multiple alignment of *Arabidopsis* Pre2 peptide with monocots (Bahia, Sudan and Resurrection grasses, sorghum, rice, and maize) and other dicots (soybean and castor bean). The order of sequences shown in the alignment is SEQ ID NOS: 15, 9, 5, 22, 18, 20, 3, 13, 7 and 11. The consensus regions are shown at the end of the alignment. A few exemplary conserved regions are indicated by horizontal bars.

FIG. 11(A-C) shows conserved domain sequences from Pre2 polypeptide sequences.

Figure 12:
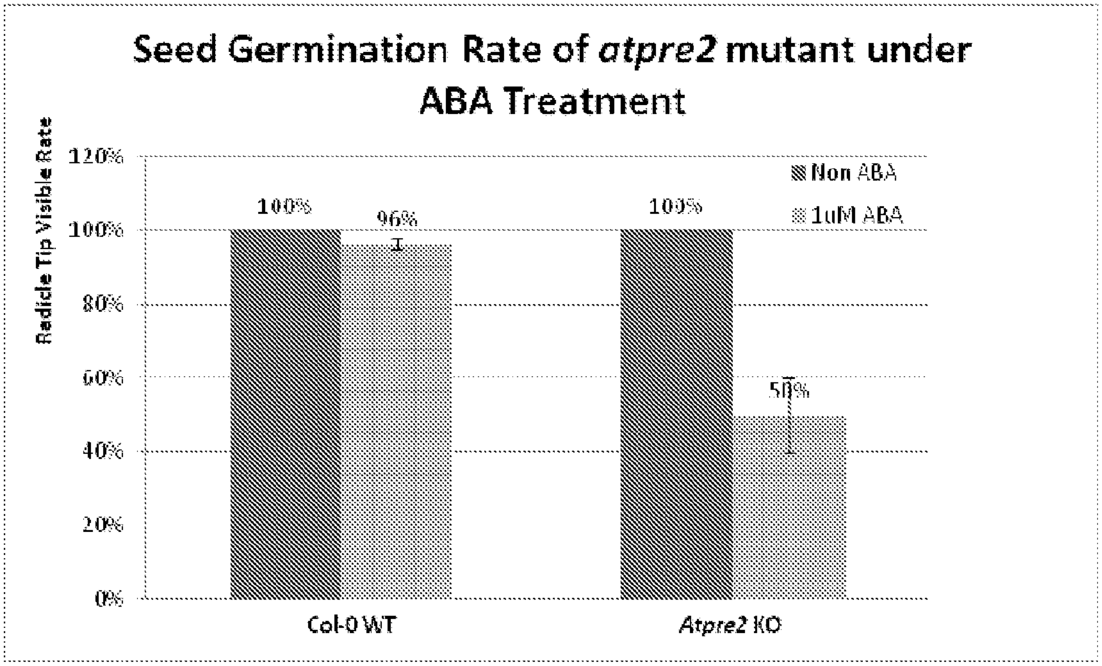

FIG. 12 shows germination rate on media containing 1 μM ABA. Col-0 and Atpre2 are represented as dark and light boxes, respectively. The data are averages of germination rate with standard deviations from three replications.

SUMMARY OF SEQ ID NOS

| Description and Abbreviation | SEQ ID NO. |
|---|---|
| Maize (ZmPre2 genomic sequence) | 1 |
| Maize (ZmPre2 cDNA sequence) | 2 |
| Maize (ZmPRE2 amino acid sequence) | 3 |
| Rice (OsPre2 cDNA) | 4 |
| Rice (OsPRE2 aa sequence) | 5 |
| Sorghum (SbPre2 cDNA) | 6 |
| Sorghum (SbPRE2_aa sequence) | 7 |
| BahiaGrass cDNA sequence | 8 |
| BahiaGrass PRE2 aa | 9 |
| SudanGrass_CDS (partial length sequence) | 10 |
| SudanGrass_aa partial length sequence | 11 |
| ResurrectionGrass CDS | 12 |
| ResurrectionGrass_aa | 13 |
| At1g72390FL cDNA *Arabidopsis* | 14 |
| AtPRE2_aa sequence | 15 |
| At1g72390genomic *Arabidopsis* | 16 |
| GM_chr16_Pre2 CDS | 17 |
| GM_chr16_Pre2 (amino acid) | 18 |
| GM_chr7_Pre2 (CDS) | 19 |
| GM_chr7_Pre2 (amino acid) | 20 |
| Castor bean Pre2 CDS | 21 |
| Castor bean PRE2 amino acid | 22 |
| BrassicaOleracea_Pre2(gi_17734666_gb_BH526581.1) CDS | 23 |
| BrassicaRapa_Pre2(PBR136351) CDS | 24 |
| Canola(PBN029307) CDS | 25 |
| Soybean GM-Pre2 (PSO423639) DNA | 26 |
| ZmPre2 TR1 (Fwd) | 49 |
| ZmPre2 TR1 (Rev) | 50 |
| Soybean Pre2 RNAi target sequence | 51 |
| Conserved Domain 1 | 27 |
| Conserved Domain 2 | 28 |
| Conserved Domain 3 | 29 |
| Conserved Domain 4 | 30 |
| Conserved Domain 5 | 31 |

| Description and Abbreviation | Consensus sequences (amino acid) | SEQ ID NO: |
|---|---|---|
| Conserved Region 1 | MSLENIVKDIPSISDNSWTYGDLMEVESKILKALQPK LHLDPTPKLDRL | 32 |
| Conserved Region 2 | SWTYGDLMEVES | 33 |
| Conserved Region 3 | SWTYGDLMEVESKILKALQP | 34 |
| Conserved Region 4 | GKKVCIDRVQESS | 35 |
| Conserved Region 5 | QSPRLSAGALPQSPLSSKSGEFS | 36 |

-continued

| Description and Abbreviation | Consensus sequences (amino acid) | SEQ ID NO: |
|---|---|---|
| Conserved Region 6 | SPLSSKSGEFS | 37 |
| Conserved Region 7 | AQLAAKRRSNSLPKT | 38 |
| Conserved Region 8 | VGSPVSVGTTSVPLNANSP | 39 |
| Conserved Region 9 | RFSKIEMVTMRHQLNFKK | 40 |
| Conserved Region 10 | LPNTHSADLLAQQFCSLMVREG | 41 |
| Conserved Region 11 | QALQMSQGLLSGVSM | 42 |
| Conserved Region 12 | SPQQMSQRTPMSPQISSGAIHAMSAGNPEACPASP QLSSQTLGSVSSITNSPM | 43 |
| Conserved Region 13 | CPASPQLSSQTLGSVSSITNSPM | 44 |
| Conserved Region 14 | HEVSFTFSLYDRGYLISKSAAMDPSQTSIQDGKTLH PYDRASEKLFSAIEAGRLPGDILDEIPSKYYNGSVVC EIRDYRKHVSNQAPASSAELGLPIVNKVRLRMTFEN VVKDITLLSDDSWSYRDFVEAEARIVRALQPELCLD PTPKLDRLCQDPVPHKLSLGIGKKRRLRQNPEVVVT SSNMSHGKKVCIDR | 45 |
| Conserved Region 15 | LCLDPTPKLDRLCQDPVPHKLSLGIGKKRRLRQNP | 46 |
| Conserved Region 16 | LCLDPTPKLDRL | 47 |
| Conserved Region 17 | QDPVPHKLSLGIGKKRRLRQNP | 48 |

The sequence descriptions and Sequence Listing attached hereto comply with the rules governing nucleotide and/or amino acid sequence disclosures in patent applications as set forth in 37 C.F.R. §1.821-1.825.

The Sequence Listing contains the one letter code for nucleotide sequence characters and the three letter codes for amino acids as defined in conformity with the IUPAC-IUBMB standards described in *Nucleic Acids Res.* 13:3021-3030 (1985) and in the *Biochemical J.* 219(2):345-373 (1984) which are herein incorporated by reference. The symbols and format used for nucleotide and amino acid sequence data comply with the rules set forth in 37 C.F.R. §1.822.

DETAILED DESCRIPTION

Pre2 nucleotide sequences and polypeptide sequences improve stress tolerance and yield of agronomically important crop plants and vegetables. Reduced expression of Pre2 mRNA results in enhanced tolerance to drought and improved utilization of nitrogen (NUE) under nitrogen limiting conditions. Suppressing of one or more Pre2 endogenous genes results in improved agronomic performance. One way of suppressing endogenous Pre2 gene expression is through RNAi. Other modes of suppression include antisense, co-suppression, promoter inverted repeats, and micro RNA. Another non-transgenic approach is to generate native variation in the expression levels of endogenous Pre2.

One or more of the plant Pre2 polypeptides disclosed herein include an Spt20 domain that is found in the Spt20 family of proteins from both human and yeast. The Spt20 protein is part of the SAGA complex which is a large complex that may be involved in histone deacetylation. Yeast Spt20 has been shown to play a role in structural integrity of the SAGA complex as no intact SAGA could be purified in spt20 deletion strains. The Spt20 domain or a sub-region thereof may be involved in DNA binding. For example, in an embodiment, the Spt20 domain comprises amino acid positions 69-227 of the castor bean Pre2 polypeptide. Relative positions in other Pre2 homologs or orthologs from one or more other species also contain this conserved region. In an embodiment, this conserved region is designated as "pfam12090".

Figure 5A:
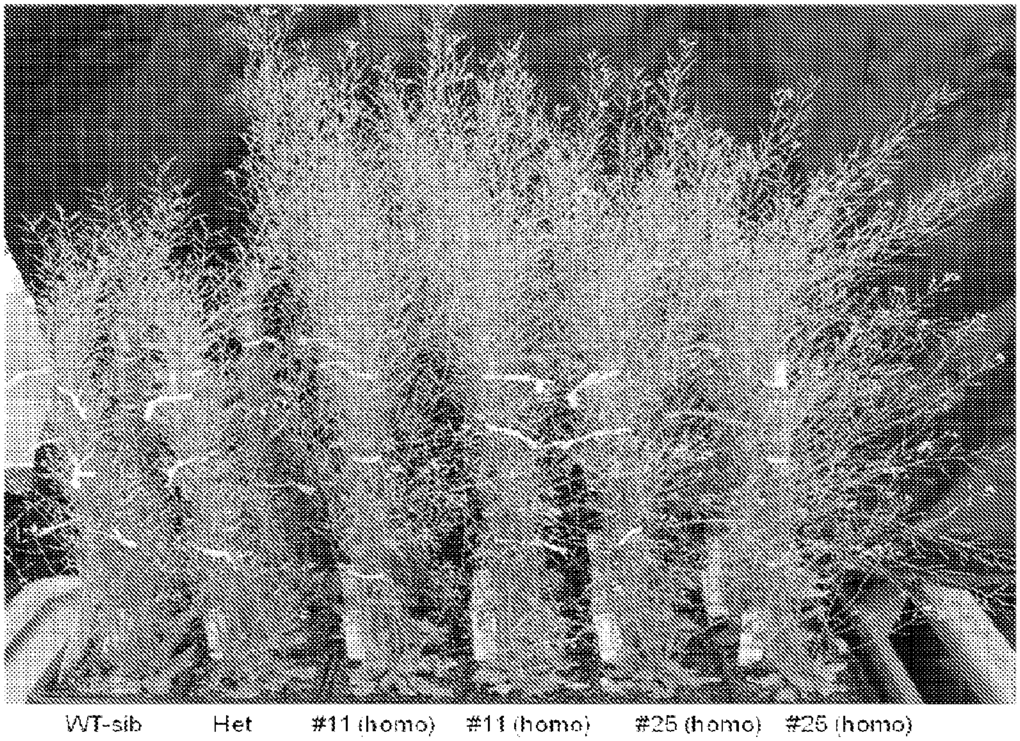
FIG. 5A shows that homozygous (pre2/pre2) knockout mutants (#11 and #25) exhibit robust growth and more siliques at flowering as compared to its both wild-type (+/+) and heterozygous (+/pre2) sibs.
Figure 5B:
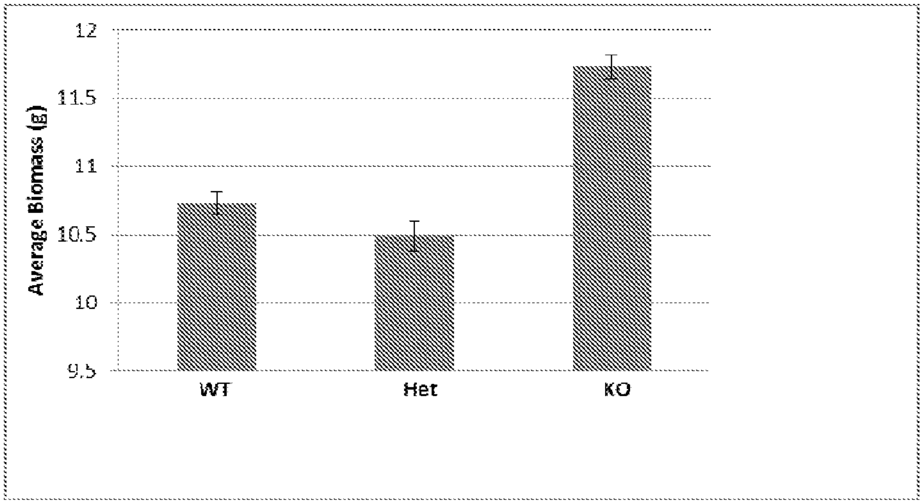
FIG. 5B shows average biomass of homozygous T-DNA knockout mutant (KO) plants is significantly higher as compared to its homozygous WT-sibs (WT) and heterozygous WT-sibs (Het).
Figures 9A, 9B:
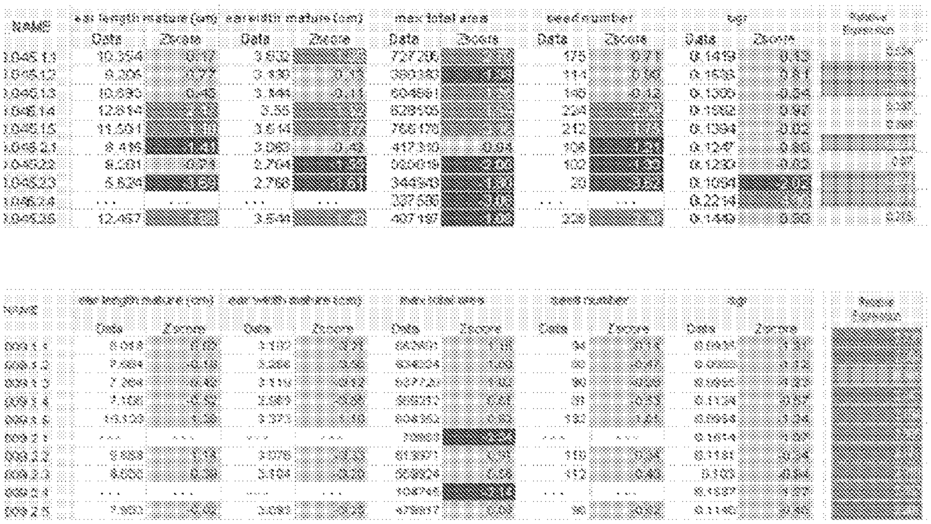
FIG. 9 shows trait summary of T0 plants for ear characteristics and seed number along with their molecular analysis (A) and the T1 reproductive assays results for three events (B). Significantly positive attributes are shown in bold.

Pre2 homozygous mutants were robust in growth with more pod numbers but were late in maturity by 4 to 5 days as compared to its WT-sibs (FIG. 5A). For measuring total biomass, 9 whole plants, each of knock out #11, knock out #25, homozygous WT, and heterozygous WT-sibs, were harvested and air dried for 14 days at room temperature. Total weight was determined by weighing and average and standard deviation were calculated for statistical analysis. The total biomass of both knockouts (combined) was found to be significantly higher (t test at $P<0.01$) when compared to both homozygous and heterozygous WT-sibs (FIG. 5B). In an embodiment, three maize gene suppression events (e.g., RNAi events namely 1.4, 1.5, and 2.5) exhibited improved agronomic parameters in an NUE Reproductive Assay in T1 generation under 4.0 mMol Nitrate-suboptimal nitrogen conditions. Two of three events (1.5 and 2.5) showed significant increase (percent change vs. Null) in silk count, ear length, ear width, and ear area (FIG. 9B). In addition to these traits, event 2.5 also showed significant difference for Days to shed and days to silk as compared to its nulls. Thus, transgenic plants where the expression of the Pre2 mRNA has been modulated exhibit significant differences in one or more agronomic parameters of interest for crop plants.

In ABA-sensitivity experiments, Atpre2 mutant showed a hypersensitive response to ABA in a dosage dependent manner. The seed germination in mutant was reduced or delayed by more than 50% as compare to wild type in presence of 1 uM ABA (FIG. x). Endogenous AT-PRE2 gene expression was higher in guard cells in wild type plants and was down-regulated by ABA treatment both in seedling and leaf based on gene expression databases. In addition AtPRE2 was also up-regulated by nitrate in roots. These results indicate a direct or indirect role of AtPRE2 in ABA and N signaling/pathway.

The disclosure of each reference set forth herein is hereby incorporated by reference in its entirety. Some of the agronomic parameters that correlate with nitrogen use efficiency analysis and/or include for e.g., root dwt (g), root: shoot dwt ratio, shoot dwt (g), shoot nitrogen (mg/g dwt), shoot total nitrogen (mg) and total plant dwt (g). Some of the variables that for nitrogen use efficiency reproductive assay include e.g., anthesis to silking interval (days), days to shed, days to silk, ear area 8 days after silk (sq cm), ear length 8 days after silk (cm), ear width 8 days after silk (cm), max total area, specific growth rate, and silk count.

As used herein and in the appended claims, the singular forms "a", "an", and "the" include plural reference unless the context clearly dictates otherwise. Thus, for example, reference to "a plant" includes a plurality of such plants, reference to "a cell" includes one or more cells and equivalents thereof known to those skilled in the art, and so forth.

As used herein:

The terms "monocot" and "monocotyledonous plant" are used interchangeably herein. A monocot of the current disclosure includes the Gramineae.

The terms "dicot" and "dicotyledonous plant" are used interchangeably herein. A dicot of the current disclosure includes the following families: Brassicaceae, Leguminosae, and Solanaceae.

The terms "full complement" and "full-length complement" are used interchangeably herein, and refer to a complement of a given nucleotide sequence, wherein the complement and the nucleotide sequence consist of the same number of nucleotides and are 100% complementary.

"*Arabidopsis*" and "*Arabidopsis thaliana*" are used interchangeably herein, unless otherwise indicated.

An "Expressed Sequence Tag" ("EST") is a DNA sequence derived from a cDNA library and therefore is a sequence which has been transcribed. An EST is typically obtained by a single sequencing pass of a cDNA insert. The sequence of an entire cDNA insert is termed the "Full-Insert Sequence" ("FIS"). A "Contig" sequence is a sequence assembled from two or more sequences that can be selected from, but not limited to, the group consisting of an EST, FIS and PCR sequence. A sequence encoding an entire or functional protein is termed a "Complete Gene Sequence" ("CGS") and can be derived from an FIS or a contig.

"Agronomic characteristic" or "agronomic parameter" is a measurable parameter including but not limited to, greenness, yield, growth rate, biomass, fresh weight at maturation, dry weight at maturation, fruit yield, seed yield, total plant nitrogen content, fruit nitrogen content, seed nitrogen content, nitrogen content in a vegetative tissue, total plant free amino acid content, fruit free amino acid content, seed free amino acid content, free amino acid content in a vegetative tissue, total plant protein content, fruit protein content, seed protein content, protein content in a vegetative tissue, drought tolerance, nitrogen uptake, root lodging, harvest index, stalk lodging, plant height, ear height, ear length, salt tolerance, early seedling vigor and seedling emergence under low temperature stress.

"Transgenic" refers to any cell, cell line, callus, tissue, plant part or plant, the genome of which has been altered by the presence of a heterologous nucleic acid, such as a recombinant DNA construct, including those initial transgenic events as well as those created by sexual crosses or asexual propagation from the initial transgenic event. The term "transgenic" as used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition or spontaneous mutation.

"Genome" as it applies to plant cells encompasses not only chromosomal DNA found within the nucleus, but organelle DNA found within subcellular components (e.g., mitochondrial, plastid) of the cell.

"Plant" includes reference to whole plants, plant organs, plant tissues, seeds and plant cells and progeny of same. Plant cells include, without limitation, cells from seeds, suspension cultures, embryos, meristematic regions, callus tissue, leaves, roots, shoots, gametophytes, sporophytes, pollen, and microspores.

"Progeny" comprises any subsequent generation of a plant.

"Transgenic plant" includes reference to a plant which comprises within its genome a heterologous polynucleotide. For example, the heterologous polynucleotide is stably integrated within the genome such that the polynucleotide is passed on to successive generations. The heterologous polynucleotide may be integrated into the genome alone or as part of a recombinant DNA construct.

"Heterologous" with respect to sequence means a sequence that originates from a foreign species, or, if from the same species, is substantially modified from its native form in composition and/or genomic locus by deliberate human intervention.

"Polynucleotide", "nucleic acid sequence", "nucleotide sequence", or "nucleic acid fragment" are used interchangeably and is a polymer of RNA or DNA that is single- or double-stranded, optionally containing synthetic, non-natural or altered nucleotide bases. Nucleotides (usually found in their 5'-monophosphate form) are referred to by their single letter designation as follows: "A" for adenylate or deoxyadenylate (for RNA or DNA, respectively), "C" for cytidylate or deoxycytidylate, "G" for guanylate or deoxyguanylate, "U" for uridylate, "T" for deoxythymidylate, "R" for purines (A or G), "Y" for pyrimidines (C or T), "K" for G or T, "H" for A or C or T, "I" for inosine and "N" for any nucleotide.

"Polypeptide", "peptide", "amino acid sequence" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers. The terms "polypeptide", "peptide", "amino acid sequence", and "protein" are also inclusive of modifications including, but not limited to, glycosylation, lipid attachment, sulfation, gamma-carboxylation of glutamic acid residues, hydroxylation and ADP-ribosylation.

"Messenger RNA (mRNA)" refers to the RNA that is without introns and that can be translated into protein by the cell.

"cDNA" refers to a DNA that is complementary to and synthesized from a mRNA template using the enzyme reverse transcriptase. The cDNA can be single-stranded or converted into the double-stranded form using the Klenow fragment of DNA polymerase I.

"Mature" protein refers to a post-translationally processed polypeptide; i.e., one from which any pre- or pro-peptides present in the primary translation product have been removed.

Nitrogen utilization efficiency (NUE) genes affect yield and have utility for improving the use of nitrogen in crop plants, especially maize. Increased nitrogen use efficiency can result from enhanced uptake and assimilation of nitrogen fertilizer and/or the subsequent remobilization and reutilization of accumulated nitrogen reserves, as well as increased tolerance of plants to stress situations such as low nitrogen environments. The genes can be used to alter the genetic composition of the plants, rendering them more productive with current fertilizer application standards or maintaining their productive rates with significantly reduced fertilizer or reduced nitrogen availability. Improving NUE in corn would increase corn harvestable yield per unit of input nitrogen fertilizer, both in developing nations where access to nitrogen fertilizer is limited and in developed nations where the level of nitrogen use remains high. Nitrogen utilization improvement also allows decreases in on-farm input costs, decreased use and dependence on the non-renewable energy sources required for nitrogen fertilizer production and reduces the environmental impact of nitrogen fertilizer manufacturing and agricultural use "Precursor" protein refers to the primary product of translation of mRNA; i.e., with pre- and pro-peptides still present. Pre- and pro-peptides may be and are not limited to intracellular localization signals.

"Isolated" refers to materials, such as nucleic acid molecules and/or proteins, which are substantially free or otherwise removed from components that normally accompany or interact with the materials in a naturally occurring environment. Isolated polynucleotides may be purified from a host cell in which they naturally occur. Conventional nucleic acid purification methods known to skilled artisans may be used to obtain isolated polynucleotides. The term also embraces recombinant polynucleotides and chemically synthesized polynucleotides.

"Recombinant" refers to an artificial combination of two otherwise separated segments of sequence, e.g., by chemical synthesis or by the manipulation of isolated segments of nucleic acids by genetic engineering techniques. "Recombinant" also includes reference to a cell or vector, that has been modified by the introduction of a heterologous nucleic acid or a cell derived from a cell so modified, but does not encompass the alteration of the cell or vector by naturally occurring events (e.g., spontaneous mutation, natural transformation/transduction/transposition) such as those occurring without deliberate human intervention.

"Recombinant DNA construct" refers to a combination of nucleic acid fragments that are not normally found together in nature. Accordingly, a recombinant DNA construct may comprise regulatory sequences and coding sequences that are derived from different sources, or regulatory sequences and coding sequences derived from the same source, but arranged in a manner different than that normally found in nature.

The terms "entry clone" and "entry vector" are used interchangeably herein.

"Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include, but are not limited to, promoters, translation leader sequences, introns, and polyadenylation recognition sequences. The terms "regulatory sequence" and "regulatory element" are used interchangeably herein.

"Promoter" refers to a nucleic acid fragment capable of controlling transcription of another nucleic acid fragment.

"Promoter functional in a plant" is a promoter capable of controlling transcription in plant cells whether or not its origin is from a plant cell.

"Tissue-specific promoter" and "tissue-preferred promoter" are used interchangeably, and refer to a promoter that is expressed predominantly but not necessarily exclusively in one tissue or organ, but that may also be expressed in one specific cell.

"Developmentally regulated promoter" refers to a promoter whose activity is determined by developmental events.

"Operably linked" refers to the association of nucleic acid fragments in a single fragment so that the function of one is regulated by the other. For example, a promoter is operably linked with a nucleic acid fragment when it is capable of regulating the transcription of that nucleic acid fragment.

"Expression" refers to the production of a functional product. For example, expression of a nucleic acid fragment may refer to transcription of the nucleic acid fragment (e.g., transcription resulting in mRNA or functional RNA) and/or translation of mRNA into a precursor or mature protein.

"Phenotype" means the detectable characteristics of a cell or organism.

"Introduced" in the context of inserting a nucleic acid fragment (e.g., a recombinant DNA construct) into a cell, means "transfection" or "transformation" or "transduction" and includes reference to the incorporation of a nucleic acid fragment into a eukaryotic or prokaryotic cell where the nucleic acid fragment may be incorporated into the genome of the cell (e.g., chromosome, plasmid, plastid or mitochondrial DNA), converted into an autonomous replicon, or transiently expressed (e.g., transfected mRNA).

A "transformed cell" is any cell into which a nucleic acid fragment (e.g., a recombinant DNA construct) has been introduced.

"Transformation" as used herein refers to both stable transformation and transient transformation.

"Stable transformation" refers to the introduction of a nucleic acid fragment into a genome of a host organism resulting in genetically stable inheritance. Once stably transformed, the nucleic acid fragment is stably integrated in the genome of the host organism and any subsequent generation.

"Transient transformation" refers to the introduction of a nucleic acid fragment into the nucleus, or DNA-containing organelle, of a host organism resulting in gene expression without genetically stable inheritance.

"Allele" is one of several alternative forms of a gene occupying a given locus on a chromosome. When the alleles present at a given locus on a pair of homologous chromosomes in a diploid plant are the same that plant is homozygous at that locus. If the alleles present at a given locus on a pair of homologous chromosomes in a diploid plant differ that plant is heterozygous at that locus. If a transgene is present on one of a pair of homologous chromosomes in a diploid plant that plant is hemizygous at that locus.

The percent identity between two amino acid or nucleic acid sequences may be determined by visual inspection and mathematical calculation.

Sequence alignments and percent identity calculations may be determined using a variety of comparison methods designed to detect homologous sequences including, but not limited to, the MEGALIGN® program of the LASERGENE® bioinformatics computing suite (DNASTAR® Inc., Madison, Wis.). Unless stated otherwise, multiple alignment of the sequences provided herein were performed using the Clustal W method of alignment (Thompson, et al., (1994). *Nucleic Acids Research* 22:4673-80) with the default parameters (GAP PENALTY=10, GAP LENGTH PENALTY=0.2, DELAY DEVERGENT SEQS (%)=30%, DNA TRANSITION WEIGHT=0.5, PROTEIN WEIGHT MATRIX "Gonnet Series").

Default parameters for pairwise alignments using the Clustal W method were SLOW-ACCURATE, GAP PENALTY=10, GAP LENGTH=0.10, PROTEIN WEIGHT MATRIX "Gonnet 250". After alignment of the sequences, using the Clustal W program, it is possible to obtain "percent identity" and "divergence" values by viewing the "sequence distances" table on the same program; unless stated otherwise, percent identities and divergences provided and claimed herein were calculated in this manner.

Alternatively, sequence alignments and percent identity calculations may be determined using a variety of comparison methods designed to detect homologous sequences including, but not limited to, the Clustal V method of alignment (Higgins and Sharp, (1989) CABIOS 5:151-153) with the default parameters (GAP PENALTY=10, GAP LENGTH PENALTY=10). Default parameters for pairwise alignments and calculation of percent identity of protein sequences using the Clustal V method are KTUPLE=1, GAP PENALTY=3, WINDOW=5 and DIAGONALS SAVED=5. For nucleic acids these parameters are KTUPLE=2, GAP PENALTY=5, WINDOW=4 and DIAGONALS SAVED=4.

Alternatively, the percent identity of two protein sequences may be determined by comparing sequence information based on the algorithm of Needleman and Wunsch, (*J. Mol. Biol.* 48:443-453, 1970) and using the GAP computer program available from the University of Wisconsin Genetics Computer Group (UWGCG). The preferred default parameters for the GAP program include: (1) a scoring matrix, blosum62, as described by Henikoff and Henikoff, (*Proc. Natl. Acad. Sci. USA* 89:10915-10919 1992); (2) a gap weight of 12; (3) a gap length weight of 4; and (4) no penalty for end gaps.

Other programs used by those skilled in the art of sequence comparison may also be used. The percent identity can be determined by comparing sequence information using, e.g., the BLAST program described by Altschul, et al., (*Nucl. Acids. Res.* 25:3389-3402 1997). This program is available on the Internet at the web site of the National Center for Biotechnology Information (NCBI) or the DNA Data Bank of Japan (DDBJ). The details of various conditions (parameters) for identity search using the BLAST program are shown on these web sites, and default values are commonly used for search although part of the settings may be changed as appropriate. Alternatively, the percent identity of two amino acid sequences may be determined by using a program such as genetic information processing software GENETYX Ver.7 (Genetyx Corporation, Japan) or using an algorithm such as FASTA. In this case, default values may be used for search.

The percent identity between two nucleic acid sequences can be determined by visual inspection and mathematical calculation, or more preferably, the comparison is done by comparing sequence information using a computer program. An exemplary, preferred computer program is the Genetic Computer Group (GCG®; Madison, Wis.) WISCONSIN PACKAGE® version 10.0 program, "GAP" (Devereux, et al., (1984) *Nucl. Acids Res.* 12:387). In addition to making a comparison between two nucleic acid sequences, this "GAP" program can be used for comparison between two amino acid sequences and between a nucleic acid sequence and an amino acid sequence. The preferred default parameters for the "GAP" program include: (1) the GCG® implementation of a unary comparison matrix (containing a value of 1 for identities and 0 for non-identities) for nucleotides, and the weighted amino acid comparison matrix of Gribskov and Burgess, (1986) *Nucl. Acids Res.* 14:6745, as described by Schwartz and Dayhoff, eds., "Atlas of Polypeptide Sequence and Structure," National Biomedical Research Foundation, pp. 353-358, (1979), or other comparable comparison matrices; (2) a penalty of 30 for each gap and an additional penalty of 1 for each symbol in each gap for amino acid sequences, or penalty of 50 for each gap and an additional penalty of 3 for each symbol in each gap for nucleotide sequences; (3) no penalty for end gaps; and (4) no maximum penalty for long gaps. Other programs used by those skilled in the art of sequence comparison can also be used, such as, for example, the BLASTN program version 2.2.7, available for use via the National Library of Medicine website, or the WU-BLAST 2.0 algorithm (Advanced Biocomputing, LLC). In addition, the BLAST algorithm uses the BLOSUM62 amino acid scoring matrix, and optional parameters that can be used are as follows: (A) inclusion of a filter to mask segments of the query sequence that have low compositional complexity (as determined by the SEG program of Wootton and Federhen (Computers and Chemistry, 1993); also see, Wootton and Federhen, (1996) *Methods Enzymol.* 266:554-71) or segments consisting of short-periodicity internal repeats (as determined by the XNU program of Clayerie and States (Computers and Chemistry, 1993)), and (B) a statistical significance threshold for reporting matches against database sequences, or E-score (the expected probability of matches being found merely by chance, according to the stochastic model of Karlin and Altschul, 1990; if the statistical significance ascribed to a match is greater than this E-score threshold, the match will not be reported); preferred E-score threshold values are 0.5, or in order of increasing preference, 0.25, 0.1, 0.05, 0.01, 0.001, 0.0001, 1e−5, 1e−10, 1e−15, 1e−20, 1e−25, 1e−30, 1e−40, 1e−50, 1e−75 or 1e−100.

Standard recombinant DNA and molecular cloning techniques used herein are well known in the art and are described more fully in Sambrook, et al., *Molecular Cloning: A Laboratory Manual*; Cold Spring Harbor Laboratory Press: Cold Spring Harbor, 1989 (hereinafter "Sambrook").

The term "consisting essentially of" in the context of a polypeptide sequence generally refers to the specified portion of the amino acid sequence and those other sequences that do not materially affect the basic and novel characteristics of the disclosed sequences herein. For example, in the context of an RNAi sequence, the term consisting essentially generally refers to that portion of the target sequence and those other nucleotide sequences that do not materially affect the binding and suppressing properties of the sequence targets disclosed herein.

Embodiments include isolated polynucleotides and polypeptides, recombinant DNA constructs useful for conferring drought tolerance, compositions (such as plants or seeds) comprising these recombinant DNA constructs, and methods utilizing these recombinant DNA constructs.

Isolated Polynucleotides and Polypeptides:

The present disclosure includes the following isolated polynucleotides and polypeptides:

An isolated polypeptide having an amino acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity, based on the Clustal W method of alignment, when compared to a sequence selected from the group consisting of SEQ ID NOS: 3, 5, 7, 9, 11, 13, 15, 18, 20 and 22. The polypeptide is preferably a PRE2 polypeptide.

An isolated polypeptide wherein the amino acid sequence is a sequence selected from the group consisting of SEQ ID NOS: 3, 5, 7, 9, 11, 13, 15, 18, 20 and 22; by alteration of one or more amino acids by at least one method selected from the group consisting of: deletion, substitution, addition and insertion; and (c) a polypeptide wherein the amino acid sequence of the polypeptide comprises a sequence selected from the group consisting of SEQ ID NOS: 3, 5, 7, 9, 11, 13, 15, 18, 20 and 22. The polypeptide is preferably a PRE2 polypeptide.

An isolated polynucleotide comprising a nucleotide sequence encoding a polypeptide with drought tolerance activity, wherein the nucleotide sequence is hybridizable under stringent conditions with a DNA molecule comprising the full complement of a sequence selected from the group consisting of SEQ ID NOS: 1, 2, 4, 6, 8, 10, 12, 14, 16, 17, 19, 21, 23-26;

An isolated polynucleotide comprising a nucleotide sequence encoding a polypeptide with drought tolerance activity, wherein the nucleotide sequence is a sequence selected from the group consisting of SEQ ID NOS: 1, 2, 4, 6, 8, 10, 12, 14, 16, 17, 19, 21, 23-26; by alteration of one or more nucleotides by at least one method selected from the group consisting of: deletion, substitution, addition and insertion.

Recombinant DNA Constructs:

In one aspect, the present disclosure includes recombinant DNA constructs.

In one embodiment, a recombinant DNA construct comprises a polynucleotide operably linked to at least one regulatory sequence (e.g., a promoter functional in a plant), wherein the polynucleotide comprises (i) a nucleic acid sequence encoding an amino acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity, based on the Clustal W method of alignment, when compared to a sequence selected from the group consisting of SEQ ID NOS: 3, 5, 7, 9, 11, 13, 15, 18, 20 and 22; or (ii) a full complement of the nucleic acid sequence of (i).

In another embodiment, a recombinant DNA construct comprises a polynucleotide operably linked to at least one regulatory sequence (e.g., a promoter functional in a plant), wherein said polynucleotide encodes a PRE2 polypeptide. The PRE2 polypeptide may be from *Arabidopsis thaliana, Zea mays, Glycine max, Glycine tabacina, Glycine soja* and *Glycine tomentella.*

It is understood, as those skilled in the art will appreciate, that the disclosure encompasses more than the specific exemplary sequences. Alterations in a nucleic acid fragment which result in the production of a chemically equivalent amino acid at a given site, but do not affect the functional properties of the encoded polypeptide, are well known in the art. For example, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the polypeptide molecule would also not be expected to alter the activity of the polypeptide. Each of the proposed modifications is well within the routine skill in the art, as is determination of retention of biological activity of the encoded products.

The protein of the current disclosure may also be a protein which comprises an amino acid sequence comprising deletion, substitution, insertion and/or addition of one or more amino acids in an amino acid sequence selected from the group consisting of SEQ ID NOS: 3, 5, 7, 9, 11, 13, 15, 18, 20 and 22. The substitution may be conservative, which means the replacement of a certain amino acid residue by another residue having similar physical and chemical characteristics. Non-limiting examples of conservative substitution include replacement between aliphatic group-containing amino acid residues such as Ile, Val, Leu or Ala, and replacement between polar residues such as Lys-Arg, Glu-Asp or Gln-Asn replacement.

Proteins derived by amino acid deletion, substitution, insertion and/or addition can be prepared when DNAs encoding their wild-type proteins are subjected to, for example, well-known site-directed mutagenesis (see, e.g., *Nucleic Acid Research,* 10(20):6487-6500, (1982), which is hereby incorporated by reference in its entirety). As used herein, the term "one or more amino acids" is intended to mean a possible number of amino acids which may be deleted, substituted, inserted and/or added by site-directed mutagenesis.

Site-directed mutagenesis may be accomplished, for example, as follows using a synthetic oligonucleotide primer that is complementary to single-stranded phage DNA to be mutated, except for having a specific mismatch (i.e., a desired mutation). Namely, the above synthetic oligonucleotide is used as a primer to cause synthesis of a complementary strand by phages, and the resulting duplex DNA is then used to transform host cells. The transformed bacterial culture is plated on agar, whereby plaques are allowed to form from phage-containing single cells. As a result, in theory, 50% of new colonies contain phages with the mutation as a single strand, while the remaining 50% have the original sequence. At a temperature which allows hybridization with DNA completely identical to one having the above desired mutation, but not with DNA having the original strand, the resulting plaques are allowed to hybridize with a synthetic probe labeled by kinase treatment. Subsequently, plaques hybridized with the probe are picked up and cultured for collection of their DNA.

Techniques for allowing deletion, substitution, insertion and/or addition of one or more amino acids in the amino acid sequences of biologically active peptides such as enzymes while retaining their activity include site-directed mutagenesis mentioned above, as well as other techniques such as those for treating a gene with a mutagen and those in which a gene is selectively cleaved to remove, substitute, insert or add a selected nucleotide or nucleotides, and then ligated. Alternatively, random mutagenesis approaches may be used to disrupt or "knock-out" the expression of a Pre2 gene using either chemical or insertional mutagenesis or irradiation. A mutagenesis and mutant identification system known as TILLING (for targeting induced local lesions in genomes) can also be used. In this method, mutations are induced in the seed of a plant of interest, for example, using EMS treatment. The resulting plants are grown and self-fertilized, and the progeny are assessed. For example, the plants may be assed using PCR to identify whether a mutated plant has a Pre2 mutation, e.g., that reduces expression of a Pre2 gene. See, e.g., Colbert, et al., (2001) *Plant Physiol* 126:480-484; McCallum, et al., (2000) *Nature Biotechnology* 18:455-457.

The term "under stringent conditions" means that two sequences hybridize under moderately or highly stringent conditions. More specifically, moderately stringent conditions can be readily determined by those having ordinary skill in the art, e.g., depending on the length of DNA. The basic conditions are set forth by Sambrook, et al., Molecular Cloning: A Laboratory Manual, Third Edition, Chapters 6 and 7, Cold Spring Harbor Laboratory Press, 2001 and include the use of a prewashing solution for nitrocellulose filters 5×SSC, 0.5% SDS, 1.0 mM EDTA (pH 8.0), hybridization conditions of about 50% formamide, 2×SSC to 6×SSC at about 40-50°

C. (or other similar hybridization solutions, such as Stark's solution, in about 50% formamide at about 42° C.) and washing conditions of, for example, about 40-60° C., 0.5-6×SSC, 0.1% SDS. Preferably, moderately stringent conditions include hybridization (and washing) at about 50° C. and 6×SSC. Highly stringent conditions can also be readily determined by those skilled in the art, e.g., depending on the length of DNA.

Generally, such conditions include hybridization and/or washing at higher temperature and/or lower salt concentration (such as hybridization at about 65° C., 6×SSC to 0.2×SSC, preferably 6×SSC, more preferably 2×SSC, most preferably 0.2×SSC), compared to the moderately stringent conditions. For example, highly stringent conditions may include hybridization as defined above, and washing at approximately 65-68° C., 0.2×SSC, 0.1% SDS. SSPE (1×SSPE is 0.15 M NaCl, 10 mM NaH2PO4, and 1.25 mM EDTA, pH 7.4) can be substituted for SSC (1×SSC is 0.15 M NaCl and 15 mM sodium citrate) in the hybridization and washing buffers; washing is performed for 15 minutes after hybridization is completed.

It is also possible to use a commercially available hybridization kit which uses no radioactive substance as a probe. Specific examples include hybridization with an ECL direct labeling & detection system (Amersham). Stringent conditions include, for example, hybridization at 42° C. for 4 hours using the hybridization buffer included in the kit, which is supplemented with 5% (w/v) Blocking reagent and 0.5 M NaCl, and washing twice in 0.4% SDS, 0.5×SSC at 55° C. for 20 minutes and once in 2×SSC at room temperature for 5 minutes.

The protein of the present disclosure is preferably a protein with drought tolerance activity.

"Suppression DNA construct" is a recombinant DNA construct which when transformed or stably integrated into the genome of the plant, results in "silencing" of a target gene in the plant. The target gene may be endogenous or transgenic to the plant. "Silencing," as used herein with respect to the target gene, refers generally to the suppression of levels of mRNA or protein/enzyme expressed by the target gene and/or the level of the enzyme activity or protein functionality. The terms "suppression", "suppressing" and "silencing", used interchangeably herein, include lowering, reducing, declining, decreasing, inhibiting, eliminating or preventing. "Silencing" or "gene silencing" does not specify mechanism and is inclusive, and not limited to, anti-sense, cosuppression, viral-suppression, hairpin suppression, stem-loop suppression, RNAi-based approaches and small RNA-based approaches.

A suppression DNA construct may comprise a region derived from a target gene of interest (e.g., Pre2) and may comprise all or part of the nucleic acid sequence of the sense strand (or antisense strand) of the target gene of interest. Depending upon the approach to be utilized, the region may be 100% identical or less than 100% identical (e.g., at least 50%, 51%, 52%, 53%, 54%, 55%, 56%, 57%, 58%, 59%, 60%, 81%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% identical) to all or part of the sense strand (or antisense strand) of the gene of interest.

For example, an RNAi target sequence includes about 20 to about 1000 contiguous bases of the disclosed Pre2 sense or anti-sense strand. In an embodiment, the target sequence includes about 50, 100, 200, 300, 400, 500, 600, 700, 800, 900, 1000, 1100 and 1200 bases of the Pre2 sense or anti-sense strand. Within those contiguous bases, there can be variations and the target RNAi sequences need not be identical and as described above, the similarity level can range from 50% to about 99%.

Suppression DNA constructs are well-known in the art, are readily constructed once the target gene of interest is selected, and include, without limitation, cosuppression constructs, antisense constructs, viral-suppression constructs, hairpin suppression constructs, stem-loop suppression constructs, double-stranded RNA-producing constructs and more generally, RNAi (RNA interference) constructs and small RNA constructs such as siRNA (short interfering RNA) constructs and miRNA (microRNA) constructs.

"Antisense inhibition" refers to the production of antisense RNA transcripts capable of suppressing the expression of the target gene or gene product. "Antisense RNA" refers to an RNA transcript that is complementary to all or part of a target primary transcript or mRNA and that blocks the expression of a target isolated nucleic acid fragment (U.S. Pat. No. 5,107,065). The complementarity of an antisense RNA may be with any part of the specific gene transcript, i.e., at the 5' non-coding sequence, 3' non-coding sequence, introns or the coding sequence.

"Cosuppression" refers to the production of sense RNA transcripts capable of suppressing the expression of the target gene or gene product. "Sense" RNA refers to RNA transcript that includes the mRNA and can be translated into protein within a cell or in vitro. Cosuppression constructs in plants have been previously designed by focusing on overexpression of a nucleic acid sequence having homology to a native mRNA, in the sense orientation, which results in the reduction of all RNA having homology to the overexpressed sequence (see, Vaucheret, et al., (1998) *Plant J.* 16:651-659 and Gura, (2000) *Nature* 404:804-808).

Another variation describes the use of plant viral sequences to direct the suppression of proximal mRNA encoding sequences (PCT Publication Number WO 1998/36083 published on Aug. 20, 1998).

Promoter inverted repeats are also suitable to suppress the expression of endogenous genes including Pre2. Such targeted promoter inactivation is possible by identifying the promoter region of Pre2 and constructing promoter inverted repeat constructs.

Genome editing or genome engineering through site-directed mutagenesis by custom meganucleases with unique DNA-recognition and cleavage properties is possible (e.g., WO 2007/047859 and WO 2009/114321). This technique provides the ability to specifically modify a defined target of interest within a genome, e.g., Pre2 genomic region. Another site-directed engineering is through the use of zinc finger domain recognition coupled with the restriction properties of restriction enzyme. See, e.g., Urnov, et al., (2010) *Nat Rev Genet.* 11(9):636-46; Shukla, et al., (2009) *Nature* 459(7245):437-41. These citations are incorporated herein to the extent they relate to materials and methods to enable genome editing through site-specific modification. Such genome editing techniques are used to engineer site-directed changes including increasing gene expression of an endogenous gene (e.g., placing an enhancer element in control of the transcription), transcriptionally silencing an endogenous gene, creating mutants, variants of the encoded polypeptide, removing one or more genomic regions and other methods to modulate the gene expression and/or its activity.

Knock-out or gene knock-out refers to an inhibition or substantial suppression of endogenous gene expression either by a transgenic or a non-transgenic approach. For example, knock-outs can be achieved by a variety of approaches including transposons, retrotransposons, deletions, substitutions, mutagenesis of the endogenous coding sequence and/or a regulatory sequence such that the expression is substantially suppressed; and any other methodology that suppresses the activity of the target of interest.

Exogenous application of nucleotides including synthetic nucleotide molecules to induce RNAi-mediated silencing of the endogenous Pre2 gene is possible. See e.g., US 2008/0248576, US 2011/0296556 and WO 2011/112570. Exogenously applied agents are capable of inducing the downregulation of the endogenous gene.

Regulatory Sequences:

A recombinant DNA construct of the present disclosure may comprise at least one regulatory sequence. A regulatory sequence may be a promoter.

A number of promoters can be used in recombinant DNA constructs of the present disclosure. The promoters can be selected based on the desired outcome, and may include constitutive, tissue-specific, inducible or other promoters for expression in the host organism.

Promoters that cause a gene to be expressed in most cell types at most times are commonly referred to as "constitutive promoters".

High level, constitutive expression of the candidate gene under control of the 35S or UBI promoter may have pleiotropic effects, although candidate gene efficacy may be estimated when driven by a constitutive promoter. Use of tissue-specific and/or stress-specific promoters may eliminate undesirable effects but retain the ability to enhance drought tolerance. This effect has been observed in *Arabidopsis* (Kasuga, et al., (1999) *Nature Biotechnol.* 17:287-91).

Suitable constitutive promoters for use in a plant host cell include, for example, the core promoter of the Rsyn7 promoter and other constitutive promoters disclosed in WO 1999/43838 and U.S. Pat. No. 6,072,050; the core CaMV 35S promoter (Odell, et al., (1985) *Nature* 313:810-812); rice actin (McElroy, et al., (1990) *Plant Cell* 2:163-171); ubiquitin (Christensen, et al., (1989) *Plant Mol. Biol.* 12:619-632 and Christensen, et al., (1992) *Plant Mol. Biol.* 18:675-689); pEMU (Last, et al., (1991) *Theor. Appl. Genet.* 81:581-588); MAS (Velten, et al., (1984) *EMBO J.* 3:2723-2730); ALS promoter (U.S. Pat. No. 5,659,026), and the like. Other constitutive promoters include, for example, those discussed in U.S. Pat. Nos. 5,608,149; 5,608,144; 5,604,121; 5,569,597; 5,466,785; 5,399,680; 5,268,463; 5,608,142 and 6,177,611.

In choosing a promoter to use in the methods of the disclosure, it may be desirable to use a tissue-specific or developmentally regulated promoter.

A tissue-specific or developmentally regulated promoter is a DNA sequence which regulates the expression of a DNA sequence selectively in the cells/tissues of a plant critical to tassel development, seed set, or both, and limits the expression of such a DNA sequence to the period of tassel development or seed maturation in the plant. Any identifiable promoter may be used in the methods of the present disclosure which causes the desired temporal and spatial expression.

Promoters which are seed or embryo-specific and may be useful in the disclosure include soybean Kunitz trypsin inhibitor (Kti3, Jofuku and Goldberg, (1989) *Plant Cell* 1:1079-1093), patatin (potato tubers) (Rocha-Sosa, et al., (1989) *EMBO J.* 8:23-29), convicilin, vicilin, and legumin (pea cotyledons) (Rerie, et al., (1991) *Mol. Gen. Genet.* 259:149-157; Newbigin, et al., (1990) *Planta* 180:461-470; Higgins, et al., (1988) *Plant. Mol. Biol.* 11:683-695), zein (maize endosperm) (Schemthaner, et al., (1988) *EMBO J.* 7:1249-1255), phaseolin (bean cotyledon) (Segupta-Gopalan, et al., (1985) *Proc. Natl. Acad. Sci. U.S.A.* 82:3320-3324), phytohemagglutinin (bean cotyledon) (Voelker, et al., (1987) *EMBO J.* 6:3571-3577), B-conglycinin and glycinin (soybean cotyledon) (Chen, et al., (1988) *EMBO J.* 7:297-302), glutelin (rice endosperm), hordein (barley endosperm) (Marris, et al., (1988) *Plant Mol. Biol.* 10:359-366), glutenin and gliadin (wheat endosperm) (Colot, et al., (1987) *EMBO J.* 6:3559-3564) and sporamin (sweet potato tuberous root) (Hattori, et al., (1990) *Plant Mol. Biol.* 14:595-604). Promoters of seed-specific genes operably linked to heterologous coding regions in chimeric gene constructions maintain their temporal and spatial expression pattern in transgenic plants. Such examples include *Arabidopsis thaliana* 2S seed storage protein gene promoter to express enkephalin peptides in *Arabidopsis* and *Brassica napus* seeds (Vanderkerckhove, et al., (1989) *Bio/Technology* 7:L929-932), bean lectin and bean beta-phaseolin promoters to express luciferase (Riggs, et al., (1989) *Plant Sci.* 63:47-57) and wheat glutenin promoters to express chloramphenicol acetyl transferase (Colot, et al., (1987) *EMBO J.* 6:3559-3564).

Inducible promoters selectively express an operably linked DNA sequence in response to the presence of an endogenous or exogenous stimulus, for example by chemical compounds (chemical inducers) or in response to environmental, hormonal, chemical and/or developmental signals. Inducible or regulated promoters include, for example, promoters regulated by light, heat, stress, flooding or drought, phytohormones, wounding or chemicals such as ethanol, jasmonate, salicylic acid or safeners.

Promoters for use in the current disclosure include the following: 1) the stress-inducible RD29A promoter (Kasuga, et al., (1999) *Nature Biotechnol.* 17:287-91); 2) the barley promoter, B22E; expression of B22E is specific to the pedicel in developing maize kernels (Klemsdal, et al., (1991) *Mol. Gen. Genet.* 228 (1/2):9-16) and 3) maize promoter, Zag2 (Schmidt, et al., (1993) *Plant Cell* 5(7):729-737; Theissen, et al., (1995) *Gene* 156(2):155-166; NCBI GenBank Accession Number X80206)). Zag2 transcripts can be detected 5 days prior to pollination to 7 to 8 days after pollination ("DAP"), and directs expression in the carpel of developing female inflorescences and Ciml which is specific to the nucleus of developing maize kernels. Ciml transcript is detected 4 to 5 days before pollination to 6 to 8 DAP. Other useful promoters include any promoter which can be derived from a gene whose expression is maternally associated with developing female florets.

Additional promoters for regulating the expression of the nucleotide sequences of the present disclosure in plants are stalk-specific promoters. Such stalk-specific promoters include the alfalfa S2A promoter (GenBank Accession Number EF030816; Abrahams, et al., (1995) *Plant Mol. Biol.* 27:513-528) and S2B promoter (GenBank Accession Number EF030817) and the like, herein incorporated by reference.

Promoters may be derived in their entirety from a native gene or be composed of different elements derived from different promoters found in nature or even comprise synthetic DNA segments.

Promoters for use in the current disclosure may include: RIP2, mLIP15, ZmCOR1, Rab17, CaMV 35S, RD29A, B22E, Zag2, SAM synthetase, ubiquitin, CaMV 19S, nos, Adh, sucrose synthase, R-allele, the vascular tissue preferred promoters S2A (Genbank Accession Number EF030816) and S2B (Genbank Accession Number EF030817) and the constitutive promoter GOS2 from *Zea mays*. Other promoters include root preferred promoters, such as the maize NAS2 promoter, the maize Cyclo promoter (US 2006/0156439, published Jul. 13, 2006), the maize ROOTMET2 promoter (WO 2005/063998, published Jul. 14, 2005), the CR1BIO promoter (WO 2006/055487, published May 26, 2006), the CRWAQ81 (WO 2005/035770, published Apr. 21, 2005) and the maize ZRP2.47 promoter (NCBI Accession Number: U38790; GI Number 1063664).

Recombinant DNA constructs of the present disclosure may also include other regulatory sequences, including but not limited to, translation leader sequences, introns, and polyadenylation recognition sequences. In another embodiment of the present disclosure, a recombinant DNA construct of the present disclosure further comprises an enhancer or silencer.

An intron sequence can be added to the 5' untranslated region, the protein-coding region or the 3' untranslated region to increase the amount of the mature message that accumulates in the cytosol. Inclusion of a spliceable intron in the transcription unit in both plant and animal expression constructs has been shown to increase gene expression at both the mRNA and protein levels up to 1000-fold. Buchman and Berg, (1988) *Mol. Cell Biol.* 8:4395-4405; Callis, et al., (1987) *Genes Dev.* 1:1183-1200.

Any plant can be selected for the identification of regulatory sequences and PRE2 polypeptide genes to be used in recombinant DNA constructs of the present disclosure. Examples of suitable plant targets for the isolation of genes and regulatory sequences would include but are not limited to alfalfa, apple, apricot, *Arabidopsis*, artichoke, arugula, asparagus, avocado, banana, barley, beans, beet, blackberry, blueberry, broccoli, brussels sprouts, cabbage, canola, cantaloupe, carrot, cassava, castorbean, cauliflower, celery, cherry, chicory, cilantro, citrus, clementines, clover, coconut, coffee, corn, cotton, cranberry, cucumber, Douglas fir, eggplant, endive, escarole, eucalyptus, fennel, figs, garlic, gourd, grape, grapefruit, honey dew, jicama, kiwifruit, lettuce, leeks, lemon, lime, Loblolly pine, linseed, mango, melon, mushroom, nectarine, nut, oat, oil palm, oil seed rape, okra, olive, onion, orange, an ornamental plant, palm, papaya, parsley, parsnip, pea, peach, peanut, pear, pepper, persimmon, pine, pineapple, plantain, plum, pomegranate, poplar, potato, pumpkin, quince, radiata pine, radicchio, radish, rapeseed, raspberry, rice, rye, sorghum, Southern pine, soybean, spinach, squash, strawberry, sugarbeet, sugarcane, sunflower, sweet potato, sweetgum, tangerine, tea, tobacco, tomato, triticale, turf, turnip, a vine, watermelon, wheat, yams and zucchini.

Compositions:

A composition of the present disclosure is a plant comprising in its genome any of the recombinant DNA constructs of the present disclosure (such as any of the constructs discussed above). Compositions also include any progeny of the plant, and any seed obtained from the plant or its progeny, wherein the progeny or seed comprises within its genome the recombinant DNA construct. Progeny includes subsequent generations obtained by self-pollination or out-crossing of a plant. Progeny also includes hybrids and inbreds.

In hybrid seed propagated crops, mature transgenic plants can be self-pollinated to produce a homozygous inbred plant. The inbred plant produces seed containing the newly introduced recombinant DNA construct. These seeds can be grown to produce plants that would exhibit an altered agronomic characteristic (e.g., an increased agronomic characteristic optionally under water limiting conditions), or used in a breeding program to produce hybrid seed, which can be grown to produce plants that would exhibit such an altered agronomic characteristic. The seeds may be maize seeds.

The plant may be a monocotyledonous or dicotyledonous plant, for example, a maize, rice or soybean plant, such as a maize hybrid plant or a maize inbred plant. The plant may also be sunflower, sorghum, canola, wheat, alfalfa, cotton, barley, millet, sugarcane, switchgrass, tobacco, potato and sugar beet.

The recombinant DNA construct may be stably integrated into the genome of the plant.

Particularly embodiments include but are not limited to the following:

1. A plant (for example, a maize, rice or soybean plant) comprising in its genome a recombinant DNA construct comprising a polynucleotide operably linked to at least one regulatory sequence, wherein said polynucleotide encodes a polypeptide having an amino acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity, based on the Clustal W method of alignment, when compared to a sequence selected from the group consisting of SEQ ID NOS: 3, 5, 7, 9, 11, 13, 15, 18, 20 and 22; and wherein said plant exhibits increased drought tolerance when compared to a control plant not comprising said recombinant DNA construct. The plant may further exhibit an alteration of at least one agronomic characteristic when compared to the control plant.

2. A plant (for example, a maize, rice or soybean plant) comprising in its genome a recombinant DNA construct comprising a polynucleotide operably linked to at least one regulatory sequence, wherein said polynucleotide encodes a PRE2 polypeptide, and wherein said plant exhibits increased drought tolerance when compared to a control plant not comprising said recombinant DNA construct. The plant may further exhibit an alteration of at least one agronomic characteristic when compared to the control plant.

3. A plant (for example, a maize, rice or soybean plant) comprising in its genome a recombinant DNA construct comprising a polynucleotide operably linked to at least one regulatory sequence, wherein said polynucleotide encodes a PRE2 polypeptide, and wherein said plant exhibits an alteration of at least one agronomic characteristic when compared to a control plant not comprising said recombinant DNA construct.

4. A plant (for example, a maize, rice or soybean plant) comprising in its genome a recombinant DNA construct comprising a polynucleotide operably linked to at least one regulatory element, wherein said polynucleotide encodes a polypeptide having an amino acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity, based on the Clustal W method of alignment, when compared to a sequence selected from the group consisting of SEQ ID NOS: 1, 2, 4, 6, 8, 10, 12, 14, 16, 17, 19, 21, 23-26, and wherein said plant exhibits an alteration of at least one agronomic characteristic when compared to a control plant not comprising said recombinant DNA construct.

5. A plant (for example, a maize, rice or soybean plant) comprising in its genome a recombinant DNA construct comprising a polynucleotide operably linked to at least one regulatory element, wherein said polynucleotide comprises a nucleotide sequence encoding a polypeptide with drought tolerance activity, wherein the nucleotide sequence is: (a) hybridizable under stringent conditions with a DNA molecule comprising the full complement of a sequence selected from the group consisting of SEQ ID NOS: 1, 2, 4, 6, 8, 10, 12, 14, 16, 17, 19, 21, 23-26; or (b) a sequence selected from the group consisting of SEQ ID NOS: 1, 2, 4, 6, 8, 10, 12, 14, 16, 17, 19, 21, 23-26; by alteration of one or more nucleotides by at least one method selected from the group consisting of: deletion, substitution, addition and insertion; and wherein said plant exhibits increased drought tolerance when compared to a control plant not comprising said recombinant DNA construct.

6. A plant (for example, a maize, rice or soybean plant) comprising in its genome a recombinant DNA construct comprising a polynucleotide operably linked to at least one regulatory element, wherein said polynucleotide comprises a nucleotide sequence encoding a polypeptide with drought tolerance activity, wherein the nucleotide sequence is: (a) hybridizable under stringent conditions with a DNA molecule comprising the full complement of a sequence selected from the group consisting of SEQ ID NOS: 1, 2, 4, 6, 8, 10, 12, 14, 16, 17, 19, 21, 23-26; or (b) a sequence selected from the group consisting of SEQ ID NOS: 1, 2, 4, 6, 8, 10, 12, 14, 16, 17, 19, 21, 23-26; by alteration of one or more nucleotides by at least one method selected from the group consisting of: deletion, substitution, addition and insertion; and wherein said plant exhibits an alteration of at least one agronomic characteristic when compared to a control plant not comprising said recombinant DNA construct.

8. Any progeny of the above plants in embodiments 1-7, any seeds of the above plants in embodiments 1-7, any seeds of progeny of the above plants in embodiments 1-7, and cells from any of the above plants in embodiments 1-6 and progeny thereof.

In any of the foregoing embodiments 1-8 or any other embodiments of the present disclosure, the PRE2 polypeptide may be from *Arabidopsis thaliana, Zea mays, Glycine max, Glycine tabacina, Glycine soja* or *Glycine tomentella.*

In any of the foregoing embodiments 1-8 or any other embodiments of the present disclosure, the recombinant DNA construct may comprise at least a promoter functional in a plant as a regulatory sequence.

In any of the foregoing embodiments 1-8 or any other embodiments of the present disclosure, the alteration of at least one agronomic characteristic is either an increase or decrease.

In any of the foregoing embodiments 1-8 or any other embodiments of the present disclosure, the at least one agronomic characteristic may be selected from the group consisting of greenness, yield, growth rate, biomass, fresh weight at maturation, dry weight at maturation, fruit yield, seed yield, total plant nitrogen content, fruit nitrogen content, seed nitrogen content, nitrogen content in a vegetative tissue, total plant free amino acid content, fruit free amino acid content, seed free amino acid content, free amino acid content in a vegetative tissue, total plant protein content, fruit protein content, seed protein content, protein content in a vegetative tissue, drought tolerance, nitrogen uptake, root lodging, harvest index, stalk lodging, plant height, ear height, ear length, salt tolerance, early seedling vigor and seedling emergence under low temperature stress. For example, the alteration of at least one agronomic characteristic may be an increase in yield, greenness or biomass.

In any of the foregoing embodiments 1-8 or any other embodiments of the present disclosure, the plant may exhibit the alteration of at least one agronomic characteristic when compared, under water limiting conditions, to a control plant not comprising said recombinant DNA construct.

"Drought" refers to a decrease in water availability to a plant that, especially when prolonged, can cause damage to the plant or prevent its successful growth (e.g., limiting plant growth or seed yield).

"Drought tolerance" is a trait of a plant to survive under drought conditions over prolonged periods of time without exhibiting substantial physiological or physical deterioration.

"Increased drought tolerance" of a plant is measured relative to a reference or control plant, and is a trait of the plant to survive under drought conditions over prolonged periods of time, without exhibiting the same degree of physiological or physical deterioration relative to the reference or control plant grown under similar drought conditions. Typically, when a transgenic plant comprising a recombinant DNA construct in its genome exhibits increased drought tolerance relative to a reference or control plant, the reference or control plant does not comprise in its genome the recombinant DNA construct.

One of ordinary skill in the art is familiar with protocols for simulating drought conditions and for evaluating drought tolerance of plants that have been subjected to simulated or naturally-occurring drought conditions. For example, one can simulate drought conditions by giving plants less water than normally required or no water over a period of time, and one can evaluate drought tolerance by looking for differences in physiological and/or physical condition, including (but not limited to) vigor, growth, size, or root length, or in particular, leaf color or leaf area size. Other techniques for evaluating drought tolerance include measuring chlorophyll fluorescence, photosynthetic rates and gas exchange rates.

A drought stress experiment may involve a chronic stress (i.e., slow dry down) and/or may involve two acute stresses (i.e., abrupt removal of water) separated by a day or two of recovery. Chronic stress may last 8-10 days. Acute stress may last 3-5 days. The following variables may be measured during drought stress and well watered treatments of transgenic plants and relevant control plants:

The variable "% area chg_start chronic-acute2" is a measure of the percent change in total area determined by remote visible spectrum imaging between the first day of chronic stress and the day of the second acute stress The variable "% area chg_start chronic-end chronic" is a measure of the percent change in total area determined by remote visible spectrum imaging between the first day of chronic stress and the last day of chronic stress.

The variable "% area chg_start chronic-harvest" is a measure of the percent change in total area determined by remote visible spectrum imaging between the first day of chronic stress and the day of harvest.

The variable "% area chg_start chronic-recovery24 hr" is a measure of the percent change in total area determined by remote visible spectrum imaging between the first day of chronic stress and 24 hrs into the recovery (24 hrs after acute stress 2).

The variable "psii_acute1" is a measure of Photosystem II (PSII) efficiency at the end of the first acute stress period. It provides an estimate of the efficiency at which light is absorbed by PSII antennae and is directly related to carbon dioxide assimilation within the leaf.

The variable "psii_acute2" is a measure of Photosystem II (PSII) efficiency at the end of the second acute stress period. It provides an estimate of the efficiency at which light is absorbed by PSII antennae and is directly related to carbon dioxide assimilation within the leaf.

The variable "fv/fm_acute1" is a measure of the optimum quantum yield (Fv/Fm) at the end of the first acute stress–(variable fluorescence difference between the maximum and minimum fluorescence/maximum fluorescence).

The variable "fv/fm_acute2" is a measure of the optimum quantum yield (Fv/Fm) at the end of the second acute stress–(variable flourescence difference between the maximum and minimum fluorescence/maximum fluorescence).

The variable "leaf rolling_harvest" is a measure of the ratio of top image to side image on the day of harvest.

The variable "leaf rolling_recovery24 hr" is a measure of the ratio of top image to side image 24 hours into the recovery.

The variable "Specific Growth Rate (SGR)" represents the change in total plant surface area (as measured by an imaging instrument) over a single day ($Y(t)=Y0*e^{r*t}$). $Y(t)=Y0*e^{r*t}$ is equivalent to % change in $Y/\Delta t$ where the individual terms are as follows: Y(t)=Total surface area at t; Y0=Initial total surface area (estimated); r=Specific Growth Rate $day^{-1}$, and t=Days After Planting ("DAP").

The variable "shoot dry weight" is a measure of the shoot weight 96 hours after being placed into a 104° C. oven.

The variable "shoot fresh weight" is a measure of the shoot weight immediately after being cut from the plant.

The Examples below describe some representative protocols and techniques for simulating drought conditions and/or evaluating drought tolerance.

One can also evaluate drought tolerance by the ability of a plant to maintain sufficient yield (at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% yield) in field testing under simulated or naturally-occurring drought conditions (e.g., by measuring for substantially equivalent yield under drought conditions compared to non-drought conditions, or by measuring for less yield loss under drought conditions compared to a control or reference plant).

One of ordinary skill in the art would readily recognize a suitable control or reference plant to be utilized when assessing or measuring an agronomic characteristic or phenotype of a transgenic plant in any embodiment of the present disclosure in which a control plant is utilized (e.g., compositions or methods as described herein). For example, by way of non-limiting illustrations:

1. Progeny of a transformed plant which is hemizygous with respect to a recombinant DNA construct, such that the progeny are segregating into plants either comprising or not comprising the recombinant DNA construct: the progeny comprising the recombinant DNA construct would be typically measured relative to the progeny not comprising the recombinant DNA construct (i.e., the progeny not comprising the recombinant DNA construct is the control or reference plant).

2. Introgression of a recombinant DNA construct into an inbred line, such as in maize, or into a variety, such as in soybean: the introgressed line would typically be measured relative to the parent inbred or variety line (i.e., the parent inbred or variety line is the control or reference plant).

3. Two hybrid lines, where the first hybrid line is produced from two parent inbred lines and the second hybrid line is produced from the same two parent inbred lines except that one of the parent inbred lines contains a recombinant DNA construct: the second hybrid line would typically be measured relative to the first hybrid line (i.e., the first hybrid line is the control or reference plant).

4. A plant comprising a recombinant DNA construct: the plant may be assessed or measured relative to a control plant not comprising the recombinant DNA construct but otherwise having a comparable genetic background to the plant (e.g., sharing at least 90%, 91%, 92%, 93%, 94%, 95%, 96%, 97%, 98%, 99% or 100% sequence identity of nuclear genetic material compared to the plant comprising the recombinant DNA construct. There are many laboratory-based techniques available for the analysis, comparison and characterization of plant genetic backgrounds; among these are Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length Polymorphisms (AFLP®s) and Simple Sequence Repeats (SSRs) which are also referred to as Microsatellites.

Furthermore, one of ordinary skill in the art would readily recognize that a suitable control or reference plant to be utilized when assessing or measuring an agronomic characteristic or phenotype of a transgenic plant would not include a plant that had been previously selected, via mutagenesis or transformation, for the desired agronomic characteristic or phenotype.

Methods:

Methods include but are not limited to methods for increasing drought tolerance in a plant, methods for evaluating drought tolerance in a plant, methods for altering an agronomic characteristic in a plant, methods for determining an alteration of an agronomic characteristic in a plant, and methods for producing seed. The plant may be a monocotyledonous or dicotyledonous plant, for example, a maize, rice or soybean plant. The plant may also be sunflower, sorghum, canola, wheat, alfalfa, cotton, barley or millet. The seed may be a maize, rice or soybean seed, for example, a maize hybrid seed or maize inbred seed.

Methods include but are not limited to the following:

A method for transforming a cell comprising transforming a cell with any of the isolated polynucleotides of the present disclosure. The cell transformed by this method is also included. In particular embodiments, the cell is eukaryotic cell, e.g., a yeast, insect or plant cell or prokaryotic, e.g., a bacterial cell.

A method for producing a transgenic plant comprising transforming a plant cell with any of the isolated polynucleotides or recombinant DNA constructs of the present disclosure and regenerating a transgenic plant from the transformed plant cell. The disclosure is also directed to the transgenic plant produced by this method and transgenic seed obtained from this transgenic plant.

A method for isolating a polypeptide of the disclosure from a cell or culture medium of the cell, wherein the cell comprises a recombinant DNA construct comprising a polynucleotide of the disclosure operably linked to at least one regulatory sequence and wherein the transformed host cell is grown under conditions that are suitable for expression of the recombinant DNA construct.

A method of altering the level of expression of a polypeptide of the disclosure in a host cell comprising: (a) transforming a host cell with a recombinant DNA construct of the present disclosure; and (b) growing the transformed host cell under conditions that are suitable for expression of the recombinant DNA construct wherein expression of the recombinant DNA construct results in production of altered levels of the polypeptide of the disclosure in the transformed host cell.

A method of increasing drought tolerance in a plant, comprising: (a) introducing into a regenerable plant cell a recombinant DNA construct comprising a polynucleotide operably linked to at least one regulatory sequence (for example, a promoter functional in a plant), wherein the polynucleotide encodes a polypeptide having an amino acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity, based on the Clustal W method of alignment, when compared to a sequence selected from the group consisting of SEQ ID NOS: 3, 5, 7, 9, 11, 13, 15, 18, 20 and 22; and (b) regenerating a transgenic plant from the regenerable plant cell after step (a), wherein the transgenic plant comprises in its genome the recombinant DNA construct and exhibits increased drought tolerance when compared to a control plant not comprising the recombinant DNA construct. The method may further comprise (c) obtaining a progeny plant derived from the transgenic plant, wherein said progeny plant comprises in its genome the recombinant DNA construct and exhibits increased drought tolerance when compared to a control plant not comprising the recombinant DNA construct.

A method of increasing drought tolerance in a plant, comprising: (a) introducing into a regenerable plant cell a recombinant DNA construct comprising a polynucleotide operably linked to at least one regulatory element, wherein said polynucleotide comprises a nucleotide sequence encoding a polypeptide with drought tolerance activity, wherein the nucleotide sequence is: (a) hybridizable under stringent conditions with a DNA molecule comprising the full complement of a sequence selected from the group consisting of SEQ ID NOS: 1, 2, 4, 6, 8, 10, 12, 14, 16, 17, 19, 21, 23-26; or (b) a sequence selected from the group consisting of SEQ ID NOS: 1, 2, 4, 6, 8, 10, 12, 14, 16, 17, 19, 21, 23-26; by alteration of one or more nucleotides by at least one method selected from the group consisting of: deletion, substitution, addition and insertion; and (b) regenerating a transgenic plant from the regenerable plant cell after step (a), wherein the transgenic plant comprises in its genome the recombinant DNA construct and exhibits increased drought tolerance when compared to a control plant not comprising the recombinant DNA construct. The method may further comprise (c) obtaining a progeny plant derived from the transgenic plant, wherein said progeny plant comprises in its genome the recombinant DNA construct and exhibits increased drought tolerance when compared to a control plant not comprising the recombinant DNA construct.

A method of evaluating drought tolerance in a plant, comprising (a) obtaining a transgenic plant, wherein the transgenic plant comprises in its genome a recombinant DNA construct comprising a polynucleotide operably linked to at least one regulatory sequence (for example, a promoter functional in a plant), wherein said polynucleotide encodes a polypeptide having an amino acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity, based on the Clustal W method of alignment, when compared to a sequence selected from the group consisting of SEQ ID NOS: 3, 5, 7, 9, 11, 13, 15, 18, 20 and 22; (b) obtaining a progeny plant derived from said transgenic plant, wherein the progeny plant comprises in its genome the recombinant DNA construct; and (c) evaluating the progeny plant for drought tolerance compared to a control plant not comprising the recombinant DNA construct.

A method of evaluating drought tolerance in a plant, comprising (a) obtaining a transgenic plant, wherein the transgenic plant comprises in its genome a recombinant DNA construct comprising a polynucleotide operably linked to at least one regulatory element, wherein said polynucleotide comprises a nucleotide sequence encoding a polypeptide with drought tolerance activity, wherein the nucleotide sequence is: (a) hybridizable under stringent conditions with a DNA molecule comprising the full complement of a sequence selected from the group consisting of SEQ ID NOS: 1, 2, 4, 6, 8, 10, 12, 14, 16, 17, 19, 21, 23-26; or (b) a sequence selected from the group consisting of SEQ ID NOS: 1, 2, 4, 6, 8, 10, 12, 14, 16, 17, 19, 21, 23-26; by alteration of one or more nucleotides by at least one method selected from the group consisting of: deletion, substitution, addition and insertion; (b) obtaining a progeny plant derived from said transgenic plant, wherein the progeny plant comprises in its genome the recombinant DNA construct; and (c) evaluating the progeny plant for drought tolerance compared to a control plant not comprising the recombinant DNA construct.

A method of determining an alteration of an agronomic characteristic in a plant, comprising (a) obtaining a transgenic plant, wherein the transgenic plant comprises in its genome a recombinant DNA construct comprising a polynucleotide operably linked to at least one regulatory sequence (for example, a promoter functional in a plant), wherein said polynucleotide encodes a polypeptide having an amino acid sequence of at least 50%, 51%, 52%, 53%, 54%, 55%, 56%, 57%, 58%, 59%, 60%, 81%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity, based on the Clustal W method of alignment, when compared to a sequence selected from the group consisting of SEQ ID NOS: 3, 5, 7, 9, 11, 13, 15, 18, 20 and 22; (b) obtaining a progeny plant derived from said transgenic plant, wherein the progeny plant comprises in its genome the recombinant DNA construct; and (c) determining whether the progeny plant exhibits an alteration in at least one agronomic characteristic when compared, optionally under water limiting conditions, to a control plant not comprising the recombinant DNA construct.

A method of determining an alteration of an agronomic characteristic in a plant, comprising (a) obtaining a transgenic plant, wherein the transgenic plant comprises in its genome a recombinant DNA construct comprising a polynucleotide operably linked to at least one regulatory element, wherein said polynucleotide comprises a nucleotide sequence encoding a polypeptide with drought tolerance activity, wherein the nucleotide sequence is: (a) hybridizable under stringent conditions with a DNA molecule comprising the full complement of a sequence selected from the group consisting of SEQ ID NOS: 1, 2, 4, 6, 8, 10, 12, 14, 16, 17, 19, 21, 23-26; or (b) a sequence selected from the group consisting of SEQ ID NOS: 1, 2, 4, 6, 8, 10, 12, 14, 16, 17, 19, 21, 23-26; by alteration of one or more nucleotides by at least one method selected from the group consisting of: deletion, substitution, addition and insertion; (b) obtaining a progeny plant derived from said transgenic plant, wherein the progeny plant comprises in its genome the recombinant DNA construct; and (c) determining whether the progeny plant exhibits an alteration in at least one agronomic characteristic when compared, optionally under water limiting conditions, to a control plant not comprising the recombinant DNA construct.

A method of producing seed (for example, seed that can be sold as a drought tolerant product offering) comprising any of the preceding methods and further comprising obtaining seeds from said progeny plant, wherein said seeds comprise in their genome said recombinant DNA construct.

In any of the preceding methods or any other embodiments of methods of the present disclosure, in said introducing step said regenerable plant cell may comprise a callus cell, an embryogenic callus cell, a gametic cell, a meristematic cell or a cell of an immature embryo. The regenerable plant cells may derive from an inbred maize plant.

In any of the preceding methods or any other embodiments of methods of the present disclosure, said regenerating step may comprise the following: (i) culturing said transformed plant cells in a media comprising an embryogenic promoting hormone until callus organization is observed; (ii) transferring said transformed plant cells of step (i) to a first media which includes a tissue organization promoting hormone; and (iii) subculturing said transformed plant cells after step (ii) onto a second media, to allow for shoot elongation, root development or both.

In any of the preceding methods or any other embodiments of methods of the present disclosure, the at least one agronomic characteristic may be selected from the group consisting of greenness, yield, growth rate, biomass, fresh weight at maturation, dry weight at maturation, fruit yield, seed yield, total plant nitrogen content, fruit nitrogen content, seed nitrogen content, nitrogen content in a vegetative tissue, total plant free amino acid content, fruit free amino acid content, seed free amino acid content, amino acid content in a vegetative tissue, total plant protein content, fruit protein content, seed protein content, protein content in a vegetative tissue, drought tolerance, nitrogen uptake, root lodging, harvest index, stalk lodging, plant height, ear height, ear length, salt tolerance, early seedling vigor and seedling emergence under low temperature stress. The alteration of at least one agronomic characteristic may be an increase in yield, greenness or biomass.

In any of the preceding methods or any other embodiments of methods of the present disclosure, the plant may exhibit the alteration of at least one agronomic characteristic when compared, under water limiting conditions, to a control plant not comprising said recombinant DNA construct.

In any of the preceding methods or any other embodiments of methods of the present disclosure, alternatives exist for introducing into a regenerable plant cell a recombinant DNA construct comprising a polynucleotide operably linked to at least one regulatory sequence. For example, one may introduce into a regenerable plant cell a regulatory sequence (such as one or more enhancers, optionally as part of a transposable element) and then screen for an event in which the regulatory sequence is operably linked to an endogenous gene encoding a polypeptide of the instant disclosure.

Transgenic plants comprising or derived from plant cells or native plants with reduced Pre2 expression or activity of this disclosure can be further enhanced with stacked traits, e.g. a crop plant having an enhanced trait resulting from expression of DNA disclosed herein in combination with herbicide tolerance and/or pest resistance traits. For example, plants with reduced Pre2 expression can be stacked with other traits of agronomic interest, such as a trait providing herbicide resistance and/or insect resistance, such as using a gene from *Bacillus thuringensis* to provide resistance against one or more of lepidopteran, coliopteran, homopteran, hemiopteran and other insects. Known genes that confer tolerance to herbicides such as e.g., auxin, HPPD, glyphosate, dicamba, glufosinate, sulfonylurea, bromoxynil and norflurazon herbicides can be stacked either as a molecular stack or a breeding stack with plants expressing the traits disclosed herein. Polynucleotide molecules encoding proteins involved in herbicide tolerance include, but are not limited to, a polynucleotide molecule encoding 5-enolpyruvylshikimate-3-phosphate synthase (EPSPS) disclosed in U.S. Pat. Nos. 39,247; 6,566,587 and for imparting glyphosate tolerance; polynucleotide molecules encoding a glyphosate oxidoreductase (GOX) disclosed in U.S. Pat. No. 5,463,175 and a glyphosate-N-acetyl transferase (GAT) disclosed in U.S. Pat. Nos. 7,622,641; 7,462,481; 7,531,339; 7,527,955; 7,709,709; 7,714,188 and 7,666,643 also for providing glyphosate tolerance; dicamba monooxygenase disclosed in U.S. Pat. No. 7,022,896 and WO 2007/146706 A2 for providing dicamba tolerance; a polynucleotide molecule encoding AAD12 disclosed in US Patent Application Publication Number 2005/731044 or WO 2007/053482 A2 or encoding AAD1 disclosed in US 2011/0124503 A1 or U.S. Pat. No. 7,838,733 for providing tolerance to auxin herbicides (2,4-D); a polynucleotide molecule encoding hydroxyphenylpyruvate dioxygenase (HPPD) for providing tolerance to HPPD inhibitors (e.g., hydroxyphenylpyruvate dioxygenase) disclosed in e.g., U.S. Pat. No. 7,935,869; US 2009/0055976 A1 and US 2011/0023180 A1, each publication is herein incorporated by reference in its entirety.

Other examples of herbicide-tolerance traits that could be combined with the traits disclosed herein include those conferred by polynucleotides encoding an exogenous phosphinothricin acetyltransferase, as described in U.S. Pat. Nos. 5,969,213; 5,489,520; 5,550,318; 5,874,265; 5,919,675; 5,561,236; 5,648,477; 5,646,024; 6,177,616 and 5,879,903. Plants containing an exogenous phosphinothricin acetyltransferase can exhibit improved tolerance to glufosinate herbicides, which inhibit the enzyme glutamine synthase. Other examples of herbicide-tolerance traits include those conferred by polynucleotides conferring altered protoporphyrinogen oxidase (protox) activity, as described in U.S. Pat. Nos. 6,288,306 B1; 6,282,837 B1 and 5,767,373 and International Patent Publication WO 2001/12825. Plants containing such polynucleotides can exhibit improved tolerance to any of a variety of herbicides which target the protox enzyme (also referred to as “protox inhibitors”).

The introduction of recombinant DNA constructs of the present disclosure into plants may be carried out by any suitable technique, including but not limited to direct DNA uptake, chemical treatment, electroporation, microinjection, cell fusion, infection, vector-mediated DNA transfer, bombardment or *Agrobacterium*-mediated transformation. Techniques for plant transformation and regeneration have been described in International Patent Publication WO 2009/006276, the contents of which are herein incorporated by reference.

The development or regeneration of plants containing the foreign, exogenous isolated nucleic acid fragment that encodes a protein of interest is well known in the art. The regenerated plants may be self-pollinated to provide homozygous transgenic plants. Otherwise, pollen obtained from the regenerated plants is crossed to seed-grown plants of agronomically important lines. Conversely, pollen from plants of these important lines is used to pollinate regenerated plants. A transgenic plant of the present disclosure containing a desired polypeptide is cultivated using methods well known to one skilled in the art.

TABLE 1A

Expression of maize Pre2 in different tissues as compiled from MPSS-Signature Platform

| Tissue | Expression (PPTM) | Dev. Stage | Treatment |
|---|---|---|---|
| Leaf | 2880 | V5 | ECB |
| Kernel | 1750 | R1 | Drought Stress |
| Anther | 1270 | VT | Control |
| Apical Meristem, pre-floral | 1110 | V3 | |
| Endosperm | 1080 | R1 | In vitro |

TABLE 1A-continued

Expression of maize Pre2 in different tissues as compiled from MPSS-Signature Platform

| Tissue | Expression (PPTM) | Dev. Stage | Treatment |
|---|---|---|---|
| Immature Ear | 800 | V9 | |
| Pedicel and Basal Layer | 710 | R3 | |
| Root | 560 | V12 | Hydroponic |
| Lateral Branch Meristem | 540 | V8 | |
| Pericarp | 460 | R4 | |
| Stalk | 390 | Vn | Colletotrichum |
| Leaf midrib | 370 | V7 | Nitrate 4 h |
| Stalk internode meristematic zone | 350 | V10-V11 | |
| Germination Embryo | 320 | VE | |
| Root cortex | 320 | V1 | Nitrate-4 hr |
| Aleurone | 280 | R3 | |
| Stalk nodal plate | 270 | V10-V11 | |
| Vegetative Lateral Meristems | 200 | V8 | |
| Stalk rind | 170 | V10-V11 | |
| Root stele | 100 | V1 | Nitrate-4 hr |
| Germination Scutellum | 90 | VE | |
| Tassel Spikelet | 90 | VT | Tilt Herbicide |
| Pollen | 70 | VT | |
| Silk | 30 | R1 | |

TABLE 1B

Expression of maize Pre2 in different tissues as compiled from MPSS-Classic Platform

| Tissue | Expression (PPTM) | Dev. Stage | Treatment |
|---|---|---|---|
| Embryo | 990 | R2 | |
| Aerial Vegetative | 950 | Vn | |
| Apical Meristem | 820 | Vn | |
| Root | 770 | V6-V8 | |
| Stalk | 760 | V6 | |
| Immature ear | 760 | Vn | |
| Stalk Node | 580 | V12-V13 | |
| Ear Shoot | 530 | V11 | |
| Leaf | 500 | V6-V8 | Transgene |
| Pericarp | 490 | R4 | |
| Stalk Internode Rind | 440 | V12-V13 | |
| Leaf-base | 390 | V3 | |
| Leaf Whorl ECB | 390 | V5 | ECB infestation |
| Endosperm | 380 | R5 | |
| Stalk Internode | 340 | VT | |
| Pedicel | 340 | R1-R2 | Drought stress |
| Kernel | 340 | R2 | |
| Tassel Spikelet | 320 | VT | |
| Root Tip Meristem | 300 | V6 | |
| Ovary | 290 | Vn | |
| Silk | 290 | VT | |
| Tassel | 280 | Vn | |
| Pollen | 280 | VT | |
| Stem, Sheath | 260 | V7-V8 | |
| Ear | 230 | V15-R1 | |
| Stalk Internode Pith | 220 | VT | |
| Mesocotyl | 110 | VE | |
| Stalk Leaf Pulvinus | 100 | VT | |
| Husk | 80 | R1 | |
| Stalk Node | 40 | V12-V13 | |

TABLE 1C

Expression of maize Pre2 in different tissues as compiled from Solexa-WgT Platform

| Tissue | Expression (PPTM) | Dev. Stage |
|---|---|---|
| Tassel | 359.04 | V6 |
| Root | 349.75 | V19 |
| Immature Ear | 319.93 | V8 |
| Embryo | 270.21 | VE |
| Leaf | 230.42 | V19 |
| Kernel | 211.82 | R2 |
| Root Hair | 188.91 | V1 |
| Endosperm | 173.4 | R4 |
| Pericarp | 137.11 | R4 |
| Stalk | 94.79 | V8 |
| Pollen | 52.79 | R1 |

EXAMPLES

The Examples described below form part of the detailed description of the disclosure. The present disclosure is further illustrated in the following Examples, in which parts and percentages are by weight and degrees are Celsius, unless otherwise stated. It should be understood that these Examples, while indicating preferred embodiments of the disclosure, are given by way of illustration only. From the above discussion and these Examples, one skilled in the art can ascertain the essential characteristics of this disclosure, and without departing from the spirit and scope thereof, can make various changes and modifications of the disclosure to adapt it to various usages and conditions. Thus, various modifications of the disclosure in addition to those shown and described herein will be apparent to those skilled in the art from the foregoing description. Such modifications are also intended to fall within the scope of the appended claims.

Example 1

Characterization of the Pre-Mature Senescence2 (Pre2) Mutation in Maize

Figure 2A:
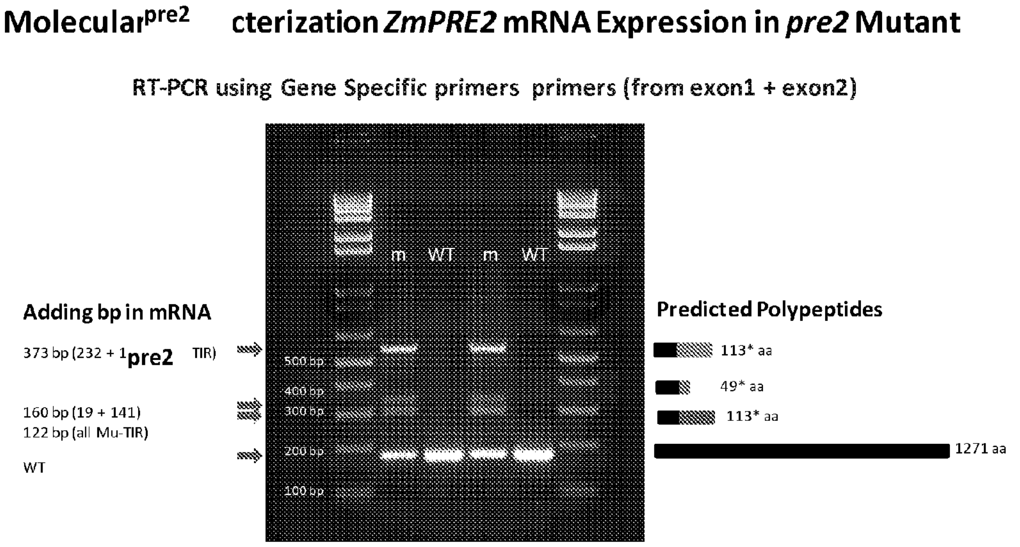
Figure 2B:
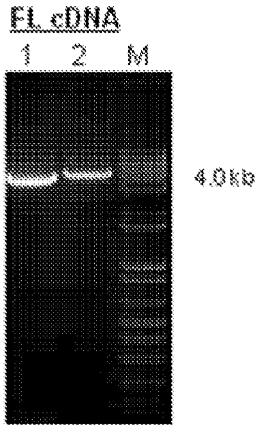
Figure 2C:
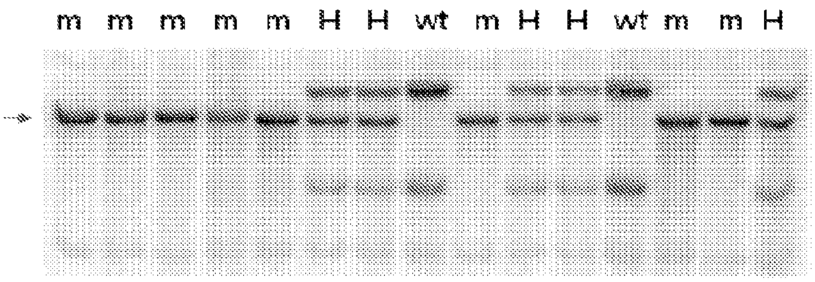

Forward genetics was used to clone a pre-mature senescence2 (pre2) mutation isolated from a highly Mu-active stock. The senescing phenotype of pre2, which inherits in a recessive manner, is apparent 2-3 weeks prior to anthesis. Like natural senescence, the pre2 phenotype starts from the lowermost leaves and then spreads to the top of the plant in a progressive fashion (FIG. 1A). We have cloned a candidate gene for pre2 mutation using SAIFF protocol (Selective Amplification of Insertion Flanking Fragments). The candidate gene co-segregates completely with the phenotype in a population of 500 segregating F2 plants (FIG. 1B). The pre2 encodes a conserved protein of no previously known function and is expressed at very low level (less than 100 PPM) in almost all parts of corn plant. The pre2 mutant phenotype was found to be the result of an interference of the insertion in differential splicing of intron1 in the transcript (FIG. 2A), which further leads to an early termination codon in its peptide. The Mu insertion in the mutant resulted in expression 4 different species of mRNA with variable expression levels (FIG. 2A). In addition to wild type mRNA, the mutant also expresses mRNAs with 122, 170 and 373 by insertions which due to pre mature stop codons translated into predicted polypeptides of 113, 49 and 113 amino acid residues in addition to 1271 amino acid wild type polypeptide (FIG. 2A). Reverse genetics and allelic test of two independent mutant alleles (pre2-2 and pre2-3) provided proof-of-validation that the right gene for pre2 mutation had been cloned (FIG. 2C).

Only a few partial ESTs representing 3' end of the gene were found in the database, thus a full length cDNA of 3.9 kb was amplified using RT-PCR (FIG. 2B) and cloned into a cloning vector. The maize pre2 gene includes of 13 exons and 12 introns and has 1271 amino acid long peptide. The Zmpre2 gene was mapped to chr4 on bin 189 cM. The maize Pre2 gene expression was compiled from different libraries developed by DuPont-Pioneer using various corn tissues at different developmental stages under different treatments. The gene expression value measured in PPTM by using three platforms, MPSS-Signature, MPSS-Classic and Solexa-WgT, is summarized in Table 1A, 1B, and 10. The Pre2 gene expression is enhanced under drought stress, insect infestation, disease inoculation, herbicide spray, and Nitrate application. The Pre2 is expressing in almost all plant parts of corn with maximum expression in leaf at V5 stage followed by kernel, anther, embryo, apical meristem, and root at V6-V8 stage.

Example 2

Identification and Characterization of the Pre2 Knock-Out Mutant in *Arabidopsis*

Figure 3:
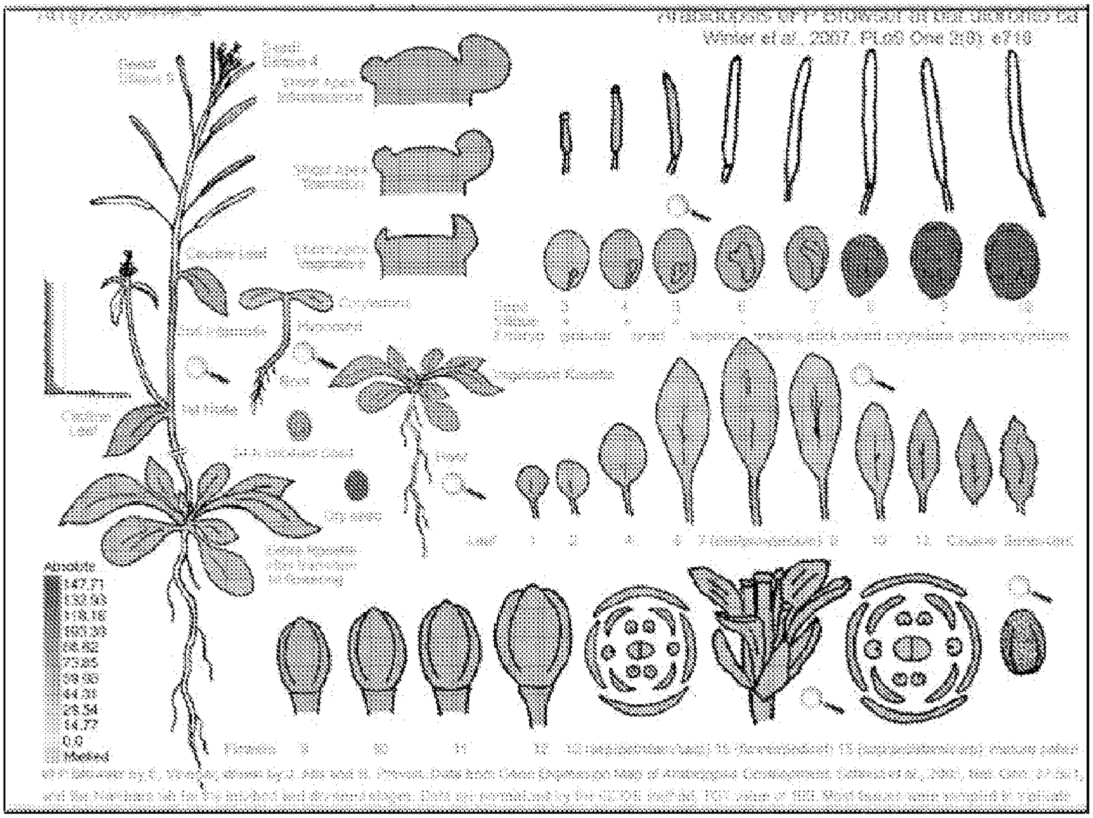
FIG. 3 shows a diagramatic representation of gene expression of Pre2 gene in different plant parts of *Arabidopsis*. Red (dark shade) and yellow (light shade) colors depict the highest and lowest gene expression, respectively.
Figure 4:
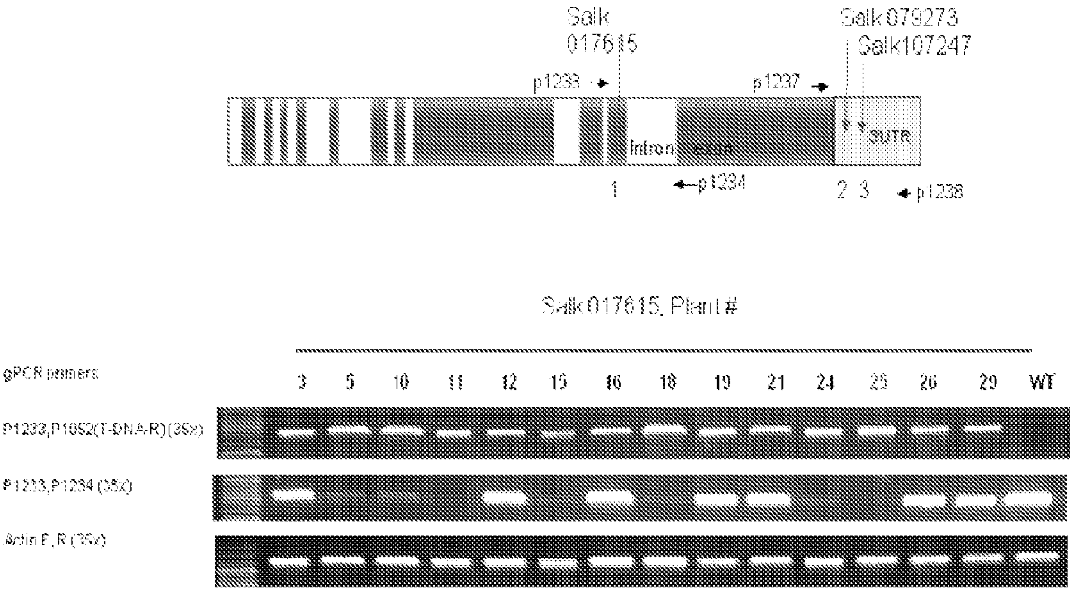
FIG. 4 show PCR fingerprinting of T-DNA insertion plants of *Arabidopsis*: PCR-FP analysis to identify homozygous knockouts, heterozygous and wild-type plants for T-DNA insertion of pre2 gene.

Homologous sequence of Pre2 in *Arabidopsis* was identified by using corn candidate gene sequence for pre-mature senescence2 as query. Then by using Atpre2 gene sequence, three independent T-DNA insertional alleles (Salk_017615, Salk_079273, Salk_107247) were identified in the *Arabidopsis* T-DNA mutant database. As in both SALK_079273 and SALK_107247 lines the T-DNA is situated in the 3' UTR region of the candidate gene (FIG. 4; top panel), Salk_017615 was analyzed in which the T-DNA is present in the coding sequence. This mutant line was obtained from ABRC and plants were grown and subjected to PCR fingerprinting and RT-PCR analyses. PCR amplification of the T-DNA flanking sequences using gene specific primer along with T-DNA primer confirmed that the T-DNA insertion is present in exon10 of At-PRE2 gene (FIG. 4; upper panel). Genomic PCRs using gene and T-DNA specific primers also showed that all plants were having T-DNA in the Atpre2 gene (FIG. 3, $2^{nd}$ panel from top). The gene specific primers flanking the T-DNA insertion will amplify DNA region in wild-type (WT) plants and right size PCR product was present in all plant except plant #11 and #25 (FIG. 3, $3^{rd}$ panel from top) indicating that all plants except #11 and #25 were heterozygous for this insertion. PCR amplification of Actin in both mutant and wild type plants was used as control (FIG. 4; $4^{th}$ panel from top). Based on these genotyping results plant #11 and 25 were identified as homozygous for T-DNA insertion. Expression of Pre2 is low in *Arabidopsis* and almost present in plant parts but highest was noticed in siliques and maturing seeds (FIG. 3). Furthermore, Reverse Transcriptase Polymerase Chain Reaction (RT-PCR) was performed on these plants and, but a full length transcript of AtPre2 mRNA was not detected in plant #11 and #25 (35 cycles) indicating that AtPre2 gene expression is knocked out in these two T-DNA mutants. We harvested seed from the two homozygous and all heterozygous plants. In order to identify and multiply the seed of WT-sib (+/+), seeds from the next generation from a self progeny of heterozygous plant were grown and PCR fingerprinting was repeated. The homozygous nature of T-DNA knock out in plant #11 and #25 was confirmed and the seeds were multiplied. Morphological traits from both homozygous plant #11 and #25 were compared with homozygous WT-sib (+/+) and heterozygous WT-sib (+/Pre2) at flowering. Both homozygous mutants were robust in growth with more pod numbers but were late in maturity by 4 to 5 days as compared to its WT-sibs (FIG. 5A). For measuring total biomass, 9 whole plants, each of knock out #11, knock out #25, homozygous WT, and heterozygous WT-sibs, were harvested and air dried for 14 days at room temperature. Total weight was determined by weighing and average and standard deviation were calculated for statistical analysis. The total biomass of both knockouts (combined) was found to be significantly higher (t test at $P<0.01$) when compared to both homozygous and heterozygous WT-sibs (FIG. 5B).

Example 3

Overexpression of Atpre2 in *Arabidopsis*

Multisite Gateway (Invitrogen) technology was used to generate plant expression vectors. A 3978 bp coding sequence of AtPre2 (at1g72390) was amplified by PCR using forward and reverse gene specific primers (GSP-F+GSP-R) and cloned in pENTR.D.TOPO. The final expression vector (pRG1261) contained herbicide and fluorescent marker for transgenic seed sorting. Quality check was performed on the resulting expression vector by restriction digestion mapping and transferred into *Agrobacterium tumefaciens* LB4404JT by electroporation. The co-integrated DNA from transformed *Agrobacterium* was transferred in *E. coli* DH10B and the plasmid DNA from this strain was used to check its quality again by restriction digestion. These overexpression vectors were transformed in to *Arabidopsis thaliana* ecotype Columbia-0 by *Agobacterium* mediated 'Floral-Dip' method (Clough and Bent, (1998) *Plant Journal* 16:735). $T_0$ seeds were screened for T1 transformants in soil for herbicide resistance. For molecular analysis of the transgenic T1 events, RT-PCRs were conducted to detect the transgene expression, actin control and the presence of genomic DNA in the RNA preparations. Transgene expressing events were advanced for further studies. Overexpression of ZmPre2 coding sequence in *Arabidopsis* resulted in a hypersensitive response to drought. (See, FIG. 6B).

Example 4

Sub-Cellular Localization and Regulation of Expression of Atpre2

In order to determine the sub-cellular localization AcGFP was fused in the c-terminal of AtPRE2. This fusion cassette was either driven by 35S promoter (pRG1263) or by ATPRE2 promoter (518 by region upstream of start codon of Atpre2) in pRG1264. Similarly, in order to study the regulation of expression of AtPre2 in details, this 518 by promoter region of Atpre2 was fused to GUS:RFP (a dual reporter) to generate pRG1265. All these constructs were transformed into *Arabidopsis* as described in Example 3.

Example 5

Drought Analysis of T-DNA Knockout Mutant and Over-Expressed Pre2 in *Arabidopsis*

Drought assay was performed on total 72 mutants and 72 wild-type sibs (WT) by using 8 pots (cells) for each. Each pot was shown to produce 9 mutant s or WT seedlings in a 3×3 array. Flats are configured with 8 square pots each in one experiment. Each pot was filled with Scotts® Metro-Mix® 200 soil. The soil was watered to saturation and then plants were grown under standard conditions of 16 hour light, 8 hour dark cycle; 22° C.; ~60% relative humidity). No additional water was given after day $16^{th}$.

Figure 6:
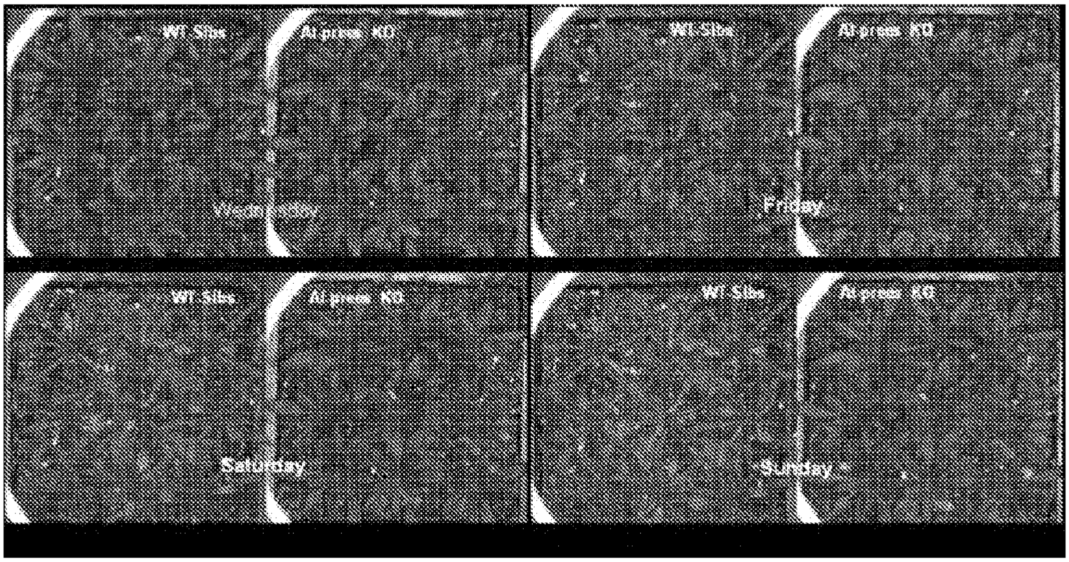
FIG. 6 shows *Arabidopsis* knockout mutant (homozygous) for corn homolog of pre2 candidate gene and its WT-sib were screened for drought assay. The Atpre2 mutant was an outlier in this assay with a score (2 sigma) higher than 0.9 and with positive deviation. *Arabidopsis* transgene with corn native gene was a control and was hypersensitive to drought stress.

Digital images of the plants were taken at the onset of visible drought stress symptoms. Images were taken once a day (at the same time of day), until the plants appear dessicated. Typically, four consecutive days of data is captured. Color analysis was employed for identifying potential drought tolerant lines. Color analysis can be used to measure the increase in the percentage of leaf area that falls into a yellow color bin. Using hue, saturation and intensity data ("HSI"), the yellow color bin consists of hues 35 to 45. Maintenance of leaf area was also used as another criterion for identifying potential drought tolerant lines, since *Arabidopsis* leaves wilt during drought stress. Maintenance of leaf area can be measured as reduction of rosette leaf area over time. Leaf area was measured in terms of the number of green pixels obtained using an imaging system. Mutant and control (e.g. wild-type) plants were grown side by side in flats and when wilting begins. From these data wilting profiles are determined based on the green pixel counts obtained over four consecutive days for activation-tagged or knockout mutant plants and accompanying control plants. The profile was selected from a series of measurements over the four day period that provided the largest degree of wilting. The ability to withstand drought was measured by the tendency of plants to resist wilting compared to control their WT-sib plants (FIG. 6A).

Software was used to analyze CCD images. Estimates of the leaf area of the *Arabidopsis* plants were obtained in terms of the number of green pixels. The data for each image was averaged to obtain estimates of mean and standard deviation for the green pixel counts for activation-tagged and wild-type plants. Parameters for a noise function were obtained by straight line regression of the squared deviation versus the mean pixel count using data for all images in a batch. Error estimates for the mean pixel count data were calculated using the fit parameters for the noise function. The mean pixel counts for activation-tagged and wild-type plants are summed to obtain an assessment of the overall leaf area for each image. The four-day interval with maximal wilting was obtained by selecting the interval that corresponds to the maximum difference in plant growth. The individual wilting responses of the activation-tagged, knockout mutants, and wild-type plants were obtained by normalization of the data using the value of the green pixel count of the first day in the interval. The drought tolerance of the activation-tagged or ko mutant plants compared to the wild-type plant was scored by summing the weighted difference between the wilting response of mutant or activation-tagged plants and wild-type plants over day two to day four; the weights were estimated by propagating the error in the data. A positive drought tolerance score corresponds to an activation-tagged or mutant plant with slower wilting compared to the wild-type plant. Significance of the difference in wilting response between activation-tagged and wild-type plants was obtained from the weighted sum of the squared deviations.

In drought assay the Atpre2 mutant plants were showing positive score greater than 0.9 with positive standard deviation in all flats. This demonstrated that these mutant plants outperformed significantly better than their wild type sibs used as control (FIG. 6B). The second control used in this experiment was ZmPre2 gene over expressed under 35S promoter in *Arabidopsis*. These plants became hypersensitive to drought stress (FIG. 6B) further authenticated these drought assay results.

Example 6

Analysis of Atpre2 Mutants on Low and High Nitrogen

Figure 7:
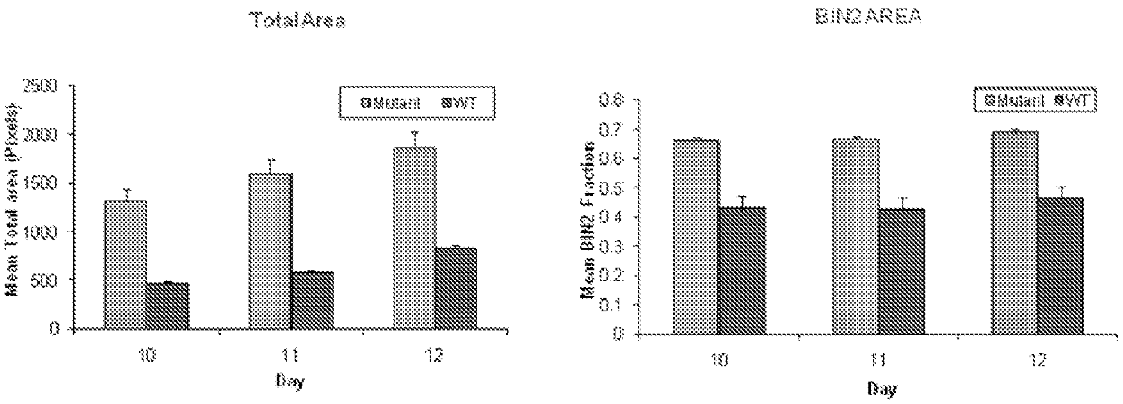
FIG. 7 shows phenotypic response of *Arabidopsis* knockout mutant (homozygous) for homolog of corn pre2 along with its WT-sib screened on Low N.

For low nitrogen (Low N) plate assays, 32 mutant and 32 wild type plants were grown on square plates (15 mm×15 mm) containing 0.5×N-Free Hoagland's, 0.4 mM potassium nitrate, 0.1% sucrose, 1 mM MES and 0.25% Phytagel™ (Low N medium). Plates were kept for three days in the dark at 4° C. to stratify seeds and then placed horizontally for nine days at 22° C. light and 20° C. dark. Plates were placed under sixteen hours light and eight hours dark, with an average light intensity of ~200 mmol/$m^2$/s. Plates were rotated and shuffled daily within each shelf. At day twelve (nine days of growth), seedling status was evaluated by imaging the entire plate. After masking the plate image to remove background color, two different measurements were collected for each individual plant: total rosette area, and the percentage of color that falls into a green color bin using hue, saturation and intensity data (HSI). The green color bin consists of hues 50 to 66. Total rosette area was used as a measure of plant biomass, whereas the green color bin was shown by dose-response studies to be an indicator of nitrogen assimilation. In this assay Atpre2 mutant plants showed a significantly higher total area (biomass) and green color (Bin2 area) (FIG. 7).

Figure 8:
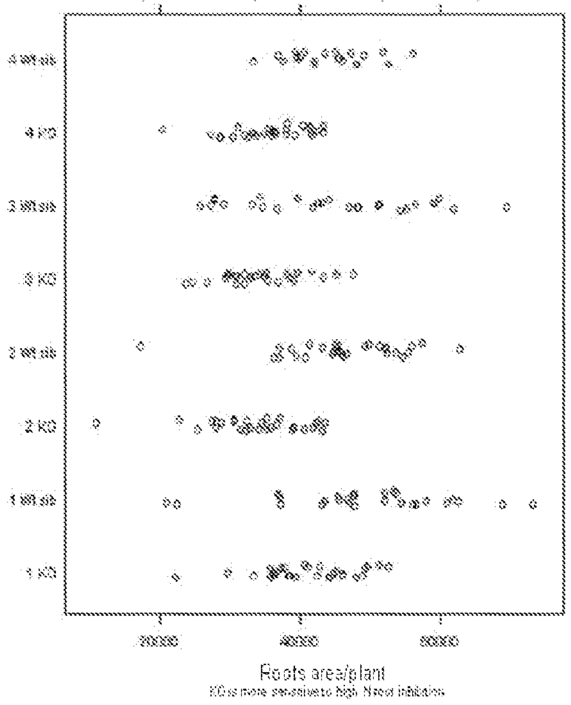
FIG. 8 shows screening of pre2 knockout mutant for pre2 of *Arabidopsis* showing root inhibition (sensitivity) to high N.

For high nitrogen (High N) root assays, 16 mutants and 16 wild type plants instead of 32 each were grown on plates in the same light and temperature conditions as described above. The plates were having the same medium except it was containing 60 mM of potassium nitrate. N and root biomass was measured by imaging. Four independent experiments were performed and the data revealed that in each case mutant plants were hyper-sensitive to higher concentration of nitrogen which leads to severe root growth inhibition as compared to its wild type sib plants (FIG. 8).

Example 7

Down-Regulation of Endogenous ZmPre2 mRNA by RNAi Studies

A genomic fragment of 450 bp (from 1189 to 1638 nt of ZmPre2 CDS) was used in sense and antisense orientation with an intron (ST-SL2 intron2) as a spacer to make an inverted repeat/RNAi cassette. This cassette was driven by either Zm-UBI (constitutive promoter) and/or a putative ZM-SEE1 (senescence induced promoter) promoters. MOPAT driven by Zm-UBI promoter and PMI driven by OsACTIN promoter was used as selectable markers. In addition, RFP driven by a pericarp specific promoter LTP2 was also used to sort out the transgenic seeds (red) from their segregating non-transgenic sib seeds. Transgenic lines for the constructs were generated and molecular analyses, such as PCR-FP and RT-PCR, were performed for selection of transgenic events. Several lines with significantly reduced expression of ZmPre2 have been identified and are characterized in further experiments.

Example 8

Down-Regulation of Endogenous ZmPre2-mRNA by RNAi Studies

ZmPre2 RNAi suppression construct is transformed into a fast cycling corn line (FASTCORN) for further transgenic validation. A full length mRNA amplified by RT-PCR (FIG.

2A) was used to make both for over-expression (Ox) and RNAi constructs using Ubi promoter. Ten transgenic events for both were screened molecularly for copy number and Pre2 gene expression by QPCR. For phenotypic data on leaf area, leaf color, height etc. digital images of the plants at various growth stages were taken as described above. Data on total biomass and stay green traits were calculated by measuring the leaf area in terms of the number of green pixels obtained using a commercially available imaging system. Data for other traits such as ear length, ear width, maximum ear area and total seed number were obtained at the time of harvesting. Data was analyzed by applying paired t-test and presented as Z-score in FIG. 9. All ten events (RNAi construct) and all but two of the (Ox) had single copy and the relative gene expression in five out ten RNAi events was significantly low (ranging from 0.07 to 0.554) as compared to internal transgenic and non-transgenic controls. All but one Ox events had 2× more relative expression ranging from 2.171 to 2.897. Three RNAi events (1.4, 1.5 and 2.5) were found to have significantly higher ear length, ear width and total seed numbers (FIG. 9), which is relevant to their relative gene expression. However, pre-mature senescence phenotype was not observed in these events. This could be due to the fact that all the insertion mutant alleles for the native Pre2 gene were resulting from the partial interference and differential splicing of the introns in their mature transcript, whereas the RNAi mechanism is different than Mutator insertion mutants. On the other hand, these four RNAi events with higher seed numbers as compared to all overexpression (Ox) events are behaving similar to T-DNA knockouts in *Arabidopsis*. These four events also show higher biomass (FIG. 9A). Three RNAi events (namely 1.4, 1.5 and 2.5) were selected for conducting NUE Reproductive Assay in T1 generation under 4.0 mMol Nitrate-suboptimal nitrogen conditions. Two of three events (1.5 and 2.5) showed significant increase (percent change vs. Null) in silk count, ear length, ear width and ear area (FIG. 9B). In addition to these traits, event 2.5 also showed significant difference for Days to shed and days to silk as compared to its nulls. Thus, transgenic plants where the expression of the Pre2 mRNA has been modulated exhibit significant differences in one or more agronomic parameters of interest for crop plants.

Example 9

Characterization of Polypeptides Homologous to Pre2

The protein-coding regions of other genes homologous to the PRE2 amino acid sequences disclosed herein. FIGS. 10-11 present an alignment of a plurality of amino acid sequences set forth in SEQ ID NOS: 1-48.

Sequence alignments and percent identity calculations were performed using the MEGALIGN® program of the LASERGENE® bioinformatics computing suite (DNASTAR® Inc., Madison, Wis.). Multiple alignment of the sequences was performed using the Clustal W method of alignment (Higgins and Sharp (1989) *CABIOS.* 5:151-153) with the default parameters (GAP PENALTY=10, GAP LENGTH PENALTY=10). Default parameters for pairwise alignments using the Clustal method were KTUPLE=1, GAP PENALTY=3, WINDOW=5 and DIAGONALS SAVED=5.

The amino acid sequence of corn Pre2 peptide (ZmPRE2) has the following percent sequence identity with the homologs presented in FIGS. 10 and 11: Pre2 peptides of sorghum and grasses such as Sudan, Bahia and Resurrection were found to be 83% to 90% identical with corn at amino acid level whereas the rice peptide diverged from corn and showed 68%. Homologs in dicots including *Arabidopsis*, Soybean and Canola have 34%, 36%, and 35% identity, respectively at the global alignment level.

Example 10

Molecular Analysis of the PRE2 Homologs

Molecular analysis revealed several conserved regions/domain in the Pre2 homologs. Despite the overall sequence divergence along the full-length of the Pre2 polypeptides across a variety of species shown in FIG. 10 for example, several highly conserved domains were observed (FIG. 11). SEQ ID NOS: 27-48 represent a subset of conserved regions and domains across the Pre2 polypeptide region.

Example 11

Expression of Transgenes or Downregulation of Endogenous Genes in Soybean

Local Blast results using AtPre2 full length gene sequence as query showed that there are two copies of Pre2 gene in soybean and their partial sequences is aligned in a multiple alignment (FIG. 10). A partial EST sequence (PSO423639) of about 2800 bp in length was cloned. The expression pattern distribution of the ESTs or full-length cDNAs in the Tissue Library Browser indicate that Pre2 gene expression is very low in soybean and Pre2-ESTs have been expressed highest in seedling, mostly in shoot under biotic and abiotic stresses. Medium numbers of ESTs (20-30) have been detected in leaf, root, young cotyledons, low levels in reproductive tissues such as pod, seed and seed coat.

Sequences of both the partial Pre2 copies in soybean were aligned and the following consensus sequence of 147 bp (SEQ ID NO: 51) was selected to use in an RNAi construct using *Arabidopsis* UBI promoter. This construct is transformed into soybean.

Soybean embryos are bombarded with a plasmid comprising a preferred promoter operably linked to a heterologous nucleotide sequence comprising a suitable target RNAi sequence against Pre2 polynucleotide sequence or subsequence (e.g., SEQ ID NOS: 14, 16, 17 and 19), as follows. To induce somatic embryos, cotyledons of 3 to 5 mm in length are dissected from surface-sterilized, immature seeds of the soybean cultivar A2872, then cultured in the light or dark at 26° C. on an appropriate agar medium for six to ten weeks. Somatic embryos producing secondary embryos are then excised and placed into a suitable liquid medium. After repeated selection for clusters of somatic embryos that multiply as early, globular-staged embryos, the suspensions are maintained as described below.

Soybean embryogenic suspension cultures can be maintained in 35 ml liquid media on a rotary shaker, 150 rpm, at 26° C. with fluorescent lights on a 16:8 hour day/night schedule. Cultures are sub-cultured every two weeks by inoculating approximately 35 mg of tissue into 35 ml of liquid medium.

Soybean embryogenic suspension cultures may then be transformed by the method of particle gun bombardment (Klein, et al., (1987) *Nature* (*London*) 327:70-73, U.S. Pat. No. 4,945,050). A DuPont Biolistic™ PDS1000/HE instrument (helium retrofit) can be used for these transformations.

A selectable marker gene that can be used to facilitate soybean transformation is a transgene composed of the 35S promoter from Cauliflower Mosaic Virus (Odell, et al., (1985) *Nature* 313:810-812), the hygromycin phosphotransferase gene from plasmid pJR225 (from *E. coli*; Gritz, et al., (1983) *Gene* 25:179-188) and the 3' region of the nopaline synthase gene from the T-DNA of the Ti plasmid of *Agrobacterium tumefaciens*. The expression cassette of interest, comprising the preferred promoter and a heterologous Pre2 polynucleotide e.g., in the sense or anti-sense or hairpin orientation, can be isolated as a restriction fragment. This fragment can then be inserted into a unique restriction site of the vector carrying the marker gene.

To 50 μl of a 60 mg/ml 1 μm gold particle suspension is added (in order): 5 μl DNA (1 μg/μl), 20 μl spermidine (0.1 M) and 50 μl CaCl2 (2.5 M). The particle preparation is then agitated for three minutes, spun in a microfuge for 10 seconds and the supernatant removed. The DNA-coated particles are then washed once in 400 μl 70% ethanol and resuspended in 40 μl of anhydrous ethanol. The DNA/particle suspension can be sonicated three times for one second each. Five microliters of the DNA-coated gold particles are then loaded on each macro carrier disk.

Approximately 300-400 mg of a two-week-old suspension culture is placed in an empty 60×5 mm petri dish and the residual liquid removed from the tissue with a pipette. For each transformation experiment, approximately 5-10 plates of tissue are normally bombarded. Membrane rupture pressure is set at 1100 psi, and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media and eleven to twelve days post-bombardment with fresh media containing 50 mg/ml hygromycin. This selective media can be refreshed weekly. Seven to eight weeks post-bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

Example 12

Transformation of Maize Using *Agrobacterium*

*Agrobacterium*-mediated transformation of maize is performed for example, as described by Zhao, et al., (2006) *Meth. Mol. Biol.* 318:315-323 (see also, Zhao, et al., (2001) *Mol. Breed.* 8:323-333 and U.S. Pat. No. 5,981,840 issued Nov. 9, 1999, incorporated herein by reference). The transformation process involves bacterium innoculation, co-cultivation, resting, selection and plant regeneration.

1. Immature Embryo Preparation:

Immature maize embryos are dissected from caryopses and placed in a 2 mL microtube containing 2 mL PHI-A medium.

2. *Agrobacterium* Infection and Co-Cultivation of Immature Embryos:

2.1 Infection Step:

PHI-A medium of (1) is removed with 1 mL micropipettor, and 1 mL of *Agrobacterium* suspension is added. The tube is gently inverted to mix. The mixture is incubated for 5 min at room temperature.

2.2 Co-culture Step:

The *Agrobacterium* suspension is removed from the infection step with a 1 mL micropipettor. Using a sterile spatula the embryos are scraped from the tube and transferred to a plate of PHI-B medium in a 100×15 mm Petri dish. The embryos are oriented with the embryonic axis down on the surface of the medium. Plates with the embryos are cultured at 20° C., in darkness, for three days. L-Cysteine can be used in the co-cultivation phase. With the standard binary vector, the co-cultivation medium supplied with 100-400 mg/L L-cysteine is critical for recovering stable transgenic events.

3. Selection of Putative Transgenic Events:

To each plate of PHI-D medium in a 100×15 mm Petri dish, 10 embryos are transferred, maintaining orientation and the dishes are sealed with PARAFILM®. The plates are incubated in darkness at 28° C. Actively growing putative events, as pale yellow embryonic tissue, are expected to be visible in six to eight weeks. Embryos that produce no events may be brown and necrotic, and little friable tissue growth is evident. Putative transgenic embryonic tissue is subcultured to fresh PHI-D plates at two-three week intervals, depending on growth rate. The events are recorded.

4. Regeneration of T0 plants:

Embryonic tissue propagated on PHI-D medium is subcultured to PHI-E medium (somatic embryo maturation medium), in 100×25 mm Petri dishes and incubated at 28° C., in darkness, until somatic embryos mature, for about ten to eighteen days. Individual, matured somatic embryos with well-defined scutellum and coleoptile are transferred to PHI-F embryo germination medium and incubated at 28° C. in the light (about 80 μE from cool white or equivalent fluorescent lamps). In seven to ten days, regenerated plants, about 10 cm tall, are potted in horticultural mix and hardened-off using standard horticultural methods.

Media for Plant Transformation:

1. PHI-A: 4 g/L CHU basal salts, 1.0 mL/L 1000× Eriksson's vitamin mix, 0.5 mg/L thiamin HCl, 1.5 mg/L 2,4-D, 0.69 g/L L-proline, 68.5 g/L sucrose, 36 g/L glucose, pH 5.2. Add 100 μM acetosyringone (filter-sterilized).
2. PHI-B: PHI-A without glucose, increase 2,4-D to 2 mg/L, reduce sucrose to 30 g/L and supplemented with 0.85 mg/L silver nitrate (filter-sterilized), 3.0 g/L GELRITE®, 100 μM acetosyringone (filter-sterilized), pH 5.8.
3. PHI-C: PHI-B without GELRITE® and acetosyringone, reduce 2,4-D to 1.5 mg/L and supplemented with 8.0 g/L agar, 0.5 g/L 2-[N-morpholino]ethane-sulfonic acid (MES) buffer, 100 mg/L carbenicillin (filter-sterilized).
4. PHI-D: PHI-C supplemented with 3 mg/L bialaphos (filter-sterilized).
5. PHI-E: 4.3 g/L of Murashige and Skoog (MS) salts, (Gibco, BRL 11117-074), 0.5 mg/L nicotinic acid, 0.1 mg/L thiamine HCl, 0.5 mg/L pyridoxine HCl, 2.0 mg/L glycine, 0.1 g/L myo-inositol, 0.5 mg/L zeatin (Sigma, Cat. No. Z-0164), 1 mg/L indole acetic acid (IAA), 26.4 μg/L abscisic acid (ABA), 60 g/L sucrose, 3 mg/L bialaphos (filter-sterilized), 100 mg/L carbenicillin (filter-sterilized), 8 g/L agar, pH 5.6.
6. PHI-F: PHI-E without zeatin, IAA, ABA; reduce sucrose to 40 g/L; replacing agar with 1.5 g/L GELRITE® pH 5.6.

Plants can be regenerated from the transgenic callus by first transferring clusters of tissue to N6 medium supplemented with 0.2 mg per liter of 2,4-D. After two weeks the tissue can be transferred to regeneration medium (Fromm, et al., (1990) *Bio/Technology* 8:833-839).

Transgenic T0 plants can be regenerated and their phenotype determined. T1 seed can be collected. T1 plants, and/or their progeny, can be grown and their phenotype determined.

Example 13

Transformation of *Brassica* with Pre2 Homoloqs Disclosed Herein

Canola transformation is accomplished for example, as described in Chen and Tulsieram, US Patent Application Publication Number 2007/0107077, incorporated herein by reference. Buds are collected from a donor line and sterilized. Buds are then homogenized, filtered, and washed to collect the microspores. The resultant microspore suspension was adjusted to a specified density and cultured for 2 days. Embryogenic microspores were then isolated via gradient centrifugation and cultured.

Gold particles coated with the DNA fragment were used for transformation. Biolistic transformation is carried out using the PDS-1000/He Particle Delivery System (Bio-Rad, Hercules, Calif.) as described by Klein, et al., (1987) *Nature* 327:70-73. Transformed embryogenic microspores are cultured in fresh medium in dark conditions for 10-12 days, then under dim light for 1-3 weeks. Green embryos are transferred to fresh medium and cultured for two weeks to select based on the marker gene used. Germinated shoots and/or plants were transferred to growth medium supplemented with selection component.

Example 14

Yield Analysis of Plants Transformed with Pre2 Targeting Constructs

A recombinant DNA construct containing a Pre2 down-regulating construct can be introduced into plants either by direct transformation or introgression from a separately transformed line.

Transgenic plants, either inbred or hybrid, can undergo more vigorous field-based experiments to study yield enhancement and/or stability under well-watered and water-limiting conditions.

Subsequent yield analysis can be done to determine whether plants that contain the constructs/sequences disclosed herein have an improvement in yield performance under water-limiting conditions, when compared to the control plants that do not contain the validated drought tolerant lead gene. Specifically, drought conditions can be imposed during the flowering and/or grain fill period for plants that contain the constructs/sequences disclosed herein and the control plants. Reduction in yield can be measured for both. Plants containing the constructs/sequences disclosed herein have less yield loss relative to the control plants, for example, at least 25% less yield loss, under water limiting conditions, or would have increased yield relative to the control plants under water non-limiting conditions.

The above method may be used to select transgenic plants with increased yield, under water-limiting conditions and/or well-watered conditions, when compared to a control plant not comprising said recombinant DNA construct.

Example 15

At-Pre2 Mutant is Hypersensitive to ABA

In earlier experiments At-Pre2 T-DNA knock out mutant showed a significant increase in biomass, improved growth on low N plates, and drought tolerant phenotype in soil. AT-PRE2 is a large protein of 1326 amino acid residues with unknown function. To elucidate the function of this protein, several experiments were conducted. One of such experiments included ABA response of Atpre2 mutant. Seeds of Atpre2 mutant and Col-0 WT (36 seeds of each WT and mutant with 3 replications) were grown on half MS media (without sucrose) with or without abscisic acid (1 μM±-cis, trans-ABA). The plates with seeds were kept at 4° C. in dark for 3 days and then incubated in growth chamber under the long day growth conditions (16-h-light/8-h-dark cycle at 120-150 μmol m−2 sec−1 and 20° C. to 22° C., with 75% humidity). Visible radicle tips (1-2 mm) were counted after 48 hrs as a germinated seed. In these multiple experiments Atpre2 mutant showed a hypersensitive response to ABA in a dosage dependent manner. The seed germination in mutant was reduced or delayed by more than 50% as compare to wild type in presence of 1 μM ABA (FIG. 12). Searches of expression databases revealed that the endogenous AT-PRE2 gene expression was higher in guard cells in wild type plants and was down-regulated by ABA treatment both in seedling and leaf. In addition AtPRE2 was also up-regulated by nitrate in roots. These results indicate a direct or indirect role of AtPRE2 in ABA and N signaling/pathway.

The invention claimed is:

1. A method of altering an agronomic parameter of a maize plant, the method comprising transforming a maize plant with a recombinant DNA construct that downregulates the endogenous expression of a nucleotide encoding a polypeptide, wherein the polypeptide comprises an amino acid sequence that is at least 95% identical to SEQ ID NO:3 and thereby altering the agronomic parameter of the plant.

2. The method of claim 1, wherein the agronomic parameter is selected from the group consisting of greenness, yield, growth rate, biomass, plant nitrogen content, drought tolerance, nitrogen uptake, root lodging, harvest index, stalk lodging, plant height, ear height, ear width, ear length, ear area, salt tolerance, early seedling vigor and seedling emergence under low temperature stress, drought tolerance, increased nitrogen use efficiency, silk count, inducing early maturity, delaying maturity, days to shed and days to silk.

3. The method of claim 1, wherein the downrequlation of endogenous expression of the nucleotide is by RNAi.

* * * * *